US012104181B2

(12) United States Patent
Schoggins et al.

(10) Patent No.: US 12,104,181 B2
(45) Date of Patent: Oct. 1, 2024

(54) COMPOSITIONS AND METHODS FOR TREATING VIRAL INFECTIONS TARGETING TRIM7

(71) Applicant: THE BOARD OF REGENTS OF THE UNIVERSITY OF TEXAS SYSTEM, Austin, TX (US)

(72) Inventors: John W. Schoggins, Dallas, TX (US);
Wenchun Fan, Dallas, TX (US);
Daniel J. Siegwart, Dallas, TX (US);
Qiang Cheng, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 3 days.

(21) Appl. No.: 17/710,464

(22) Filed: Mar. 31, 2022

(65) Prior Publication Data
US 2022/0325255 A1   Oct. 13, 2022

Related U.S. Application Data

(60) Provisional application No. 63/168,898, filed on Mar. 31, 2021.

(51) Int. Cl.
*A61P 31/14*     (2006.01)
*A61K 9/51*      (2006.01)
*A61K 48/00*     (2006.01)
*C12N 9/10*      (2006.01)

(52) U.S. Cl.
CPC ............ *C12N 9/104* (2013.01); *A61K 9/5123* (2013.01); *A61K 48/0066* (2013.01); *A61P 31/14* (2018.01)

(58) Field of Classification Search
None
See application file for complete search history.

(56) References Cited

U.S. PATENT DOCUMENTS 10,562,849 B2    2/2020  Siegwart et al.
2014/0010861 A1* 1/2014  Bancel ................ C07K 14/485
                                                   536/23.4

OTHER PUBLICATIONS

Nurgun Kose et al., A lipid-encapsulated mRNA encoding a potently neutralizing human monoclonal antibody protects against chikungunya infection.Sci. Immunol.4,eaaw6647(2019) (Year: 2019).*
Wang, Y., Hao, L., Pan, L. et al. Age, primary symptoms, and genotype characteristics of norovirus outbreaks in Shanghai schools in 2017. Sci Rep 8, 15238 (2018). (Year: 2018).*
Rajsbaum, R., García-Sastre, A. and Versteeg, G.A., 2014. TRIMmunity: the roles of the TRIM E3-ubiquitin ligase family in innate antiviral immunity. Journal of molecular biology, 426(6), pp. 1265-1284. (Year: 2014).*
Nozawa, R.S., et al. (2017). SAF-A Regulates Interphase Chromosome Structure through Oligomerization with Chromatin-Associated RNAs. Cell 169, 1214-1227.e18.
Ode, H., et al. (2012). Molecular dynamics simulation in virus research. Front. Microbiol. 3, 1-9.
Orchard, R.C., et al. (2018). Identification of Antinorovirus Genes in Human Cells Using Genome-Wide CRISPR Activation Screening. J. Virol. 93, 1-12.
Pacheco, B., et al. (2010). Adaptation of HIV-1 to cells expressing rhesus monkey TRIM5α. Virology 408, 204-212.
Parrinello, M., et al. (1981). Polymorphic transitions in single crystals: A new molecular dynamics method. J. Appl. Phys. 52(12), 7182.
Patel, K., et al. (2015). Lipolysis of visceral adipocyte triglyceride by pancreatic lipases converts mild acute pancreatitis to severe pancreatitis independent of necrosis and inflammation. Am. J. Pathol. 185, 808-819.
Patil, G., et al. (2019). Tripartite motif proteins: an emerging antiviral protein family Girish. Future Virol. 14, 107-122.
Patil G, et al. (2018). TRIM41-Mediated Ubiquitination of Nucleoprotein Limits Influenza A Virus Infection. J. Virol. 92, 1-12.
Di Pietro, A., et al. (2013). TRIM22 Inhibits Influenza A Virus Infection by Targeting the Viral Nucleoprotein for Degradation. J. Virol. 87, 4523-4533.
Robert, X., et al. (2014). Deciphering key features in protein structures with the new ENDscript server. Nucleic Acids Res. 42, 320-324.
Robinson, C.M., et al. (2017). Sex-Dependent Intestinal Replication of an Enteric Virus. J. Virol. 91, 1-10.
Schindelin, J., et al. (2012). Fiji—an Open platform for biological image analysis. Nat. Methods 9(7), 676-682.
Schoggins, J.W. (2019). Interferon-Stimulated Genes: What Do They All Do? Annu. Rev. Virol. 6, 567-584.
Schoggins, J.W., et al. (2011). A diverse range of gene products are effectors of the type i interferon antiviral response. Nature 472, 481-485.
Schoggins, J.W., et al. (2012). Dengue reporter viruses reveal viral dynamics in interferon receptor-deficient mice and sensitivity to interferon effectors in vitro. Proc. Natl. Acad. Sci. U. S. A. 109, 14610-14615.
Schoggins, et al. (2014). Pan-viral specificity of IFN-induced genes reveals new roles for cGAS in innate immunity. Nature 505, 691-695.

(Continued)

*Primary Examiner* — Neil P Hammell
*Assistant Examiner* — Khaleda B Hasan
(74) *Attorney, Agent, or Firm* — POLSINELLI PC

(57) ABSTRACT

Embodiments of the instant disclosure relate to novel antiviral compositions and methods for treating viral infections. In accordance with these embodiments, antiviral compositions can include at least one mRNA encoding for a TRIM7 protein encapsulated into a lipid nanoparticle (LNP). In other embodiments, methods of making antiviral compositions are disclosed as well as methods of administering a composition having at least one mRNA encoding for a TRIM7 protein encapsulated into LNP into a subject.

10 Claims, 41 Drawing Sheets

(7 of 41 Drawing Sheet(s) Filed in Color)

Specification includes a Sequence Listing.

(56) References Cited

OTHER PUBLICATIONS

Schwarz, M.C., et al. (2016). Rescue of the 1947 Zika Virus Prototype Strain with a Cytomegalovirus Promoter-Driven cDNA Clone. MSphere 1, 1-12.
Si, X., et al. (2008). Ubiquitination is required for effective replication of Coxsackievirus B3. PLoS One 3(7), e2585.
Skurat, A. V., et al. (2002). GNIP, a novel protein that binds and activates glycogenin, the self-glucosylating initiator of glycogen biosynthesis. J. Biol. Chem. 277, 19331-19338.
Suhy, D.A., et al. (2000). Remodeling the Endoplasmic Reticulum by Poliovirus Infection and by Individual Viral Proteins: an Autophagy-Like Origin for Virus-Induced Vesicles. J. Virol. 74, 8953-8965.
Tamura, K., et al. (2013). MEGA6: Molecular evolutionary genetics analysis version 6.0. Mol. Biol. Evol. 30, 2725-2729.
Tan, G., et al. (2019). Type-I-IFN-Stimulated Gene TRIM5 g Inhibits HBV Replication by Promoting HBx Degradation Article Type-I-IFN-Stimulated Gene TRIM5 g Inhibits HBV Replication by Promoting HBx Degradation. CellReports 29, 3551-3563.e3.
Taylor, R.T., et al. (2011). TRIM79α, an interferon-stimulated gene product, restricts tick-borne encephalitis virus replication by degrading the viral RNA polymerase. Cell Host Microbe 10, 185-196.
Tracy, S., et al. (2000). Group B coxsackievirus myocarditis and pancreatitis: Connection between viral virulence phenotypes in mice. J. Med. Virol. 62, 70-81.
Vourinen, T., et al. (1989). Coxsackievirus B3-induced acute pancreatitis: Analysis of histopathological and viral parameters in a mouse model. Br. J. Exp. Pathol. 70, 395-403.
Wang, T., et al. (2017). Enterovirus 71 protease 2Aproand 3Cprodifferentially inhibit the cellular endoplasmic reticulum-associated degradation (ERAD) pathway via distinct mechanisms, and enterovirus 71 hijacks ERAD component p97 to promote its replication.PLoS Pathog. 13(10). e1006674.
Wu, X., et al. (2019). Inhibition of influenza A virus replication by TRIM14 via its multifaceted protein-protein interaction with NP. Front. Microbiol. 10, 1-14.
Yang, B., et al. (2020). RNF90 negatively regulates cellular antiviral responses by targeting MITA for degradation. PLoS Pathog. 16, 1-20.
Zhai, L., et al. (2004). Structure-function analysis of GNIP, the glycogenin-interacting protein. Arch. Biochem. Biophys. 421, 236-242.
Zhou, K., et al. (2016). Modular degradable dendrimers enable small RNAs to extend survival in an aggressive liver cancer model. Proc. Natl. Acad. Sci. U. S. A. 113, 520-525.
Zhu, L., et al. (2019). The E3 ubiquitin ligase TRIM7 suppressed hepatocellular carcinoma progression by directly targeting Src protein. Cell Death Differ. 27(6), 1819-1831.
Abraham, M.J., et al. (2015). Gromacs: High performance molecular simulations through multi-level parallelism from laptops to supercomputers. SoftwareX 1-2, 19-15.
Aguilera, E.R., et al. (2019). Bacterial Stabilization of a Panel of Picornaviruses. MSphere 4(2), e00183-19.
Althof, N., et al. (2014). In Vivo Ablation of Type I Interferon Receptor from Cardiomyocytes Delays Coxsackieviral Clearance and Accelerates Myocardial Disease. J. Virol. 88, 5087-5099.
Amadei, A., et al. (1993). Essential dynamics of proteins. Proteins Struct. Funct. Bioinforma. 17(4), 412-425.
Amamuddy, O.S., et al. (2020). Impact of early pandemic stage mutations on molecular dynamics of SARS-COV-2 MPro. J. Chem. Inf. Model. 60, 5080-5102.
Amjad, A., FarooquiRahman, et al. (2019). The host cell ubiquitin ligase protein CHIP is a potent suppressor of HIV-1 replication. J. Biol. Chem. 294, 7283-7295.
Baggen, J., et al.. (2018). The life cycle of non-polio enteroviruses and how to target it. Nat. Rev. Microbiol. 16, 368-381.
Calistri, A., et al. (2014). The Ubiquitin-Conjugating System: Multiple Roles in Viral Replication and Infection. Cells 3 (2), 386-417.

Chakraborty, A., et al. (2015). The E3 ubiquitin ligase Trim7 mediates c-Jun/AP-1 activation by Ras signalling. Nat. Commun. 6, 1-12.
Cheng, Q., et al. (2018). Dendrimer-Based Lipid Nanoparticles Deliver Therapeutic FAH mRNA to Normalize Liver Function and Extend Survival in a Mouse Model of Hepatorenal Tyrosinemia Type I. Adv Mater 30, e1805308.
Cheng, Q., et al. (2020). Selective organ targeting (SORT) nanoparticles for tissue-specific mRNA delivery and CRISPR-Cas gene editing. Nat. Nanotechnol. 15, 313-320.
Chiramel, A.I., et al. (2019). TRIM5α Restricts Flavivirus Replication by Targeting the Viral Protease for Proteasomal Degradation. Cell Rep. 27, 3269-3283.e6.
Cornell, C.T., et al. (2007). Coxsackievirus B3 Proteins Directionally Complement Each Other To Downregulate Surface Major Histocompatibility Complex Class I. J. Virol. 81, 6785-6797.
Darden, T., et al. (1993). Particle mesh Ewald: An N-log(N) method for Ewald sums in large systems. J. Chem. Phys. 98(12), 10089-10092.
David, C.C., et al. (2014). Principal component analysis: A method for determining the essential dynamics of proteins. Methods Mol. Biol. 1084, 193-226.
Duggal, N.K., et al. (2012). Evolutionary conflicts between viruses and restriction factors shape immunity. Nat. Rev. Immunol. 12, 687-695.
Emsley, P., et al. (2010). Features and development of Coot. Acta Crystallogr. Sect. D Biol. Crystallogr. 66, 486-501.
Eslami, H., et al. (2010). Molecular dynamics simulation with weak coupling to heat and material baths. J. Chem. Phys. 133(8), 084105.
Fan, W., et al. (2016). TRIM52 inhibits Japanese Encephalitis Virus replication by degrading the viral NS2A. Sci. Rep. 6, 1-11.
Feuer, R., et al. (2002). Cell Cycle Status Affects Coxsackievirus Replication, Persistence, and Reactivation In Vitro. J. Virol. 76, 4430-4440.
Fu, B., et al. (2015). TRIM32 Senses and Restricts Influenza A Virus by Ubiquitination of PB1 Polymerase. PLoS Pathog. 11, 1-23.
Ganser-Pornillos, B.K., et al. (2019). Restriction of HIV-1 and other retroviruses by TRIM5. Nat. Rev. Microbiol. 17, 546-556.
Van Gent, M., et al. (2018). TRIM Proteins and Their Roles in Antiviral Host Defenses. Annu. Rev. Virol. 5, 385-405.
Giraldo, M.I., et al. (2020). Envelope protein ubiquitination drives entry and pathogenesis of Zika virus. Nature 585, 414-419.
Grice, G.L., et al. (2016). The recognition of ubiquitinated proteins by the proteasome. Cell. Mol. Life Sci. 73, 3497-3506.
Guan, H., et al. (2017). Crystal structure of 2C helicase from enterovirus 71. Sci. Adv. 3, 1-10.
Guan, H., et al. (2018). Crystal structure of a soluble fragment of poliovirus 2CATPase. PLoS Pathog. 14, 1-24.
Gustin, et al. (2011). Viral takeover of the host ubiquitin system. 2, 1-24.
Hage, A., et al. (2019). To TRIM or not to TRIM: the balance of host-virus interactions mediated by the ubiquitin system. J. Gen. Virol. 1641-1662.
Hashim, A., et al. (2019). Cellular TRIM33 restrains HIV-1 infection by targeting viral integrase for proteasomal degradation. Nat. Commun. 10, 1-15.
Hrecka, K., et al. (2011). Vpx relieves inhibition of HIV-1 infection of macrophages mediated by the SAMHD1 protein. Nature 474, 658-661.
Hu, X., et al. (2019). Tripartite motif-containing protein 7 regulates hepatocellular carcinoma cell proliferation via the DUSP6/p38 pathway. Biochem. Biophys. Res. Commun. 511, 889-895.
Huber, S., et al. (2004). Review Coxsackievirus-Induced Pancreatitis. 17, 358-369.
Ji, R., et al. (2019). TRIM7 promotes proliferation and migration of vascular smooth muscle cells in atherosclerosis through activating c-Jun/AP-1. IUBMB Life 1-12.
Johannsdottir, H.K., et al. (2009). Host Cell Factors and Functions Involved in Vesicular Stomatitis Virus Entry. J. Virol. 83, 440-453.
Kallewaard, N.L., et al. (2009). Tissue-Specific Deletion of the Coxsackievirus and Adenovirus Receptor Protects Mice from Virus-Induced Pancreatitis and Myocarditis. Cell Host Microbe 6, 91-98.

(56) References Cited

OTHER PUBLICATIONS

Kimura, T., et al. (2019). Biphasic and cardiomyocyte-specific IFIT activity protects cardiomyocytes from enteroviral infection. PLoS Pathog. 15, 1-22.

Krumbholz, A., et al. (2016). Analysis of an echovirus 18 outbreak in Thuringia, Germany: insights into the molecular epidemiology and evolution of several enterovirus species B members. Med. Microbiol. Immunol. 205, 471-483.

Laguette, N., et al. (2011). SAMHD1 is the dendritic- and myeloid-cell-specific HIV-1 restriction factor counteracted by Vpx. Nature 474, 654-657.

Laufman, O., et al. (2019). Viral Generated Inter-Organelle Contacts Redirect Lipid Flux for Genome Replication. Cell 178, 275-289. e16.

Lee, H.K., et al. (2007). Autophagy-dependent viral recognition by plasmacytoid dendritic cells. Science (80-. ). 315, 1398-1401.

Lindorff-Larsen, K., et al. (2010). Improved side-chain torsion potentials for the Amber ff99SB protein force field. Proteins Struct. Funct. Bioinforma. 78, 1950-1958.

Ma, Z., et al. (2017). Tandem affinity purification of protein complexes from eukaryotic cells. J. Vis. Exp. 119, 55236.

Mar, K.B., et al. (2018). LY6E mediates an evolutionarily conserved enhancement of virus infection by targeting a late entry step. Nat. Commun. 9(1), 3603.

Marin, M., et al. (2003). HIV-1 Vif protein binds the editing enzyme APOBEC3G and induces its degradation. Nat. Med. 9, 1398-1403.

Mena, I., et al. (2000). Coxsackievirus infection of the pancreas: Evaluation of receptor expression, pathogenesis, and immunopathology. Virology 271, 276-288.

Mombo, I.M., et al. (2017). African non-human primates host diverse enteroviruses. PLoS One 12, 1-18.

Montori-Grau, M., et al. (2018). GNIP1 E3 ubiquitin ligase is a novel player in regulating glycogen metabolism in skeletal muscle. Metabolism. 83, 177-187.

Morosky, S., et al. (2019). The neonatal Fc receptor is a pan-echovirus receptor. Proc. Natl. Acad. Sci. U. S. A. 116, 3758-3763.

Neil, S.J.D., et al. (2007). An Interferon-α-Induced Tethering Mechanism Inhibits HIV-1 and Ebola Virus Particle Release but Is Counteracted by the HIV-1 Vpu Protein. Cell Host Microbe 2, 193-203.

\* cited by examiner

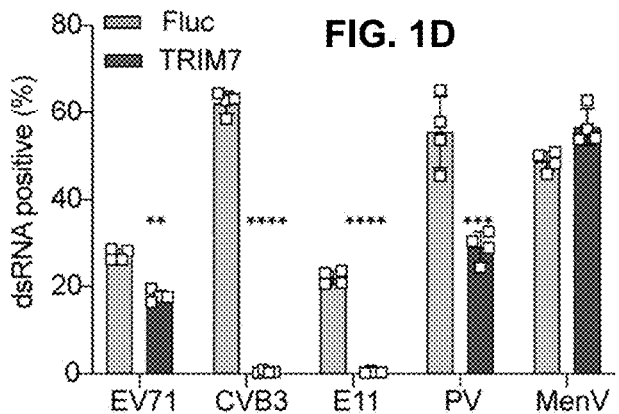
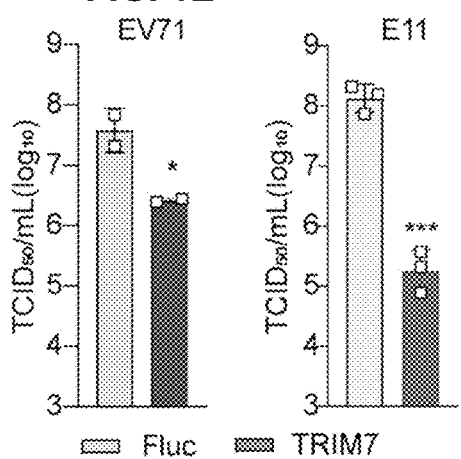
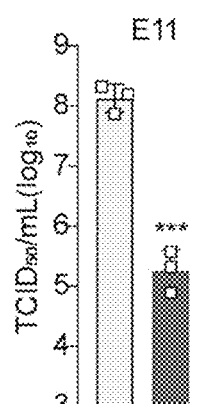
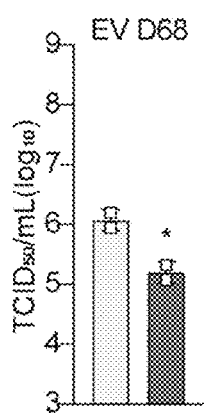
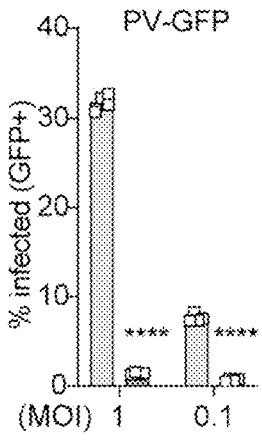
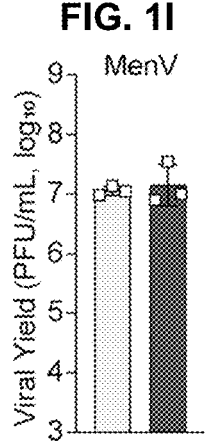
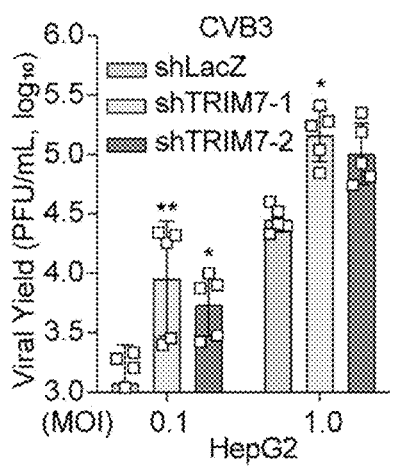

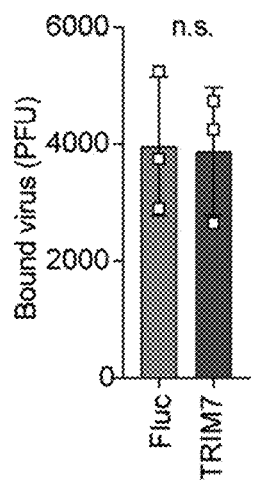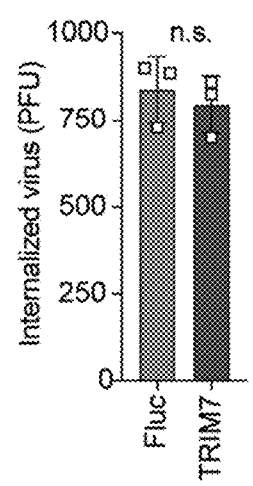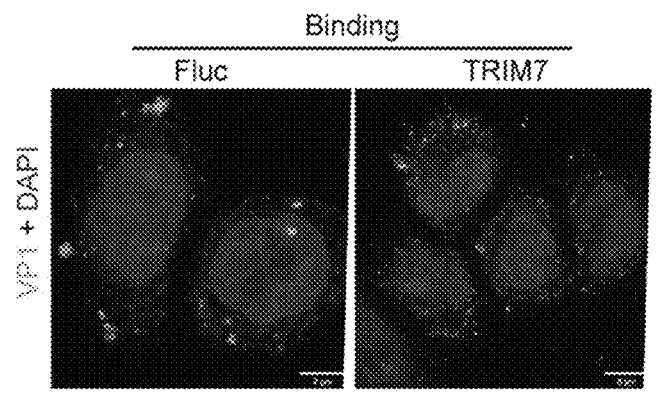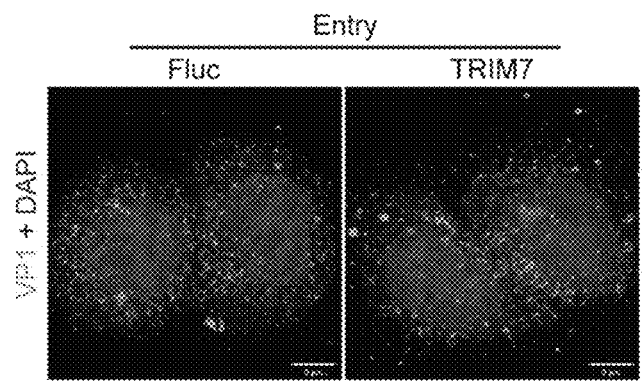

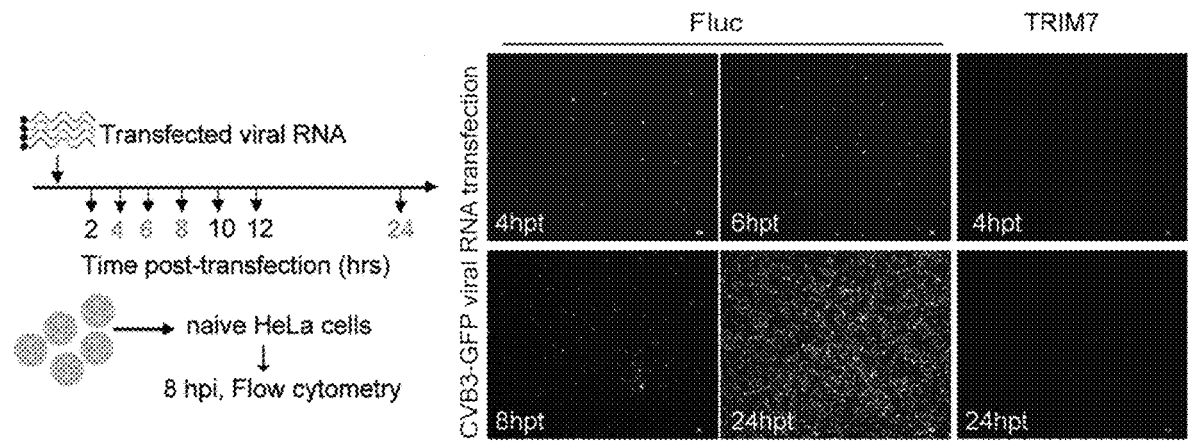
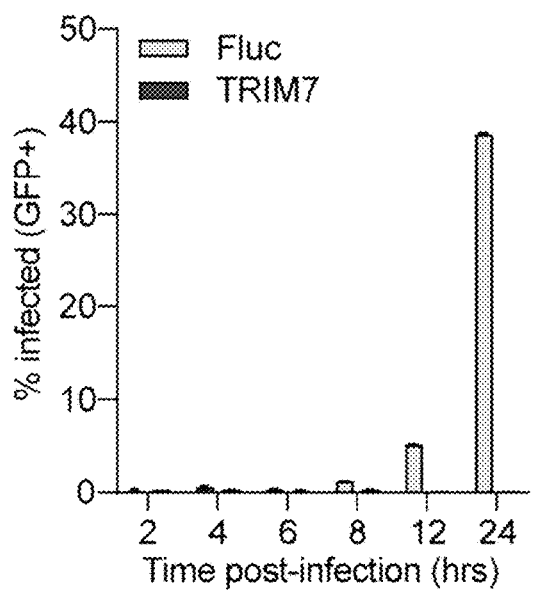
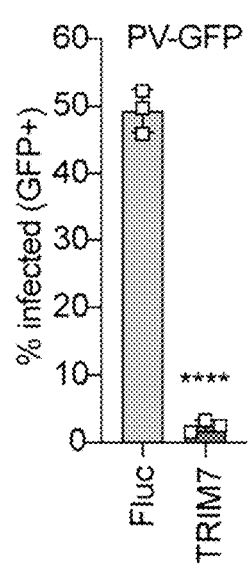

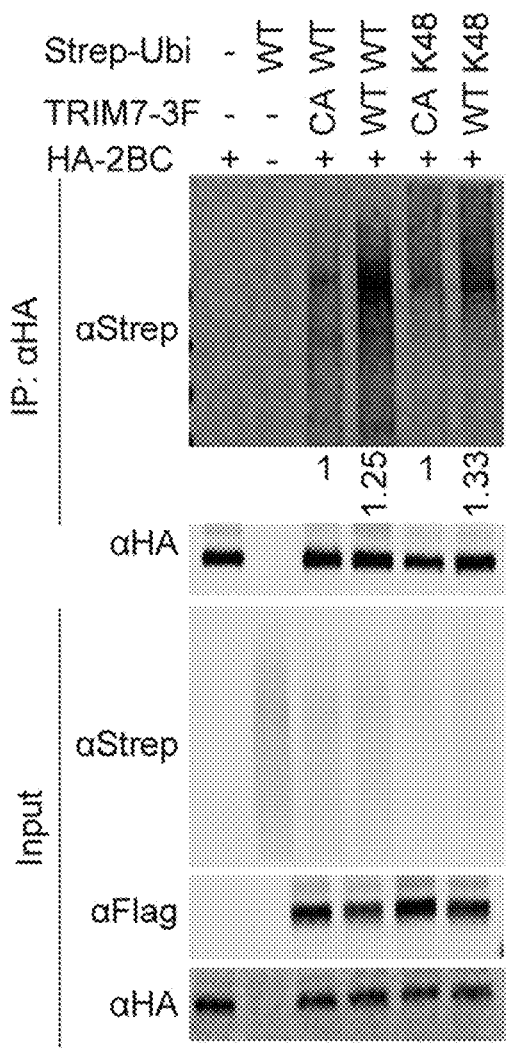
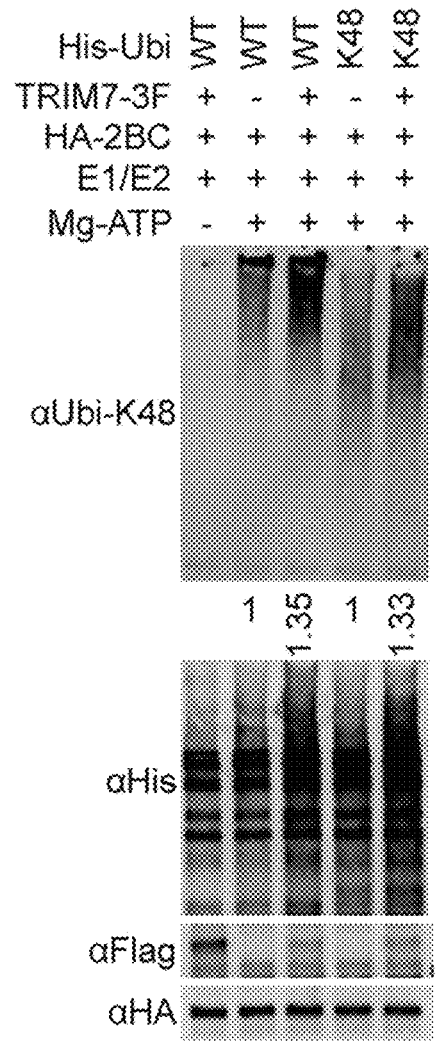

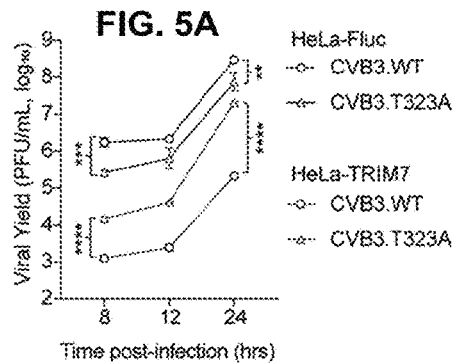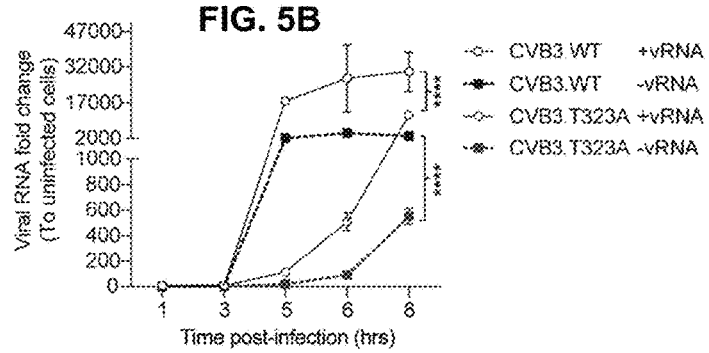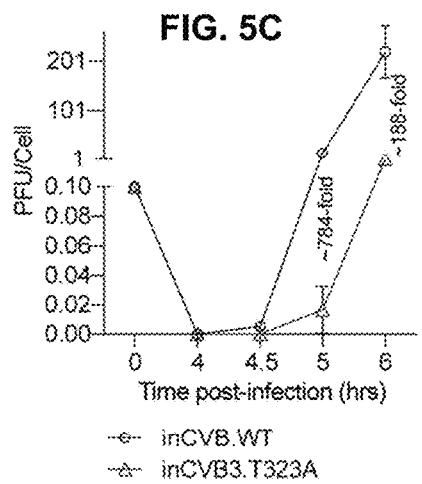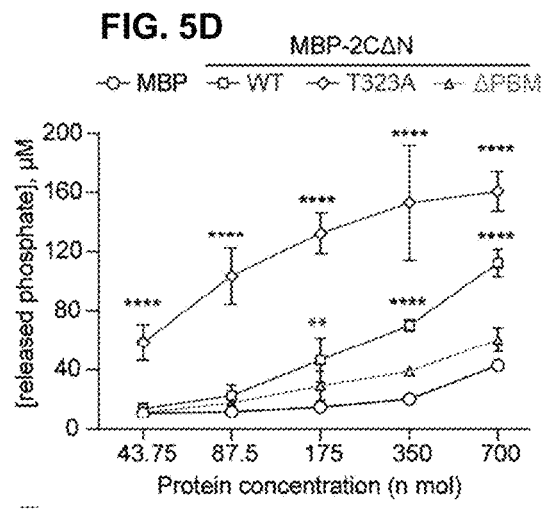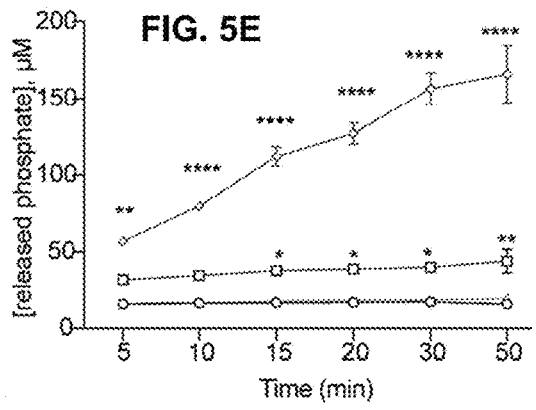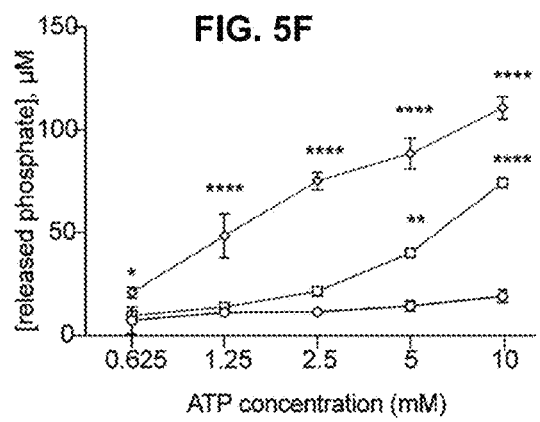

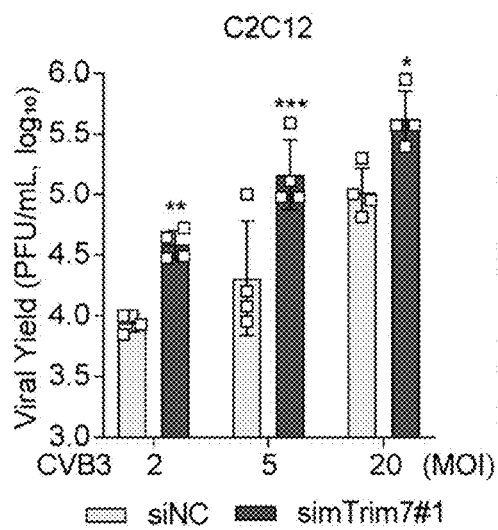
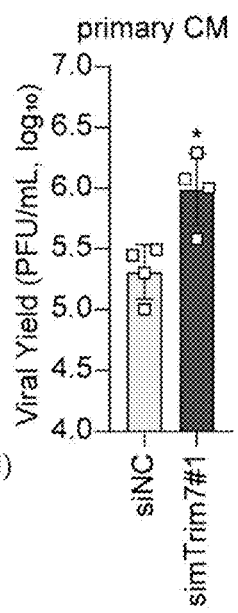
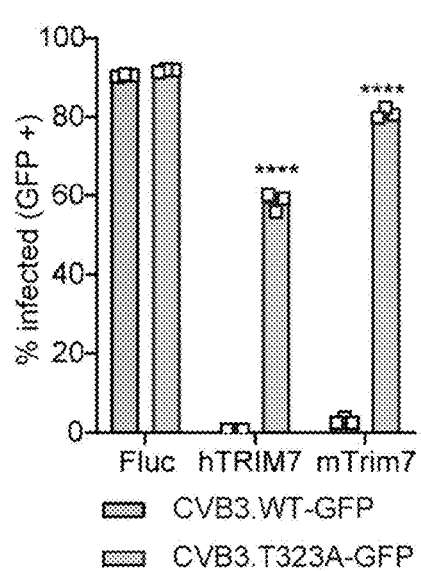
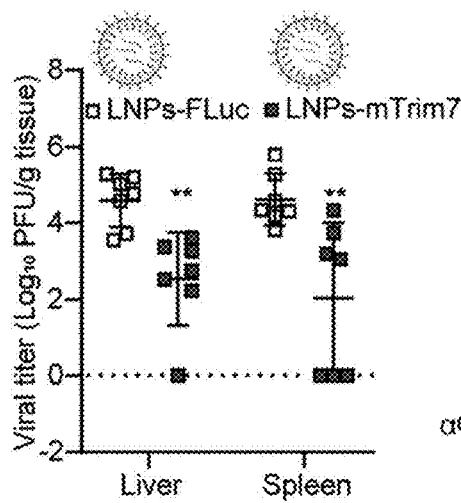
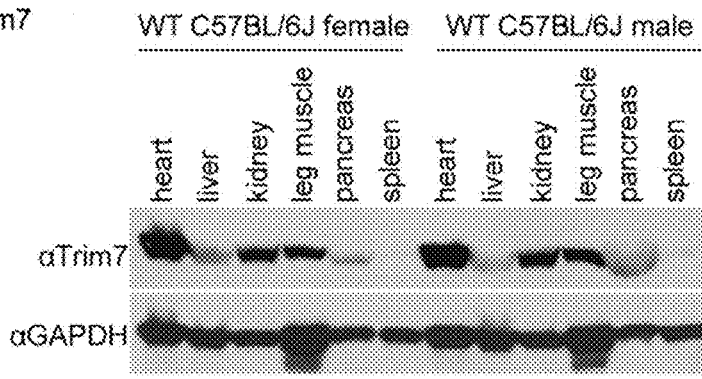

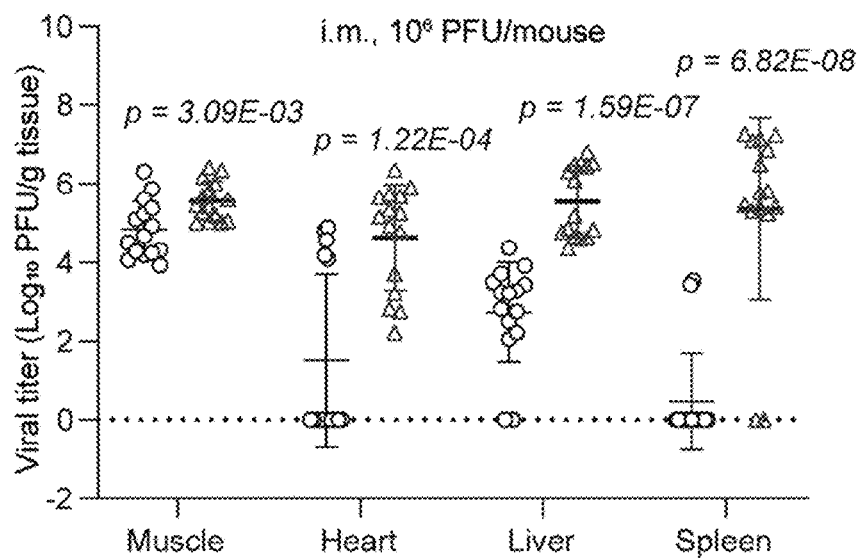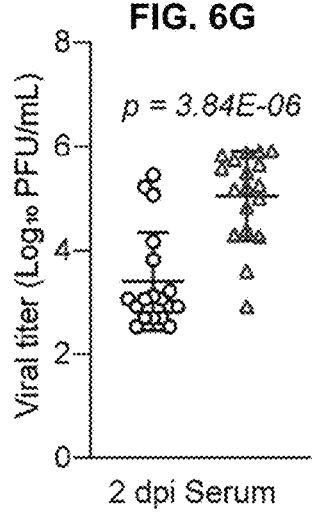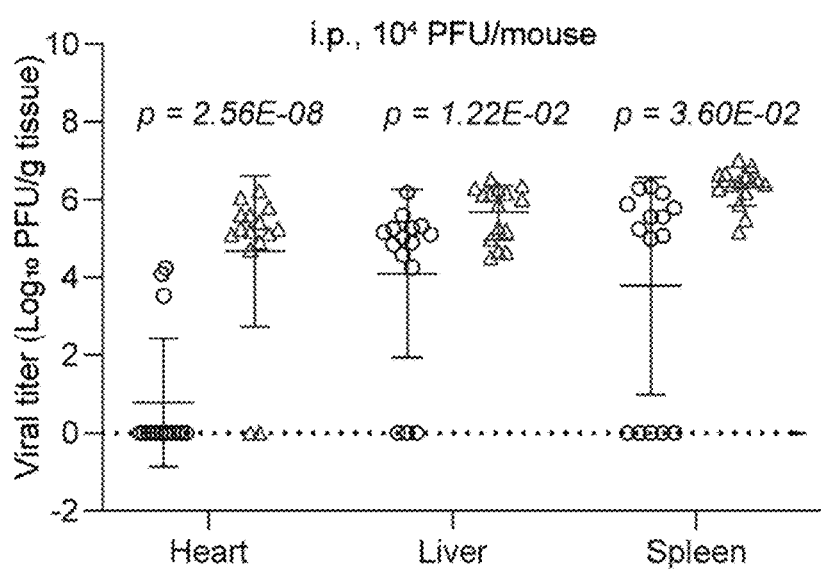

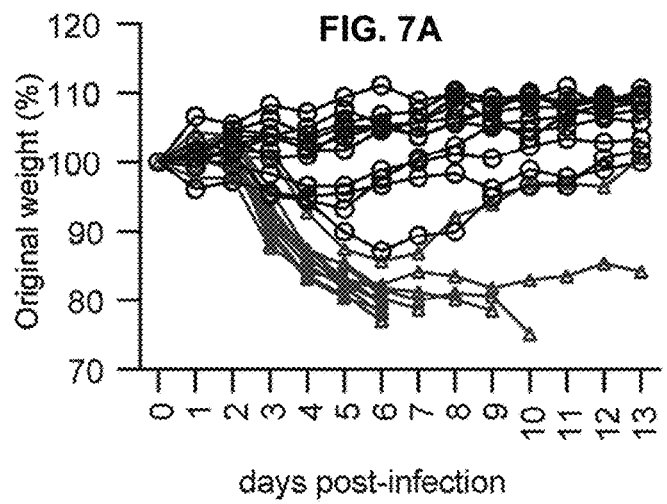
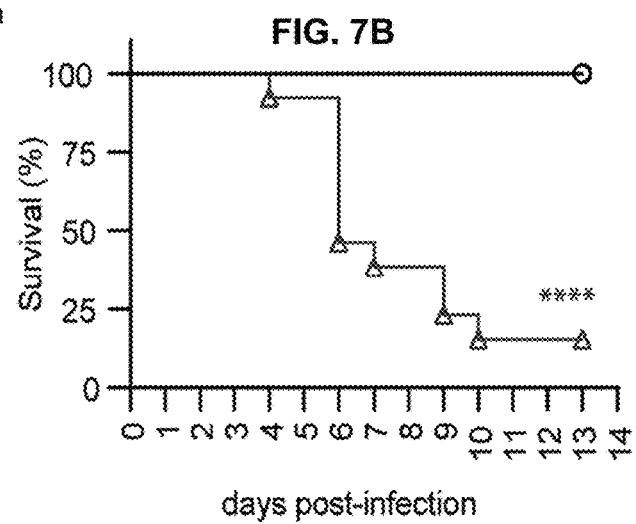
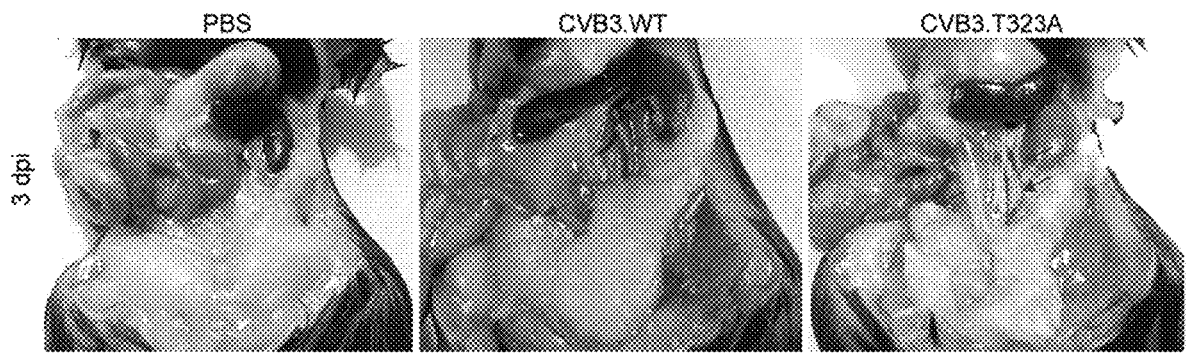

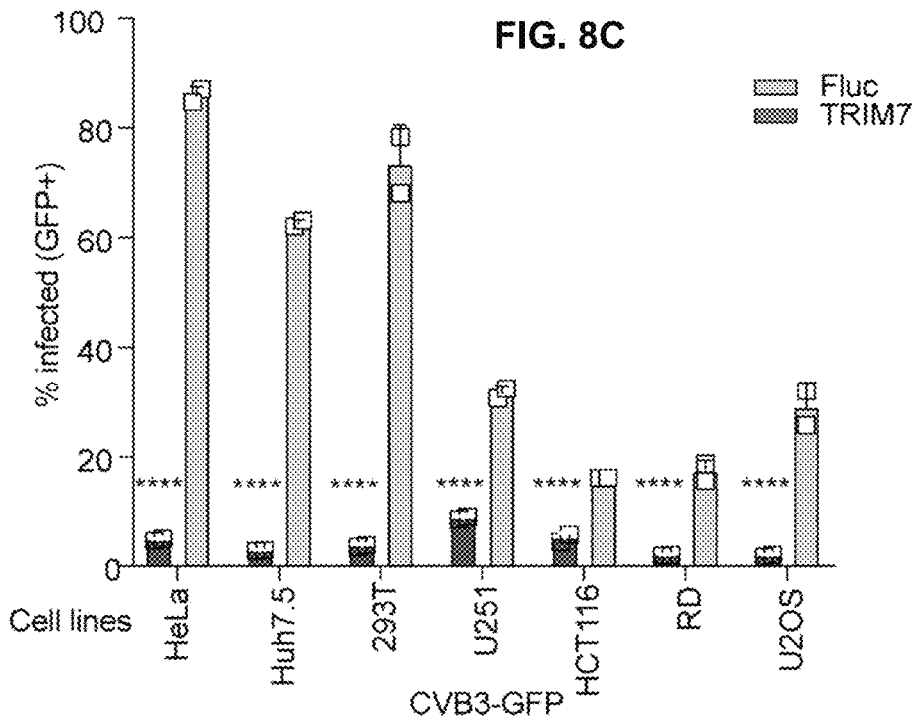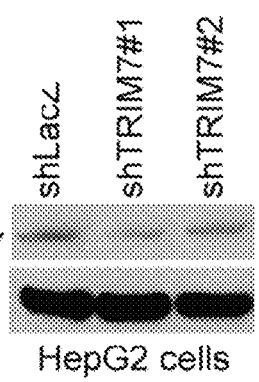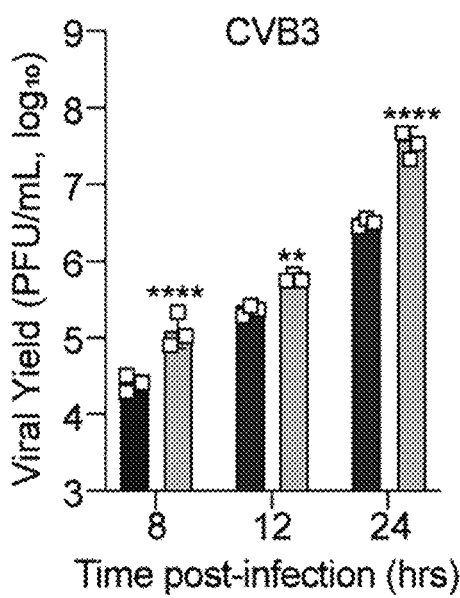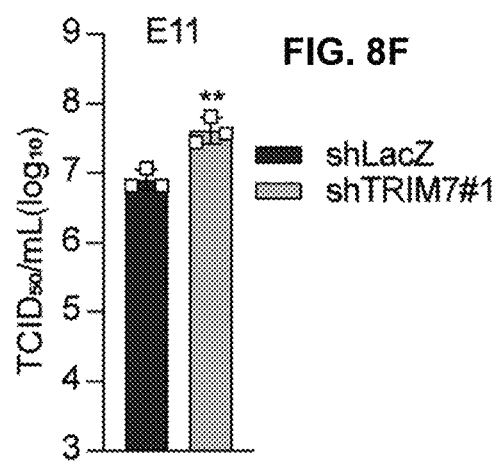

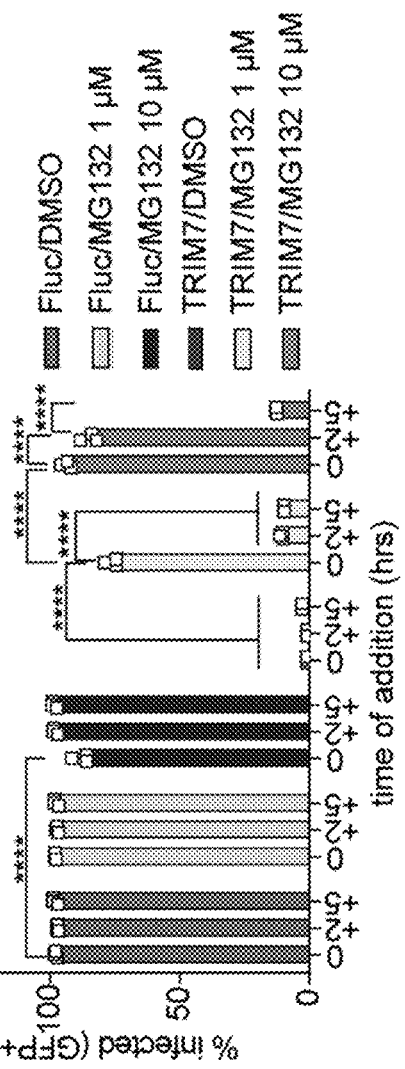
FIG. 9A
FIG. 9B
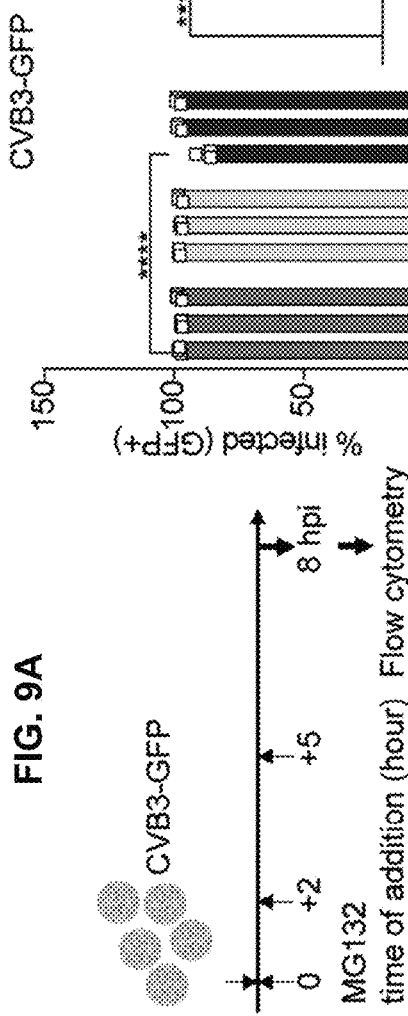
FIG. 9C
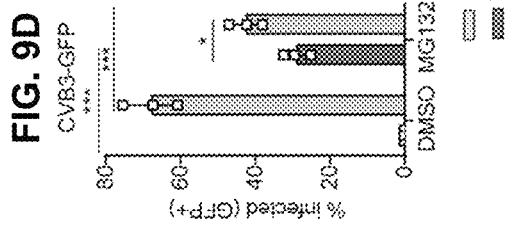
FIG. 9D
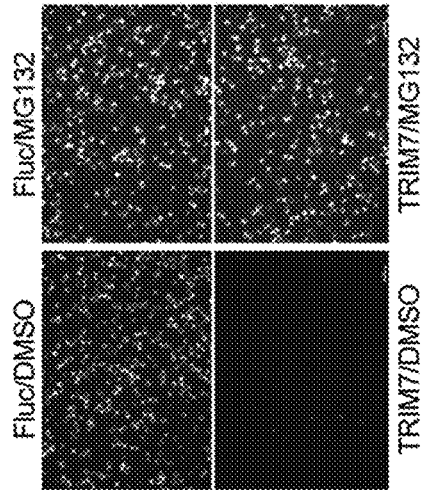

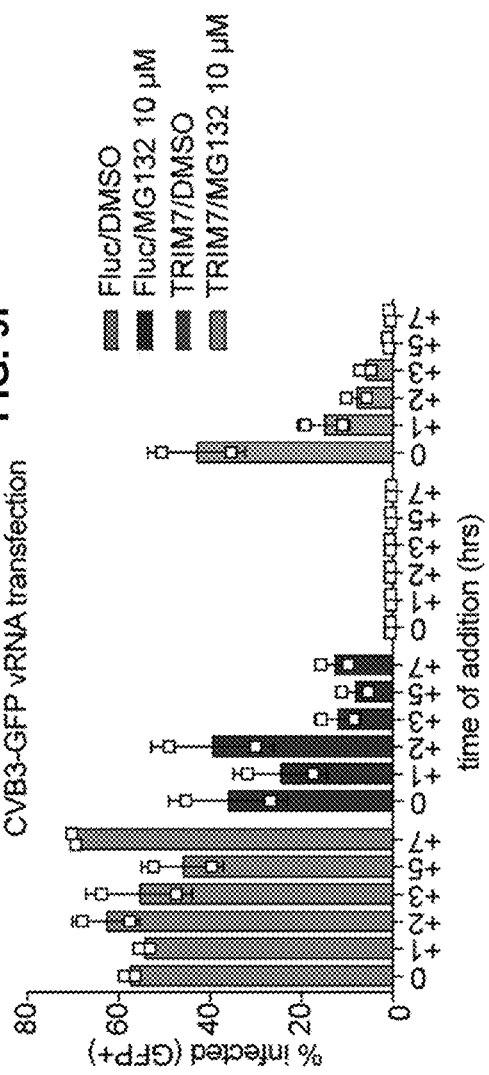
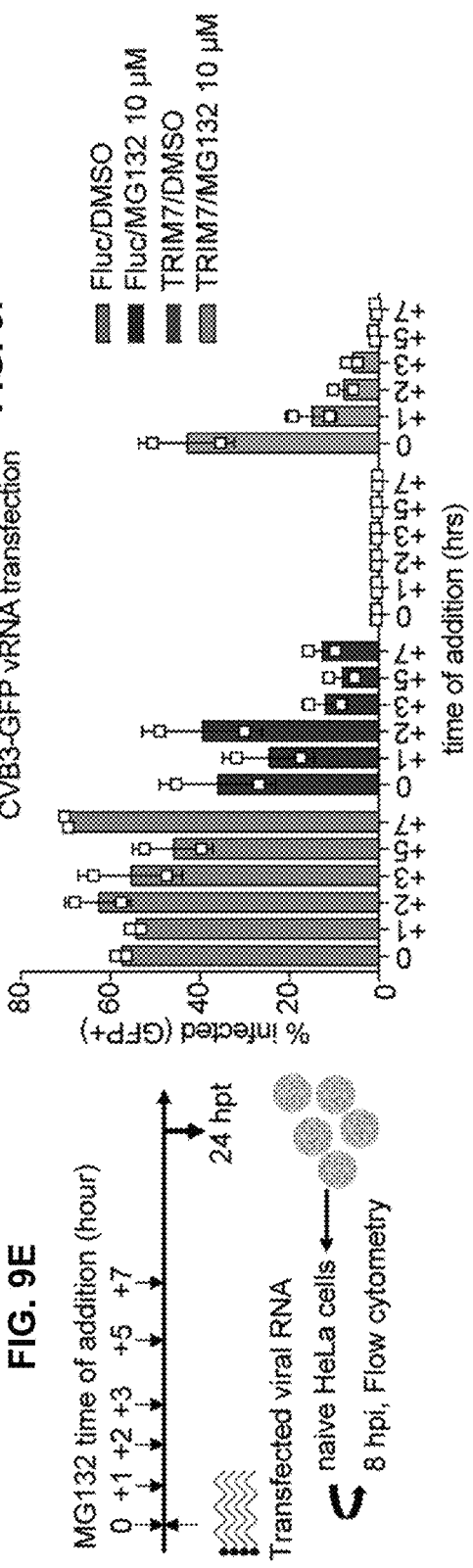
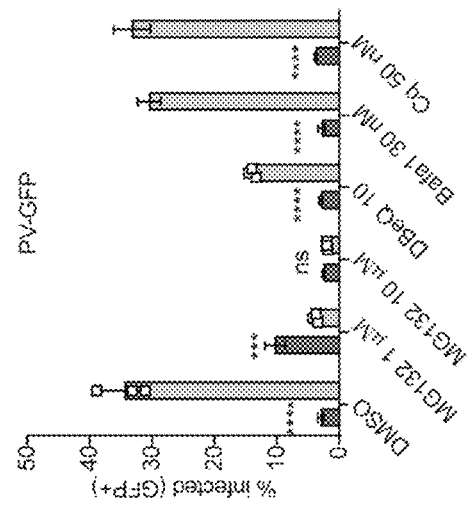
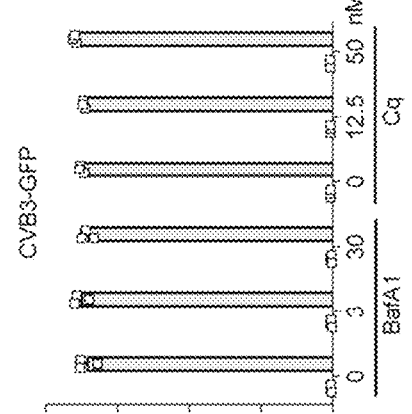
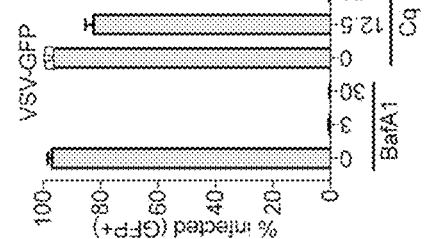
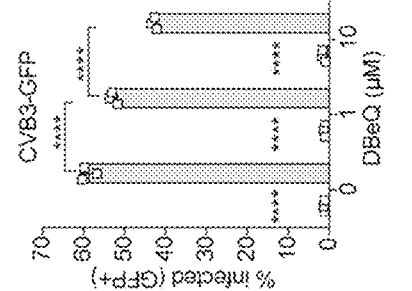

| Species | Enterovirus B | Position 323 in 2C protein |
|---|---|---|
| Human | Coxaskievirus B: 1-3, 6 | T323 |
| | Coxaskievirus A9 | |
| | Echovirus: 1-9, 11-21, 24-33 | |
| | Enterovirus B69 | |
| | Enterovirus B: 73-75, 77, 79-86, 97, 98, 100, 101,106,111 | |
| Non-Human primate | Enterovirus B: 112-114 | V323 |
| Bovine | BEV | V323 |

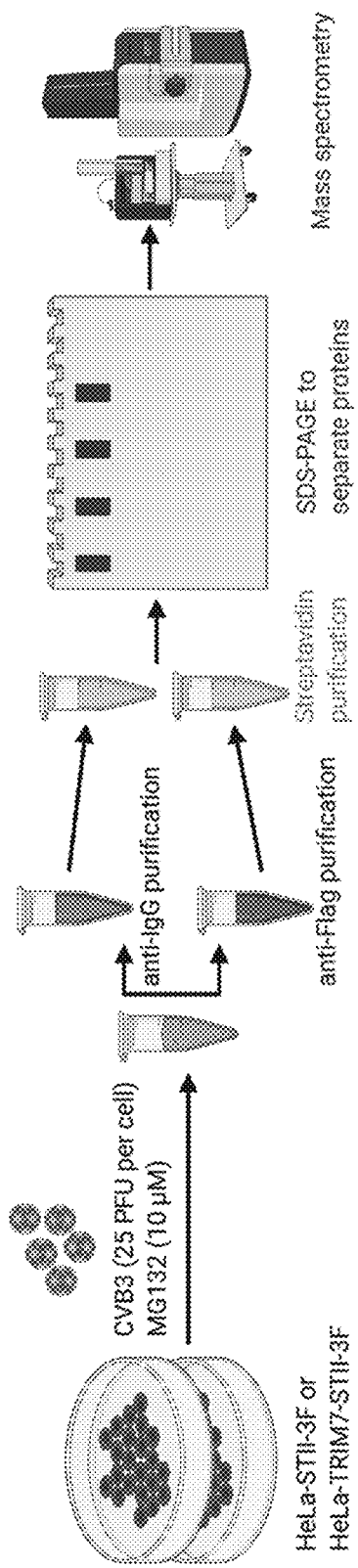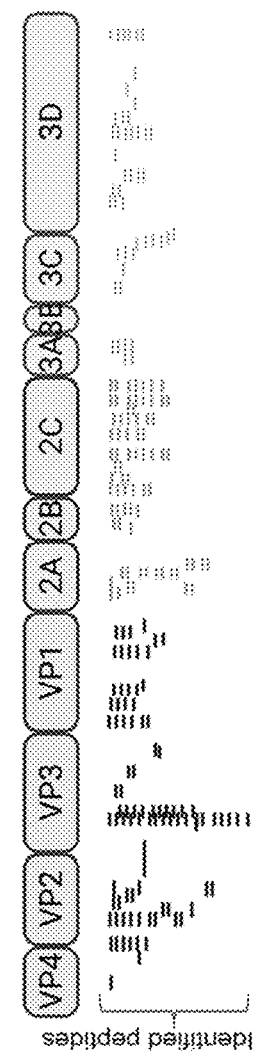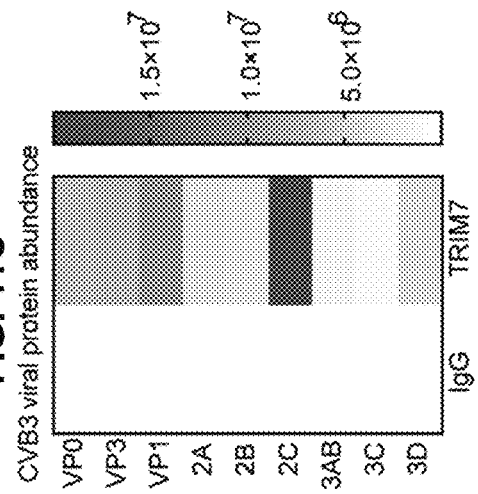

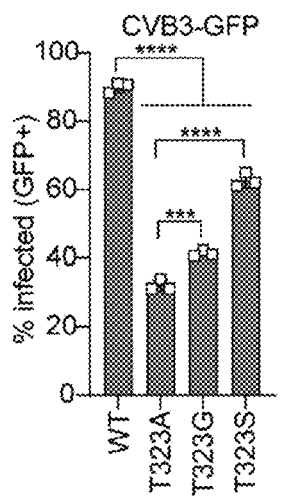
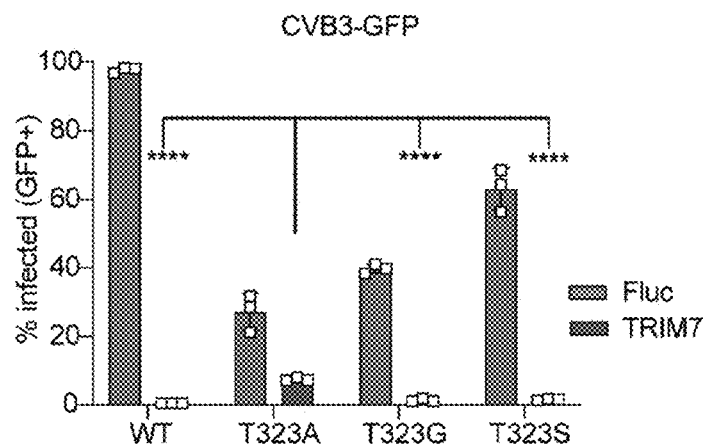
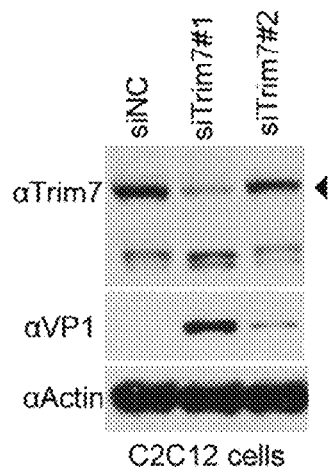
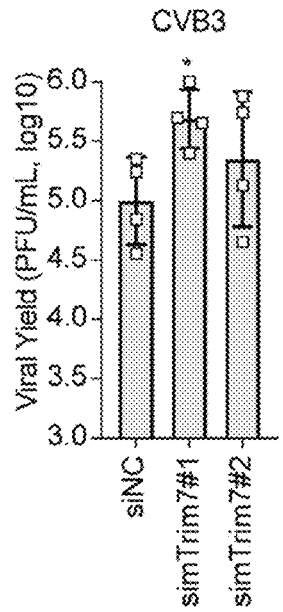
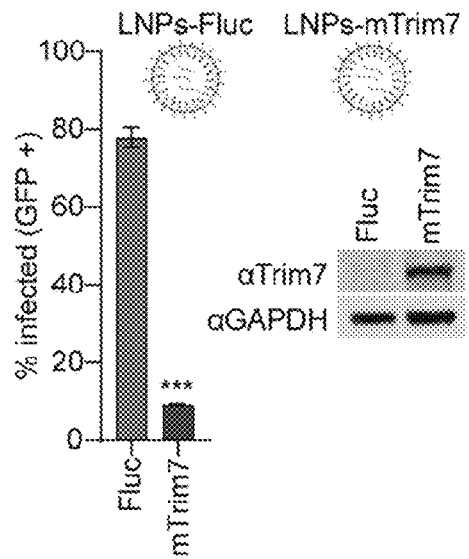
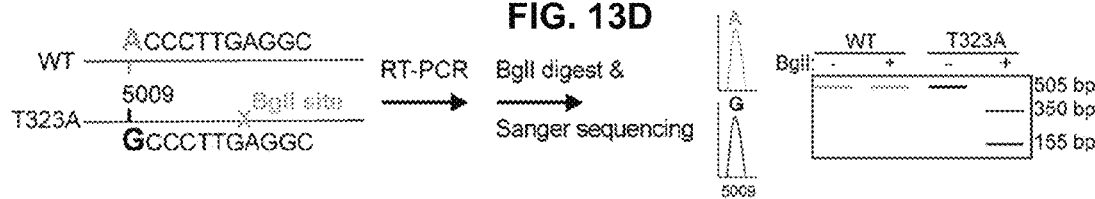

FIG. 13O

| | Liver | | | Muscle | | | |
|---|---|---|---|---|---|---|---|
| | PBS | WT | T323A | PBS | WT | T323A | |
| | -1.4 | -0.7 | 2.1 | -1.9 | 0.1 | 1.9 | Adaptive |
| | -1.3 | -0.4 | 1.9 | -2.0 | -0.1 | 1.7 | Antigen Processing |
| | 0.6 | 0.2 | -1.2 | -0.5 | -0.2 | 0.3 | Cell Cycle |
| | -1.0 | -0.2 | 1.1 | -1.1 | -0.2 | 1.6 | Chemokines & Receptors |
| | -1.6 | -0.9 | 2.3 | -1.1 | -0.3 | 1.7 | Cytokines & Receptors |
| | -1.4 | -0.7 | 2.0 | -1.5 | -0.5 | 2.1 | Inflammation |
| | -3.1 | -1.3 | 4.4 | -2.8 | -0.2 | 3.3 | Innate |
| | -2.3 | -0.9 | 3.5 | -2.4 | 0.1 | 2.6 | Interferon |
| | -0.4 | -0.2 | 0.8 | -0.9 | -0.2 | 1.0 | Pathogen Response |
| | | CVB3 | | | CVB3 | | |

Row Z Score

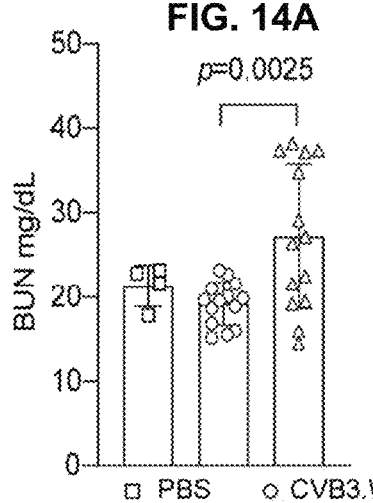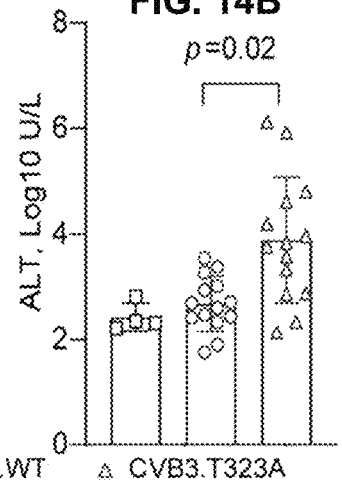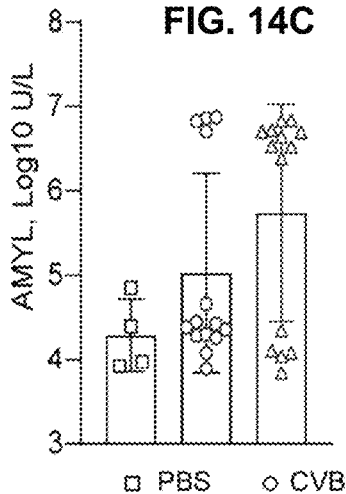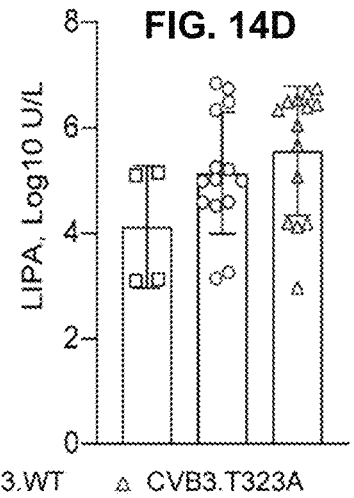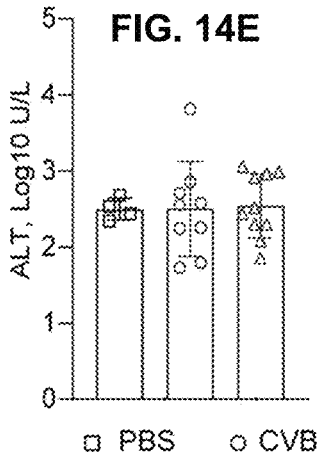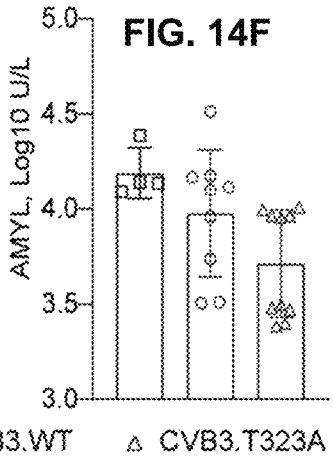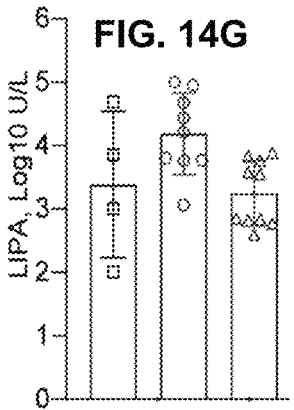

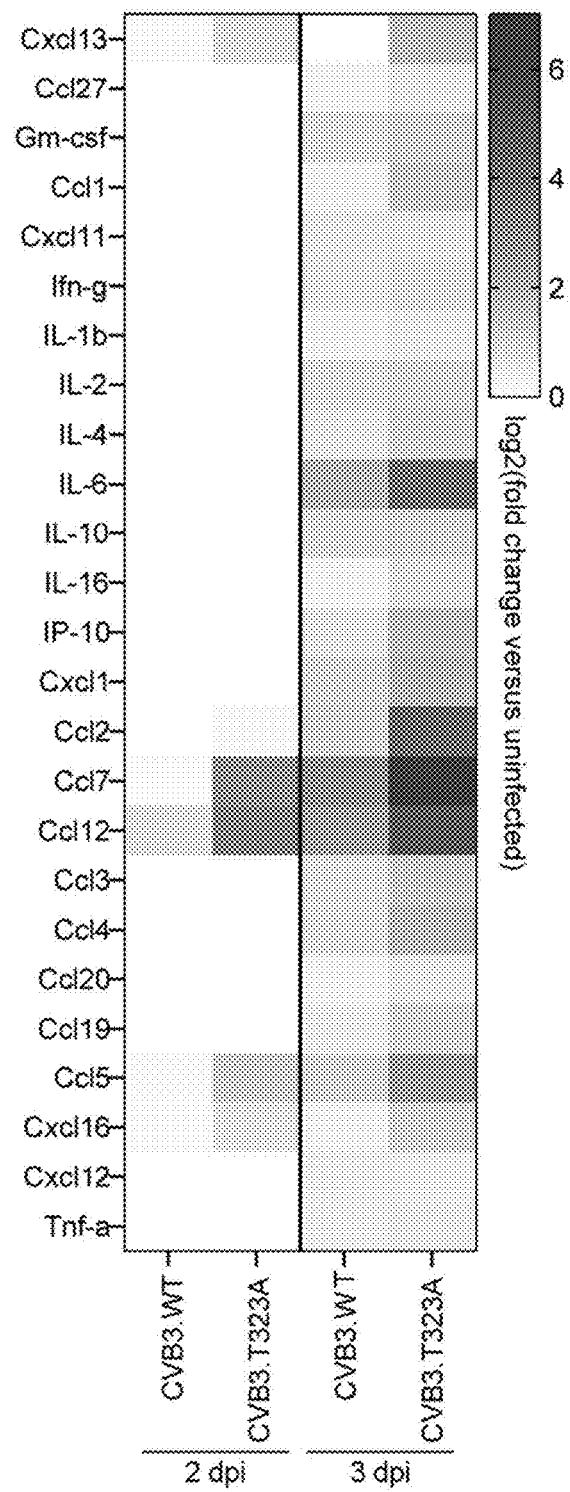

○ CVB3.WT  △ CVB3.T323A

COMPOSITIONS AND METHODS FOR TREATING VIRAL INFECTIONS TARGETING TRIM7

CROSS REFERENCE TO RELATED APPLICATION

This application claims the benefit of U.S. Provisional Application No. 63/168,898 filed on Mar. 31, 2021, the disclosure of which is hereby incorporated by reference in its entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file created on Dec. 19, 2023, is 40,000 bytes in size, and titled 106546-722205_UTSD-3894-US_SequenceListing_Revised_ST25.txt.

BACKGROUND

1. Field

The present inventive concept is directed to compositions and methods of using the compositions herein for impairing viral replication.

2. Discussion of Related Art

Enterovirus is a genus of small RNA viruses that contains more than 100 viruses, including, but not limited to, poliovirus, rhinovirus, enterovirus A71, coxsackievirus, echovirus, and enterovirus D68. Enteroviruses cause a broad spectrum of diseases, including non-specific acute febrile illness, skin rash, acute respiratory distress, and severe neurological complications in humans. Currently, there are no approved preventative therapies or vaccines against the majority of enteroviruses. Where available, current treatments focus on reducing host response-mediated symptoms rather than targeting the virus to limit replication and duration of infection. Accordingly, there is a need in the art for new treatment regimens that target enteroviruses.

SUMMARY OF THE INVENTION

The present disclosure is based, at least in part, on the surprising discovery that tripartite motif containing 7 (TRIM7) suppresses enterovirus replication. The present disclosure provides for the first E3 ligase targeting an enterovirus protein and the first demonstration that a viral membrane remodeling protein is subject to degradation as a host antiviral strategy. Accordingly, the present disclosure provides for new antiviral treatments which allow for new methods of treating RNA viruses, such as enteroviruses.

In certain embodiments, the present disclosure provides for compositions comprising at least one mRNA encoding a tripartite motif containing 7 (TRIM7) protein and at least one lipid nanoparticle (LNP) wherein the at least one mRNA encoding a TRIM7 protein may be encapsulated in the at least one LNP. In some embodiments, compositions disclosed herein may include at least one mRNA encoding a TRIM7 protein wherein the mRNA comprises a polynucleotide sequence at least about 80% identical to SEQ ID NOs: 1-6. In some aspects, compositions disclosed herein may include at least one mRNA encoding a TRIM7 protein wherein the mRNA comprises a polynucleotide sequence of any one of SEQ ID NOs: 1-6. In some aspects, compositions disclosed herein may comprise at least one mRNA having an optimized codon. In some embodiments, compositions disclosed herein may include at least one LNP comprising an ionizable cationic lipid, an ionizable phospholipid, a cholesterol, a cholesterol derivative, or any combination thereof. In some embodiments, compositions disclosed herein may further comprise at least one pharmaceutically acceptable excipient.

In certain embodiments, the present disclosure provides for methods of treating, preventing, and/or attenuating a viral infection. In some embodiments, methods disclosed herein may comprise administering to a subject a composition comprising an mRNA encoding a tripartite motif containing 7 (TRIM7) protein and at least one lipid nanoparticle (LNP), wherein the subject has or is suspected of having a viral infection. In some embodiments, the composition used in the methods disclosed herein may be administered at an effective dose and/or at an administration interval such that at least one symptom of the viral infection is reduced in intensity, severity, frequency, onset, or any combination thereof. In accordance with these embodiments, viral infection symptoms that can be treated by methods disclosed herein may include fever, chills, sore throat, nasal congestion, cough, or any combination thereof. In some embodiments, an effective dose may comprise a dose ranging from about 0.01 mg/kg mRNA to about 5.0 mg/kg mRNA to body weight. In some embodiments, methods herein may include administering a composition disclosed herein intravenously. In some embodiments, methods disclosed herein may result in a decreased viral titer in the subject compared to an untreated subject with identical viral infection and predicted outcome.

In certain embodiments, the present disclosure provides methods for attenuating and/or preventing a viral infection in a subject wherein the methods may comprise administering to the subject a composition effective for modulating tripartite motif containing 7 (TRIM7), wherein modulating TRIM7 comprises increasing TRIM7 gene expression, increasing TRIM7 protein expression, increasing TRIM7 activity, or any combination thereof. In accordance with these embodiments, methods disclosed herein may comprise administering a composition effective for modulating TRIM7 wherein the composition may include at least one of a peptide, an antibody, a chemical, a compound, an oligo, a nucleic acid molecule, or any combination thereof. In some aspects, composition may include nucleic acid molecule, wherein the nucleic acid molecule may comprise a single-stranded RNA effective for increasing the expression of TRIM7. In some aspects, a single-stranded RNA effective for increasing the expression of TRIM7 may be a messenger RNA (mRNA). In some embodiments, methods of administering compositions effective for modulating TRIM7 as disclosed herein may be administered to the subject topically, systemically, subcutaneously, intravenously, and/or intranasally.

In some embodiments, methods of administering compositions effective for modulating TRIM7 as disclosed herein may be administered to a subject who has or is suspected of having a viral infection. In some aspects, a subject may have a viral infection resulting from an infection by one or more single-stranded RNA viruses. In some aspects, one or more single-stranded RNA viruses causing a viral infection in a subject of the methods disclosed herein may be bymoviruses, comoviruses, nepoviruses, nodaviruses, picornaviruses, potyviruses, sobemoviruses, luteoviruses, carmoviruses, dianthoviruses, flaviviruses, pestiviruses, statoviruses, tombusviruses, single-stranded RNA bacteriophages, hepatitis C virus, hepatitis E virus, alphaviruses, carlaviruses, furoviruses, hordeiviruses, potexviruses, rubiviruses, tobraviruses, tricornaviruses, tymoviruses, enteroviruses, or any combination thereof. In some aspects, the one or more single-stranded RNA viruses comprises an enterovirus.

The present disclosure also provides for kits having compositions disclosed herein and for use in methods disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present inventive concept are illustrated by way of example in which like reference numerals indicate similar elements.

FIGS. 1A-1J are images and graphs illustrating the identification of TRIM7 as an antiviral effector against human enteroviruses. FIG. 1A shows HeLa cells transduced with lentivirus co-expressing RFP and 118 different human RING type E3 ubiquitin ligases infected with GFP-expressing viruses. Virus infectivity was determined as the percentage of GFP-positive cells within the RFP-positive gate using flow cytometry. All percent infection values were normalized to the Fluc-expressing control. FIG. 1B shows titers of supernatants from HeLa-Fluc or HeLa-TRIM7 cells infected with 0.01 or 0.1 MOI CVB3 for 12 hours and 24 hours, quantified by plaque assay. FIG. 1C shows titers of supernatants from HeLa-Fluc or HeLa-TRIM7 cells infected with 10 MOI CVB3 for 4 hours and 8 hours, quantified by plaque assay. FIG. 1D shows HeLa-Fluc or HeLa-TRIM7 cells infected with indicated viruses at 1 MOI. Cells were harvested at the following time points: EV71 and E11 at 12 h and CVB3, PV, and MenV at 8 hours. Production of viral dsRNA was assessed by flow cytometry using J2 antibody staining. FIGS. 1E-1G show titers of supernatants from HeLa-Fluc or HeLa-TRIM7 cells infected with EV71, E11, or EVD68 at 1 MOI for 24 hours, quantified by tissue culture infectivity dose 50% (TCID50) assay. FIG. 1H shows infectivity of 1 MOI PV-GFP in HeLa-Fluc or HeLa-TRIM7 cells, determined as percentage of GFP-positive cells by flow cytometry. FIG. 1I shows titers of supernatants from HeLa-Fluc or HeLa-TRIM7 cells infected with 1 MOI MenV for 8 hours, quantified by plaque assay. FIG. 1J shows titers of supernatants from HepG2 cells expressing shRNA targeting LacZ or TRIM7 and infected with 0.1 or 1 MOI CVB3 for 8 hours, quantified by plaque assay. Data represent averages of independent biological replicates and are presented as means±SD (n=2-5). Statistical significance was determined by 2-way ANOVA with Sidak's multiple comparisons test. ($*P<0.05$, $P<0.01$, $*P<0.001$, $****P<0.0001$; FIGS. 1B-1D, 1H, 1J). For FIGS. 1E-1G, unpaired students' t-test was used ($*P<0.05$, $P<0.01$, $*P<0.001$, $****P<0.0001$)

FIGS. 2A-2K are images and graphs illustrating TRIM7 restriction of CVB3 RNA replication. FIG. 2A shows HeLa-Fluc or HeLa-TRIM7 infected with 1000 MOI CVB3 at 4° C. for 1.5 hours, then washed five times with cold media. Bound virus was quantified by plaque assay. FIG. 2B shows HeLa-Fluc or HeLa-TRIM7 infected with 1000 MOI CVB3 at 4° C. for 1.5 hours, then cells were shifted to 37° C. for 30 minutes, then washed with cold glycine buffer. Internalized virus was quantified by plaque assay. FIGS. 2C-2D show confocal microscopy analysis of CVB3 binding or entry. HeLa-Fluc or HeLa-TRIM7 cells were infected with CVB3 at 1,000 MOI at 4° C. for 1.5 hours. For the binding assay (FIG. 2C), the cells were fixed and stained with anti-VP1 antibody. For the entry assay (FIG. 2D), the cells were incubated at 37° C. for 30 minutes after 4° C. incubation, then fixed and stained with anti-VP1 antibody. Scale bar is 8 μm. FIG. 2E shows HeLa-Fluc or HeLa-TRIM7 cells transfected with CVB3-GFP infectious viral RNA. Images were taken at 4, 6, 8, and 24 hours post-transfection. Scale bar is 50 μm. FIG. 2F shows supernatants from FIG. 2E harvested at the indicated time points post-transfection and used to infect naïve HeLa cells. Infectivity of progeny virus was assessed by flow cytometry. FIG. 2G shows HeLa-Fluc or HeLa-TRIM7 cells transfected with PV-GFP infectious viral RNA. Supernatants were harvested at 24 hours post-transfection and used to infect naïve HeLa cells. Infectivity of progeny virus was assessed by flow cytometry. FIGS. 2H-2I show HeLa-Fluc or HeLa-TRIM7 cells transfected with wild type (FIG. 2H) or replication-defective (FIG. 2I) CVB3-Rluc replicon RNA. Cells were harvested at the indicated time points post-transfection and Renilla luciferase activity was quantified. FIG. 2J shows HeLa-Fluc or HeLa-TRIM7 cells infected with 0.1 MOI CVB3. Strand-specific viral RNA was quantified by RT-PCR. +vRNA, −vRNA: positive strand and negative strand viral RNA. FIG. 2K shows HeLa-Fluc or HeLa-TRIM7 cells infected with 0.1 MOI CVB3. Intracellular and extracellular virus production from the indicated time points was determined by plaque assay. iV: intracellular virus, eV: extracellular virus. Data represent averages of independent biological replicates and are presented as means±SD (n=3). For FIGS. 2A, 2B, and 2G, statistical significance was determined by unpaired students' t-test analysis (ns, $P>0.05$, $****P<0.00001$). For FIGS. 2F, 2H-2I, statistical significance was determined by 2-way ANOVA with Sidak's multiple comparisons test. In FIG. 2J, statistical significance was determined by 2-way ANOVA with Tukey's multiple comparisons test ($*P<0.05$, $P<0.01$, $*P<0.001$, $****P<0.0001$).

FIG. 3A shows a viral polyprotein schematic depicting three major regions, P1, P2, P3, and emergence of T323A at the C terminus of 2C from CVB3 passaged in HeLa-TRIM7. FIG. 3N shows an in vitro binding analysis of the interaction between TRIM7 and wild type or mutant 2C. Left panel: schematic illustration of full-length CVB3 2C protein and its mutants used for expression and purification in *E. coli*. Right panel: Coomassie-staining showing the in vitro binding of GST-tagged TRIM7-PRY/SPRY to His-MBP-His-tagged wild type 2C and its mutants, or His-MBP control. Black arrow and red arrows denote GST-TRIM7PRY/SPRY in input or after pulldown with Ni-NTA beads, respectively. Data represent averages of independent biological replicates and are presented as means±SD (n=3). For FIGS. 3K and 3L, statistical significance was determined by 2-way ANOVA with Sidak's multiple comparisons test (****P<0.0001).

FIGS. 4A-4K are images and graphs illustrating that TRIM7 promotes proteasome-dependent degradation of 2BC from human enteroviruses. FIG. 4A shows 293T cells co-transfected with the indicated HA-tagged CVB3 viral protein expressing plasmids and TRIM7-3F or empty plasmids. The cells were harvested at 30 hours post-transfection for Western blot analysis. FIG. 4B shows 293T cells co-transfected with consistent amounts of plasmid expressing CVB3 HA-2C or HA-2BC, and with increasing amounts of WT TRIM7-3F. The cells were collected at 30 hours post-transfection for Licor analysis of band intensity. FIG. 4C shows the correlation between 2BC versus GAPDH ratio and TRIM7 versus GAPDH ratio from FIG. 4B. Three independent experiments were performed. FIG. 4D shows 293T cells co-transfected with consistent amounts of plasmid expressing CVB3 HA-2BC, and with CA mutant TRIM7-3F or increasing amounts of WT TRIM7-3F. The cells were collected at 30 hours post-transfection for Western blot analysis. FIG. 4E shows HeLa cells expressing Fluc or TRIM7 variants infected with CVB3-GFP at a 1 MOI. Virus infectivity at 8 hours post-infection was quantified by flow cytometry. FIG. 4F shows 293T cells co-transfected with consistent amounts of plasmid expressing HA-2BC and increasing amounts of plasmid expressing TRIM7-3F. The cells were treated with DMSO or MG132 (10 μM) at 24 hours post-transfection for 6 hours and then assessed by Western blot. FIG. 4G shows 293T cells co-transfected with plasmids expressing HA-tagged 2BC from EV71, EVD68, or MenV with empty plasmid or TRIM7-3F expressing plasmid. The cells were treated with DMSO or MG132 (10 μM) at 24 hours post-transfection and cells were harvested at 30 hours post-transfection for Western blot analysis. FIG. 4H shows Western blot analysis of 293T cells co-transfected with constant amounts of plasmids expressing HA-tagged 2BC from EV71 or MenV plus CA TRIM7-3F, empty plasmid, or increasing amounts of WT TRIM7-3F-expressing plasmids. The cells were harvested at 30 hours post-transfection for Western blot analysis. FIG. 4I shows co-IP analysis of lysates from 293T cell co-transfected with TRIM7-3F expressing constructs and plasmids expressing HA-tagged EV71 2BC, MenV 2BC, or empty vector. The cells were harvested at 30 hours post-transfection, followed by anti-HA co-IP and Western blot analysis. FIG. 4J shows co-IP analysis of ubiquitination of CVB3 2BC in 293T cells co-transfected with HA-2BC, TRIM7-3F (WT and CA), and the indicated StrepII-tagged ubiquitin expressing plasmids. The cells were treated with MG132 (10 μM) at 24 hours post-transfection for 6 hours. Cells were harvested at 30 hours post-transfection for anti-HA precipitation, respectively, and analyzed by Western blot. FIG. 4K shows an in vitro ubiquitination assay of 2BC. TRIM7-3F and HA-2BC were purified from 293T cells using anti-Flag beads and anti-HA beads, respectively. In FIG. 4E, data represents average of independent biological replicates and is presented as mean±SD (n=3); statistical significance was determined by 2-way ANOVA with Sidak's multiple comparisons test (****P<0.0001). Western blots are representative of three (FIG. 4J) or two (FIG. 4K) independent experiments showing similar results.

FIGS. 5A-5J are images and graphs illustrating that TRIM7-resistance mutation T323A reduces viral replication in vitro and increases plasticity and ATPase activity of 2C. FIG. 5A shows HeLa-Fluc or HeLa-TRIM7 cells infected with CVB3-WT or CVB3-T323A at 1 MOI. The supernatants were then collected at the indicated time points post-infection. Viral titers of supernatants were determined using plaque assay. FIG. 5B shows HeLa cells infected with CVB3-WT or CVB3-T323A at 1 MOI and harvested at the indicated time points post-infection. The production of strand specific viral RNA was analyzed by RT-PCR. +vRNA and −vRNA: positive strand and negative strand viral RNA. FIG. 5C shows HeLa cells infected with CVB3-WT or CVB3-T323A at 0.1 MOI. The intracellular virus production at the indicated time points were determined by plaque assay. inCVB3.WT and inCVB3.T323A: intracellular CVB3.WT and CVB3.T323A. FIGS. 5D-5F show the ATPase activity of WT and mutant CVB3 2C proteins as measured under different conditions: (FIG. 5D) enzyme dose dependence, (FIG. 5E) time course at 140 nM protein, (FIG. 5F) substrate dose dependence. His-MBP-His was used as control. The enzymatic activity was assessed at 15 minutes post incubation at room temperature (RT) with the different concentrations of the indicated proteins. FIG. 5G shows the two primary modes of protein dynamics, breathing and twisting, as obtained from principle components analysis of MD simulations. The inset shows the 'hinge' region close to the mutation site that facilitates both motions. FIG. 5H shows quantification of each mode of dynamics for WT and mutant 2C dimers as a percentage of total conformational variation during MD simulations. FIG. 5I shows a crystal structure of the ATP binding pocket from EVA71 2C (PDB: 5GRB). ATP molecule is shown by ball-and-stick representation while hydrolysis residues are depicted as van der Waals surfaces. FIG. 5J shows probability distributions of pocket size as determined by radius of gyration of hydrolysis residues calculated from MD simulations of 2C-WT and 2C-T323A bound to ATP. Data represents average of independent biological replicates and is presented as mean±SD (n=3). In FIGS. 5A-5E, statistical significance was determined by 2-way ANOVA with Tukey's multiple comparisons test (*P<0.05, P<0.01, *P<0.001, ****P<0.0001).

FIGS. 6A-6H are images and graphs illustrating that the T323A mutation in CVB3 2C confers a replicative advantage in mice. FIG. 6A shows titers of supernatants from C2C12 cells transfected with siRNA targeting Trim7 or non-targeting control and infected with CVB3 at 2, 5, or 20 MOI for 24 hours, measured by plaque assay. FIG. 6B shows titers of supernatants from mouse primary cardiomyocytes (CM) transfected with siRNA targeting mouse Trim7 or non-targeting control and infected with CVB3 at 1 MOI for 48 hours, quantified by plaque assay. FIG. 6C shows HeLa cells expressing Fluc, hTRIM7, or mTrim7 infected with WT or 2C-T323A CVB3-GFP for 8 hours. Viral infectivity was determined by flow cytometry. FIG. 6D shows wild type C57BL/6J female mice that were administrated mRNA expressing Fluc or mTrim7 in LNPs and then infected with WT or 2C-T323A CVB3 (i.p., $10^4$ PFU). Liver and spleen were harvested at 2 dpi and titers were determined by plaque assay. FIG. 6E shows a Western blot of Trim7 protein in multiple tissues from two 6-week-old wild type C57BL/6J mice, one male and one female. FIG. 6F shows C57BL/6J female mice that were challenged with WT or 2C-T323A CVB3 (i.m., $10^6$ PFU). Tissues (thigh muscle, heart, liver, and spleen) were harvested at 2 dpi and titers were determined by plaque assay. FIG. 6G shows C57BL/6J female mice that were challenged with WT or 2C-T323A CVB3 (i.m., $10^6$ PFU). Viral titers in blood at 2 dpi were determined by plaque assay. FIG. 6H shows C57BL/6J female mice that were challenged with WT or T323A CVB3 (i.p., $10^4$ PFU per mouse). Tissues (heart, liver, and spleen) were harvested at 2-day post-infection and titers were determined by plaque assay. In FIG. 6D, n=7, one experiment. In FIGS. 6F and 6H, n=4-5 mouse per group, three independent experiments. In FIG. 6E, n=3-5, three independent experiments. In FIGS. 6A, 6B, 6D, and 6G, statistical significance was determined by unpaired students' t-test analysis was used (*P<0.05, P<0.01, *P<0.001). In FIGS. 6C, 6F, and 6H, statistical significance was determined by 2-way ANOVA with Sidak's multiple comparisons test (****P<0.0001).

FIGS. 7A-7I are images and graphs illustrating that the T323A mutation in CVB3 2C causes increased pathogenicity in mice. FIG. 7A shows C57BL/6J female mice that were challenged with WT or 2C-T323A CVB3 (i.m., $10^6$ PFU). Weight was measured daily for 13 days. FIG. 7B shows survival of the mice infected as described in FIG. 7A. FIGS. 7C-7D show images of the peritoneal cavity at 3 dpi (FIG. 7C) and 7 dpi (FIG. 7D) of mice that were euthanized. Red arrow: necrotic fat. FIG. 7E shows C57BL/6J female mice that were challenged with WT or 20-T323A CVB3 (i.m., $10^6$ PFU per mouse, n=4-5, two independent experiments). Pancreata were harvested at 3 dpi and viral titers were determined by plaque assay. FIGS. 7F-7I show representative histological sections of pancreata and perigonadal white adipose tissue (3 dpi and 7 dpi) stained with hematoxylin and eosin. Scale bar is 100 μm. In FIGS. 7F and 7G, white asterisk: islets of Langerhans; black asterisk: injury; black arrowheads: inflammation. In FIGS. 7H and 7I, black asterisk: necrotic adipocytes. In FIGS. 7A and 7B, n=3-5 mice per group, three independent experiments. In FIGS. 7C and 7D, n=4-5 mice per group, three independent experiments. In FIG. 7E, n=4-5 mice per group, two independent experiments. In FIGS. 7F and 7G, n=4 mice per group. In FIGS. 7H and 7I, n=4-5 mice per group, three independent experiments. In FIG. 7B, statistical significance was determined by Log-rank (Mantel-Cox) test (**P<0.0001). In FIG. 7E, unpaired students' t-test analysis was used (*P<0.001).

FIGS. 8A-8F are images and graphs illustrating the identification of TRIM7 as antiviral protein targeting human enteroviruses. FIG. 8A shows a schematic illustration of the ectopic expression-based screen depicting cells transduced with lentiviral vectors-expressing RING type E3 ubiquitin ligases. Cells were infected with Coxsackievirus B3 virus-expressing GFP, and GFP-positive cells were quantified by flow cytometry. FIG. 8B shows Huh7.5 cells expressing Fluc or TRIM7 that were infected with the indicated GFP-expressing viruses. Viral infectivity was determined by flow cytometry. FIG. 8C shows HeLa, Huh7.5, 293T, U251, HCT116, RD, and U2OS cells expressing Fluc or TRIM7 that were infected with CVB3-GFP at 1 MOI. Viral infectivity at 8 hours (HeLa, Huh7.5, 293T, and HCT116) or 24 hours (U251, RD, and U2OS) post-infection was determined by flow cytometry. FIG. 8D shows a Western blot analysis of TRIM7 or housekeeping GAPDH in lysates from HepG2 cells expressing shRNA targeting LacZ or TRIM7. FIG. 8E shows viral titers, determined by plaque assay, in supernatants from HepG2 cells expressing shRNA targeting LacZ or TRIM7 and infected with CVB3 at 0.1 MOI for 8 hours. FIG. 8F shows viral titers, determined by plaque assay, in supernatants from HepG2 cells expressing shRNA targeting LacZ or TRIM7 and infected with E11 at 0.1 MOI for 8 hours. Data represents averages of independent biological replicates and are presented as mean±SD (n=2-3). Statistical significance was determined by 2-way ANOVA with Sidak's multiple comparisons test (FIGS. 8B, 8C, and 8E. *P<0.05, P<0.01, *P<0.001, **P<0.0001). In FIG. 8F, unpaired students' t-test analysis was used (P<0.01).

FIGS. 9A-9J are images and graphs illustrating that TRIM7-mediated inhibition of enteroviruses is proteasome-dependent. FIG. 9A shows HeLa-Fluc or HeLa-TRIM7 cells infected with CVB3-GFP at 1 MOI. DMSO or MG132 were added to culture medium before infection (0) or 2 and 5 hours pi (+2, +5). FIG. 9B shows virus infectivity at 8 hours post-infection as determined by flow cytometry. FIGS. 9C-9D show a yield of infectious CVB3-GFP virions from HeLa-Fluc or HeLa-TRIM7 cells untreated or treated with MG132 (10 μM) at 1 hpi. Viral infectivity was assessed by immunofluorescence at 8 hpi (FIG. 9C) and virus production was quantified by flow cytometry (FIG. 9D). FIG. 9E shows the effects of MG132 addition on virus production of CVB3-GFP in HeLa-Fluc or HeLa-TRIM7 cells transfected with CVB3-GFP viral RNA. FIG. 9F shows supernatants that were used to infect naïve HeLa cells and analyzed by flow cytometry. FIG. 9G shows HeLa-Fluc or HeLa-TRIM7 cells infected with CVB3-GFP at 1 MOI in the presence of DBeQ. Virus infectivity at 8 hpi was quantified by flow cytometry. FIG. 9H shows HeLa-FLuc or HeLa-TRIM7 cells infected with VSV-GFP at 1 MOI in the presence of different concentrations of BafA1 or Cq. Virus infectivity at 8 hpi was analyzed by flow cytometry. FIG. 9I shows HeLa-FLuc or HeLa-TRIM7 cells infected with CVB3-GFP at 1 MOI in the presence of different concentrations of BafA1 or Cq. Virus infectivity at 8 hpi was analyzed by flow cytometry. FIG. 9J shows HeLa-Fluc or HeLa-TRIM7 cells infected with 1 MOI PV-GFP in the presence of the indicated reagents. Virus infectivity at 8 hpi was analyzed by flow cytometry. Bafilomycin A1 (BafA1), chloroquine (Cq). Data represents average of independent biological replicates and are presented as mean±SD (n=2-3). For FIG. 9B, statistical significance was determined by 2-way ANOVA with Tukey's multiple comparisons test. For FIGS. 9D, 9F, 9G-9J statistical significance was determined by 2-way ANOVA with Sidak's multiple comparisons test (*P<0.05, P<0.01, *P<0.001, ****P<0.0001). The scale bar in FIG. 9C is 50 µm.

FIGS. 10A-10G are images and graphs illustrating how the 323rd amino acid residue in type B enterovirus 2C impacts its sensitivity to TRIM7-mediated inh infected (i.m., 10⁶ PFU) and uninfected mice at 3 dpi. FIGS. 14E-14G show (FIG. 14E) alanine aminotransferase (ALT), (FIG. 14F) amylase (AMYL), and (FIG. 14G) lipase (LIPA) in serum from infected (i.m., 10⁶ PFU) and uninfected mice at 7 dpi. FIG. 14H shows a heatmap of serum levels of indicated cytokines and chemokines 2 dpi and 3 dpi with CVB3-WT or CVB3-T323A. The $\log_2$-fold change was normalized to uninfected mice. In FIGS. 14A-14G and 14I-14N, statistical significance was determined by unpaired students' t-test analysis was used (*P<0.05, P<0.01, *P<0.001, ****P<0.0001).

Figure 1A:
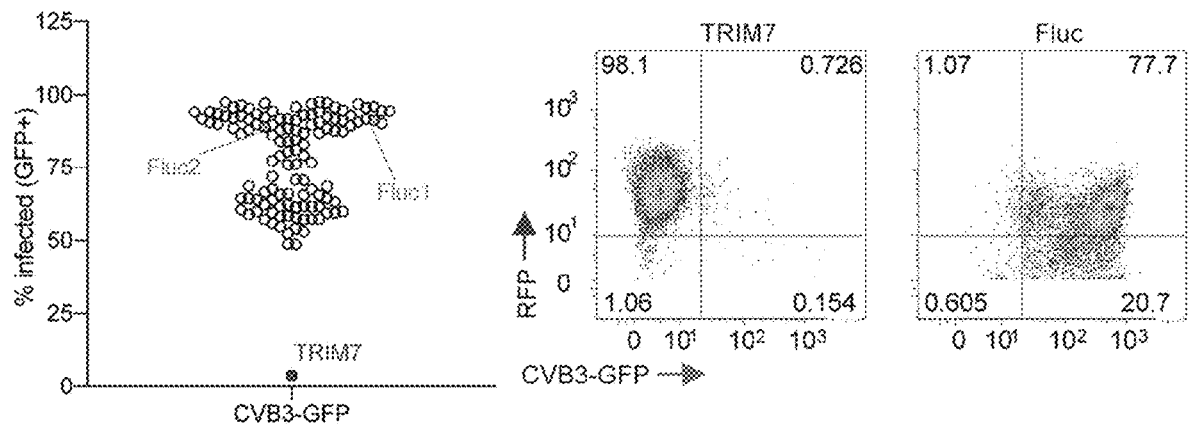

The drawing figures do not limit the present inventive concept to the specific embodiments disclosed and described herein. The drawings are not necessarily to scale, emphasis instead being placed on clearly illustrating principles of certain embodiments of the present inventive concept.

DETAILED DESCRIPTION

The following detailed description references the accompanying drawings that illustrate various embodiments of the present inventive concept. The drawings and description are intended to describe aspects and embodiments of the present inventive concept in sufficient detail to enable those skilled in the art to practice the present inventive concept. Other components can be utilized, and changes can be made without departing from the scope of the present inventive concept. The following description is, therefore, not to be taken in a limiting sense. The scope of the present inventive concept is defined only by the appended claims, along with the full scope of equivalents to which such claims are entitled.

The present disclosure is based, at least in part, on the surprising discovery that tripartite motif containing 7 (TRIM7) suppresses enterovirus replication. Disclosed herein are the first E3 ligase targeting an enterovirus protein and the first demonstration that a viral membrane remodeling protein is subject to degradation as a host antiviral strategy. The present disclosure provides for new antiviral treatments which allow for new methods of treating RNA viruses, such as enteroviruses.

I. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the present inventive concept or the appended claims.

Further, as the present inventive concept is susceptible to embodiments of many different forms, it is intended that the present disclosure be considered as an example of the principles of the present inventive concept and not intended to limit the present inventive concept to the specific embodiments shown and described. Any one of the features of the present inventive concept may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments but is not necessarily included. Thus, the present inventive concept may include a variety of combinations and/or integrations of the embodiments described herein. Additionally, all aspects of the present disclosure, as described herein, are not essential for its practice. Likewise, other systems, methods, features, and advantages of the present inventive concept will be, or become, apparent to one with skill in the art upon examination of the figures and the description. It is intended that all such additional systems, methods, features, and advantages be included within this description, be within the scope of the present inventive concept, and be encompassed by the claims.

Any term of degree such as, but not limited to, "substantially" as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 3 mM includes all values from 1 mM to 9 mM, and approximately 50 degrees includes all values from 16.6 degrees to 150 degrees. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The terms "comprising," "including" and "having" are used interchangeably in this disclosure. The terms "comprising," "including" and "having" mean to include, but not necessarily be limited to the things so described.

Lastly, the terms "or" and "and/or," as used herein, are to be interpreted as inclusive or meaning any one or any combination. Therefore, "A, B or C" or "A, B and/or C" mean any of the following: "A," "B" or "C"; "A and B"; "A and C"; "B and C"; "A, B and C." An exception to this definition will occur only when a combination of elements, functions, steps or acts are in some way inherently mutually exclusive.

The term "biomolecule" as used herein refers to, but is not limited to, proteins, enzymes, antibodies, DNA, siRNA, and small molecules. "Small molecules" as used herein can refer to chemicals, compounds, drugs, and the like.

The term "modify" or "modifying" and grammatical variations thereof, when used in reference to any of the compositions (e.g., proteins, protein domains, peptides, peptide fragments, polypeptide sequences) disclosed herein means that the modified composition deviates from a reference composition.

Lastly, a suitable "subject" as disclosed herein includes a human, a livestock animal, a companion animal, a lab animal, or a zoological animal. In some embodiments, the subject may be a rodent, e.g., a mouse, a rat, a guinea pig, etc. In some embodiments, the subject may be a livestock animal. Non-limiting examples of suitable livestock animals may include pigs, cows, horses, goats, sheep, llamas and alpacas. In some embodiments, the subject may be a companion animal. Non-limiting examples of companion animals may include pets such as dogs, cats, rabbits, and birds. In some embodiments, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

II. Compositions

The mammalian innate immune system controls viral infection in part through the actions of protein-based antiviral effectors. While many of these effectors are expressed after viral infection triggers an interferon response, cell-intrinsic restriction factors are constitutively present and variably regulated by interferon. Thus, these cell-intrinsic effectors, such as E3 ligases, may provide a frontline defense against viruses prior to transcription of interferon and interferon-stimulated genes. Tripartite-motif-containing proteins (TRIMs) constitute a small fraction of the RING-type E3 ligase protein family. The present disclosure is based, at least in part, on the surprising discovery that TRIM7 suppresses enterovirus replication. Accordingly, the present disclosure provides for compositions and methods of using the compositions herein for impairing viral replication.

(a) TRIM7

In certain embodiments, compositions herein can modulate TRIM7 (Tripartite Motif Containing 7). The TRIM7 protein encoded by the TRIM7 gene is a member of the tripartite motif (TRIM) family. The TRIM motif includes three zinc-binding domains, a RING, a B-box type 1, a B-box type 2, and a coiled-coil region. The TRIM7 protein localizes to both the nucleus and the cytoplasm and may represent a participant in the initiation of glycogen synthesis. Alternative splicing results in multiple transcript variants. Non-limiting examples of TRIM7 transcript variants (mRNA sequences; *Homo sapiens*) are provided in Table 1.

TABLE 1

| TRIM 7 transcript variant, mRNA (NCBI Reference Sequence) | Sequence | SEQ ID NO: |
|---|---|---|
| Variant 1 (NM_203293.3) | AGTGGGCCCTCGGCGCCCAGCTCCG CGTCCTGTGAGGTCCAGTGGCCGCC CAGGCGCGACCAGATCTGGGTGCGC GGAGAGCGCGCATGGCGGCTGTGGG ACCGCGGACCGGCCCCGGAACCGGC GCCGAGGCTCTAGCGCTGGCGGCAG AGCTGCAGGGCGAGGCGACGTGCTC CATCTGCCTAGAGCTCTTTCGTGAG CCGGTGTCCGTCGAGTGCGGCCACA GCTTCTGCCGCGCCTGCATAGGGCG CTGCTGGGAGCGCCCGGCGCGGGG TCTGTTGGGGCCGCCACCCGCGCGC CCCCCTTCCCACTGCCCTGTCCGCA GTGCCGCGAGCCCGCGCGCCCCAGT CAGCTGCGGCCCAACCGGCAGCTGG CGGCAGTGGCCACGCTCCTGCGGCG CTTCAGCCTGCCCGCGGCTGCCCCG GGAGAGCACGGGTCTCAGGCGGCCG CGGCCCGGGCAGCGGCTGCCCGCTG CGGGCAGCATGGCGAACCCTTCAAG CTCTACTGCCAGGACGACGGACGCG CCATCTGCGTGGTGTGCGACCGCGC CCGCGAGCACCGCGAGCACGCCGTG CTGCCGCTGGACGAGGCGGTGCAGG AGGCCAAGGAGCTCTTGGAGTCCAG GCTGAGGGTCTTGAAGAAGGAACTG GAGGACTGTGAGGTGTTCCGGTCCA CGGAAAAGAAGGAGAGCAAGGAGCT GCTGAAACAGATGGCAGCGGAGCAG GAGAAGGTGGGGGCAGAGTTCCAGG CACTGAGGGCTTTCCTGGTGGAGCA GGAGGGTCGGCTGCTAGGCCGCCTG GAGGAACTGTCCCGGGAGGTGGCAC AGAAGCAGAATGAGAACCTGGCCCA GCTCGGGGTTGAGATCACCCAGCTG TCCAAGCTCAGCAGCCAGATCCAGG AGACAGCTCAAAAGCCTGACCTTGA CTTTCTCCAGGAATTCAAAAGCACG CTGAGCAGGTGTAGCAATGTGCCTG GCCCCAAGCCAACCACAGTCTCTTC TGAGATGAAGAATAAAGTCTGGAAT GTTTCTCTCAAGACCTTTGTCTTAA AAGGGATGCTGAAGAAGTTCAAAGA GGACCTTCGGGGAGAGCTGGAGAAA GAGGAGAAAGTGGAGCTCACCTTGG ATCCCGACACGGCCAACCCGCGCCT CATCCTCTCTCTGGATCTTAAGGGC GTGCGCCTCGGCGAGCGGGCCCAGG ACCTGCCCAACCACCCCTGCCGCTT CGACACCAACACCCGCGTCCTGGCG TCCTGCGGCTTCTCCTCGGGCCGGC ATCACTGGGAGGTGGAGGTGGGCTC TAAGGACGGCTGGGCCTTTGGCGTG GCCCGCGAGAGCGTGCGCCGAAAGG GCCTGACGCCCTTCACTCCCGAGGA GGGCGTCTGGGCCCTGCAGCTCAAC GGCGGCCAGTACTGGGCCGTGACCA GCCCCGAGCGGTCGCCCCTCAGCTG CGGGCACCTGTCGCGCGTGCGGGTG GCCCTGGACCTGGAGGTGGGAGCCG TGTCCTTCTACGCTGTGGAGGACAT GCGCCACCTCTACACCTTCCGCGTC AACTTCCAGGAGCGCGTGTTCCCGC TTTTCTCTGTTTGCTCCACGGGCAC CTACTTGCGAATCTGGCCTTGAGGG GCACTGCTGGGGAGCTCCTGTCTCT GGGCTGCCGGTGGGAGGGGATGTCG CCTCCCCAGAGATGCCTGGTCCGTC TTGGGTCTGCCCTCCGTGCTCCTGA CCCCTGCTGCCCAAGAGAGCCTGCT ACAGACACAACCCGAGGCAGGAGA GTGACTGTGGCCAACCGAGCAGGGG AACAGGGGCTTTGGACTCCTGAGGG TGTTCCCTTCCTGAGGTCACATGTG GATTTGGCCAGAGCCTTCAGGAGGT | 1 |

TABLE 1-continued

| TRIM 7 transcript variant, mRNA (NCBI Reference Sequence) | Sequence | SEQ ID NO: |
|---|---|---|
| | GGAGGCCGGTGAGGTCAGGAGCCCA GCTCTCCAGGGGGCTTCTGCCCTGA CTGGGAAGGGTGCCTGGCTCCCTAA AACAATGTCAAAGCCAGTCCTGCTG TTCTCTGTTGCCAGGGGGCAGGTCT GGGCCTGGGCCAACCACGTTTGTTA TCATGGCTGCTGCCTTCTGGACAGC TGCCAGCTCTGCCTTGAGAGGTTGT GGGACCTCTGGATCCAGCTGACCTG ACAGGTCATCTACTCAGGGAGGAGC CCTGTGCTCCCAGCTCAGAGGACAG TCTGGGCCAGAACTGGAAGGAGACA TCTGTCCCGTCTTTGAGTGACAAGC CCGGGACAACAGCCAGTGGGCATCA CGGCTCTCCAGCACTCCTTAGCCGG AGGATACAGAGTGATGGGTGCATCC TGACCAATGCGACAACCAACACGTG CTCTCACAAACCCCTGACTCCCGCA CTTTCCAGTGCCAAAGTACAAACGC TGCTTGGATAAGGAGAGCAAAGCTT CTGGAACTTTATTTACTCTTTCTTT TTAATTTTCTTTTAAGAGACTGGGT CTTGCTATGTTGCCCAGGCTGGTCT TGAACTCCTGCCTCAAGTGATCCT CCAGTTTCCATCTCCCTAAGAGCTG GGATTACAGGTGTGAGCCGCTGTAC CCGAACTTTTTTGTTTTTGCTTCT GGAACTTTGAAACACAAAACACAAG TTGGCACTTACAATTTTAAAGATGC AGCCAGCTCTAAACAACACACAGAG CACAAATATGCTCCTGACGGACTCA GGAAAATGCCAACAGCAGAGCACCC TGGTGCCAAGGCCTTCTCAGCCCAT GCCCTGGAGGGCATTCCCCTGGCCA GCCTCAGCCCCTTGTCTACTTGTTC TCCAGCTTCTGGGTAGCTGGGCTTC TGGAAGGGTGGCAGTGGGCTACTCC CTGCTCAGCGCTCCCCTGGGAAGGG GGTGAGGAGATGAAAATGAAACTAT GAGCTGTCTTTGGA | |
| Variant 2 NM_203297.2 | CTGCAGCCTGCCTGGAAGCTGAAGG AAAGGTGGGGGCATTGTAGGCACCC TTGAACCCAGGTCTCCCAACTTCAC AGGACTCCCTTCCTCCGCCCAGGAG TTTTAAGGAAGAGGAACTTCCTGGT GGGACATATTGAGTGCCAAACGTGT GTTCACATAAAAAATCAAGAGATCA GGGCATGAGTCTGCATCTGAAAACT CGAGTAAAAAATCCGGTGTATGCTG TTAATGAAAGAACAGAATATGACA CTTGCATGCCGCATATTCTCACTTC GTTCCTTGGGGGTGTGCTGCTACCT CTGGTCACTGGCATCGGACTTTTCT TCCTTCTTTCTACTTTCCTACATCT CCCAAGTTTTGTATTTTGAGCATGT GTTAGCATTATAACTGCTAAACAGG AAAGATGGCCTTTAAAAAGAAAGTG AAGTGTAAAAGTTTGAGGGTGATGA AATAAATGTCTTGAGGAAGAAAAA GCAATCTCAGTTTAATCCTATGGTT GCCCCAGGAGCTACTAATTTATCCC TTCTGCTTTTCAAGTGAGGAAGCTG CAGCTTGGCGTAGTTCTGGGGGGAG TATGAAGCTGCCTTGGTTTAGGTGA TGGAGCACAGGTCCACAGACATGTG TGGGTGCATCTGTGGCAGGGGAGAA AAGAGCATGTGTCCAGACTACAGCT TGTTCAGAGCTGGGACACTGACAAT AGAGCACGCACTGCGTGCTAGGTG GGTGTGTCTCCGATCCTCCAGCAGT GACAGGGACGAAGCCTTGCCCTGTG GGATGACTCAGGCCACTGGCCAAAT GTTATGTCTCCATGTTCAAGTCCCT CTCCAACTTCTCCTCCTGGGACAGA | 2 |
| | AACAGATGGCAGCGGAGCAGGAGAA GGTGGGGGCAGAGTTCCAGGCACTG AGGGCTTTCCTGGTGGAGCAGGAGG GTCGGCTGCTAGGCGCCTGGAGGA ACTGTCCCGGGAGGTGGCACAGAAG CAGAATGAGAACCTGGCCCAGCTCG GGGTTGAGATCACCCAGCTGTCCAA GCTCAGCAGCCAGATCCAGGAGACA GCTCAAAAGCCTGACCTTGACTTTC TCCAGGAATTCAAAAGCACGCTGAG CAGGTGTAGCAATGTGCCTGGCCCC AAGCCAACCACAGTCTCTTCTGAGA TGAAGAATAAAGTCTGGAATGTTTC TCTCAAGACCTTTGTCTTAAAAGGG ATGCTGAAGAAGTTCAAAGAGGACC TTCGGGGAGAGCTGGAGAAAGAGGA GAAAGTGGAGCTCACCTTGGATCCC GACACGGCCAACCCGCGCCTCATCC TCTCTCTGGATCTTAAGGGCGTGCG CCTCGGCCGAGCGGGCCCAGGACCTG CCCAACCACCCGTGCCGCTTCGACA CCAACACCCGCGTCCTGGCGTCCTG CGGCTTCTCCTCGGGCCGGCATCAC TGGGAGGTGGAGGTGGGCTCTAAGG ACGGCTGGGCCTTTGGCGTGGCCCG CGAGAGCGTGCGCCGAAAGGGCCTG ACGCCCTTCACTCCCGAGGAGGGCG TCTGGGCCCTGCAGCTCAACGGCGG CCAGTACTGGGCCGTGACCAGCCCC GAGCGGTCGCCCCTCAGCTGCGGGC ACCTGTCGCGCGTGCGGGTGGCCCT GGACCTGGAGGTGGGAGCCGTGTCC TTCTACGCTGTGGAGGACATGCGCC ACCTCTACACCTTCCGCGTCAACTT CCAGGAGCGCGTGTTCCCGCTTTTC TCTGTTTGCTCCACGGGCACCTACT TGCGAATCTGGCCTTGAGGGGCACT GCTGGGGAGCTCCTGTCTCTGGGCT GCCGGTGGGAGGGGATGTCGCCTCC CCAGAGATGCCTGGTCCGTCTTGGG TCTGCCCTCCGTGCTCCTGACCCCT GCTGCCCAAGAGAGCCTGCTACAGA CACAACCCCGAGGCAGGAGAGTGAC TGTGGCCAACCGAGCAGGGGAACAG GGGCTTTGGACTCCTGAGGGTGTTC CCTTCCTGAGGTCACATGTGGATTT GGCCAGAGCCTTCAGGAGGTGGAGG CCGGTGAGGTCAGGAGCCCAGCTCT CCAGGGGGCTTCTGCCCTGACTGGG AAGGGTGCCTGGCTCCCTAAACAA TGTCAAAGCCAGTCCTGCTGTTCTC TGTTGCCAGGGGGCAGGTCTGGGCC TGGGCCAACCACGTTTGTTATCATG GCTGCTGCCTTCTGGACAGCTGCCA GCTCTGCCTTGAGAGGTTGTGGGAC CTCTGGATCCAGCTGACCTGACAGG TCATCTACTCAGGGAGGAGCCCTGT GCTCCCAGCTCAGAGGACAGTCTGG GCCAGAACTGGAAGGAGACATCTGT CCCGTCTTTGAGTGACAAGCCCGGG ACAACAGCCAGTGGGCATCACGGCT CTCCAGCACTCCTTAGCCGGAGGAT ACAGAGTGATGGGTGCATCCTGACC AATGCGACAACCAACACGTGCTCTC ACAAACCCCTGACTCCCGCACTTTC CAGTGCCAAAGTACAAACGCTGCTT GGATAAGGAGAGCAAAGCTTCTGGA ACTTTATTTACTCTTTCTTTTAAT TTTCTTTTAAGAGACTGGGTCTTGC TATGTTGCCCAGGCTGGTCTTGAAC TCCTGGCCTCAAGTGATCCTCCAGT TTCCATCTCCCTAAGAGCTGGGATT ACAGGTGTGAGCCGCTGTACCCGAA CTTTTTTTGTTTTTGCTTCTGGAAC TTTGAAACACAAAACACAAGTTGGC | |

TABLE 1-continued

| TRIM 7 transcript variant, mRNA (NCBI Reference Sequence) | Sequence | SEQ ID NO: |
|---|---|---|
| | ACTTACAATTTTAAAGATGCAGCCA GCTCTAAACAACACACAGAGCACAA ATATGCTCCTGACGGACTCAGGAAA ATGCCAACAGCAGAGCACCCTGGTG CCAAGGCCTTCTCAGCCCATGCCCT GGAGGGCATTCCCCTGGCCAGCCTC AGCCCCTTGTCTACTTGTTCTCCAG CTTCTGGGTAGCTGGGCTTCTGGAA GGGTGGCAGTGGGCTACTCCCTGCT CAGCGCTCCCCTGGGAAGGGGGTGA GGAGATGAAAATGAAACTATGAGCT GTCTTTGGA | |
| Variant 3 (NM_203296.2) | TGCGCGACGTCCCCCACGGACTTGG CGATGTTCTTCCTGTCTGTTCGGAG CCTCTAGCCTGGTCTGCGTCTCCGC AGCTCTCTGCCCGCGGGAAGTCTCC GGCACAGCCACGCAGCCGCTGCCCC CACTCTTATCTCTTTCCCCGAAGCG GGCTCTGCTCAAAGTCCCCACCTCG TGGAACTGAGTGAGAGGACCTCGCC AAGATGTCCAGGGAGGGGCTCCCG GGTTAAGCCGCGCACCTAGAGCCGT CTGACTGTGCCAACGCTGTCGATTC TGGGGGCCCTTTCTTTGCTATTTTC TCGCTGAGCCTCAGCGAGGGTGTGT GCAGGGGTGAGGGCGGGGCGGGGAG GCTCGGGCGGCAGTCCCCAGTCTCT CCTTGCTGGCCCATCCTGCTCCAAC TCTCCCAGCCACGGGGCTTCCTGGT GGGGGGGCGGAGAGTAGAGGAGACG ACTAGGGGTAGGGCTGCCGGAGCTT GTGTTTCAGTCTGGCTGGTCCAGCA GATGCTTTTGGGGAAGCAAGATCCC GAGACCTTCAGAGTCACCTCGCAGT GTAACCTGTAGCCTGTAGAGATGAC TTCTACCCGGCCTCCCCGTCAGAGC TCTTGGAGTCCAGGCTGAGGGTCTT GAAGAAGGAACTGGAGGACTGTGAG GTGTTCCGGTCCACGGAAAAGAAGG AGAGCAAGGAGCTGCTGAAACAGAT GGCAGCGGAGCAGGAGAAGGTGGGG GCAGAGTTCCAGGCACTGAGGGCTT TCCTGGTGGAGCAGGAGGGTCGGCT GCTAGGCCGCTGGAGGAACTGTCC CGGGAGGTGGCACAGAAGCAGAATG AGAACCTGGCCCAGCTCGGGGTTGA GATCACCCAGCTGTCCAAGCTCAGC AGCCAGATCCAGGAGACAGCTCAAA AGCCTGACCTTGACTTTCTCCAGGA ATTCAAAAGCACGCTGAGCAGGTGT AGCAATGTGCCTGGCCCCAAGCCAA CCACAGTCTCTTCTGAGATGAAGAA TAAAGTCTGGAATGTTTCTCTCAAG ACCTTTGTCTTAAAAGGGATGCTGA AGAAGTTCAAAGAGGACCTTCGGGG AGAGCTGGAGAAAGAGGAGAAAGTG GAGCTCACCTTGGATCCCGACACGG CCAACCCGCGCCTCATCCTCTCTCT GGATCTTAAGGGCGTGCGCCTCGGC GAGCGGGCCCAGGACCTGCCCAACC ACCCCTGCCGCTTCGACACCAACAC CCGCGTCCTGGCGTCCTGCGGCTTC TCCTCGGCCGGCATCACTGGGAGG TGGAGGTGGGCTCTAAGGACGGCTG GGCCTTTTGGCGTGGCCCGCGAGGC GTGCGCCGAAAGGGCCTGACGCCCT TCACTCCCGAGGAGGGCGTCTG GGCCCTGCAGCTCAACGGCGGCCAG TACTGGGCCGTGACCAGCCGCGAGC GGTCGCCCCTCAGCTGCGGGCACCT GTCGCGCGTGCGGGTGCCCTGGAC CTGGAGGTGGGAGCCGTGTCCTTCT ACGCTGTGGAGGACATGCGCCACCT CTACACCTTCCGCGTCAACTTCCAG | 3 |
| | GAGCGCGTGTTCCCGCTTTTCTCTG TTTGCTCCACGGGCACCTACTTGCG AATCTGGCCTTGAGGGGCACTGCTG GGGAGCTCCTGTCTCTGGGCTGCCG GTGGGAGGGGATGTCGCCTCCCCAG AGATGCCTGGTCCGTCTTGGGTCTG CCCTCCGTGCTCCTGACCCCTGCTG CCCAAGAGAGCCTGCTACAGACACA ACCCCGAGGCAGGAGAGTGACTGTG GCCAACCGAGCAGGGGAACAGGGGC TTTGGACTCCTGAGGGTGTTCCCTT CCTGAGGTCACATGTGGATTTGGCC AGAGCCTTCAGGAGGTGGAGGCCGG TGAGGTCAGGAGCCCAGCTCTCCAG GGGGCTTCTGCCCTGACTGGGAAGG GTGCCTGGCTCCCTAAAACAATGTC AAAGCCAGTCCTGCTGTTCTCTGTT GCCAGGGGGCAGGTCTGGGCCTGGG CCAACCACGTTTGTTATCATGGCTG CTGCCTTCTGGACAGCTGCCAGCTG TGCCTTGAGAGGTTGTGGGACCTCT GGATCCAGCTGACCTGACAGGTCAT CTACTCAGGGAGGAGCCCTGTGCTC CCAGCTCAGAGGACAGTCTGGGCCA GAACTGGAAGGAGACATCTGTCCCG TCTTTGAGTGACAAGCCCGGGACAA CAGCCAGTGGGCATCACGGCTCTCC AGCACTCCTTAGCCGGAGGATACAG AGTGATGGGTGCATCCTGACCAATG CGACAACCAACACGTGCTCTCACAA ACCCCTGACTCCCGCACTTTCCAGT GCCAAAGTACAAACGCTGCTTGGAT AAGGAGAGCAAAGCTTCTGGAACTT TATTTACTCTTTCTTTTTAATTTTC TTTTAAGAGACTGGGTCTTGCTATG TTGCCCAGGCTGGTCTTGAACTCCT GGCCTCAAGTGATCCTCCCAGTTTCC ATCTCCCTAAGAGCTGGGATTACAG GTGTGAGCCGCTGTACCCGAACTTT TTTTGTTTTTGCTTCTGGAACTTTG AAACACAAAACAAGTTGGCACTT ACAATTTTAAAGATGCAGCCAGCTC TAAACAACACACAGAGCACAAATAT GCTCCTGACGGACTCAGGAAAATGC CAACAGCAGAGCACCCTGGTGCCAA GGCCTTCTCAGCCCATGCCCTGGAG GGCATTCCCCTGGCCAGCCTCAGCC CCTTGTCTACTTGTTCTCCAGCTTC TGGGTAGCTGGGCTTCTGGAAGGGT GGCAGTGGGCTACTCCCTGCTCAGC GCTCCCCTGGGAAGGGGGTGAGGAG ATGAAAATGAAACTATGAGCTGTCT TTGGA | |
| Variant 4 (NM_203295.2) | TGCGCGACGTCCCCCACGGACTTGG CGATGTTCTTCCTGTCTGTTCGGAG CCTCTAGCCTGGTCTGCGTCTCCGC AGCTCTCTGCCCGCGGGAAGTCTCC GGCACAGCCACGCAGCCGCTGCCCC CACTCTTATCTCTTTCCCCGAAGCG GGCTCTGCTCAAAGTCCCCACCTCG TGGAACTGAGTGAGAGGACCTCGCC AAGATGTCCAGGGAGGGGCTCCCG GGTTAAGCCGCGCACCTAGAGCCGT CTGACTGTGCCAACGCTGTCGATTC TGGGGGCCCTTTCTTTGCTATTTTC TCGCTGAGCCTCAGCGAGGGAGCTC TTGGAGTCCAGGCTGAGGGTCTTGA AGAAGGAACTGGAGGACTGTGAGGT GTTCCGGTCCACGGAAAAGAAGGAG AGCAAGGAGCTGCTGGTGAGCCAGG CACCCGCAGGCCCCCGTGGGACAT TACAGAGGCCTGAGAACTCAGCACC AGGGCTCGAAACAGATGGCAGCGGA GCAGGAGAAGGTGGGGGCAGAGTTC | 4 |

TABLE 1-continued

| TRIM 7 transcript variant, mRNA (NCBI Reference Sequence) | Sequence | SEQ ID NO: |
|---|---|---|
| | CAGGCACTGAGGGCTTTCCTGGTGG<br>AGCAGGAGGGTCGGCTGCTAGGCCG<br>CCTGGAGGAACTGTCCCGGGAGGTG<br>GCACAGAAGCAGAATGAGAACCTGG<br>CCCAGCTCGGGGTTGAGATCACCCA<br>GCTGTCCAAGCTCAGCAGCCAGATC<br>CAGGAGACAGCTCAAAAGCCTGACC<br>TTGACTTTCTCCAGGAATTCAAAAG<br>CACGCTGAGCAGGTGTAGCAATGTG<br>CCTGGCCCCAAGCCAACCACAGTCT<br>CTTCTGAGATGAAGAATAAAGTCTG<br>GAATGTTTCTCTCAAGACCTTTGTC<br>TTAAAAGGGATGCTGAAGAAGTTCA<br>AAGAGGACCTTCGGGGAGAGCTGGA<br>GAAAGAGGAGAAAGTGGAGCTCACC<br>TTGGATCCCGACACGGCCAACCCGC<br>GCCTCATCCTCTCTCTGGATCTTAA<br>GGGCGTGCGCCTCGGCGAGCGGGCC<br>CAGGACCTGCCCAACCACCCCTGCC<br>GCTTCGACACCAACACCCGCGTCCT<br>GGCGTCCTGCGGCTTCTCCTCGGGC<br>CGGCATCACTGGGAGGTGGAGGTGG<br>GCTCTAAGGACGGCTGGGCCTTTGG<br>CGTGGCCCGCGAGAGCGTGCGCCGA<br>AAGGGCCTGACGCCCTTCACTCCCG<br>AGGAGGGCGTCTGGGCCCTGCAGCT<br>CAACGGCGGCCAGTACTGGGCCGTG<br>ACCAGCCCCGAGCGGTCGCCCCTCA<br>GCTGCGGGCACCTGTCGCGCGTGCG<br>GGTGGCCCTGGACCTGGAGGTGGG<br>AGCCGTGTCCTTCTACGCTGTGGAG<br>GACATGCGCCACCTCTACACCTTCC<br>GCGTCAACTTCCAGGAGCGCGTGTT<br>CCCGCTTTTCTCTGTTTGCTCCACG<br>GGCACCTACTTGCGAATCTGGCCTT<br>GAGGGGCACTGCTGGGGAGCTCCTG<br>TCTCTGGGCTGCCGGTGGGAGGGGA<br>TGTCGCCTCCCCAGAGATGCCTGGT<br>CCGTCTTGGGTCTGCCCTCCGTGCT<br>CCTGACCCCTGCTGCCCAAGAGAGC<br>CTGCTACAGACACAACCCCGAGGCA<br>GGAGAGTGACTGTGGCCAACCGAGC<br>AGGGGAACAGGGGCTTTGGACTCCT<br>GAGGGTGTTCCCTTCCTGAGGTCAC<br>ATGTGGATTTGGCCAGAGCCTTCAG<br>GAGGTGGAGGCCGGTGAGGTCAGGA<br>GCCCAGCTCTCAGGGGGCTTCTGC<br>CCTGACTGGGAAGGGTGCCTGGCTC<br>CCTAAAACAATGTCAAAGCCAGTCC<br>TGCTGTTCTCTGTTGCCAGGGGGCA<br>GGTCTGGGCCTGGGCCAACCACGTT<br>TGTTATCATGGCTGCTGCCTTCTGG<br>ACAGCTGCCAGCTCTGCCTTGAGAG<br>GTTGTGGGACCTCTGGATCCAGCTG<br>ACCTGACAGGTCATCTACTCAGGGA<br>GGAGCCCTGTGCTCCCAGCTCAGAG<br>GACAGTCTGGGCCAGAACTGGAAGG<br>AGACATCTGTCCCGTCTTTGAGTGA<br>CAAGCCCGGACAACAGCCAGTGGG<br>CATCACGGCTCTCCAGCACTCCTTA<br>GCCGGAGGATACAGAGTGATGGGTG<br>CATCCTGACAATGCGACAACCAAC<br>ACGTGCTCTCACAAACCCCTGACTC<br>CCGCACTTTCCAGTGCCAAAGTACA<br>AACGCTGCTTGGATAAGGAGAGCAA<br>AGCTTCTGGAACTTTATTTACTCTT<br>TCTTTTTAATTTTCTTTTAAGAGAC<br>TGGGTCTTGCTATGTTGCCCAGGCT<br>GGTCTTGAACTCCTGGCCTCAAGTG<br>ATCCTCCAGTTTCCATCTCCCTAAG<br>AGCTGGGATTACAGGTGTGAGCCGC<br>TGTACCCGAACTTTTTTTGTTTTTG<br>CTTCTGGAACTTTGAAACACAAAAC<br>ACAAGTTGGCACTTACAATTTTAAA<br>GATGCAGCCAGCTCTAAACAACACA | |
| Variant 5 (NM_203294.2) | TGCGCGACGTCCCCCACGGACTTGG<br>CGATGTTCTTCCTGTCTGTTCGGAG<br>CCTCTAGCCTGGTCTGCGTCTCCGC<br>AGCTCTCTGCCCGCGGGAAGTCTCC<br>GGCACAGCCACGCAGCCGCTGCCCC<br>CACTCTTATCTCTTTCCCCGAAGCG<br>GGCTCTGCTCAAAGTCCCCACCTCG<br>TGGAACTGAGTGAGAGGACCTCGCC<br>AAGATGTCCAGGGAGGGGCTCCCG<br>GGTTAAGCCGCGCACCTAGAGCCGT<br>CTGACTGTGCCAACGCTGTCGATTC<br>TGGGGGCCCTTTCTTTGCTATTTTC<br>TCGCTGAGCCTCAGCGAGGGAGCTC<br>TTGGAGTCCAGGCTGAGGGTCTTGA<br>AGAAGGAACTGGAGGACTGTGAGGT<br>GTTCCGGTCCACGGAAAAGAAGGAG<br>AGCAAGGAGCTGCTGAAACAGATGG<br>CAGCGGAGCAGGAGAAGGTGGGGGC<br>AGAGTTCCAGGCACTGAGGGCTTTC<br>CTGGTGGAGCAGGAGGGTCGGCTGC<br>TAGGCCGCCTGGAGGAACTGTCCCG<br>GGAGGTGGCACAGAAGCAGAATGAG<br>AACCTGGCCCAGCTCGGGGTTGAGA<br>TCACCCAGCTGTCCAAGCTCAGCAG<br>CCAGATCCAGGAGACAGCTCAAAAG<br>CCTGACCTTGACTTTCTCCAGGAAT<br>TCAAAAGCACGCTGAGCAGGTGTAG<br>CAATGTGCCTGGCCCCAAGCCAACC<br>ACAGTCTCTTCTGAGATGAAGAATA<br>AAGTCTGGAATGTTTCTCTCAAGAC<br>CTTTGTCTTAAAAGGGATGCTGAAG<br>AAGTTCAAAGAGGACCTTCGGGGAG<br>AGCTGGAGAAAGAGGAGAAAGTGGA<br>GCTCACCTTGGATCCCGACACGGCC<br>AACCCGCGCCTCATCCTCTCTCTGG<br>ATCTTAAGGGCGTGCGCCTCGGCGA<br>GCGGGCCCAGGACCTGCCCAACCAC<br>CCCTGCCGCTTCGACACCAACACCC<br>GCGTCCTGGCGTCCTGCGGCTTCTC<br>CTCGGGCCGGCATCACTGGGAGGTG<br>GAGGTGGGCTCTAAGGACGGCTGGG<br>CCTTTGGCGTGGCCCGCGAGAGCGT<br>GCGCCGAAAGGGCCTGACGCCCTTC<br>ACTCCCGAGGAGGGCGTCTGGGCCC<br>TGCAGCTCAACGGCGGCCAGTACTG<br>GGCCGTGACCAGCCCCGAGCGGTCG<br>CCCCTCAGCTGCGGGCACCTGTCGC<br>GCGTGCGGGTGGCCCTGGACCTGGA<br>GGTGGGAGCCGTGTCCTTCTACGCT<br>GTGGAGGACATGCGCCACCTCTACA<br>CCTTCCGCGTCAACTTCCAGGAGCG<br>CGTGTTCCCGCTTTTCTCTGTTTGC<br>TCCACGGGCACCTACTTGCGAATCT<br>GGCCTTGAGGGGCACTGCTGGGGAG<br>CTCCTGTCTCTGGGCTGCCGGTGGG<br>AGGGGATGTCGCCTCCCCAGAGATG<br>CCTGGTCCGTCTTGGGTCTGC<br>CCTCCGTGCTCCTGACCCCTGCTGC<br>CCAAGAGAGCCTGCTACAGACACAA<br>CCCCGAGGCAGGAGAGTGACTGTGG<br>CCAACCGAGCAGGGGAACAGGGGCT<br>TTGGACTCCTGAGGGTGTTCCCTTC<br>CTGAGGTCACATGTGGATTTGGCCA<br>GAGCCTTCAGGAGGTGGAGGCCGGT | 5 |

TABLE 1-continued

| TRIM 7 transcript variant, mRNA (NCBI Reference Sequence) | Sequence | SEQ ID NO: |
|---|---|---|
| | GAGGTCAGGAGCCCAGCTCTCCAGG<br>GGGCTTCTGCCCTGACTGGGAAGGG<br>TGCCTGGCTCCCTAAAACAATGTCA<br>AAGCCAGTCCTGCTGTTCTCTGTTG<br>CCAGGGGGCAGGTCTGGGCCTGGGC<br>CAACCACGTTTGTTATCATGGCTGC<br>TGCCTTCTGGACAGCTGCCAGCTCT<br>GCCTTGAGAGGTTGTGGGACCTCTG<br>GATCCAGCTGACCTGACAGGTCATC<br>TACTCAGGGAGGAGCCCTGTGCTCC<br>CAGCTCAGAGGACAGTCTGGGCCAG<br>AACTGGAAGGAGACATCTGTCCCGT<br>CTTTGAGTGACAAGCCCGGGACAAC<br>AGCCAGTGGGCATCACGGCTCTCCA<br>GCACTCCTTAGCCGGAGGATACAGA<br>GTGATGGGTGCATCCTGACCAATGC<br>GACAACCAACACGTGCTCTCACAAA<br>CCCCTGACTCCCGCACTTTCCAGTG<br>CCAAAGTACAAACGCTGCTTGGATA<br>AGGAGAGCAAAGCTTCTGGAACTTT<br>ATTTACTCTTTcttttttaattttct<br>tttaagagactgggtcttgctatgt<br>tgcccaggctGGTCTTGAACTCCTG<br>GCCTCAAGTGATCCTCCAGTTTCCA<br>TCTCCCTAAGAGCTGGGATTACAGG<br>TGTGAGCCGCTGTACCCGAACTTTT<br>TTTGTTTTTGCTTCTGGAACTTTGA<br>AACACAAAACACAAGTTGGCACTTA<br>CAATTTTAAAGATGCAGCCAGCTCT<br>AAACAACACACAGAGCACAAATATG<br>CTCCTGACGGACTCAGGAAAATGCC<br>AACAGCAGAGCACCCTGGTGCCAAG<br>GCCTTCTCAGCCCATGCCCTGGAGG<br>GCATTCCCCTGGCCAGCCTCAGCCC<br>CTTGTCTACTTGTTCTCCAGCTTCT<br>GGGTAGCTGGGCTTCTGGAAGGGTG<br>GCAGTGGGCTACTCCCTGCTCAGCG<br>CTCCCCTGGGAAGGGGGTGAGGAGA<br>TGAAAATGAAACTATGAGCTGTCTT<br>TGGA | |
| Variant 6 (NM_033342.4) | AGTGGGCCCTCGGCGCCCAGCTCCG<br>CGTCCTGTGAGGTCCAGTGGCCGCC<br>CAGGCGCGACCAGATCTGGGTGCGC<br>GGAGAGCGCGCATGGCGGCTGTGGG<br>ACCGCGGACCGGCCCCGGAACCGGC<br>GCCGAGGCTCTAGCGCTGGCGGCAG<br>AGCTGCAGGGCGAGGCGACGTGCTC<br>CATCTGCCTAGAGCTCTTTCGTGAG<br>CCGGTGTCCGTCGAGTGCGGCCACA<br>GCTTCTGCCGCGCCTGCATAGGGCG<br>CTGCTGGGAGCGCCCGGGCGCGGGG<br>TCTGTTGGGGCCGCCACCCGCGCGC<br>CCCCCTTCCCACTGCCCTGTCCGCA<br>GTGCCGCGAGCCCGCGCGCCCCAGT<br>CAGCTGCGGCCCAACCGGCAGCTGG<br>CGGCAGTGGCCACGCTCCTGCGGCG<br>CTTCAGCCTGCCCGCCGGCTGCCCCG<br>GGAGAGCACGGGTCTCAGGCGGCCG<br>CGGCCCGGGCAGCGGCTGCCCGCTG<br>CGGGCAGCATGGCGAACCCTTCAAG<br>CTCTACTGCCAGGACGACGGACGCG<br>CCATCTGCGTGGTGTGCGACCGCGC<br>CCGCGAGCACCGCGAGCACGCCGTG<br>CTGCCGCTGGACGAGGCGGTGCAGG<br>AGGCCAAGGAGCTCTTGGAGTCCAG<br>GCTGAGGGTCTTGAAGAAGGAACTG<br>GAGGACTGTGAGGTGTTCCGGTCCA<br>CGGAAAAGAAGGAGAGCAAGGAGCT<br>GCTGGTGAGCCAGGCACCCGCAGGC<br>CCCCGTGGGACATTACAGAGGCCT<br>GAGAACTCAGCACCAGGGCTCGGTG<br>TGTGTGGTGTTGGAGTGTGTGCTAT<br>GGAACCGCAGAATCGATTTCAGAAA<br>GATAATAGAGTCCATATTATATAGG | 6 |
| | GTGTCCACATAATTGTTGTACAAAC<br>CAGAGCTTTTTAAAGTGAAAAGCAG<br>TGCTAAAATAATTATTGCAAAACAA<br>CTGGCTTAAACTGGAGCTGTCCCAG<br>CGAATCAGGACGCTCAGTCACTCTG<br>ATATTACGTAACATACCAGTTAGGG<br>CCTGCGGAAGCATCTTGTAATGGAA<br>CACATTACTATTTCTGCAGAGAAAC<br>ATGGATATTCAATAAGTGGGAATAT<br>TAATACAATAAAGAGCCTCATGGCA<br>TGTTTTGTCAACAAAACAGTAGTGA<br>AAAAAA | |

As used herein, compositions "modulating" TRIM7 can include any biomolecule(s) capable of increasing TRIM7 gene expression, increasing TRIM7 protein expression, increasing TRIM7 activity, or any combination thereof. In some embodiments, compositions "modulating" TRIM7 can include any biomolecule(s) that are modulators and/or activators of targets upstream or downstream of a TRIM7 signaling cascade that would effectively activate the physiological outcome of TRIM7 activation. In some embodiments, biomolecule(s) capable of modulating TRIM7 can be a peptide, an antibody, a chemical, a compound, an oligo, a nucleic acid molecule, or a combination thereof.

In certain embodiments, compositions herein can include a nucleic acid molecule. The term "nucleic acid molecule" as used herein refers to a molecule having nucleotides (i.e., a polynucleotide sequence). The nucleic acid can be single, double, or multiple stranded and may comprise modified or unmodified nucleotides or non-nucleotides or various mixtures and combinations thereof. In some embodiments, a nucleic acid molecule for use herein can be a single-stranded RNA. In some embodiments, a nucleic acid molecule for use herein can be a messenger RNA (mRNA).

As used herein, the term "messenger RNA (mRNA)" refers to a polyribonucleotide that may encode at least one polypeptide. In some embodiments, mRNA as used herein may encompass modified and/or unmodified RNA. In some embodiments, mRNA as used herein may contain one or more coding and non-coding regions. In some embodiments, mRNA as used herein can be purified from natural sources, produced using recombinant expression systems and optionally purified, in vitro transcribed, chemically synthesized, and the like. In accordance with some embodiments herein, where appropriate (e.g., in the case of chemically synthesized molecules), mRNA may comprise nucleoside analogs such as analogs having chemically modified bases or sugars, backbone modifications, and the like. An mRNA sequence disclosed herein is presented in the 5' to 3' direction unless otherwise indicated. In some embodiments, an mRNA may be or may comprise natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); modified phosphate groups (e.g., phosphorothioates and 5'-N-phosphoramidite linkages), or any combination thereof.

A suitable TRIM7 mRNA for use in any of the compositions and methods disclosed herein may encode any full length, fragment or portion of a TRIM7 protein which can be substituted for naturally occurring TRIM7 protein activity. In some embodiments, a suitable mRNA sequence is a mRNA sequence encoding a human TRIM7 protein. In some embodiments, compositions of the present disclosure may include at least one mRNA encoding a TRIM7 protein. In some aspects, a mRNA encoding a TRIM7 protein herein may have a polynucleotide sequence that is at least about 80% (e.g., about 80%, about 85%, about 90%, about 95%, about 99%) identical to SEQ ID NOs: 1-6. In some other aspects, a mRNA encoding a TRIM7 protein herein may have a polynucleotide sequence that is identical to SEQ ID NOs: 1-6.

In certain embodiments, a suitable mRNA sequence for use herein may be a mRNA sequence, a homolog, or an analog of human TRIM7 protein. For example, a homolog or an analog of human TRIM7 protein may be a modified human TRIM7 protein containing one or more amino acid substitutions, deletions, and/or insertions as compared to a wild-type or naturally occurring human TRIM7 protein while retaining substantial TRIM7 protein activity. In some embodiments, a mRNA for use in the compositions disclosed herein may encode an amino acid sequence at least about 50%, 55%, 60%, 65%, 70%, 75%, 80%, 85%, 90%, 91%, 92%, 93%, 94%, 95%, 96%, 97%, 98%, 99% or more homologous to the amino acid sequence encoded by one or more of SEQ ID NOs: 1-6. In some embodiments, a mRNA for use in the compositions disclosed herein may encode a protein substantially identical to human TRIM7 protein. In some embodiments, a mRNA for use in the compositions disclosed herein may encode a fragment or a portion of human TRIM7 protein. In some embodiments, a mRNA for use in the compositions disclosed herein may encode a fragment or a portion of human TRIM7 protein, wherein the fragment or portion of the protein still maintains TRIM7 activity similar to that of the wild-type protein. In some embodiments, a suitable mRNA for use in the compositions disclosed herein may encode a fusion protein comprising a full length, fragment, or portion of a TRIM7 protein fused to another protein (e.g., a N or C terminal fusion). In some embodiments, the protein fused to the mRNA encoding a full length, fragment, or portion of a TRIM7 protein may encode a signal or a cellular targeting sequence.

(b) TRIM7 mRNAs

In some embodiments, TRIM7 mRNAs disclosed herein (also referred to herein as "mRNAs" interchangeably) may be synthesized according to any of a variety of known methods. For example, but not limited to, mRNAs disclosed herein may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In certain embodiments, mRNA sequence(s) disclosed herein may be determined and incorporated into a DNA template using standard methods. In some aspects, a mRNA suitable for use herein may be a codon-optimized sequence. As used herein, the terms "codon optimization" and "codon-optimized" refer to modifications of the codon composition of a naturally occurring or wild-type nucleic acid encoding a peptide, polypeptide or protein that do not alter its amino acid sequence, thereby improving protein expression of said nucleic acid. Optimization algorithms may then be used for selection of suitable codons. Typically, the G/C content can be optimized to achieve the highest possible G/C content, to adjust codon usage to avoid rare or rate-limiting codons, to remove destabilizing nucleic acid sequences or motifs, and/or to eliminate pause sites or terminator sequences. In some aspects, the optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

In some embodiments, a mRNA disclosed herein may be synthesized as unmodified or modified mRNA. In specific embodiments, a mRNA disclosed herein may comprise or consist of naturally occurring nucleosides (or unmodified nucleosides; i.e., adenosine, guanosine, cytidine, and uridine). In other embodiments, mRNAs disclosed herein may be modified to enhance stability. Examples of modifications of mRNA can include, but are not limited to, modifications of the nucleotides of the RNA. In some aspects, a modified mRNA disclosed herein can include, for example, backbone modifications, sugar modifications, and/or base modifications. In some embodiments, mRNAs disclosed herein may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, wybutoxosine, and phosphoramidates, phosphorothioates, peptide nucleotides, methylphosphonates, 7-deazaguanosine, 5-methylcytosine, and inosine.

In some embodiments, mRNAs disclosed herein may contain one or more RNA backbone modifications. A backbone modification may be a modification in which the phosphates of the backbone of the nucleotides contained in the RNA are modified chemically. Non-limited examples of backbone modifications suitable for use herein may include modifications from the group consisting of methylphosphonates, methylphosphoramidates, phosphoramidates, phosphorothioates (e.g., cytidine 5'-O-(1-thiophosphate)), boranophosphates, positively charged guanidinium groups etc., which means by replacing the phosphodiester linkage by other anionic, cationic or neutral groups.

In some embodiments, mRNAs disclosed herein may contain sugar modifications. A sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-tri phosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-tri phosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs disclosed herein may contain modifications of the bases of the nucleotides (i.e., "base modifications"). A modified nucleotide which contains a base modification can also be called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-tri phosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

In certain embodiments, mRNAs disclosed herein may include the addition of a "cap" on the N-terminal (5') end. The presence of the cap may be important in providing resistance to nucleases found in most eukaryotic cells. In some embodiments, mRNAs disclosed herein may include a 5' cap structure. In some aspects, a 5' cap can be added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, 3'-O-Me-m7G(5')ppp(5')G, m7G(5')ppp(5')A, m7G(5')ppp(5')G, (5'(A,G(5')ppp(5')A, (5'(A,G(5')ppp(5')G, G(5')ppp(5')A, and G(5')ppp(5')G. In some aspects, naturally occurring cap structures may comprise a 7-methyl guanosine that is linked via a triphosphate bridge to the 5'-end of the first transcribed nucleotide, resulting in a dinucleotide cap of m7G(5')ppp(5')N, where N is any nucleoside. In some aspects, the addition of the cap to the 5' terminal end of RNA may occur immediately after initiation of transcription. The terminal nucleoside is typically a guanosine, and is in the reverse orientation to all the other nucleotides, i.e., G(5')ppp(5')GpNpNp. Non-limiting examples of cap structures can include m7G(5')ppp(5')G; a pre-formed dinucleotide of the form m7G(5')ppp(5')G ("m7GpppG"); a synthetic dinucleotide cap (e.g., Anti-Reverse Cap Analog ("ARCA") or modified ARCA, which is generally a modified cap analog in which the 2' or 3' OH group is replaced with —OCH); a chemical structure selected from the group consisting of m7GpppG, m7GpppA, m7GpppC; unmethylated cap analogs (e.g., GpppG); a dimethylated cap analog (e.g., m$^{2'7}$GpppG); a trimethylated cap analog (e.g., m$^{2,2,7}$GpppG); a dimethylated symmetrical cap analog (e.g., m7Gpppm7G); an anti-reverse cap analog (e.g., ARCA; m$^{7,2'Ome}$GpppG, m$^{7,2'd}$GpppG, m$^{7,3'Ome}$GpppG, m$^{7,3'd}$GpppG and their tetraphosphate derivatives); a 7-methyl guanylate ("m7G") linked via a triphosphate bridge to the 5'-end of the first transcribed nucleotide, resulting in m7G(5')ppp(5')N, where N is any nucleoside, and the like. In some aspects, the cap can be a Cap0 structure. Cap0 structures lack a 2'-O-methyl residue of the ribose attached to bases 1 and 2. In some embodiments, the cap may be a Cap1 structure. Cap1 structures have a 2'-O-methyl residue at base 2. In some embodiments, the cap may be a Cap2 structure. Cap2 structures have a 2'-O-methyl residue attached to both bases 2 and 3.

In certain embodiments, mRNAs disclosed herein may include the addition of a "tail" structure on the C-terminal (3') end. The presence of a "tail" can serve to protect the mRNA from exonuclease degradation. In some embodiments, mRNAs disclosed herein may include a 3' poly(A) tail structure. In some aspects, the length of the poly A tail for use herein can be at least about 10, at least about 50, at least about 100, at least about 200, at least about 300, at least about 400, or at least about 500 nucleotides. In some embodiments, a poly-A tail on the 3' terminus of mRNA may include about 10 to about 300 adenosine nucleotides (e.g., about 10 to about 200 adenosine nucleotides, about 10 to about 150 adenosine nucleotides, about 10 to about 100 adenosine nucleotides, about 20 to about 70 adenosine nucleotides, or about 20 to about 60 adenosine nucleotides). In some embodiments, a poly(U) tail may be used instead of a poly(A) tail described herein. In some embodiments, a poly(U) tail may be added to a poly(A) tail described herein. In some embodiments, mRNAs disclosed herein may include a 3' poly(C) tail structure. A suitable poly(C) tail on the 3' terminus of mRNA may include about 10 to about 200 cytosine nucleotides (e.g., about 10 to 1 about 50 cytosine nucleotides, about 10 to about 100 cytosine nucleotides, about 20 to about 70 cytosine nucleotides, about 20 to about 60 cytosine nucleotides, or about 10 to about 40 cytosine nucleotides). The poly(C) tail may be added to a poly(A) and/or poly(U) tail or may substitute the poly(A) and/or poly(U) tail.

In certain embodiments, mRNAs disclosed herein may include a 5' and/or 3' untranslated region. In some aspects, a 5' untranslated region may include one or more elements that affect an mRNA's stability or translation, for example, an iron responsive element. In some other aspects, a 5' untranslated region may be between about 50 and about 500 nucleotides in length. In some aspects, a 3' untranslated region may include one or more of a polyadenylation signal, a binding site for proteins that affect an mRNA's stability of location in a cell, or one or more binding sites for miRNAs. In some aspects, a 3' untranslated region may be between 50 and about 500 nucleotides in length or longer. Non-limiting 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

(c) Lipid Nanoparticles (LNPs)

In certain embodiments, mRNAs disclosed herein can be formulated into lipid nanoparticles (LNPs) for delivery into cells, tissues, and/or a subject. LNPs are spherical vesicles made of ionizable lipids, which can be positively charged at low pH (enabling RNA complexation) and neutral at physiological pH (reducing potential toxic effects, as compared with positively charged lipids, such as liposomes). LNPs can be taken up by cells via endocytosis, and the ionizability of the lipids at low pH (likely) can enable endosomal escape, which allows release of the cargo into the cytoplasm.

In some embodiments, LPNs for use herein can contain ionizable cationic lipids, non-cationic lipids, sterols, and/or PEG lipids components along with mRNAs and/or expression vectors encoding a mRNAs disclosed herein. In some embodiments, LPNs herein can have about 5-25% non-cationic lipid. In some embodiments, LPNs herein can have about 5-20%, about 5-15%, about 5-10%, about 10-25%, about 10-20%, about 10-25%, about 15-25%, about 15-20%, or about 20-25% non-cationic lipid. Non-limiting examples of non-cationic lipids include distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), ioleoylphosphatidylethanolamine (DOPE), palmitoyloleoylphosphatidylcholine (POPC), palmitoyloleoyl-phosphatidylethanolamine (POPE), dipalmitoyl phosphatidyl ethanolamine (DPPE), dimyristoylphosphoethanolamine (DMPE), distearoyl-phosphatidyl-ethanolamine (DSPE), sphingolipids, cerebrosides, gangliosides, 16-O-monomethyl PE, 16-O-dimethyl P, 18-1-trans PE, 1-stearoyl-2-oleoyl-phosphatidyethanolamine (SOPE), and the like.

LNPs usually contain a helper lipid to promote cell binding, cholesterol to fill the gaps between the lipids, and a polyethylene glycol (PEG) to reduce opsonization by serum proteins and reticuloendothelial clearance. In some embodiments, LPNs for use herein can include one or more synthetic ionizable phospholipids provided herein and at least one helper lipid. In some embodiments, LPNs for use herein can include one or more synthetic ionizable phospholipids provided herein and at least one helper lipid selected from: 1,2-dioleoyl-sn-glycero-3-phosphoethanolamine (DOPE), N-methyldioctadecylamine (MDOA), 1,2-dioleoyl-3-dimethylammonium-propane (DODAP), dimethyldioctadecylammonium bromide salt (DDAB), 1,2-dioleoyl-3-trimethylammonium-propane (DOTAP), and any combination thereof. In some embodiments, LPNs for use herein can include one or more synthetic ionizable phospholipids provided herein and at least one zwitterionic helper lipid (e.g., DOPE), ionizable cationic helper lipid (e.g., MDOA, DODAP), permanently cationic helper lipid (e.g., DDAB, DOTAP), or any combination thereof.

In some embodiments, LPNs for use herein can include one or more synthetic ionizable phospholipids provided herein and at least one cholesterol and/or a cholesterol derivative. As used herein, "cholesterol derivative" refers to any compound consisting essentially of a cholesterol structure, including additions, substitutions and/or deletions thereof. The term cholesterol derivative herein can also include steroid hormones and bile acids as are generally recognized in the art. Non-limiting examples of cholesterol derivatives suitable for use herein can include dihydrocholesterol, ent-cholesterol, epi-cholesterol, desmosterol, cholestanol, cholestanone, cholestenone, cholesteryl-2'-hydroxyethyl ether, cholesteryl-4'-hydroxybutyl ether, 3β-[N—(N'N'-dimethylaminoethyl)carbamoyl cholesterol (DC-Chol), 24(S)-hydroxycholesterol, 25-hydroxycholesterol, 25(R)-27-hydroxycholesterol, 22-oxacholesterol, 23-oxacholesterol, 24-oxacholesterol, cycloartenol, 22-ketosterol, 20-hydroxysterol, 7-hydroxycholesterol, 19-hydroxycholesterol, 22-hydroxycholesterol, 25-hydroxycholesterol, 7-dehydrocholesterol, 5α-cholest-7-en-3β-ol, 3,6,9-trioxaoctan-1-ol-cholesteryl-3e-ol, dehydroergosterol, dehydroepiandrosterone, lanosterol, dihydrolanosterol, lanostenol, lumisterol, sitocalciferol, calcipotriol, coprostanol, cholecalciferol, lupeol, ergocalciferol, 22-dihydroegocalciferol, ergosterol, brassicasterol, tomatidine, tomatine, ursolic acid, cholic acid, chenodeoxycholic acid, zymosterol, diosgenin, fucosterol, fecosterol, or fecosterol, or a salt or ester thereof.

In some embodiments, LPNs for use herein can include one or more synthetic ionizable phospholipids provided herein and at least one PEG or PEG-modified lipids. As used herein, a PEG-modified lipid, or "PEG lipid" refers to a lipid modified with polyethylene glycol (PEG). Such species can be alternately referred to as PEGylated lipids. Non-limiting examples of PEG-modified lipids suitable for use herein can include PEG-modified phosphatidylethanolamines, PEG-modified phosphatidic acids, PEG-modified ceramides (PEG-CER), PEG-modified dialkylamines, PEG-modified diacylglycerols (PEG-DAG), PEG-modified dialkylglycerols, and mixtures thereof. For example, but not limited to, a PEG-modified lipid for use herein can be PEG-c-DOMG (R-3-[(ω-methoxypoly(ethyleneglycol)2000)carbamoyl]-1, 2-dimyristyloxy-propyl-3-amine poly(ethylene glycol)); PEG-DMG (1,2-dimyristoyl-rac-glycero-3-methoxypolyethylene glycol poly(ethylene glycol)); PEG-DLPE (1,2-Dilauroyl-sn-glycero-3-phosphorylglycerol sodium salt-poly(ethylene glycol)); PEG-DM PE (dimethyl-2-(dimethylphosphino)ethylphosphine-poly(ethylene glycol)); PEG-DPPC (1,2-dipalmitoyl-sn-glycero-3-phosphocholine-poly(ethylene glycol)); PEG-DSPE (1, 2-distearoyl-sn-glycero-3-phosphoethanolamine-poly(ethylene glycol)); PEG-DPPE (1, 2-dipalmitoyl-sn-glycero-3-phosphoethanolamine-N-[monomethoxy poly(ethylene glycol)), and the like.

In some embodiments, a PEG-modified lipid for use herein can comprise a PEG moiety having a size of from about 1000 daltons to about 20,000 daltons. In some embodiments, a PEG-modified lipid for use herein can comprise a PEG moiety having a size of about 1000 daltons, about 2000 daltons, about 5000 daltons, about 10,000 daltons, about 15,000 daltons, or about 20,000 daltons. In some embodiments, LNPs herein can include one or more synthetic ionizable phospholipids provided herein and at least one PEG or PEG-modified lipids wherein the PEG moiety can have a size of about 2000 daltons. Examples of useful PEG-lipids for use in making the LNPs described herein include, but are not limited to, 1,2-Diacyl-sn-Glycero-3-Phosphoethanolamine-N-[Methoxy(Polyethylene glycol)-350] (mPEG 350 PE); 1,2-Diacyl-sn-Glycero-3-Phosphoethanolamine-N-[Methoxy(Polyethylene glycol)-550] (mPEG 550 PE); 1,2-Diacyl-sn-Glycero-3-Phosphoethanolamine-N-[Methoxy(Polyethylene glycol)-750] (mPEG 750 PE); 1,2-Diacyl-sn-Glycero-3-Phosphoethanolamine-N-[Methoxy(Polyethylene glycol)-1000] (mPEG 1000 PE); 1,2-Diacyl-sn-Glycero-3-Phosphoethanolamine-N-[Methoxy(Polyethylene glycol)-2000] (mPEG 2000 PE);

1,2-Diacyl-sn-Glycero-3-Phosphoethanolamine-N-[Methoxy(Polyethylene glycol)-3000] (mPEG 3000 PE); 1,2-Diacyl-sn-Glycero-3-Phosphoethanolamine-N-[Methoxy(Polyethylene glycol)-5000] (m PEG 5000 PE); N-Acyl-Sphingosine-1-[Succinyl(Methoxy Polyethylene Glycol) 750] (m PEG 750 Ceram ide); N-Acyl-Sphingosine-1-[Succinyl(Methoxy Polyethylene Glycol) 2000] (mPEG 2000 Ceramide); and N-Acyl-Sphingosine-1-[Succinyl (Methoxy Polyethylene Glycol) 5000] (m PEG 5000 Ceramide). In some embodiments, LNPs herein can include one or more synthetic ionizable phospholipids provided herein and 1,2-dimyristoyl-rac-glycero-3-methoxy(poly(ethylene glycol-2000)) (DMG-PEG2000).

In some embodiments, LNPs herein can include one or more agents to target one or more cell types. In some embodiments, LNPs herein can make the LNPs selective for one or more cell types. In some embodiments, LNPs herein can make LNPs unload cargo at one or more selective cell types. In some embodiments, LNPs herein can selectively target one or more cell types. In some embodiments, LNPs herein can selectively target one or more tissue types. In some embodiments, LNPs herein can selectively target one or more cancers.

LNP size can impact the behavior of lipid nanoparticles in vivo. In some embodiments, LNPs herein can be about 20 nm to about 1000 nm in diameter or size. In some embodiments, LNPs herein can be about 20 nm to about 200 nm in size. In some embodiments, LNPs herein can about 20 nm to about 190 nm or about 25 nm to about 190 nm in size. In some embodiments, LNPs herein can be about 30 nm to about 180 nm in size. In some embodiments, LNPs herein can be about 35 nm to about 170 nm in size. In some embodiments, LNPs herein can be about 40 nm to about 160 nm in size. In some embodiments, LNPs herein can be about 50 nm to about 150 nm, about 60 nm to about 140 nm, about 70 nm to about 130 nm, about 80 nm to about 120 nm, or about 90 nm to about 110 nm in size. In some embodiments, LNPs herein can be about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, or about 200 nm in size or diameter.

In some embodiments, an average LNP size in a LNP composition herein can be about 20 nm to about 1000 nm (e.g., about 20 nm, about 40 nm, about 60 nm, about 80 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm) in diameter in average size. In some embodiments, LNP size in a LNP composition herein can be homogenous at about 20 nm to about 1000 nm (e.g., about 20 nm, about 40 nm, about 60 nm, about 80 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm) in diameter in size. In some embodiments, LNP size in a LNP composition herein be heterogeneous at about 20 nm to about 1000 nm (e.g., about 20 nm, about 40 nm, about 60 nm, about 80 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm) in diameter in average size. In some embodiments, LNP size in a LNP composition herein can be heterogeneous wherein about 50% to about 99% of the LNPs average at about 20 nm to about 1000 nm (e.g., about 20 nm, about 40 nm, about 60 nm, about 80 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm) in diameter in average size.

In some embodiments, LNPs disclosed herein may be designed for one or more specific applications or targets. For example, a LNP may be designed to deliver a therapeutic and/or prophylactic amount of the mRNAs disclosed herein to a particular cell, tissue, organ, or system or group thereof in a mammal's body. Physiochemical properties of lipid nanoparticles may be altered in order to increase selectivity for particular bodily targets. For instance, particle sizes may be adjusted based on the fenestration sizes of different organs. The therapeutic and/or prophylactic included in a LNP may also be selected based on the desired delivery target or targets. For example, a therapeutic and/or prophylactic may be selected for a particular indication, condition, disease, or disorder and/or for delivery to a particular cell, tissue, organ, or system or group thereof (e.g., localized or specific delivery). In certain embodiments, a LNP may include an mRNA encoding a polypeptide of interest capable of being translated within a cell to produce the polypeptide of interest. Such a composition may be designed to be specifically delivered to a particular organ. In some embodiments, a composition may be designed to be specifically delivered to a mammalian liver.

In some embodiments, the wt/wt ratio of the lipid component to a mRNA disclosed herein (e.g., TRIM7 mRNAs) in a LNP may be from about 5:1 to about 60:1. As used herein, these lipid component:mRNA ratios are set out in terms of a "wt/wt ratio." That is, for example, if the ratio is 1:1, then the same weight of each can be used. In some aspects, the wt/wt ratio of the lipid component to a mRNA disclosed herein in a LNP may be 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. The amount of a mRNA in a LNP may, for example, be measured using absorption spectroscopy (e.g., ultraviolet-visible spectroscopy).

In some embodiments, a LNP disclosed herein may encapsulate one or more RNAs, and the one or more RNAs, lipids, and amounts thereof may be selected to provide a specific N:P ratio. The N:P ratio of the composition refers to the molar ratio of nitrogen atoms in one or more lipids to the number of phosphate groups in an RNA. In general, a lower N:P ratio is preferred. In some embodiments, the one or more RNA, lipids, and amounts thereof may be selected to provide a N:P ratio herein from about 2:1 to about 60:1. In some aspects, a N:P ratio herein may be about 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, 30:1, 32:1, 34:1, 36:1, 38:1, 40:1, 42:1, 44:1, 46:1, 48:1, 50:1, 52:1, 54:1, 56:1, 58:1, or 60:1.

In some embodiments, a LNP disclosed herein may encapsulate one or more mRNAs. The efficiency of encapsulation of a mRNA describes the amount of mRNA that is encapsulated or otherwise associated with a LNP after preparation, relative to the initial amount provided. The encapsulation efficiency herein is desirably high (e.g., close to 100%). The encapsulation efficiency may be measured, for example, by comparing the amount of therapeutic and/or prophylactic in a solution containing the lipid nanoparticle before and after breaking up the lipid nanoparticle with one or more organic solvents or detergents. Fluorescence may be used to measure the amount of free therapeutic and/or prophylactic (e.g., mRNA) in a solution. In some embodiments, LNPs described herein may have an encapsulation efficiency of one or more mRNAs disclosed herein of at least about 50%, for example about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100%. In some embodiments, the encapsulation efficiency may be at least about 80%. In some other embodiments, the encapsulation efficiency may be at least about 90%.

(d) Pharmaceutical Compositions

In certain embodiments, pharmaceutical compositions are contemplated. In accordance with these embodiments, pharmaceutical compositions can include one or more of the LNPs encapsulating one or more mRNAs disclosed herein. In some embodiments, pharmaceutical compositions herein can include one or more of the LNPs encapsulating one or more mRNAs disclosed herein and at least one pharmaceutically acceptable excipient or carrier. As used herein, the term "pharmaceutically acceptable" refers to those compounds, materials, compositions, and/or dosage forms which are, within the scope of sound medical judgment, suitable for use in contact with the tissues, organs, and/or bodily fluids of a subject without excessive toxicity, irritation, allergic response, or other problems or complications commensurate with a reasonable benefit/risk ratio.

Hereinafter, the phrases "physiologically acceptable carrier" and "pharmaceutically acceptable carrier" may be interchangeably used refer to a carrier or a diluent that does not cause significant irritation to an organism and does not abrogate the biological activity and properties of the administered compound. An adjuvant is included under these phrases. As used herein, the term "pharmaceutically acceptable carrier" can refer to solvents, dispersion media, coatings, antibacterial agents, antifungal agents, isotonic and absorption delaying agents, or the like that are physiologically compatible. Pharmaceutically acceptable carriers suitable for use herein can include, but are not limited to, buffers that are well known in the art, and can be phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants.

In certain embodiments, compositions disclosed herein may further compromise one or more pharmaceutically acceptable diluent(s), excipient(s), or carrier(s). As used herein, a pharmaceutically acceptable diluent, excipient, or carrier, refers to a material suitable for administration to a subject without causing undesirable biological effects or interacting in a deleterious manner with any of the components of the composition in which it is contained. Pharmaceutically acceptable diluents, carriers, and excipients can include, but are not limited to, physiological saline, Ringer's solution, phosphate solution or buffer, buffered saline, and other carriers known in the art. Pharmaceutical compositions may also include stabilizers, anti-oxidants, colorants, other medicinal or pharmaceutical agents, carriers, adjuvants, preserving agents, stabilizing agents, wetting agents, emulsifying agents, solution promoters, salts, solubilizers, antifoaming agents, antioxidants, dispersing agents, surfactants, and combinations thereof. Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols. Techniques for formulation and administration of drugs may be found in "Remington's Pharmaceutical Sciences," Mack Publishing Co., Easton, Pa., latest edition, which is incorporated herein by reference.

In certain embodiments, pharmaceutical compositions described herein may be formulated in conventional manner using one or more physiologically acceptable carriers comprising excipients and auxiliaries to facilitate processing of genetically modified endothelial progenitor cells into preparations which can be used pharmaceutically. In other embodiments, any of the well-known techniques, carriers, and excipients may be used as suitable and as understood in the art.

In certain embodiments, pharmaceutical compositions described herein may be an aqueous suspension comprising one or more polymers as suspending agents. In some aspects, polymers that may comprise pharmaceutical compositions described herein include: water-soluble polymers such as cellulosic polymers, e.g., hydroxypropyl methylcellulose; water-insoluble polymers such as cross-linked carboxyl-containing polymers; mucoadhesive polymers, selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran; or a combination thereof. In other aspects, compositions disclosed herein may comprise at least about 5%, at least about 10%, at least about 20%, at least about 25%, at least about 30%, at least about 35%, at least about 40%, at least about 45%, at least about 50% total amount of polymers as suspending agent(s) by total weight of the composition.

In certain embodiments, pharmaceutical compositions disclosed herein may comprise a viscous formulation. In some aspects, viscosity of the composition may be increased by the addition of one or more gelling and/or thickening agents. In other aspects, compositions disclosed herein may comprise one or more gelling and/or thickening agents in an amount to provide a sufficiently viscous formulation to remain on treated tissue. In still other aspects, compositions disclosed herein may comprise at least about 5%, at least about 10%, at least about 20%, at least about 25%, at least about 30%, at least about 35%, at least about 40%, at least about 45%, at least about 50% total amount of gelling and/or thickening agent(s) by total weight of the composition. In yet other aspects, suitable thickening agents can be hydroxypropyl methylcellulose, hydroxyethyl cellulose, polyvinylpyrrolidone, carboxymethyl cellulose, polyvinyl alcohol, sodium chondroitin sulfate, sodium hyaluronate. In other aspects, viscosity enhancing agents can be acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose), or combinations thereof. In some embodiments, a suitable thickening agent may be carboxymethylcellulose.

In certain embodiments, pharmaceutical compositions disclosed herein may comprise additional agents or additives selected from a group including surface-active agents, detergents, solvents, acidifying agents, alkalizing agents, buffering agents, tonicity modifying agents, ionic additives effective to increase the ionic strength of the solution, antimicrobial agents, antibiotic agents, antifungal agents, antioxidants, preservatives, electrolytes, antifoaming agents, oils, stabilizers, enhancing agents, and the like. In some aspects, pharmaceutical compositions disclosed herein may comprise at least about 5%, at least about 10%, at least about 20%, at least about 25%, at least about 30%, at least about 35%, at least about 40%, at least about 45%, at least about 50% total amount of one or more agents by total weight of the composition. In other aspects, one or more of these agents may be added to improve the performance, efficacy, safety, shelf-life and/or other property of the muscarinic antagonist composition of the present disclosure. In some aspects, additives will be biocompatible, and will not be harsh, abrasive, or allergenic.

In certain embodiments, pharmaceutical compositions disclosed herein may comprise one or more acidifying agents. As used herein, "acidifying agents" refers to compounds used to provide an acidic medium. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art. In some aspects, any pharmaceutically acceptable organic or inorganic acid may be used. In other aspects, compositions disclosed herein may comprise at least about 5%, at least about 10%, at least about 20%, at least about 25%, at least about 30%, at least about 35%, at least about 40%, at least about 45%, at least about 50% total amount of one or more acidifying agents by total weight of the composition.

In certain embodiments, pharmaceutical compositions disclosed herein may comprise one or more alkalizing agents. As used herein, "alkalizing agents" are compounds used to provide alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art. In some aspects, any pharmaceutically acceptable organic or inorganic base can be used. In other aspects, compositions disclosed herein may comprise at least about 5%, at least about 10%, at least about 20%, at least about 25%, at least about 30%, at least about 35%, at least about 40%, at least about 45%, at least about 50% total amount of one or more alkalizing agents by total weight of the composition.

In certain embodiments, pharmaceutical compositions disclosed herein may comprise one or more antioxidants. As used herein, "antioxidants" are agents that inhibit oxidation and thus can be used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art. In some aspects, compositions disclosed herein may comprise at least about 5%, at least about 10%, at least about 20%, at least about 25%, at least about 30%, at least about 35%, at least about 40%, at least about 45%, at least about 50% total amount of one or more antioxidants by total weight of the composition.

In certain embodiments, pharmaceutical compositions disclosed herein may comprise a buffer system. As used herein, a "buffer system" is a composition comprised of one or more buffering agents wherein "buffering agents" are compounds used to resist change in pH upon dilution or addition of acid or alkali. Buffering agents include, by way of example and without limitation, potassium metaphosphate, potassium phosphate, monobasic sodium acetate and sodium citrate anhydrous and dihydrate and other materials known to one of ordinary skill in the art. In some aspects, any pharmaceutically acceptable organic or inorganic buffer can be used. In another aspect, compositions disclosed herein may comprise at least about 5%, at least about 10%, at least about 20%, at least about 25%, at least about 30%, at least about 35%, at least about 40%, at least about 45%, at least about 50% total amount of one or more buffering agents by total weight of the composition. In other aspects, the amount of one or more buffering agents may depend on the desired pH level of a composition. In some embodiments, pharmaceutical compositions disclosed herein may have a pH of about 6 to about 9. In other embodiments, pharmaceutical compositions disclosed herein may have a pH greater than about 8, greater than about 7.5, greater than about 7, greater than about 6.5, or greater than about 6. In a preferred embodiment, compositions disclosed herein may have a pH greater than about 6.8.

In certain embodiments, pharmaceutical compositions disclosed herein may comprise one or more preservatives. As used herein, "preservatives" refers to agents or combination of agents that inhibits, reduces or eliminates bacterial growth in a pharmaceutical dosage form. Non-limiting examples of preservatives include Nipagin, Nipasol, isopropyl alcohol and a combination thereof. In some aspects, any pharmaceutically acceptable preservative can be used. In other aspects, pharmaceutical compositions disclosed herein may comprise at least about 5%, at least about 10%, at least about 20%, at least about 25%, at least about 30%, at least about 35%, at least about 40%, at least about 45%, at least about 50% total amount of one or more preservatives by total weight of the composition.

In certain embodiments, pharmaceutical compositions disclosed herein may comprise one or more surface-acting reagents or detergents. In some aspects, surface-acting reagents or detergents may be synthetic, natural, or semi-synthetic. In other aspects, compositions disclosed herein may comprise anionic detergents, cationic detergents, zwitterionic detergents, ampholytic detergents, amphoteric detergents, nonionic detergents having a steroid skeleton, or a combination thereof. In still other aspects, pharmaceutical compositions disclosed herein may comprise at least about 5%, at least about 10%, at least about 20%, at least about 25%, at least about 30%, at least about 35%, at least about 40%, at least about 45%, at least about 50% total amount of one or more surface-acting reagents or detergents by total weight of the composition.

In certain embodiments, pharmaceutical compositions disclosed herein may comprise one or more stabilizers. As used herein, a "stabilizer" refers to a compound used to stabilize an active agent against physical, chemical, or biochemical process that would otherwise reduce the therapeutic activity of the agent. Suitable stabilizers include, by way of example and without limitation, succinic anhydride, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art. In some aspects, pharmaceutical compositions disclosed herein may comprise at least about 5%, at least about 10%, at least about 20%, at least about 25%, at least about 30%, at least about 35%, at least about 40%, at least about 45%, at least about 50% total amount of one or more stabilizers by total weight of the composition.

In certain embodiments, pharmaceutical compositions disclosed herein may comprise one or more tonicity agents. As used herein, a "tonicity agents" refers to a compound that can be used to adjust the tonicity of the liquid formulation. Suitable tonicity agents include, but are not limited to, glycerin, lactose, mannitol, dextrose, sodium chloride, sodium sulfate, sorbitol, trehalose and others known to those or ordinary skill in the art. Osmolarity in a composition may be expressed in milliosmoles per liter (mOsm/L). Osmolarity may be measured using methods commonly known in the art. In preferred embodiments, a vapor pressure depression method is used to calculate the osmolarity of the compositions disclosed herein. In some aspects, the amount of one or more tonicity agents comprising a pharmaceutical composition disclosed herein may result in a composition osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L. In other aspects, a composition herein may have an osmolality ranging from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a pharmaceutical composition described herein has an osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L. In still other aspects, pharmaceutical compositions disclosed herein may comprise at least about 5%, at least about 10%, at least about 20%, at least about 25%, at least about 30%, at least about 35%, at least about 40%, at least about 45%, at least about 50% total amount of one or more tonicity modifiers by total weight of the composition.

(e) Dosage Formulations

Suitable routes of administration may, for example, include oral, rectal, transmucosal, especially transnasal, intestinal or parenteral delivery, including intramuscular, subcutaneous and intramedullary injections as well as, intravenous, intraperitoneal, intranasal injections.

One may administer the pharmaceutical compositions disclosed herein in a local or systemic manner, for example, via local injection of the pharmaceutical composition directly into a tissue region of a patient. In some embodiments, a pharmaceutical composition disclosed herein can be administered parenterally, e.g., by intravenous injection, intracerebroventricular injection, intra-cisterna magna injection, intra-parenchymal injection, or a combination thereof. In some embodiments, a pharmaceutical composition disclosed herein can administered to the human patient via at least two administration routes. In some examples, the combination of administration routes by be intracerebroventricular injection and intravenous injection; intrathecal injection and intravenous injection; intra-cisterna magna injection and intravenous injection; and intra-parenchymal injection and intravenous injection.

Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present disclosure thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions. Alternatively, the active ingredient may be in powder form for constitution with a suitable vehicle, e.g., sterile, pyrogen-free water-based solution, before use.

Pharmaceutical compositions suitable for use in context of the present disclosure include compositions wherein the active ingredients are contained in an amount effective to achieve the intended purpose. In some embodiments, a therapeutically effective amount means an amount of active ingredients (i.e., TRIP7 mRNAs disclosed herein) effective to prevent, slow, alleviate or ameliorate symptoms of a viral infection (e.g., fever, chills, sore throat, nasal congestion, cough) or prolong the survival of the subject being treated. Determination of a therapeutically effective amount is well within the capability of those skilled in the art, especially in light of the detailed disclosure provided herein.

For any preparation used in the methods of the present disclosure, the therapeutically effective amount or dose can be estimated initially from in vitro and cell culture assays and or screening platforms disclosed herein. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1). The amount of a composition to be administered will, of course, be dependent on the subject being treated, the severity of the affliction, the manner of administration, the judgment of the prescribing physician, etc. Effective doses may be extrapolated from dose-responsive curves derived from in vitro or in vivo test systems.

III. Methods of Use

In certain embodiments, methods of treating or ameliorating a disease and/or a disorder in a subject are disclosed. In some embodiments, methods of treating or ameliorating a disease and/or a disorder in a subject include, but are not limited to, administration of an effective amount of any the LNPs encapsulating mRNAs (e.g., TRIM7 mRNAs) and/or pharmaceutical compositions containing these LNPs thereof as described herein. "An effective amount" as used herein refers to a dose of LNPs encapsulating mRNAs that is sufficient to confer a therapeutic effect on a subject having or suspected of having a disease and/or a disorder herein. In certain embodiments, a therapeutic effect for a subject having or suspected of having a disease and/or a disorder herein can include reducing the symptoms or consequences of the disease.

In some embodiments, methods of administering LNPs encapsulating mRNAs as disclosed herein can include placement (e.g., transplantation or implantation) of any the LNPs encapsulating mRNAs and/or pharmaceutical compositions containing these LNPs into a subject, by a method or route that results in at least partial localization of the introduced LNP at a desired site, such as a tumor, such that a desired effect(s) is produced. In some embodiments, a subject can be transfused with LNPs encapsulating mRNAs disclosed herein over the course of a day, for a few hours, daily, every other day, 2 times per week, weekly, every other week, monthly, or other appropriate treatment regimen. In accordance with the embodiments herein, the period of TRIM7 protein generated after administration of LNPs encapsulating mRNAs disclosed herein to a subject can be a few hours (e.g., about 2 hours, about 6 hours, about 12 hours, about 24 hours), a few days (e.g., about 1 day, about 2 days, about 3 days, about 4 days about 5 days, about 6 days, about 7 days), weeks (e.g., about 2 weeks, about 4 weeks, about 6 weeks, about 12 weeks, about 40 weeks, about 52 weeks), to as long as several years (e.g., about 2 years, about 5 years), or even the life time of the subject. In some embodiments, an effective amount of the LNPs encapsulating mRNAs herein can be administered via a systemic route of administration, such as an intraperitoneal or intravenous route.

In some embodiments, a subject to any of the methods herein can be any subject for whom treatment or therapy is desired. In some embodiments, a subject to any of the methods herein can be any subject having or is suspected of having a disease or a disorder in need of treatment with a TRIM7 protein generated after administration of LNPs encapsulating mRNAs disclosed herein. In some embodiments, a subject to any of the methods herein can be any subject having or is suspected of having a viral infection. In some embodiments, a subject can be a mammal. In some embodiments, a subject can be a human patient. In some embodiments, a human patient such as an adult, child, adolescent, toddler, young adult or infant or fetus who is in need of the methods herein can be identified by routine medical examination, e.g., laboratory tests, biopsy, magnetic resonance imaging (MRI) scans, ultrasound exams, and the like.

In some embodiments, a subject to any of the methods herein can be any subject having or is suspected of having an infection. In some embodiments, a subject to any of the methods herein can be any subject having or is suspected of having an infection resulting from an infectious organism comprising a virus, a bacteria, or a combination thereof. In some embodiments, a subject to any of the methods herein can be any subject having or is suspected of having an infection resulting from a virus.

In certain embodiments, a viral infection to be treated by the methods disclosed herein may result from an infection of a subject by one or more single-stranded RNA viruses. Viruses with a single-stranded RNA (ssRNA) genome include viruses with a segmented negative-sense ssRNA genome (e.g., families Bunyaviridae and Orthomyxoviridae) and viruses with a positive-sense ssRNA genome (e.g., families Togaviridae and Flaviviridae). In some aspects, a viral infection to be treated by the methods disclosed herein may result from an infection of a subject by one or more single-stranded RNA viruses including, but not limited to, bymoviruses, comoviruses, nepoviruses, nodaviruses, picornaviruses, potyviruses, sobemoviruses, luteoviruses, carmoviruses, dianthoviruses, flaviviruses, pestiviruses, statoviruses, tombusviruses, single-stranded RNA bacteriophages, hepatitis C virus, hepatitis E virus, alphaviruses, carlaviruses, furoviruses, hordeiviruses, potexviruses, rubiviruses, tobraviruses, tricornaviruses, tymoviruses, enteroviruses, or any combination thereof. In some aspects, a viral infection to be treated by the methods disclosed herein may result from an infection of a subject by one ore more enteroviruses. Enterovirus is a genus of small RNA viruses that contains more than 100 viruses, including poliovirus, rhinovirus, enterovirus A71, coxsackievirus, echovirus, and enterovirus D68. Enteroviruses cause a broad spectrum of diseases, including non-specific acute febrile illness, skin rash, acute respiratory distress, and severe neurological complications in humans.

In certain embodiments, LNPs encapsulating mRNAs and/or pharmaceutical compositions disclosed herein can be administered in dosages and by techniques well known to those skilled in the medical and veterinary arts. In accordance with these embodiments, healthcare professions will take into consideration such factors as the age, sex, weight, and condition of the particular patient, and the composition form used for administration (e.g., solid vs. liquid). Dosages for humans or other mammals can be determined without undue experimentation by the skilled artisan, from this disclosure, and the knowledge in the art.

In certain embodiments, methods of administering LNPs encapsulating mRNAs and/or pharmaceutical compositions disclosed herein may decrease viral titer in a subject compared to an untreated subject with identical viral infection and predicted outcome. In some aspects, methods disclosed herein may decrease viral titer by at least about 5% to about 99%, about 10% to about 95%, or about 15% to about 90% in subject who was administered LNPs encapsulating mRNAs and/or pharmaceutical compositions disclosed herein compared to an untreated subject with identical viral infection and predicted outcome. In some aspects, methods disclosed herein may decrease viral titer by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or more in subject who was administered LNPs encapsulating mRNAs and/or pharmaceutical compositions disclosed herein compared to an untreated subject with identical viral infection and predicted outcome.

In certain embodiments, methods of administering LNPs encapsulating mRNAs and/or pharmaceutical compositions disclosed herein may reduce in intensity, severity, frequency, onset, or any combination thereof at least one symptom of a viral infection. Non-limiting examples of symptoms of a viral infection can include fever, chills, sore throat, nasal congestion, cough, and the like. In certain embodiments, methods of administering LNPs encapsulating mRNAs and/or pharmaceutical compositions disclosed herein may prevent, attenuate, and/or treat one or more infectious illnesses that can result from an enteroviral infection. Non-limiting examples of such infectious illnesses can include echovirus, coxsackievirus, polio, hand, foot and mouth disease (HFMD), and the like. In certain embodiments, methods of administering LNPs encapsulating mRNAs and/or pharmaceutical compositions disclosed herein may prevent, attenuate, and/or treat one or more severe diseases that can develop from an enteroviral infection. Non-limiting examples of such severe diseases can include brain and heart conditions, pneumonia, hepatitis, diabetes, and the like.

In some embodiments, methods of administering LNPs encapsulating mRNAs and/or pharmaceutical compositions disclosed herein may prevent, attenuate, and/or treat type 1 diabetes. Enteroviruses have been found in the blood and pancreas of type 1 diabetic patients in several studies, and they have also been associated with increased risk of type 1 diabetes. In some aspects, methods of administering LNPs encapsulating mRNAs and/or pharmaceutical compositions disclosed herein may prevent and/or decrease pancreatic destruction in a subject compared to an untreated subject with identical viral infection and predicted outcome. In some other aspects, methods of administering LNPs encapsulating mRNAs and/or pharmaceutical compositions disclosed herein may prevent and/or decrease acini injury in a subject compared to an untreated subject with identical viral infection and predicted outcome. In still some other aspects, methods of administering LNPs encapsulating mRNAs and/or pharmaceutical compositions disclosed herein may prevent and/or decrease pancreatic islet beta cell destruction in a subject compared to an untreated subject with identical viral infection and predicted outcome. In some aspects, methods of administering LNPs encapsulating mRNAs and/or pharmaceutical compositions disclosed herein may prevent and/or decrease visceral fat necrosis in a subject compared to an untreated subject with identical viral infection and predicted outcome.

IV. Kits

In some embodiments, kits are contemplated of use to generate the LNPs encapsulating mRNAs disclosed herein. In some embodiments, kits can include LNPs encapsulating mRNAs where the LNPs can be used immediately or frozen and stored for transport and later use. In some embodiments, a kit herein can include any of vectors encoding mRNAs herein, LNPs encapsulating mRNAs and/or pharmaceutical compositions disclosed herein.

In some embodiments, kits are provided for use in treating or alleviating a targeted disease or condition treatable by use of LNPs encapsulating mRNAs disclosed herein. In some embodiments, kits can include instructions for use in accordance with any of the methods described herein. The included instructions can include a description of administration of any the LNPs encapsulating mRNAs and/or pharmaceutical compositions described herein and optionally one or more additional therapies to treat, delay the onset, or alleviate a target disease (e.g., viral infection) as those described herein. In some embodiments, kits herein can further include a description of selecting an individual suitable for treatment based on identifying whether that individual has the target disease, e.g., applying one or more diagnostic methods. In some embodiments, the instructions can include a description of administering LNPs encapsulating mRNAs to a subject at risk of the target disease.

In some embodiments, kits include instructions for using the components of the kit, for example relating to the use of LNPs encapsulating mRNAs. Instructions for using the components of the kit can generally include information as to dosage, dosing schedule, and/or route of administration for the intended treatment. In some embodiments, containers can be unit doses, bulk packages (e.g., multi-dose packages) or sub-unit doses. In some embodiments, instructions supplied in the kits of the invention can be written instructions on a label or package insert (e.g., a paper sheet included in the kit), but machine-readable instructions (e.g., instructions carried on a magnetic or optical storage disk) are also acceptable.

In certain embodiments, a label or package insert herein can indicate that the composition is used for treating, delaying the onset and/or alleviating the disease (e.g., viral infection). Instructions can be provided for practicing any of the methods described herein.

In certain embodiments, kits disclosed herein include suitable packaging. Suitable packaging includes, but is not limited to, vials, bottles, jars, flexible packaging (e.g., sealed Mylar or plastic bags), and the like. Also contemplated herein are packages for use in combination with a specific device, such as an inhaler, nasal administration device (e.g., an atomizer) or an infusion device such as a minipump. A kit can have a sterile access port (for example the container can be an intravenous solution bag or a vial having a stopper pierceable by a hypodermic injection needle). The container can also have a sterile access port (for example the container can be an intravenous solution bag or a vial having a stopper pierceable by a hypodermic injection needle). At least one active agent in the composition can be an antibody generated by LNPs encapsulating mRNAs disclosed herein.

EXAMPLES

The following examples are included to demonstrate preferred embodiments of the disclosure. It should be appreciated by those of skill in the art that the techniques disclosed in the examples that follow represent techniques discovered by the inventor to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Introduction to Examples 1-8

The mammalian innate immune system controls viral infection in part through the actions of protein-based antiviral effectors. While many of these effectors are only expressed after viral infection triggers an interferon response, cell-intrinsic restriction factors are constitutively present and variably regulated by interferon. These cell-intrinsic effectors provide a frontline defense against viruses prior to transcription of interferon and interferon-stimulated genes. Several E3 ligases have been identified as cell-intrinsic antiviral effectors. In many, but not all, cases, E3 ligases target viral proteins for degradation by the ubiquitin-proteasome system. Because TRIM proteins target RNA viruses, Examples 1-8 herein examine whether enteroviruses in the Picornaviridae family may also be susceptible to antiviral E3 ligases. The Picornaviridae family includes important human pathogens and model laboratory viruses, such as coxsackieviruses, poliovirus (PV), enterovirus A71 (EV71), and echoviruses. Outbreaks of enteroviral infections are associated with morbidity and mortality in susceptible individuals worldwide. There are still no antiviral drugs or vaccines against most enteroviruses. Accordingly, Examples 1-8 demonstrate, in part, a novel method of treating enteroviruses by discovering a novel antiviral E3 ligase target, TRIM7. To date, this was the first E3 ligase targeting an enterovirus protein, and the first demonstration that a viral membrane remodeling protein was subject to degradation as a host antiviral strategy. The TRIM7-resistant coxsackievirus highlights a unique mechanism of viral innovation and may also serve as a novel tool in experimental animal models of severe pancreatitis.

Example 1: TRIM7 Restricts Multiple Human Enteroviruses

To identify E3 ubiquitin ligases that modulate viral infection, 118 human RING type E3 ligases were cloned into a bicistronic lentiviral vector co-expressing a red fluorescent protein (TagRFP) (Table 2).

TABLE 2

| Gene | Percent Infected | | Z score | |
|---|---|---|---|---|
| | R1 | R2 | R1 | R2 |
| RNF38 | 88.2 | 87.8 | −0.01 | −0.02 |
| RNF141 | 87.2 | 87.8 | −0.02 | −0.02 |
| RLIM | 82 | 83.9 | −0.08 | −0.07 |
| RNF41 | 93.5 | 93.3 | 0.06 | 0.05 |
| RNF170 | 97.3 | 97.6 | 0.11 | 0.1 |
| RNF144B | 93.9 | 95 | 0.07 | 0.07 |
| RNF122 | 90.3 | 89.4 | 0.02 | 0 |
| RNF40 | 97.1 | 86.6 | 0.11 | −0.04 |
| RNF212 | 91.1 | 94 | 0.03 | 0.06 |
| RNF25 | 90.6 | 88.5 | 0.03 | −0.01 |
| RNF111 | 84.2 | 83.7 | −0.06 | −0.07 |
| RNF139 | 77.5 | 80.6 | −0.14 | −0.11 |
| RNF146 | 89.7 | 90 | 0.01 | 0.01 |
| RNFT2 | 86.5 | 87.5 | −0.03 | −0.03 |
| RNF2 | 87.4 | 88.2 | −0.02 | −0.02 |
| RNF11 | 90.7 | 89.1 | 0.03 | −0.01 |
| RNF167 | 89.8 | 90.3 | 0.02 | 0.01 |
| RNF113B | 88 | 89 | −0.01 | −0.01 |

TABLE 2-continued

| Gene | Percent Infected | | Z score | |
|---|---|---|---|---|
| | R1 | R2 | R1 | R2 |
| RNF25 | 89.2 | 96.3 | 0.01 | 0.09 |
| RNF148 | 82.3 | 94.7 | −0.08 | 0.07 |
| RNF133 | 94.9 | 86.4 | 0.08 | −0.04 |
| RNF10 | 88.9 | 88.4 | 0 | −0.01 |
| RFFL | 88.2 | 87.7 | −0.01 | −0.02 |
| RNF13 | 97.9 | 93.5 | 0.12 | 0.05 |
| RSPRY1 | 91.4 | 90.1 | 0.04 | 0.01 |
| RFPL3 | 78.3 | 80 | −0.13 | −0.12 |
| MARCH3 | 91.4 | 92.4 | 0.04 | 0.04 |
| RCHY1 | 97.6 | 94.4 | 0.11 | 0.06 |
| RNF103 | 96.9 | 97 | 0.11 | 0.1 |
| RNF112 | 86.6 | 86 | −0.03 | −0.04 |
| RNF145 | 94.2 | 94.2 | 0.07 | 0.06 |
| RNF135 | 86.2 | 87.1 | −0.03 | −0.03 |
| RNF126 | 94.5 | 94.1 | 0.08 | 0.06 |
| RNF182 | 97.9 | 92.9 | 0.12 | 0.04 |
| RNF166 | 94.5 | 94.6 | 0.08 | 0.07 |
| RNF180 | 93.2 | 92.3 | 0.06 | 0.04 |
| RNF151 | 92.8 | 92.2 | 0.05 | 0.03 |
| RNF152 | 97.4 | 97.2 | 0.11 | 0.1 |
| MARCH1 | 97.7 | 97.7 | 0.12 | 0.1 |
| TRIM72 | 88.1 | 88.1 | −0.01 | −0.02 |
| RI NG1 | 92.9 | 93.1 | 0.05 | 0.05 |
| RNF121 | 84.1 | 84.9 | −0.06 | −0.06 |
| RNF14 | 95.5 | 96.3 | 0.09 | 0.09 |
| RNF8 | 82.8 | 85.3 | −0.07 | −0.05 |
| RCHY1 | 91.2 | 92 | 0.03 | 0.03 |
| MARCH2 | 92.4 | 92 | 0.05 | 0.03 |
| RNF144A | 97.7 | 97 | 0.12 | 0.1 |
| RNF150 | 91.1 | 90.1 | 0.03 | 0.01 |
| RFPL2 | 93.8 | 93.6 | 0.07 | 0.05 |
| RNFT1 | 95.2 | 94.4 | 0.08 | 0.06 |
| RNF220 | 96.6 | 96.4 | 0.1 | 0.09 |
| TRIM75 | 89.7 | 90.8 | 0.01 | 0.02 |
| MUL1 | 80.1 | 80.7 | −0.11 | −0.11 |
| RNF5 | 96.1 | 95.8 | 0.1 | 0.08 |
| ZNRF1 | 95.8 | 96.3 | 0.09 | 0.09 |
| MARCH5 | 91.5 | 92.1 | 0.04 | 0.03 |
| RNF130 | 91.4 | 91.4 | 0.04 | 0.02 |
| RNF4 | 93.3 | 93.1 | 0.06 | 0.05 |
| PCGF6 | 94.6 | 94.7 | 0.08 | 0.07 |
| CHFR | 87.2 | 86.6 | −0.02 | −0.04 |
| RNF20 | 91.8 | 91.9 | 0.041 | 0.0307 |
| RAD18 | 91.2 | 91.5 | 0.033 | 0.0256 |
| MKRN2 | 93.3 | 93.6 | 0.06 | 0.0524 |
| BIRC4 | 96.9 | 97.2 | 0.106 | 0.0985 |
| RNF214 | 93.9 | 94.5 | 0.067 | 0.0639 |
| RNF113 | 92 | 91.6 | 0.043 | 0.0269 |
| TRIM1 | 82.1 | 79.8 | −0.083 | −0.124 |
| TRIM2 | 62.1 | 64.4 | −0.337 | −0.321 |
| TRIM4 | 67.8 | 65.4 | −0.265 | −0.308 |
| TRIM5 | 56.2 | 51.9 | −0.412 | −0.481 |
| TRIM6 | 67.4 | 69.8 | −0.27 | −0.252 |
| TRIM7 | 3.2 | 4.05 | −1.086 | −1.093 |
| TRIM8 | 70.1 | 71.6 | −0.235 | −0.229 |
| TRIM9 | 81.3 | 73.5 | −0.093 | −0.205 |
| TRIM10 | 58.7 | 69.3 | −0.38 | −0.258 |
| TRIM11 | 58.2 | 64.8 | −0.387 | −0.316 |
| TRIM13 | 53 | 61.6 | −0.453 | −0.357 |
| TRIM14 | 70.6 | 73.1 | −0.229 | −0.21 |
| TRIM15 | 66.8 | 60.9 | −0.277 | −0.366 |
| TRIM17 | 75.9 | 75.9 | −0.162 | −0.174 |
| TRIM18 | 71.6 | 63.2 | −0.216 | −0.336 |
| TRIM19 | 60.8 | 63.7 | −0.354 | −0.33 |
| TRIM20 | 78.8 | 73.3 | −0.125 | −0.207 |
| TRIM21 | 65.7 | 69.3 | −0.291 | −0.258 |
| TRIM22 | 49.4 | 48 | −0.499 | −0.531 |
| TRIM23 | 61.5 | 57.3 | −0.345 | −0.412 |
| TRIM24 | 69.5 | 67.5 | −0.243 | −0.281 |
| TRIM25 | 53.7 | 60.6 | −0.444 | −0.37 |
| TRIM26 | 49.3 | 48.5 | −0.5 | −0.524 |
| TRIM27 | 60.7 | 56.2 | −0.355 | −0.426 |
| TRIM29 | 68 | 60.7 | −0.262 | −0.368 |
| TRIM32 | 58.4 | 53.5 | −0.384 | −0.46 |
| TRIM33 | 55.3 | 54 | −0.424 | −0.454 |

TABLE 2-continued

| Gene | Percent Infected | | Z score | |
|---|---|---|---|---|
| | R1 | R2 | R1 | R2 |
| TRIM34 | 62.2 | 61 | −0.336 | −0.364 |
| TRIM35 | 66.3 | 64.7 | −0.284 | −0.317 |
| TRIM37 | 58.8 | 57.6 | −0.379 | −0.408 |
| TRIM38 | 60.7 | 59.3 | −0.355 | −0.386 |
| TRIM39 | 58.6 | 64.8 | −0.382 | −0.316 |
| TRIM40 | 62.8 | 60.5 | −0.328 | −0.371 |
| TRIM43 | 61.4 | 57.5 | −0.346 | −0.409 |
| TRIM44 | 61.7 | 54 | −0.342 | −0.454 |
| TRIM45 | 63.9 | 65.1 | −0.314 | −0.312 |
| TRIM46 | 60.8 | 62.3 | −0.354 | −0.348 |
| TRIM49 | 65.7 | 65.3 | −0.291 | −0.31 |
| TRIM50 | 57.8 | 46.9 | −0.392 | −0.545 |
| TRIM52 | 67.6 | 63.9 | −0.267 | −0.327 |
| TRIM59 | 59.5 | 60.2 | −0.37 | −0.375 |
| TRIM60 | 54.3 | 60.2 | −0.436 | −0.375 |
| TRIM61 | 65.8 | 58.9 | −0.29 | −0.391 |
| TRIM62 | 51.3 | 54.7 | −0.474 | −0.445 |
| TRIM65 | 56.8 | 57.6 | −0.404 | −0.408 |
| TRIM67 | 58.9 | 59.1 | −0.378 | −0.389 |
| TRIM68 | 62 | 59 | −0.338 | −0.39 |
| TRIM72 | 60.2 | 58.9 | −0.361 | −0.391 |
| TRIM74 | 71.6 | 69.7 | −0.216 | −0.253 |
| TRIM75 | 66.8 | 62.1 | −0.277 | −0.35 |
| TRIML1 | 77.6 | 75.9 | −0.14 | −0.174 |
| TRIML2 | 68.3 | 63.7 | −0.258 | −0.33 |
| Fluc1 | 90.8 | 92 | 0.028 | 0.032 |
| Fluc2 | 88.6 | 89.5 | 0 | 0 |

Figure 1B:
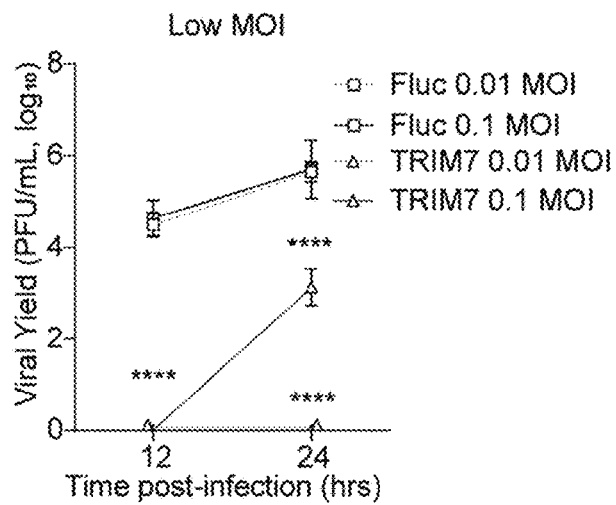
Figure 1C:
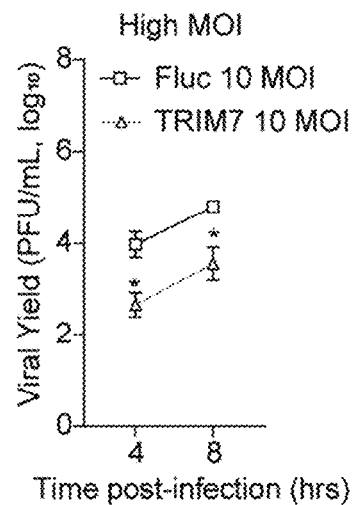
Figure 8A:
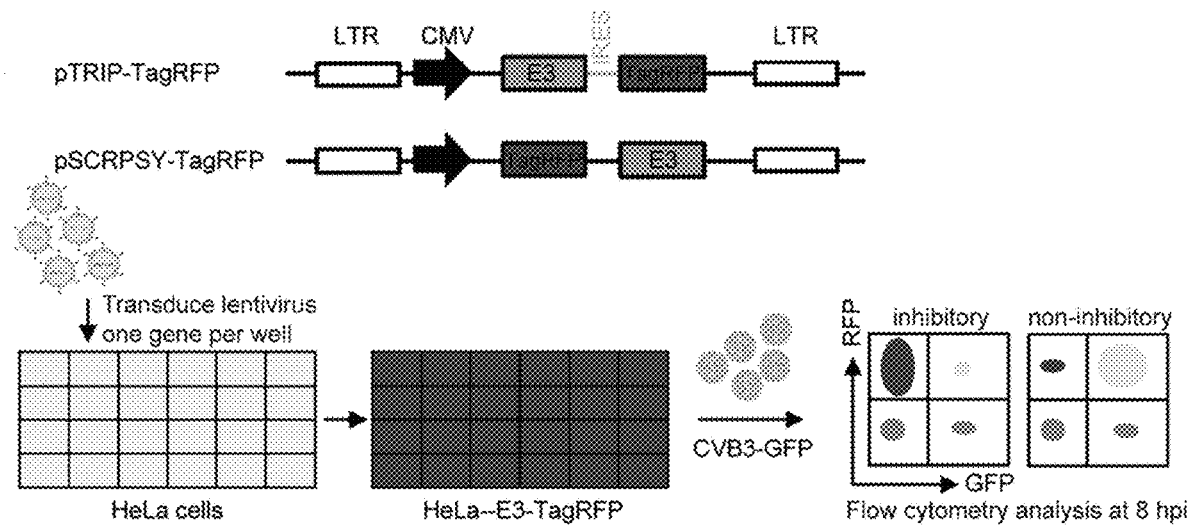
Figure 8B:
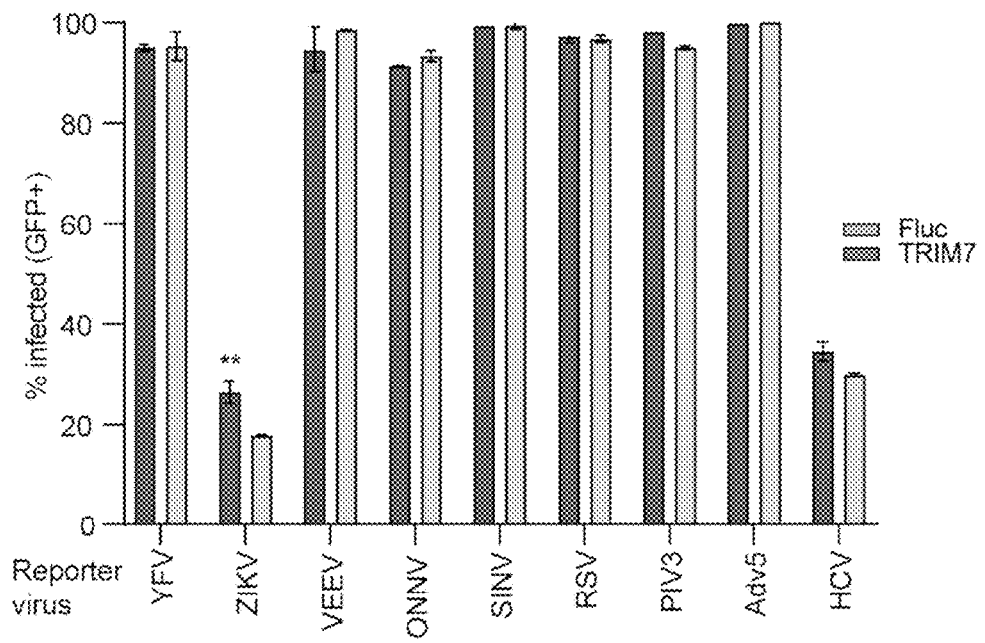

HeLa cells were transduced with lentiviral vectors in a one gene per well format (FIG. 8A). Transduced cells were infected with recombinant GFP-expressing coxsackievirus B3 (CVB3-GFP), and infectivity was quantified by the percentage of GFP-positive cells in the RFP-positive population. Strikingly, the expression of TRIM7 showed a specific and potent inhibition of CVB3 infection, with no inhibition of flaviviruses, alphaviruses, paramyxoviruses, hepatitis C virus, or a non-replicating adenovirus type 5 vector (FIGS. 1A and 8B). The antiviral effect of TRIM7 occurred independently of cell type, as TRIM7 expression in HeLa, Huh7.5, 293T, U251, HCT116, RD, and U2OS cells significantly restricted CVB3 infection (FIG. 8C). TRIM7 also inhibited non-reporter CVB3 in HeLa cells at multiple time points and multiplicities of infection, with as much as a 10,000-fold reduction in viral yield at 12 hours post-infection (FIGS. 1B-1C).

To determine whether TRIM7 inhibits other enteroviruses, HeLa cells expressing a 3x-FLAG tagged TRIM7 (HeLa-TRIM7) were infected with three different human enterovirus types, including EV71 (type A), CVB3 and E11 (type B), PV (type C), and the non-human enterovirus Mengovirus (MenV). Viral double-stranded RNA (dsRNA), which is produced during replication, was quantified by flow cytometry. TRIM7 expression significantly reduced viral dsRNA production in cells infected with EV71, CVB3, E11, and PV, but not with MenV (FIG. 1D). Accordingly, viral titers of EV71, CVB3, E11, EVD68, and PV in the supernatants of infected HeLa-TRIM7 cells were 10- to 250-fold lower than titers from control HeLa cells expressing firefly luciferase (HeLa-Fluc) (FIGS. 1E-1H). In contrast, there was no difference in the titers of MenV in HeLa-TRIM7 compared to HeLa-Fluc (FIG. 1I).

To assess whether endogenous TRIM7, as opposed to ectopically expressed protein, inhibits enterovirus, TRIM7 mRNA expression in HepG2 cells was silenced using short hairpin RNA (shRNA) and confirmed knockdown efficiency by Western blotting (FIG. 8D). Depletion of TRIM7 significantly increased production of CVB3 at 8 hours post-infection (FIG. 1J). Similar results were observed in HepG2 cells at 12 and 24 hours post-infection with CVB3 (FIG. 8E) and 8 hours post-infection with E11 (FIG. 8F). Collectively, the data demonstrates that TRIM7 was an intrinsic antiviral factor that inhibits human enteroviruses.

Example 2: TRIM7 Restricts CVB3 RNA Replication

Next assessed was which step in the viral replication cycle was targeted by TRIM7, starting with viral binding and entry. Using confocal microscopy to visualize viral particles and plaque assay to quantitate bound and internalized virions, no effect of TRIM7 on binding or entry was observed (FIGS. 2A-2D). Next, CVB3-GFP infectious viral RNA was transfected into HeLa-TRIM7 and HeLa-Fluc cells to measure replication when entry was bypassed. Compared to control HeLa-Fluc cells, which had robust GFP signal after CVB3-GFP RNA transfection, GFP was not detected in HeLa-TRIM7 cells at any time point (FIG. 2E). Accordingly, the yield of infectious virus, measured by using supernatants from RNA-transfected cells to infect naïve HeLa cells, was barely detectable from TRIM7-expressing cells (FIG. 2F). Similar results were obtained after transfection of PV-GFP RNA (FIG. 2G), indicating that TRIM7 restricts enterovirus replication after viral binding and entry.

Figure 2H:
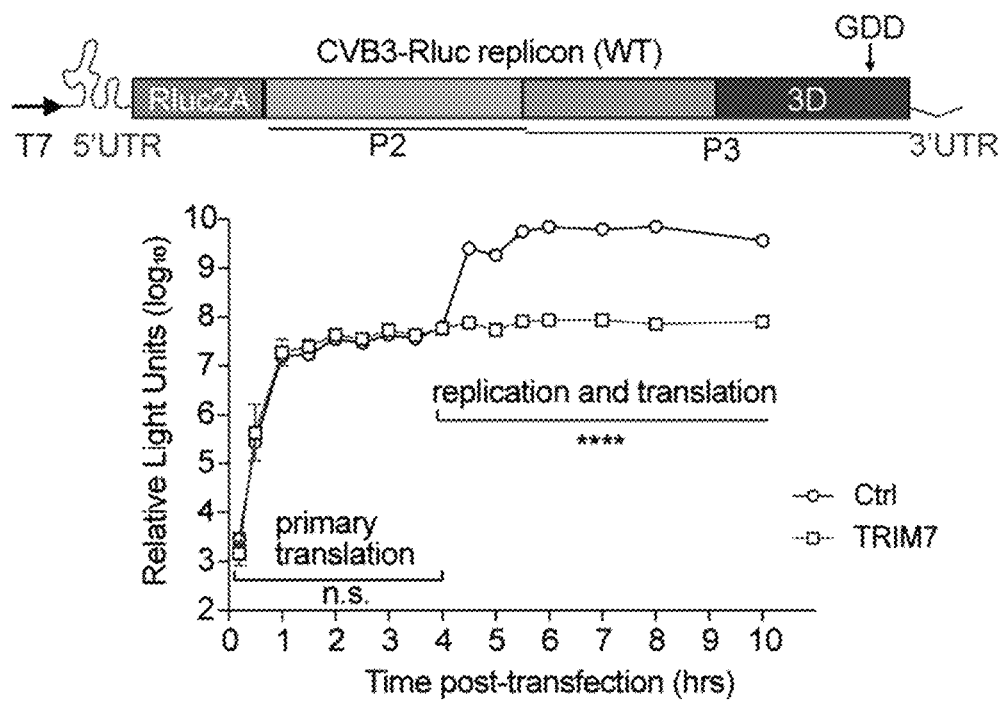
Figure 2I:
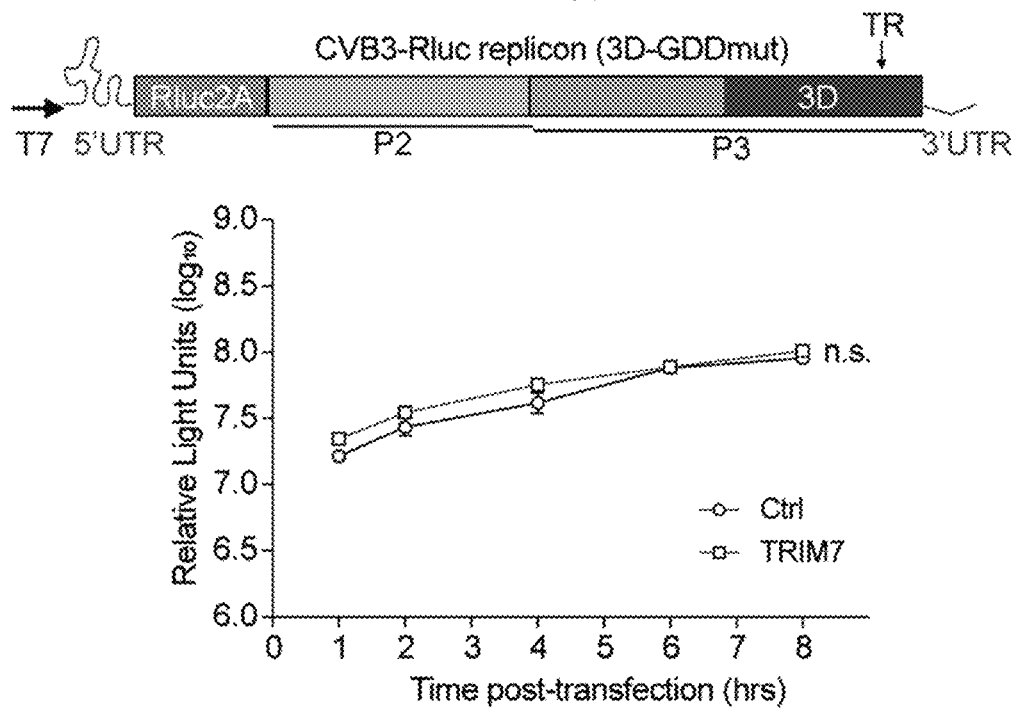
Figure 2J:
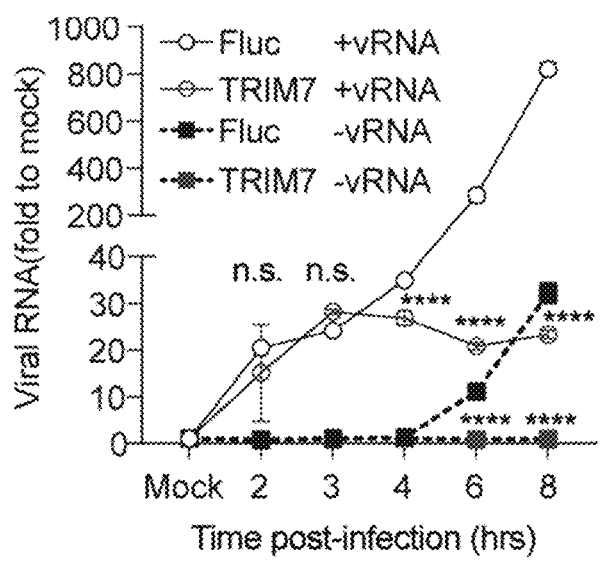
Figure 2K:
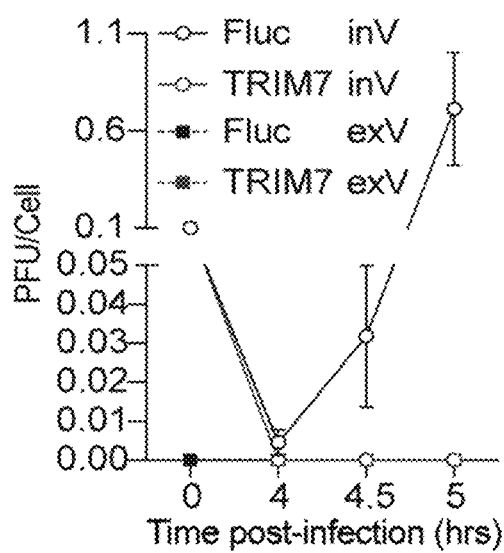

To determine whether TRIM7 targets viral RNA translation and/or replication, a subgenomic replicon expressing a Renilla luciferase (Rluc) reporter was engineered. This truncated viral RNA lacked genes that encoded structural proteins, but otherwise replicated and expressed viral proteins and Rluc reporter. Upon transfection of the wild type CVB3 replicon CVB3-Rluc (WT) into HeLa-TRIM7 or HeLa-Fluc cells, a similar luciferase signal was observed during the primary translation phase (up to 4 hours post-transfection) (FIG. 2H). Starting at 4.5 hours post-transfection, an increase in luciferase signal was observed in HeLa-Fluc, but not Hela-TRIM7. To directly monitor viral translation in the absence of replication, a replication-deficient replicon, CVB3-Rluc (3D-GDDmut) was constructed. Similar levels of Rluc signal from this replicon were observed in HeLa-TRIM7 and HeLa-Fluc cells at all time points (FIG. 2I), indicating that TRIM7 inhibited viral replication and not translation. Furthermore, strand-specific RT-PCR was used to distinguish the production of positive strand and negative strand viral RNA (+vRNA and −vRNA). In HeLa-TRIM7 cells, the production of +vRNA was significantly reduced, and −vRNA was barely detectable (FIG. 2J). In addition, the intracellular virus production of CVB3 was nearly completely restricted in HeLa-TRIM7 cells (FIG. 2K), when cells were infected with CVB3 at 0.1 MOI. Together, these results demonstrated that TRIM7 restricted CVB3 by suppressing viral RNA replication.

Example 3: The Ubiquitin-Proteasome Pathway is Required for TRIM7-Mediated Viral Restriction To determine if TRIM7 targets a viral protein or viral host dependency factor for degradation by the ubiquitin-proteasome system, TRIM7-expressing cells were treated with proteasome inhibitor MG132. A striking rescue of CVB3-GFP infection and production was observed (FIGS. 9A-9D). High doses of MG132 modestly impaired infection in control HeLa-Fluc cells. Proteasome inhibition by MG132 also rescued viral replication from transfected CVB3-GFP RNA in HeLa-TRIM7 cells (FIGS. 9E-9F). Time-of-addition studies revealed that MG132 treatment failed to rescue infection in TRIM7-expressing cells when added at later time points (post primary translation, >4 hours) (FIGS. 9A-9B and 9E-9F). This suggested that virus infection in TRIM7-expressing cells could be salvaged by inhibition of ubiquitin-mediated protein degradation before or very early during infection. Notably, DBeQ, an inhibitor of the VCP/p97-ATPase complex, failed to rescue viral replication in TRIM7-expressing cells (FIG. 9G), suggesting that TRIM7 does not inhibit viral replication by interfacing with cellular machinery involved in endoplasmic reticulum-associated degradation or autophagy. DBeQ modestly reduced CVB3 infectivity in HeLa-Fluc cells. Inhibitors of autophagosome-lysosome degradation, bafilomycin A1 and chloroquine, had no impact on CVB3 infectivity in control HeLa-Fluc cells, nor did they reverse the antiviral effects of TRIM7, although these drugs inhibited replication of vesicular stomatitis virus (FIGS. 9H-9I). Similar results with each of these drugs were observed during PV-GFP infection (FIG. 9J). These data indicated that TRIM7 functioned through a proteasome-dependent pathway to inhibit enterovirus replication.

Example 4: A Single T323A Mutation in CVB3 2C Confers Resistance to TRIM7

Figure 3A:
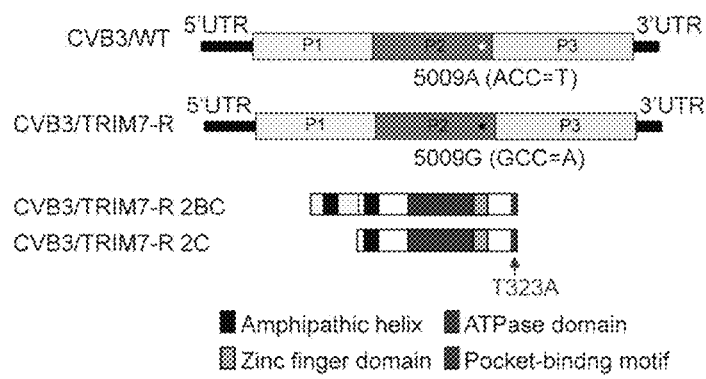
FIGS. 3A-3N are images and graphs illustrating the emergence of TRIM7-resistant virus and revelation of TRIM7 interactions with viral 2C and 2BC.
Figure 3B:
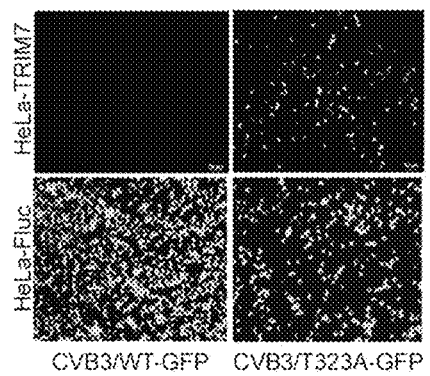
FIG. 3B shows HeLa-Fluc or HeLa-TRIM7 cells infected with CVB3.WT-GFP and CVB3.T323A-GFP at 1 MOI. Fluorescence microscopy images were collected at 8 hpi. Scale bar is 50 μm.
Figures 10A, 10B:
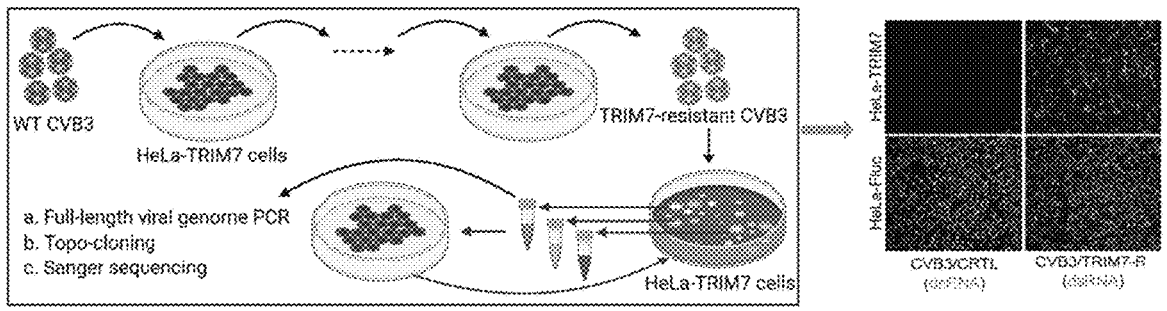

To gain insight into the mechanism of TRIM7-mediated antiviral effects, an evolutionary genetic approach was used to determine if TRIM7 imposed a selective pressure that facilitated emergence of resistant variants. CVB3 in HeLa-TRIM7 or HeLa-Fluc cells were serially passaged. The 4th passage of CVB3 from HeLa-TRIM7 cells induced cytopathic effects in HeLa-TRIM7 cells (FIG. 10A). This indicated that a TRIM7-resistant CVB3, was obtained, herein referred to as CVB3/TRIM7-R. A serially-passaged CVB3 from control HeLa-Fluc cells was named CVB3/CTRL. CVB3/TRIM7-R was verified as infectious by dsRNA immunofluorescence (FIG. 10A). CVB3/TRIM7-R was then isolated from single plaques and consensus sequencing was performed to identify potential mutations that were prevalent in the population. A unique single nucleotide A-to-G mutation was identified in all TRIM7-resistant CVB3 genomes at position 5009, resulting in a T323A missense variant in the viral 2C protein (FIG. 3A). The T323A mutation was cloned the into the CVB3-GFP molecular clone and the resulting virus, CVB3/T323A-GFP, was replicated in TRIM7-expressing cells, in contrast to the parental CVB3/WT-GFP (FIG. 3B).

Figure 10E:
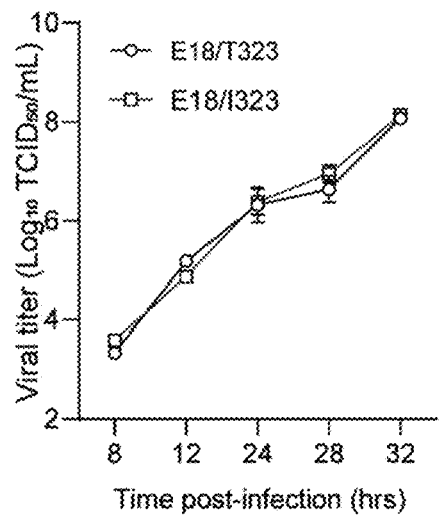
Figure 10F:
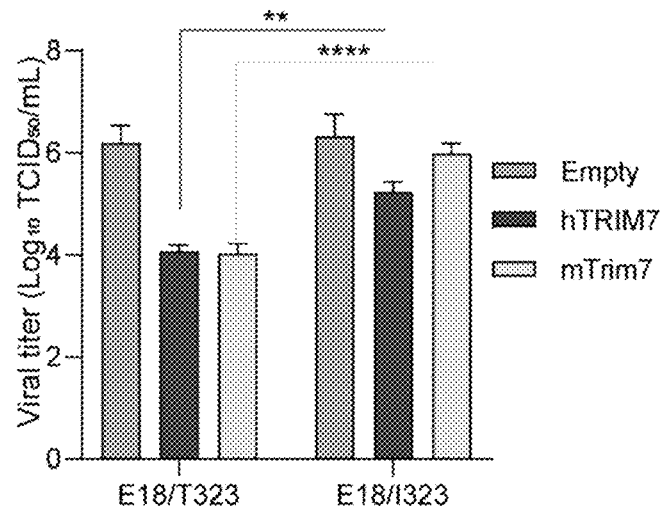
Figure 10G:
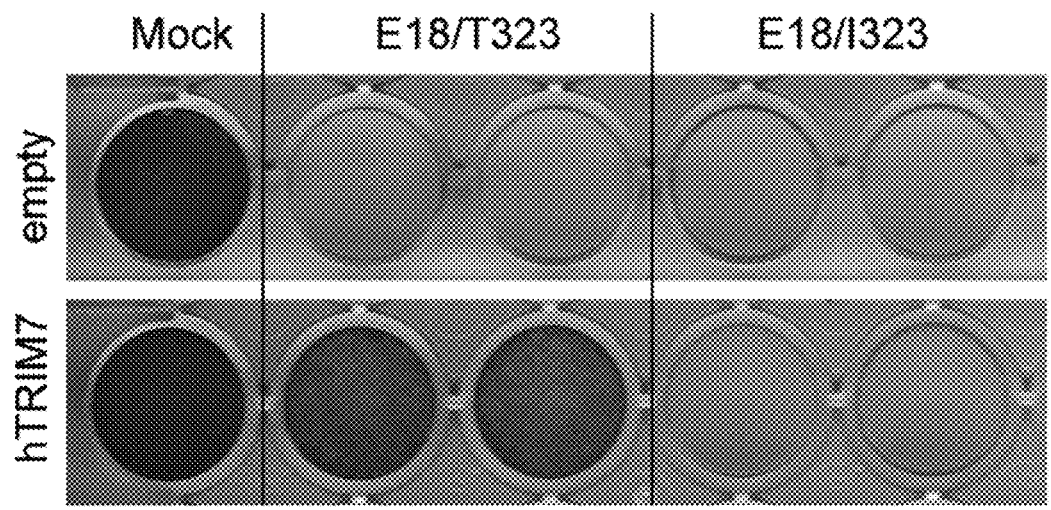

Enterovirus 2C is an ATPase/helicase that is critical for intracellular membrane rearrangement, the formation of virus-induced cytoplasmic vesicles, and for viral RNA replication. 2C is formed by proteolytic processing of the precursor 2BC, which itself is the product of a larger pre-processed 2ABC precursor generated from the viral polyprotein. The crystal structures of 2C from EV71 and PV show that T323 is part of C-terminal helix α6 (T323 or C323 to P329) of 2C, which forms the pocket-binding motif (PBM) that binds the hydrophobic pocket between the zinc finger and ATPase domains in 2C as shown in Guan et al., *Sci. Adv.* 2017; 3: e1602573, the disclosure of which is incorporated herein in its entirety. Importantly, the side chain of residue T323 of EV71 2C binds the hydrophobic pocket in 2C. Sequence alignment revealed that T323 was highly conserved in type B enteroviruses, with only 3 non-human primate enteroviruses, EV-B112, EV-B113, and EV-B114 (or SA5), differing by having valine instead of threonine at this position (FIG. 10B). Next, TRIM7 antiviral activity was assessed on SA5, and it was found that TRIM7 expression restricted SA5 replication, but only about 10-fold more than Fluc control, as compared to the 10,000-fold inhibition of CVB3 replication (FIGS. 1B and 10C). Consistent with the variable antiviral effects of TRIM7 on non-type B human enteroviruses (FIGS. 1A-1J), these data raised the possibility that TRIM7 exerts a range of antiviral activities depending on the enterovirus 2C sequence. Surprisingly, a single clinical isolate of human echovirus 18 (E18) from an outbreak in Germany has an isoleucine (Ile/I) at position 323 in 2C (FIG. 10D) was observed, whereas other E18 isolates have a conserved T323. To test whether this amino acid modulated E18 sensitivity to TRIM7, an infectious molecular clone of E18 bearing T323 or I323 was synthesized. Both viruses had similar growth kinetics and E18-I323 partially resisted inhibition by human TRIM7 and mouse Trim7 (FIGS. 10E-10G). These data indicated that both laboratory-adapted CVB3 and a natural variant of E18 have increased resistance to TRIM7-mediated inhibition via point mutation in 2C.

Figure 3C:
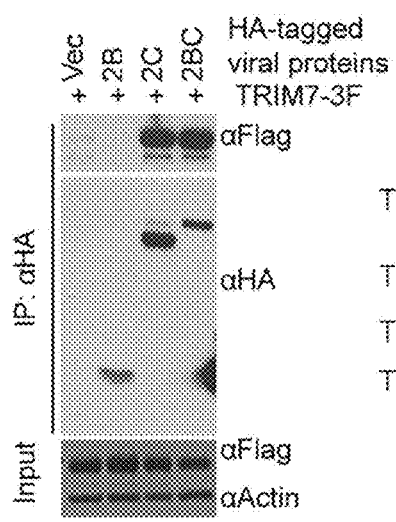
FIG. 3C shows 293T cells co-transfected with plasmids expressing TRIM7-3F (TRIM7 with C-terminal 3×FLAG epitope) or empty vector and the indicated HA-tagged CVB3 viral protein. Cells were harvested for co-IP using anti-HA beads and analyzed by Western blot.
Figure 3D:
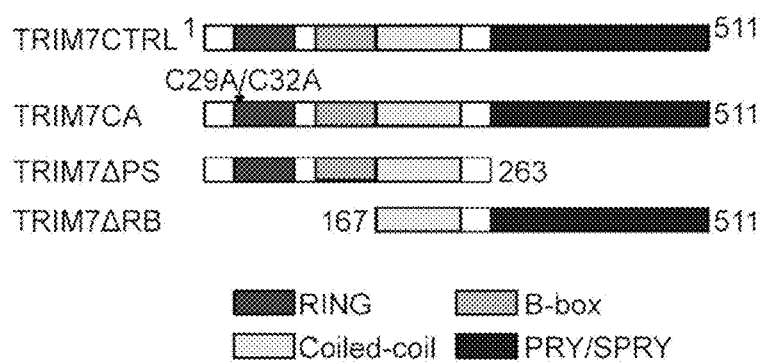
FIG. 3D shows a diagram of wild-type and mutant TRIM7 constructs.
Figure 3E:
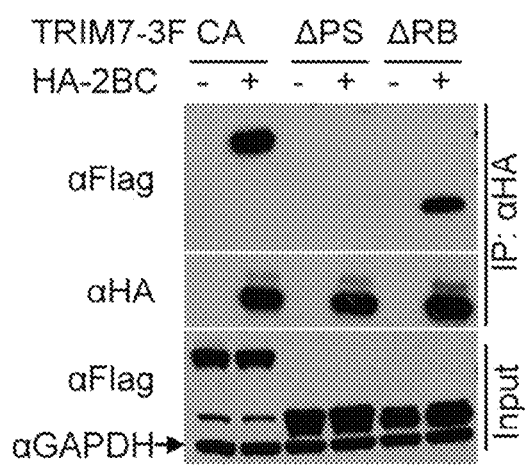
FIG. 3E shows 293T cells co-transfected with CVB3 HA-2BC plasmid or empty vector control with the indicated TRIM7-3F expressing plasmids. The cells were harvested for co-IP using anti-HA beads 30 hours post-transfection and analyzed by Western blot.
Figure 3F:
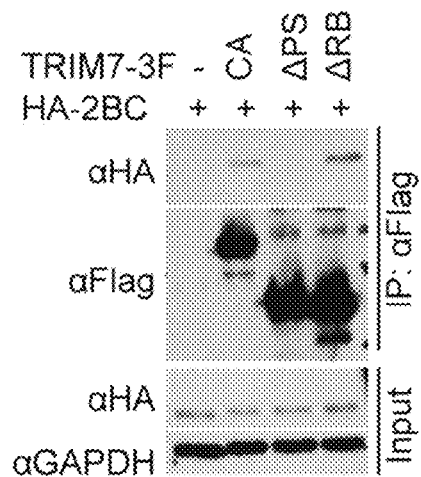
FIG. 3F shows 293T cells co-transfected with CVB3 HA-2BC plasmid and the indicated TRIM7-3F expressing plasmid or empty vector control. The cells were harvested for co-IP using anti-HA beads 30 hours post-transfection and analyzed by Western blot.
Figure 3G:
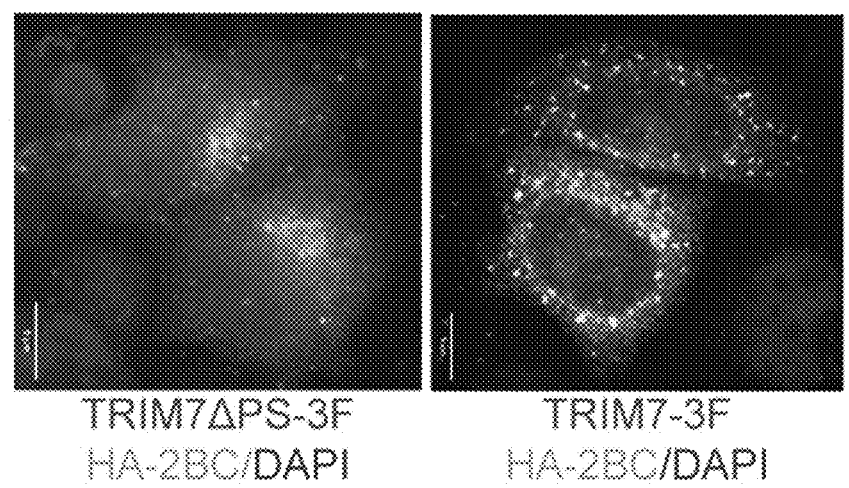
FIG. 3G shows HeLa cells co-transfected with CVB3 HA-2BC and wild type TRIM7-3F or PRY/SPRY deleted TRIM7-3F (TRIM7ΔPS). Confocal microscopy analysis was used to analyze protein localization at 24 hours post-transfection. HA-2BC (green); TRIM7-3F or TRIM7ΔPS (red). Nuclei are stained with DAPI (blue). Scale bar, 5 μm.
Figure 3H:
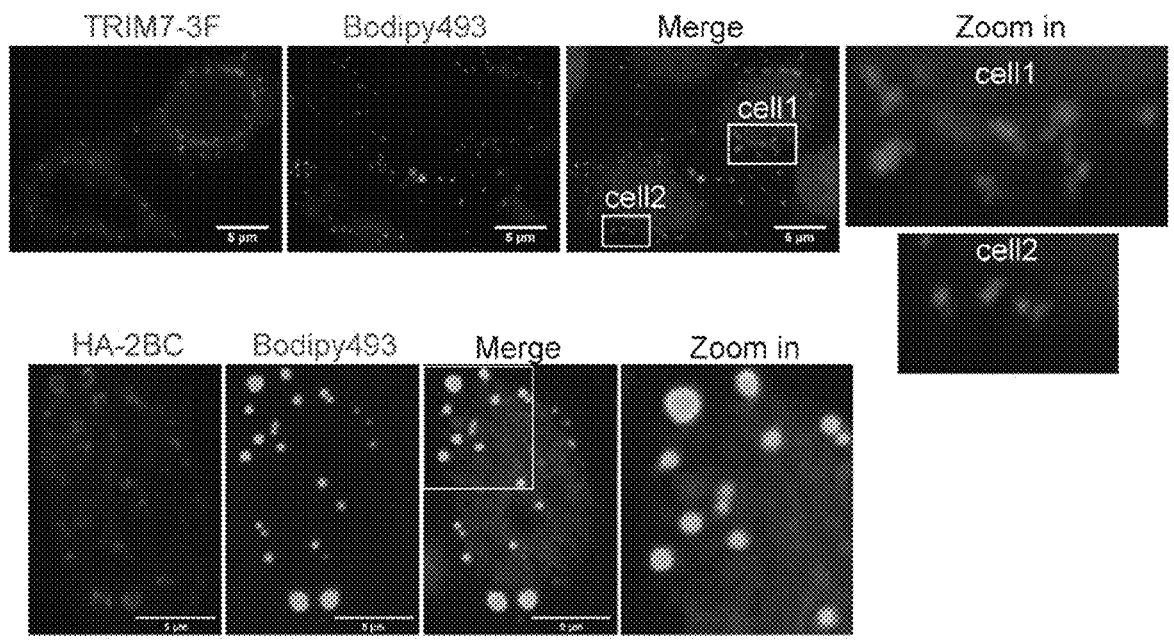
FIG. 3H shows HeLa cells transfected with plasmids expressing TRIM7-3F (top panel) or CVB3 HA-2BC (bottom panel). Co-localization of TRIM7 (top) or 2BC (bottom) and lipid droplets was assessed by confocal microscopy at 24 hours post-transfection. TRIM7-3F and HA-2BC (red); lipid droplets (Bodipy493-green); Nuclei are stained with DAPI (blue). Scale bar, 5 μm.
Figure 3I:
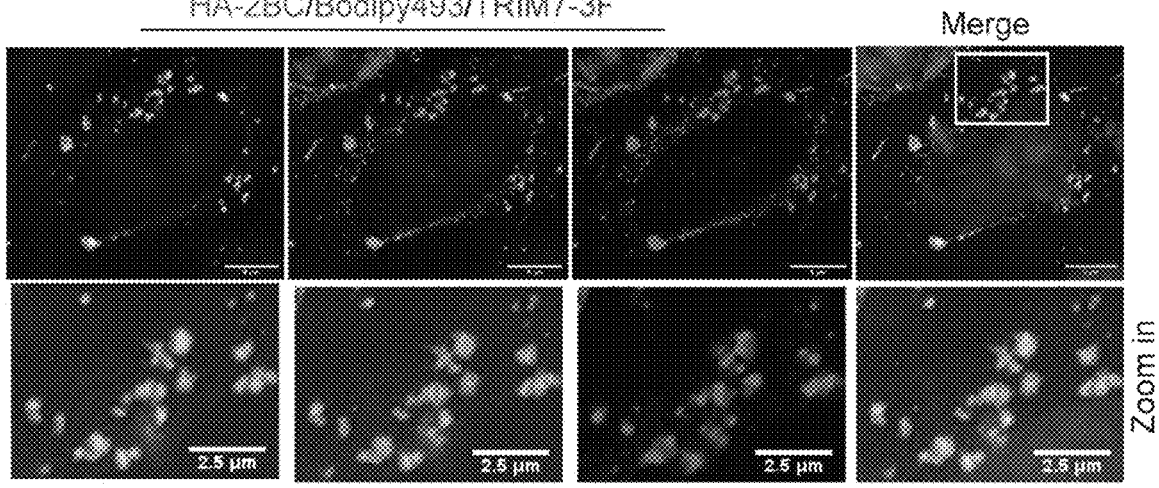
FIG. 3I shows HeLa cells co-transfected with TRIM7-3F and CVB3 HA-2BC and analyzed by confocal microscopy 24 hours post-transfection. Co-localization of HA-2BC (magenta), TRIM7-3F (red), and lipid droplets (Bodipy493: green). Nuclei are stained with DAPI (blue). Scale bar, 5 or 2.5 μm.
Figure 3J:
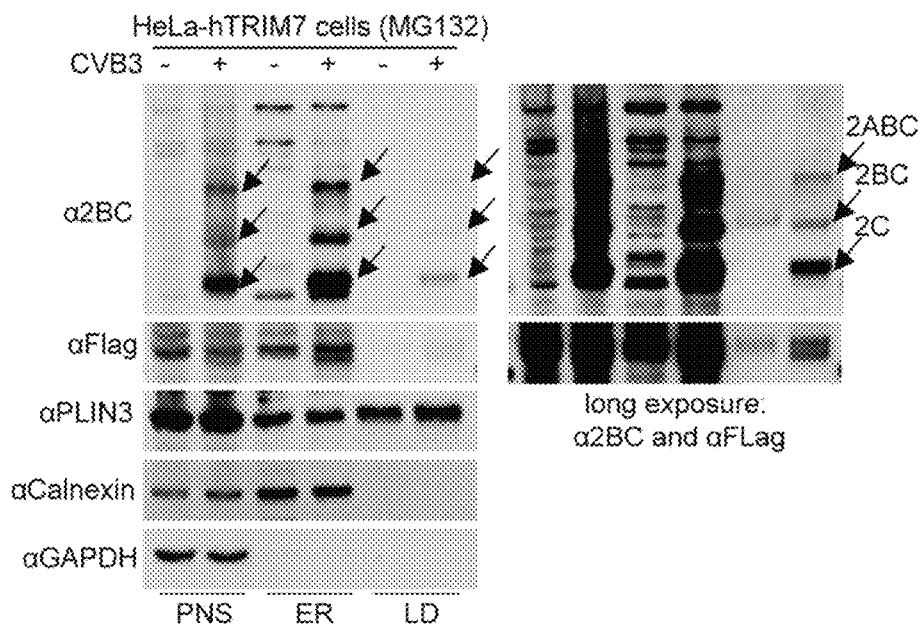
FIG. 3J shows HeLa-TRIM7CA cells infected with CVB3 at MOI of 10. 6 hpi later, post-nuclear supernatant (PNS), ER, and LD fractions were isolated and analyzed by Western blot using the indicated antibodies.
Figure 3K:
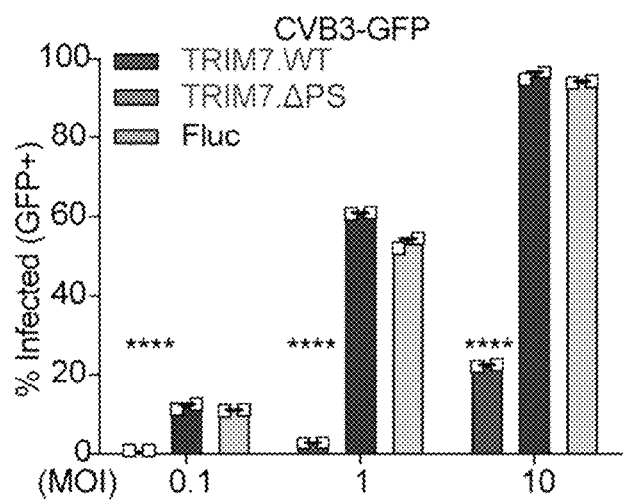
FIGS. 3K-3L show HeLa cells expressing Fluc or TRIM7 (WT or APS) infected with CVB3-GFP (FIG. 3K) or PV-GFP (FIG. 3L) for 8 hours. Virus infectivity was analyzed by flow cytometry.
Figure 3L:
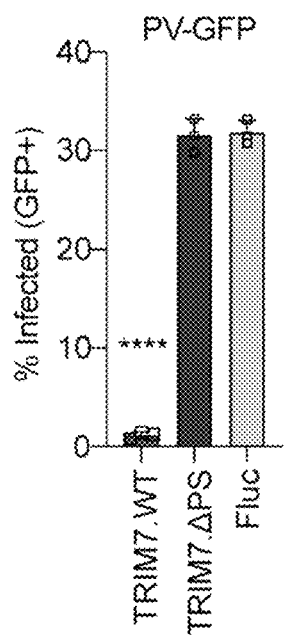

To understand how the T323A mutation confers viral resistance to TRIM7-mediated inhibition, it was examined whether TRIM7 can directly bind CVB3 2C or its precursors. Strep-11-3×Flag tandem affinity purification coupled to mass spectrometry was performed to identify viral proteins that interact with TRIM7 during infection (FIG. 11A). It was found that almost all individual CVB3 viral proteins, including structural and nonstructural proteins, can co-precipitate with TRIM7, with 2C protein being the top hit (FIGS. 11B-11C). The interaction of 2C with TRIM7 was confirmed by co-immunoprecipitation (co-IP) using HA-tagged viral 2C as bait (FIG. 3C). Also, the TRIM7 interacted with the precursor 2BC, but not 2B (FIG. 3C). Next, TRIM7 truncations were generated to determine the domain that interacts with 2BC (FIG. 3D). E3 ubiquitin "ligase-dead" TRIM7 (TRIM7-CA) were also made to prevent degradation of putative interacting factors. It was found that the C-terminal PRY/SPRY domain of TRIM7 was required for interaction with 2BC (FIGS. 3E-3F), and that a TRIM7-PRY/SPRY mutant (TRIM7-ΔPS) failed to colocalize with 2BC (FIG. 3G). Localization of 2C and 2BC to lipid droplets (LDs) is critical for formation of viral replication complexes. Thus, it was investigated whether TRIM7 localized with 2BC at LDs. It was found that when ectopically expressed alone, the majority of 2BC localized to LDs, and a small fraction of TRIM7 also localized near LDs (FIG. 3H). Notably, when TRIM7 was co-expressed with 2BC, most of the TRIM7 signal was found adjacent to 2BC on LDs (FIG. 3I). To examine TRIM7-2BC interactions during infection, biochemical fractionation of CVB3-infected cells was used. The majority of 2ABC, 2BC, and 2C was detected in ER fraction, with a smaller proportion of these proteins found in LD fractions (FIG. 3J). It was also found that compared to uninfected cells, TRIM7 was enriched in both ER and LD fractions during virus infection (FIG. 3J). Thus, while ectopic expression and bona fide viral infection resulted in distinct partitioning patterns of 2BC to LD or ER, in both cases, TRIM7 became enriched in these compartments when 2BC was present, suggesting that an interaction between the TRIM7 PRY/SPRY domain and enterovirus 2BC was critical for the observed antiviral effects.

Figure 3M:
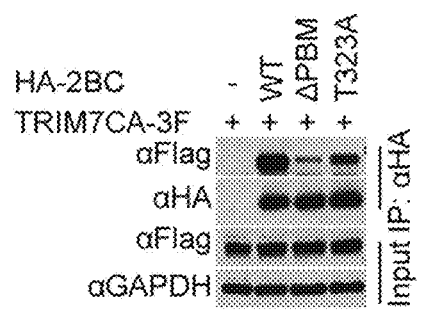
FIG. 3M shows 293T cells co-transfected with TRIM7-3F expressing plasmid and HA-tagged wild type or T323A 2BC constructs. The cells were harvested at 30 hours post-transfection and analyzed by anti-HA co-IP and Western blot.
Figure 3N:
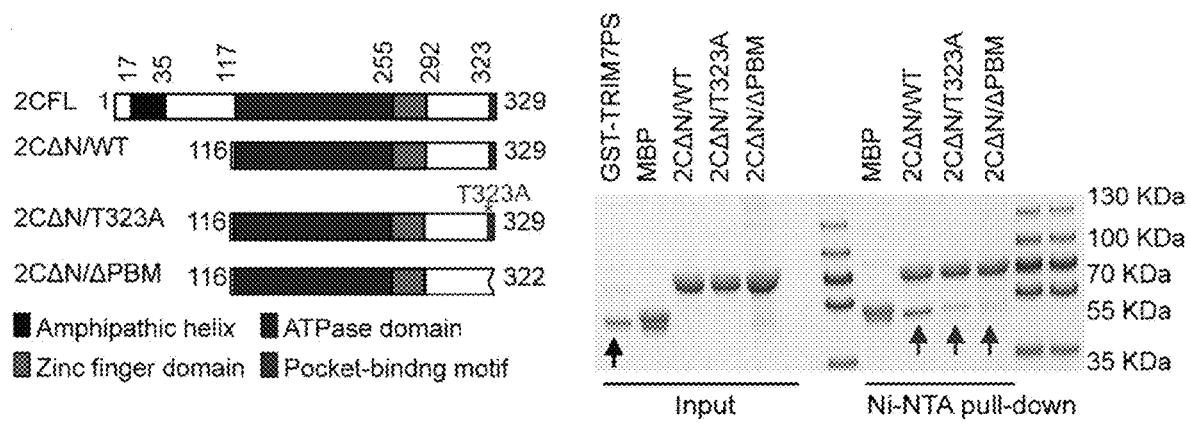

To determine how CVB3/T323A overcomes TRIM7-mediated inhibition, it was tested whether the T323A mutation in 2C modulates interactions between TRIM7 and 2BC or 2C. A co-IP assay was performed a to assess interactions between ligase-dead TRIM7-CA and 2BC, 2BC-T323A, or 2BC lacking the C-terminal pocket-binding motif (2BC-ΔPBM). Compared to wild type 2BC, it was observed that 2BC-T323A had reduced interaction with TRIM7, whereas interactions of TRIM7 and 2BC-ΔPBM were nearly ablated (FIG. 3M). The interaction between TRIM7 and 2C with an N terminal truncation was further evaluated by in vitro pull-down assay using proteins purified recombinantly in *E. coli*. Consistent with the co-IP results, TRIM7 was pulled down by 2CΔN/WT, whereas pulldown efficiency was reduced with 2CΔN/T323A (FIG. 3N). Together, these data indicated that the T323A mutation in CVB3 2C impaired the interaction between 2BC and TRIM7 that was required for TRIM7-mediated restriction of CVB3 replication.

Example 5: TRIM7 Targets Viral 2BC for Proteasome-Dependent Degradation

Figure 4A:
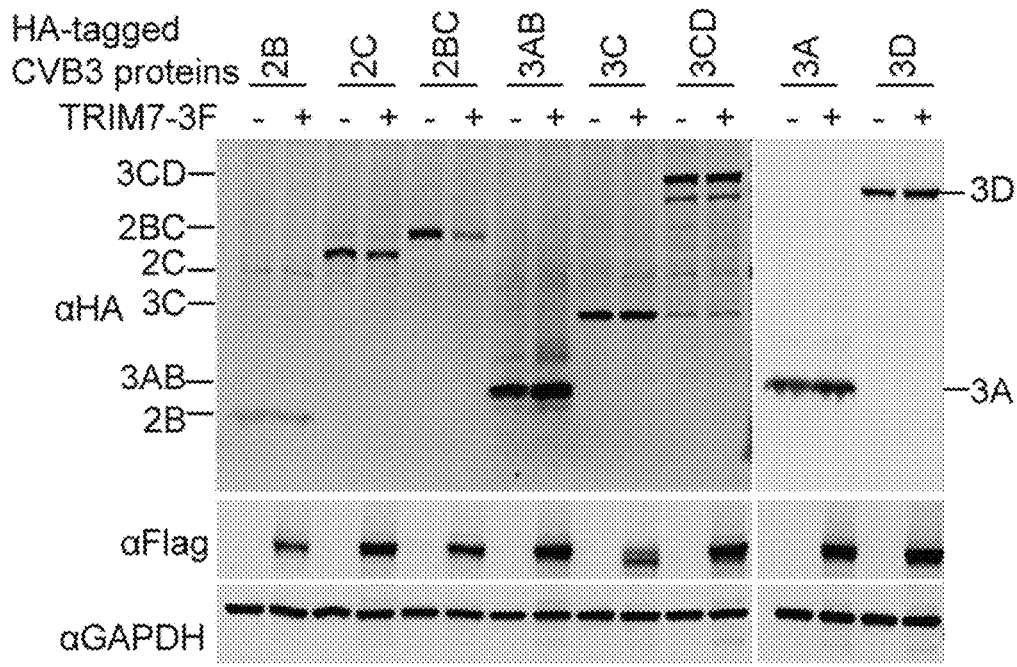
Figure 4B:
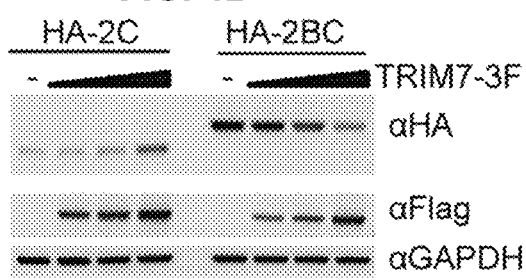
Figure 4D:
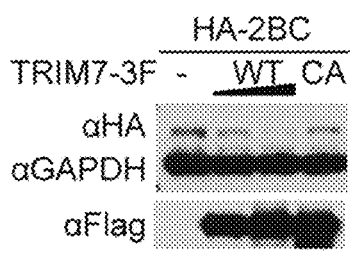
Figure 4C:
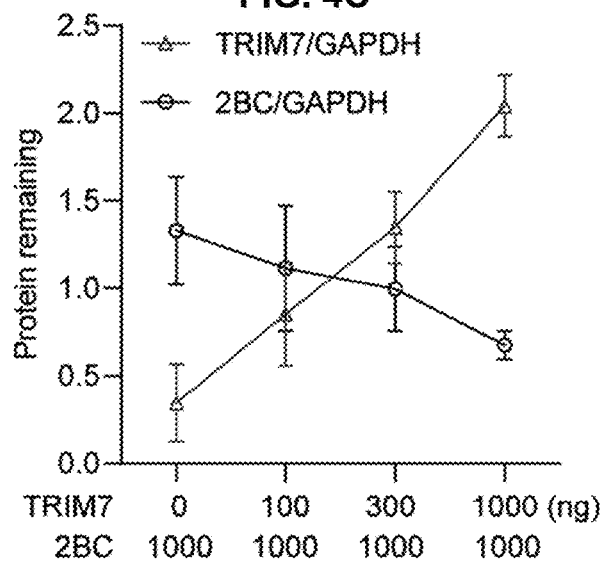
Figure 4E:
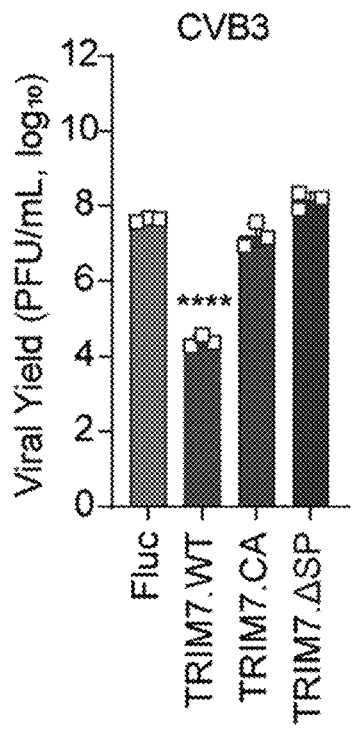
Figure 4F:
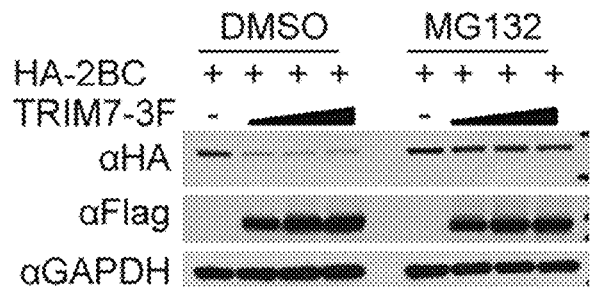
Figure 4G:
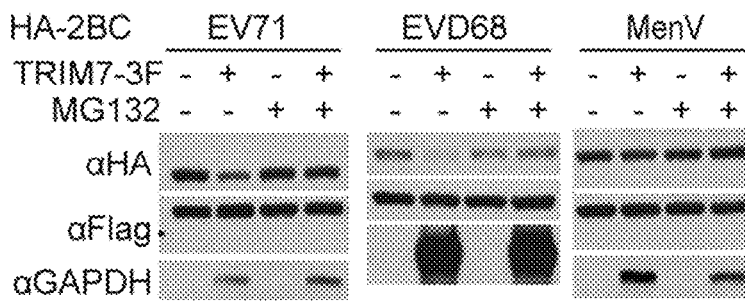
Figure 4H:
Figure 4I:
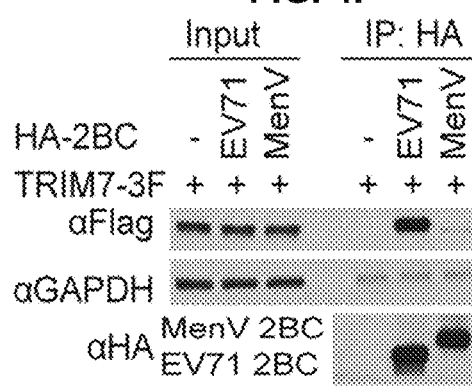

Since TRIM7 binds 2C and 2BC, it was next tested whether TRIM7 targets either protein for degradation. Also tested were other viral non-structural proteins and their immediate precursors since co-IP/mass spectrometry revealed that some of them may interact with TRIM7 (FIG. 11C). 293T cells were co-transfected with plasmids expressing HA-tagged CVB3 viral proteins and 3×Flag-tagged TRIM7 (TRIM7-3F) or Fluc-expressing vector. Expression of TRIM7 resulted in reduced levels of HA-2BC, but not other viral proteins (FIG. 4A), including HA-2C, which interacted with TRIM7 (FIG. 3C). It was also found that TRIM7 mediated 2BC degradation in a dose-dependent manner (FIGS. 4B-4C). Expression of ligase-dead TRIM7-CA did not affect HA-2BC levels, consistent with its loss of antiviral activity (FIGS. 4D-4E). Moreover, proteasome inhibition by MG132 restored HA-2BC protein in the presence of TRIM7 (FIG. 4F). Similar results were obtained with 2BC from other TRIM7-targeted enteroviruses, including EV71 and EVD68, whereas 2BC from TRIM7-insensitive MenV was unaffected (FIGS. 4G-4H). Accordingly, 2BC from EV71, but not MenV, interacted with TRIM7 in pulldown assays (FIG. 4I). These data suggested that the antiviral mechanism-of-action of TRIM7 was selective targeting of enterovirus 2BC for proteasomal degradation.

Lys48-linked ubiquitination of substrates is important for degradation by the ubiquitin-proteasome pathway. A cell-based transfection assay was used to determine whether CVB3 2BC could immunoprecipitate ubiquitin in the presence of TRIM7. Indeed, it was observed that in the presence of TRIM7, but not ligase-dead TRIM7-CA, HA-2BC pulled down more Strep-tagged wild type ubiquitin (Strep-wt.Ubi) or K48-only ubiquitin (Strep-K48.Ubi) (FIG. 4J). Furthermore, TRIM7, but not ligase-dead TRIM7-CA, promoted the ubiquitination of 2BC in an in vitro ubiquitination assay (FIG. 4K). These results further supported a model in which TRIM7 modified enterovirus 2BC protein by K48-linked ubiquitination, leading to degradation of 2BC by the proteasome.

Example 6: TRIM7 Resistance Correlates with Impaired Replication In Vitro and a Hyperactive and Structurally Plastic 2C ATPase Since adaptive mutation in 2C helped the virus overcome TRIM7-mediated restriction, it was assessed whether this mutation occurred in nature. Analysis of available genome sequences did not reveal the existence of a naturally occurring T323A variant in any human type B enterovirus 2C protein. However, as described above, a single isolate of human echovirus 18 was reported to have a T323I mutation in 2C, which conferred partial resistance to TRIM7 (FIG. 10D). The absence of a naturally occurring T323A variant resulting in examination of the impact of T323A on viral fitness. CVB3-T323A impaired viral production when compared to CVB3-WT in the absence of ectopically expressed TRIM7 (FIG. 5A). Reduced replicative fitness of CVB3-T323A in HeLa cells was further confirmed using strand-specific RT-PCR. Compared to CVB3-WT, lower levels of both positive and negative strand RNA of the mutant virus were detected (FIG. 5B). Also observed was greater than 100-fold reduction in intracellular CVB3-T323A virus production during a single replication cycle as compared to CVB3-WT (FIG. 5C).

Figure 12A:
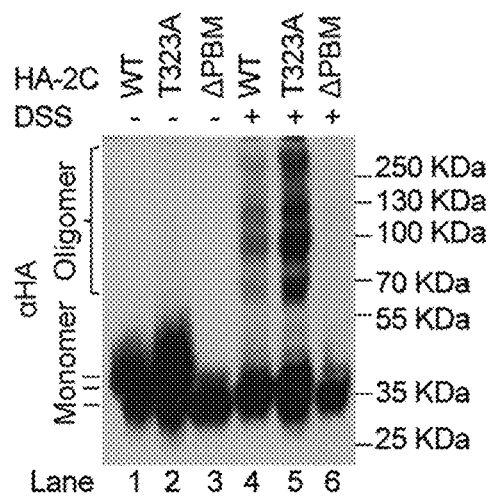
Figure 12B:
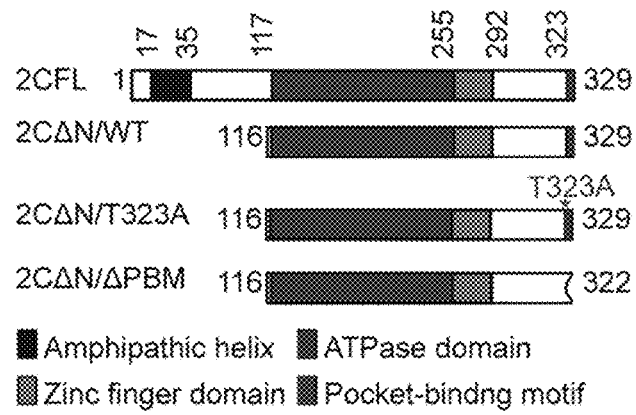
Figure 12C:
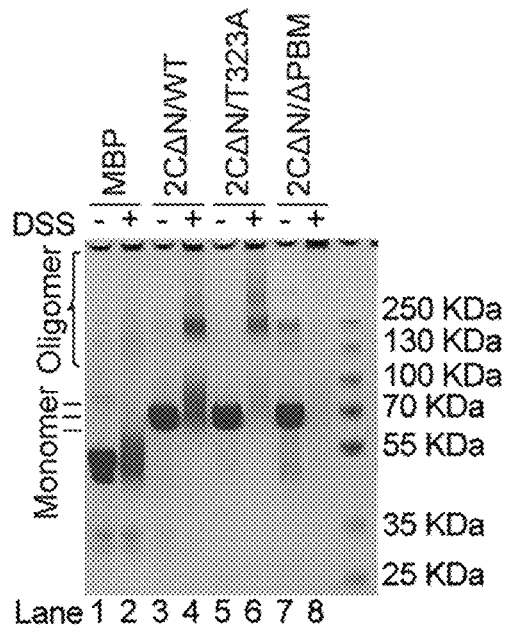

To address the molecular mechanisms underlying the fitness cost to the virus for overcoming TRIM7-mediated restriction, it was examined if the T323A mutation affected 2C oligomerization, which is required for optimal ATPase activity. An intracellular protein oligomerization assay was performed according to a method similar to that described by Nozawa et al., Cell. 2017; 169: 1214-1227.e18, the disclosure of which is incorporated herein in its entirety. Treatment of TRIM7-expressing cells with disuccinimidyl suberate (DSS) crosslinker resulted in high molecular weight oligomeric species for both 2C-WT and 2C-T323A, but not 2C lacking the pocket-binding motif (2CΔPBM), which was required for optimal interaction with TRIM7 (FIG. 12A). Notably, oligomerization was more pronounced for 2C-T323A than for 2C-WT. Next, oligomerization in vitro was investigated to corroborate this observation. The N terminally-truncated soluble regions of 2C-WT, 2C-T323A, and 2CΔPBM were expressed in *E. coli* and purified (FIG. 12B). Consistent with the cell-based assay, increased levels of high molecular weight oligomers of 2C-WT and 2C-T3232A, but not 2CΔPBM were observed (FIG. 12C). These results indicated that T323A did not abolish, and may even promoted the oligomerization of 2C protein. The ATPase activity of recombinant 2C-WT, 2C-T323A, and 2CΔPBM was next examined. In a dose response, a time course, and a substrate titration, it was found that 2C-T323A was a more catalytically active ATPase than 2C-WT (FIGS. 5D-5F), suggesting that hyperactivity in this ATPase may disfavor optimal replication.

Figure 5G:
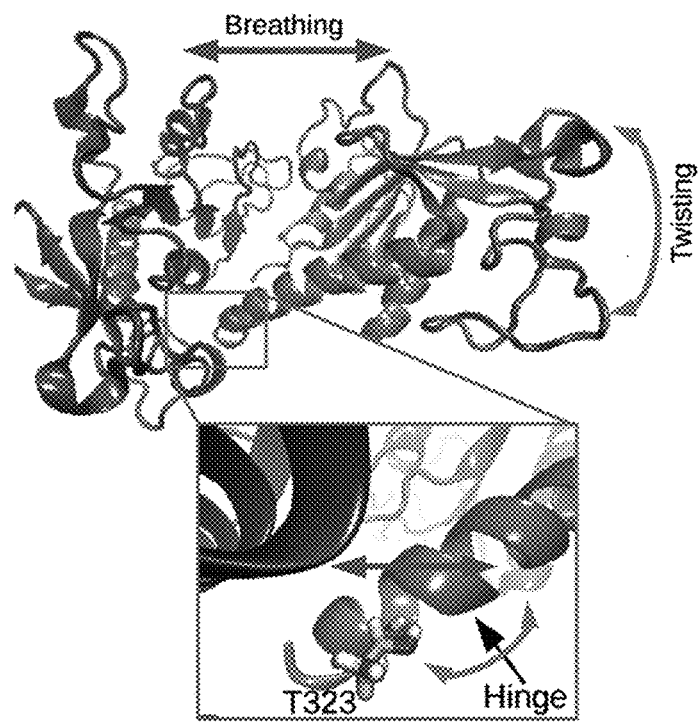
Figure 5H:
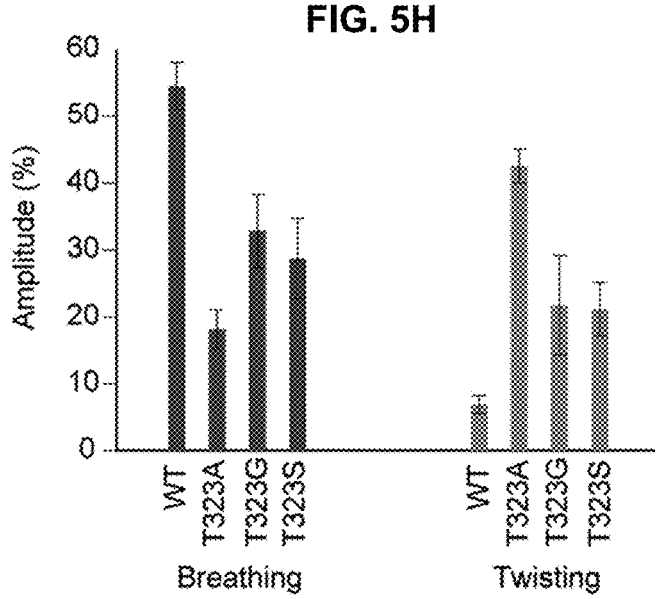
Figure 12D:
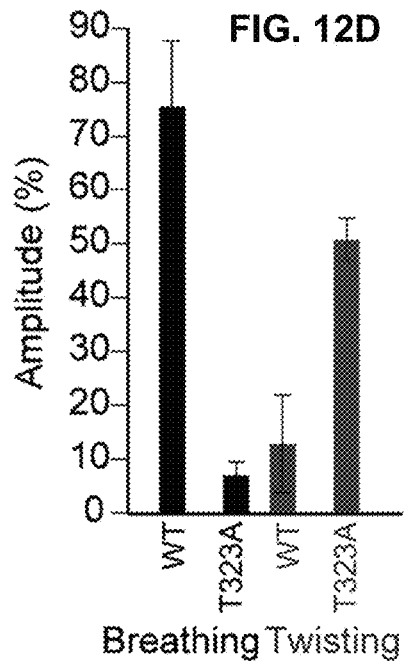

To correlate biochemical findings herein with structural data, molecular dynamics (MD) simulations were used to examine the impact of T323A on CVB3 2C dimer behavior. Starting from the crystal structure of EV71 2C, all amino acid positions were mutated to convert to CVB3 2C, followed by energy minimization and pre-equilibration of dynamics for the dimer complex. The two modes captured most (greater than 60%) of the total dynamical variation and were also mutually orthogonal motions. The remaining 40% of the variation was distributed over 800 distinct non-negligible modes. The first mode was a "breathing" motion in which the monomers move away from each other, while the second was a "twisting" motion in which monomers rotate relative to each other (FIG. 5G). Both of these motions were facilitated by a hinge region at residues S318-319, which was previously identified as a fulcrum based on multiple crystal structure configurations by Guan at al., 2017. 2C-WT had a dominant breathing mode (54.6±3.5% amplitude), with minimal twisting (6.9±1.4% amplitude). By contrast, 2C-T323A had an attenuated breathing mode (18.2±2.9%) with dominant twisting (42.6±2.5%). The same trend was observed in simulations of 2C in complex with the substrate ATP (FIG. 12D). Two other mutations, T323G and T323S, resulted in decreased breathing and increased twisting at an intermediate level between WT and T323A (FIG. 5H). Consistent with the observed increase in structural plasticity, CVB3-T323G and CVB3-T323S viruses were attenuated compared to CVB3-WT, but still replicated to higher levels than CVB3-T323A (FIG. 12E). Accordingly, both CVB3-T323G and CVB3-T323S viruses retained their sensitivity to TRIM7-mediated restriction (FIG. 12F).

Figure 5I:
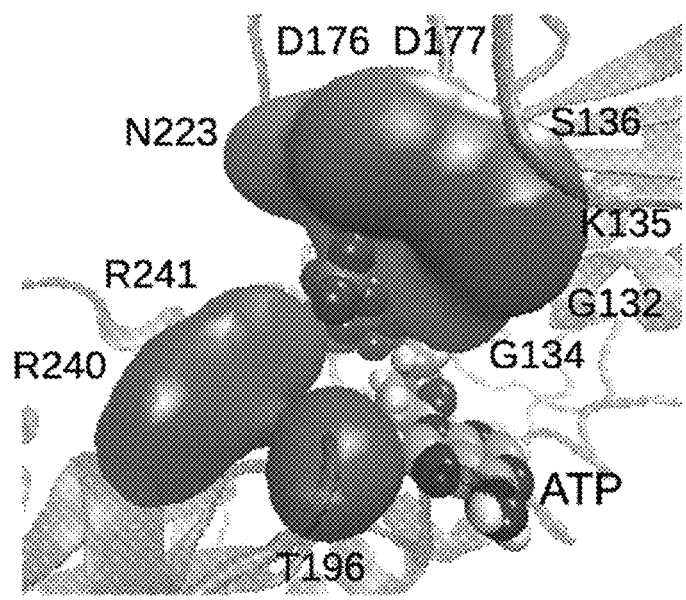
Figure 5J:
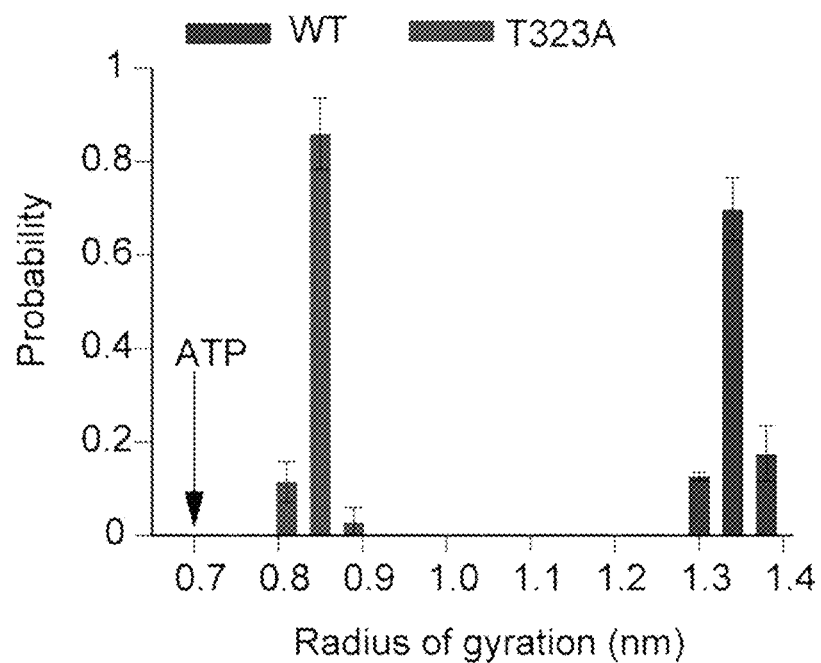

Although MD simulations cannot capture the quantum mechanical phenomenon of ATP hydrolysis, the configurational statistics of the key residues required for hydrolysis when ATP is bound to the nucleotide pocket of 2C-WT and 2C-T323A were quantified. Because ATP coordination was a rate-limiting step in hydrolysis, it can thereby be inferred the effect of the mutation on hydrolysis rate. The key residues were G132, G134, K135, S136, D176, D177, and N223 of one monomer, and T196, R240, and R241 of the other monomer (FIG. 5I). The radius of gyration of these residue sidechains was used as a metric of pocket tightness and hydrolysis-compatible coordination. By calculating the statistics of this metric over the course of the simulations, the extent of deformations in the overall shape of the pocket was quantified and inferred how tightly the ATP molecule (0.7 nm diffusion radius) coordinated with the hydrolysis residue. It was found that the 2C-T323A mutant maintained a tight radius of gyration between 0.8 nm and 0.9 nm, while 2C-WT had much looser coordination centered around a 1.35 nm radius (FIG. 5J).

Together, these data highlighted an exquisite amino acid selectivity in 2C at residue 323. CVB3 can acquire a T→A mutation which conferred resistance to TRIM7. The same 2C residue can tolerate T→S and T→G mutations but didi not benefit from these modifications. In all cases, relative to WT, these mutations compromised normal replicative fitness in the absence of TRIM7, most likely by altering optimal 2C function.

Example 7: CVB3-T323A Exhibits Augmented Replication and Immune Activation In Vivo Effects of TRIM7 resistance on viral replication and pathogenesis in a mouse model was determined. First evaluated were the effects of mouse Trim7 on CVB3 infection. RNAi-mediated knockdown of murine Trim7 reduced Trim7 protein levels in C2C12 mouse myoblast cells (FIG. 13A), resulting in increased susceptibility to CVB3 infection (FIGS. 6A and 13B). Since CVB3 is known to cause viral myocarditis, additionally shown was that siRNA-mediated silencing of Trim7 in primary mouse cardiomyocytes increased infectious CVB3 production (FIG. 6B). Conversely, ectopic expression of mTrim7 achieved similar levels of inhibition as hTRIM7 in HeLa cells (FIG. 6C). To demonstrate the antiviral potential of mTrim7, mRNA encoding mTrim7 were delivered in vitro and in vivo using validated liver-targeted lipid nanoparticles (LNPs) according to methods similar to those described in Cheng et al., Nat. Nanotechnol. 2020; 15: 313-320, the disclosure of which is incorporated herein in its entirety. mTrim7 or Fluc mRNA were encapsulated in LNPs and delivered to cultured cells. After 24 hours, mTrim7 expression was detected by Western blot and potently suppressed CVB3 infection (FIG. 13C). To further study effects in vivo, LNPs-mRNA were administered intravenously to C57BL/6J mice. At 6 hours post injection, a time point previously shown to result in the maximal level of protein expression following mRNA translation, mice were infected intraperitoneally with CVB3 and viral titers in liver were quantified at 48 hours. LNPs-mTrim7 treated mice conferred a nearly 100-fold reduction in CVB3 replication in the liver compared to control LNPs-Fluc treated mice (FIG. 6D). Together, these data suggested that mTrim7 was important for controlling CVB3 in relevant murine cells and could limit CVB3 replication in vivo.

Figure 13E:
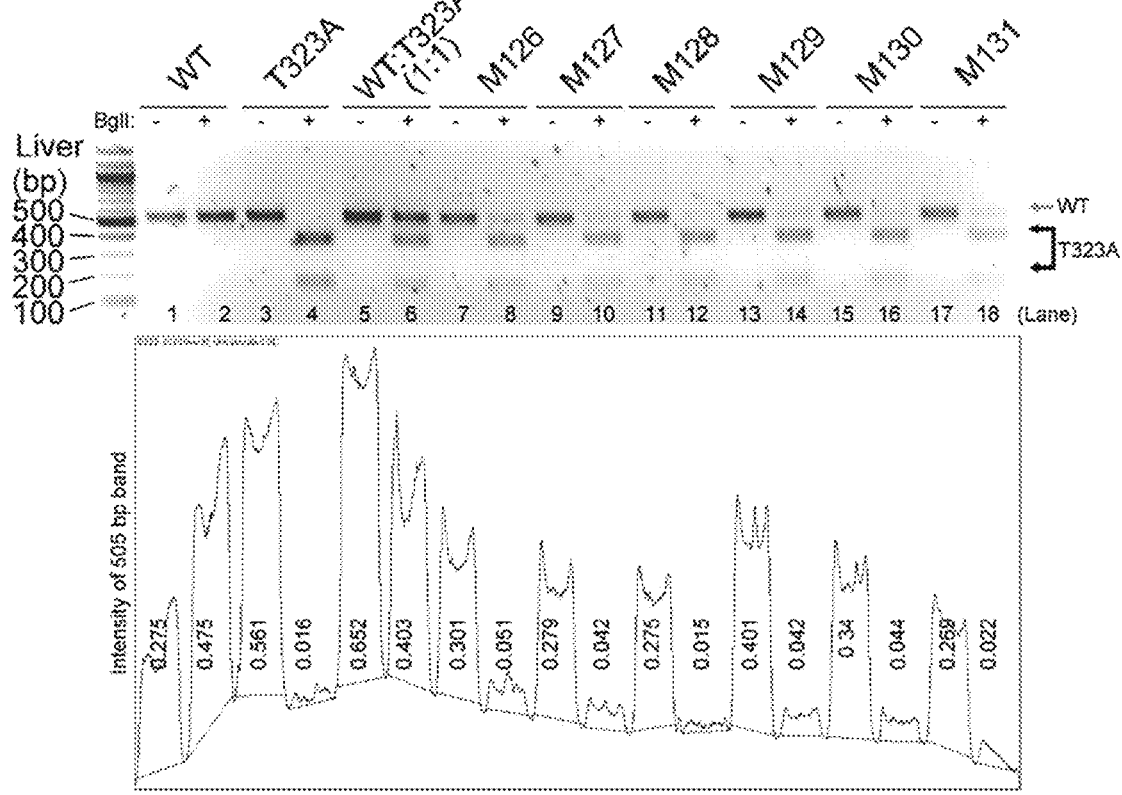
Figure 13F:
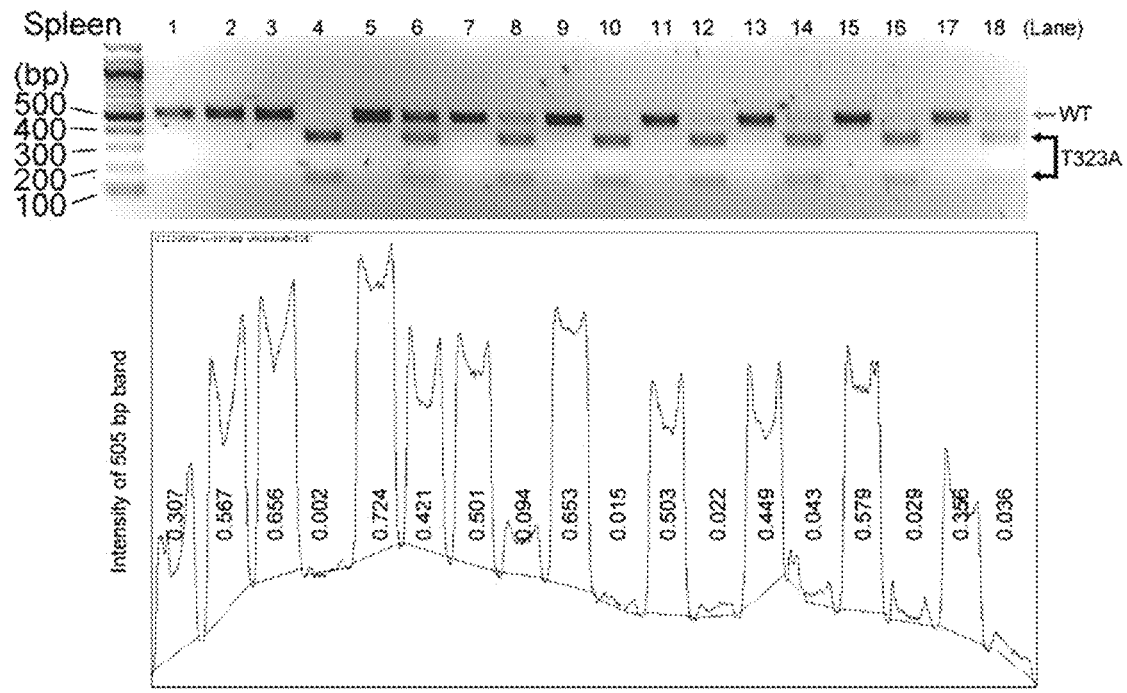
Figure 13G:
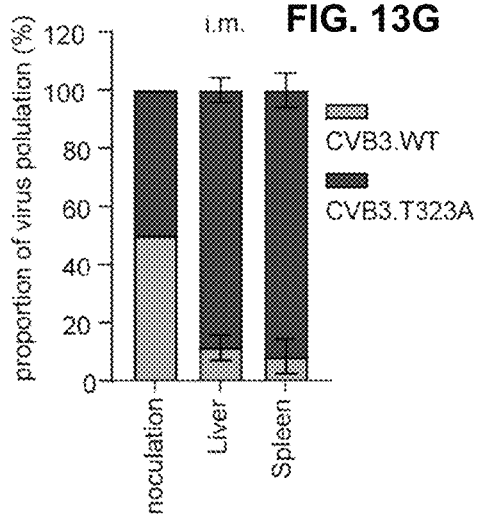
Figure 13H:
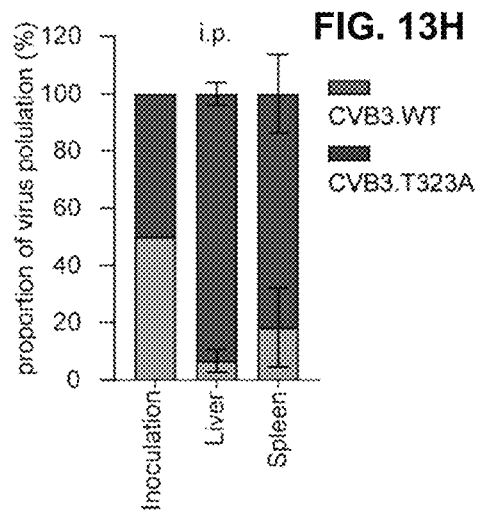

Next, Trim7 protein levels were assessed in multiple mouse tissues by Western blot. Of the tissues examined, the highest levels of Trim7 were observed in heart, kidney, and thigh muscle, while lower levels were observed in liver and pancreas and Trim7 was nearly undetectable in spleen (FIG. 6E). Since Trim7 was expressed highly in thigh muscle, if mice were inoculated via intramuscular (i.m.) injection, CVB3-T323A might replicate better than CVB3-WT in muscle and disseminate more efficiently to other tissues. To test this, i.m. administration was used to infect C57BL/6J mice with CVB3-WT and CVB3-T323A ($10^6$ PFU per mouse) and viral load was assessed in multiple tissues at 2 days post-infection. CVB3-T323A replicated to higher levels than CVB3-WT in all tested tissues (FIG. 6F), with the largest difference in spleen. Higher titers CVB3-T323A were found compared to CVB3-WT in serum at 2 dpi (FIG. 6G). Mice were next inoculated with $10^4$ PFU virus via intraperitoneal (i.p.) injection, which targeted the H3 strain of CVB3 efficiently to liver and spleen, and to variable levels in heart, depending on dose and time point. Higher titers of CVB3-T323A were again observed than CVB3-WT in heart, liver, and spleen (FIG. 6H). Most mice infected with CVB3-WT had low or undetectable levels of virus in heart after i.p. administration. Remarkably, mice infected with CVB3-T323A had a 10,000-fold increase in viral titers in heart. Since viral titers of CVB3-T323A were significantly higher than CVB3-WT in the examined tissues, it was possible that CVB3-T323A might have a competitive advantage over CVB3-WT at early time points. To test this, an in vivo viral competition assay was performed by administering both viruses together and determining whether either had a replicative advantage (FIG. 13D). It was observed that CVB3-T323A outcompeted CVB3-WT in liver and spleen (FIGS. 13E-13K). These studies demonstrated that, despite having decreased replicative fitness in normal cultured cells, CVB3-T323A had a fitness advantage in vivo.

Figure 13I:
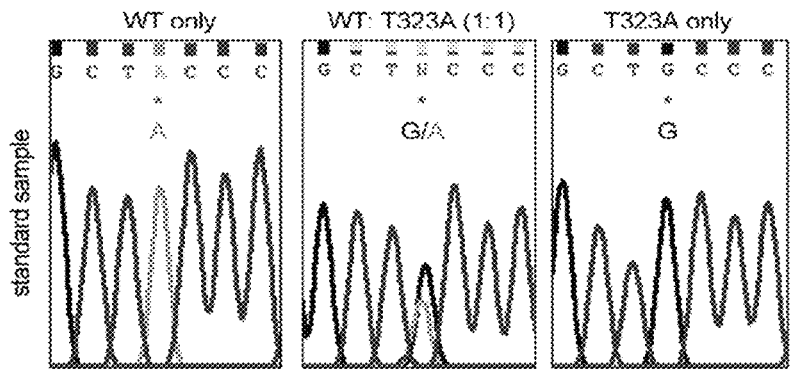
Figure 13J:
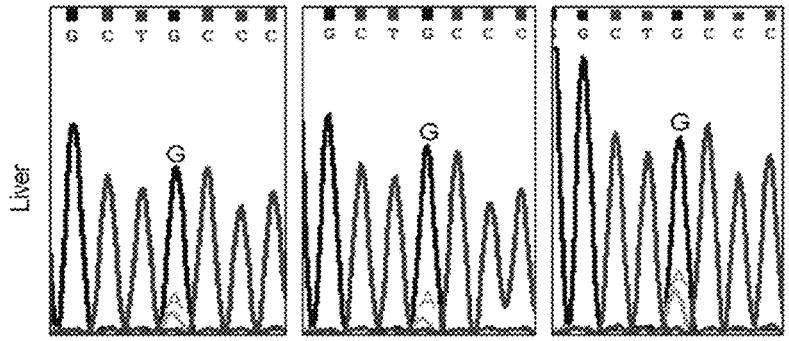
Figure 13K:
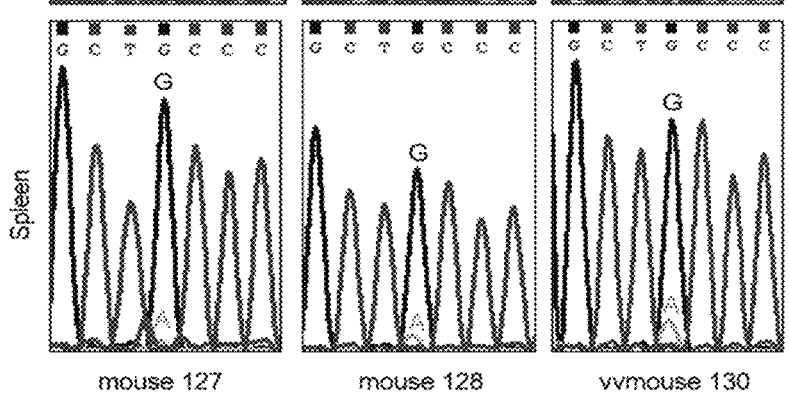
Figure 13L:
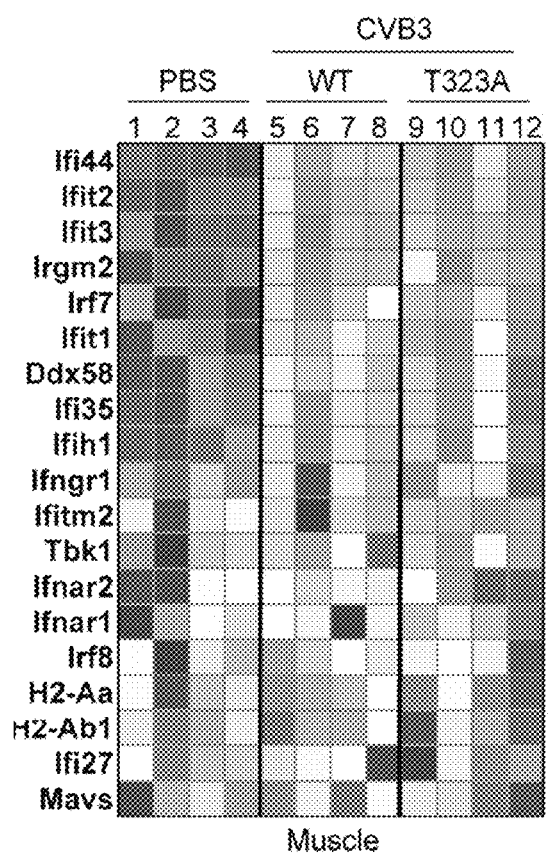
Figure 13M:
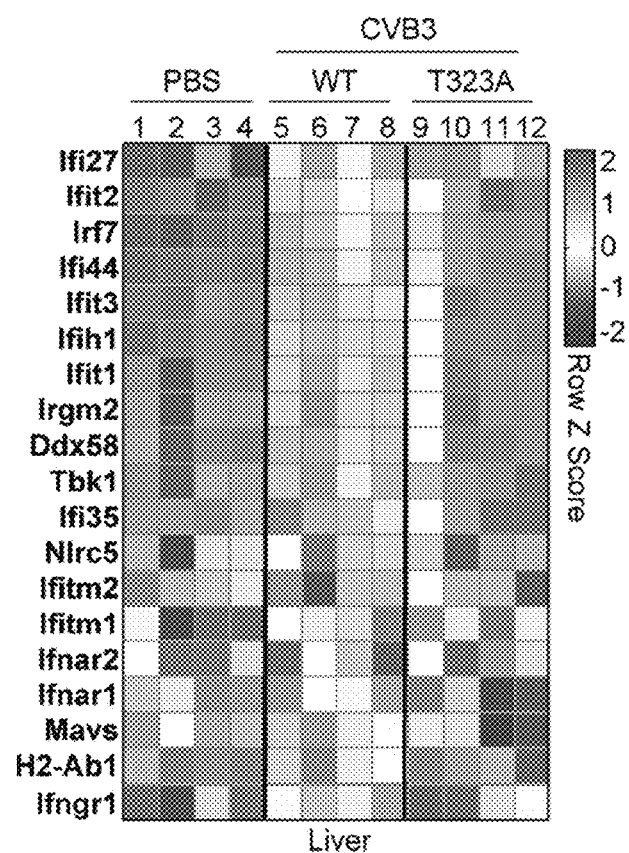
Figure 13N:
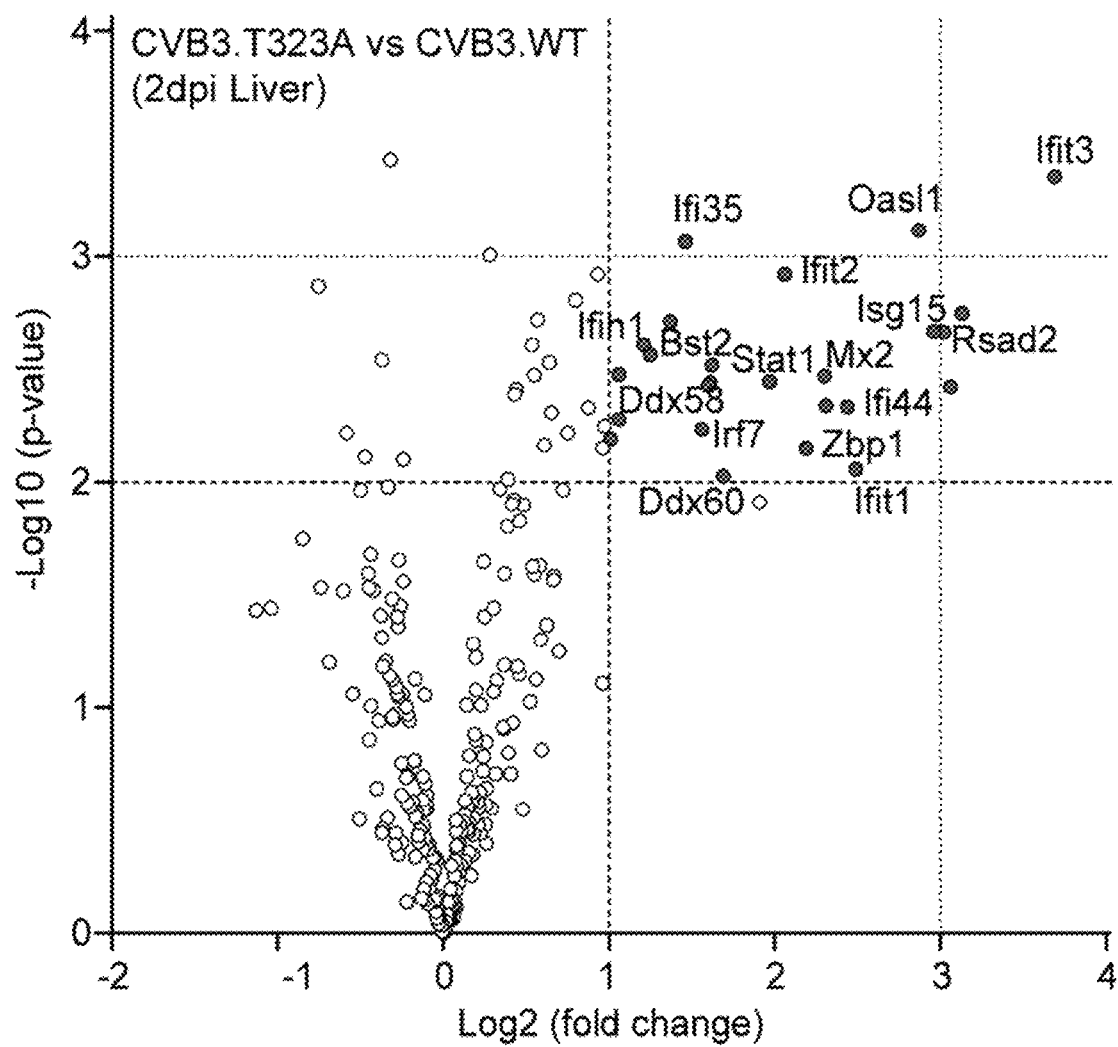

It was questioned whether this heightened replication of CVB3-T323A in vivo was due to the ability of this virus to evade triggering antiviral immune responses. NanoString transcriptional profiling of RNA from infected thigh muscle and liver at 2 days post-infection revealed that CVB3-T323A activated immune responses (interferon, inflammation, and innate and adaptive immune pathways) more robustly than CVB3-WT (FIG. 13O). CVB3-T323A induced higher levels of antiviral genes than CVB3-WT, including viral sensors (Ddx58/Rig-I; Ifih1/Mda5), transcription factors (Irf7; Stat1), and ISGs (e.g. Ifit1, Isg15, Oasl1) (FIGS. 13L-13N). These data suggested that the high replication levels of CVB3-T323A in vivo is likely not due to impaired triggering of antiviral immune responses.

Figure 7D:
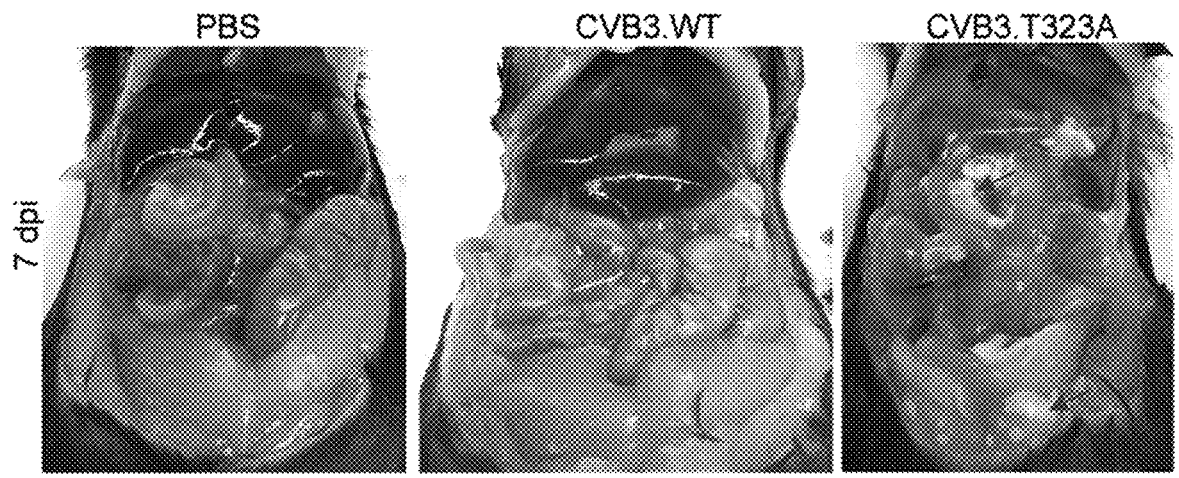

Example 8: CVB3-T323A Infection Causes Severe Pathogenesis and Lethality in Mice Pathogenic outcomes in mice infected with CVB3-WT and CVB3-T323A were next assessed. Mice infected with CVB3-T323A rapidly lost weight starting from 3 days post-infection and most mice succumbed to infection by day 10 (FIGS. 7A-7B). Notably, significant visceral fat necrosis was observed in CVB3-T323A-infected mice at 3 days post-infection (FIG. 7C), and this outcome worsened by day 7 (FIG. 7D). Visceral fat necrosis can result from enzymatic release from injured pancreatic cells. Since CVB3 can also replicate in the pancreas and cause pancreatic damage, replication of CVB3-T323A was examined in this organ.

Figure 7E:
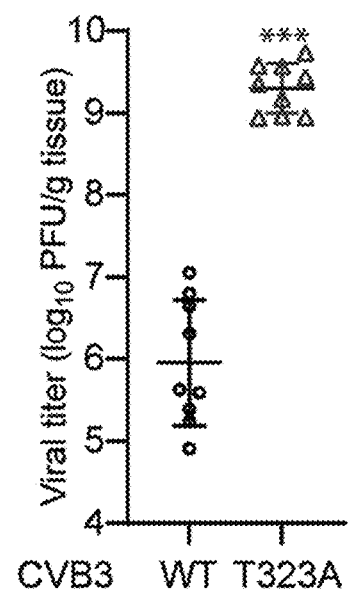
Figure 14I:
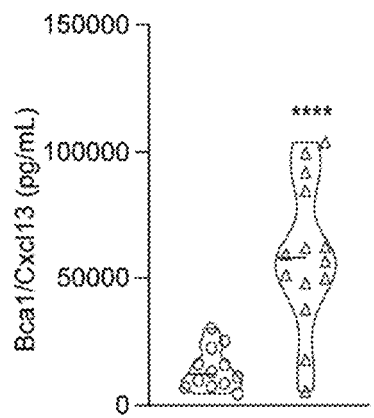
FIGS. 14I-14N show concentration of (FIG. 14I) Bca1/Cxcl13, (FIG. 14J) IP-10, (FIG. 14K) Ccl1, (FIG. 14L) Mcp-1/Ccl2, (FIG. 14M) Rantes/Ccl5, (FIG. 14N) Mcp-3/Ccl7 in serum from infected mice at 3 dpi. Each symbol indicates individual mice.
Figure 14J:
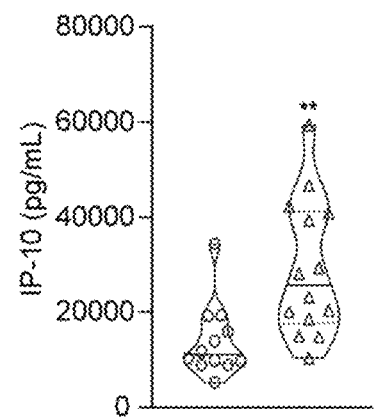
Figure 14K:
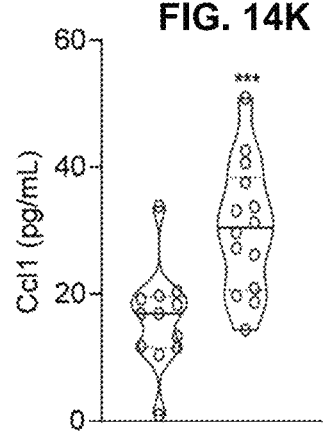
Figure 14L:
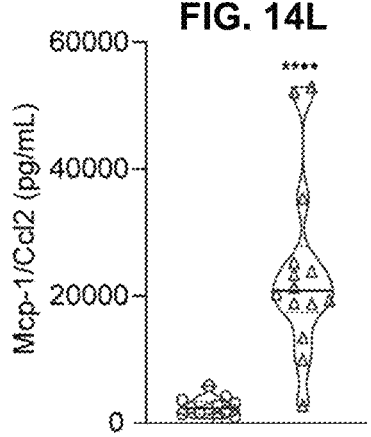
Figure 14M:
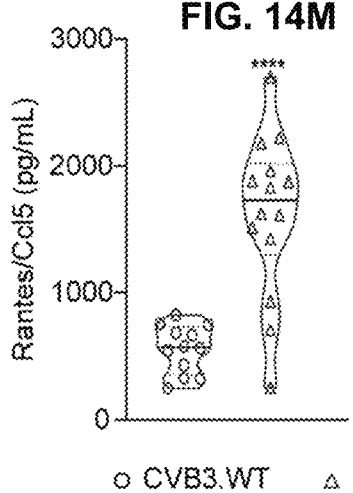
Figure 14N:
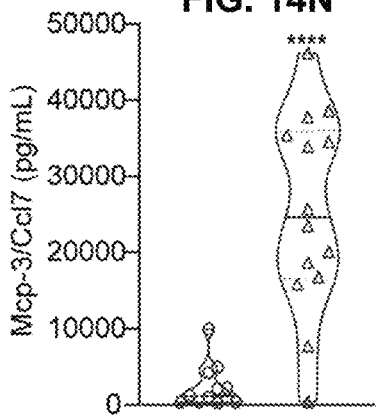

Indeed, the titer of CVB3-T323A in pancreas was nearly 200-fold higher than CVB3-WT (FIG. 7E). Also assessed were kidney, liver, and pancreas damage by measuring blood urea nitrogen (BUN), alanine transaminase (ALT), amylase (AMYL), and lipase (LIPA) from serum. Compared to CVB3-WT, CVB3-T323A infection resulted in significantly elevated serum levels of BUN and ALT, and trended toward a non-significant increase of AMYL and LIPA at 3 days post-infection (FIGS. 14A-14D). By 7 days post-infection, serum ALT levels were similar in infected and uninfected mice. However, both AMYL and LIPA from CVB3-T323 trended toward a non-significant reduction relative to CVB-WT (FIGS. 14E-14G).

Figure 14O:
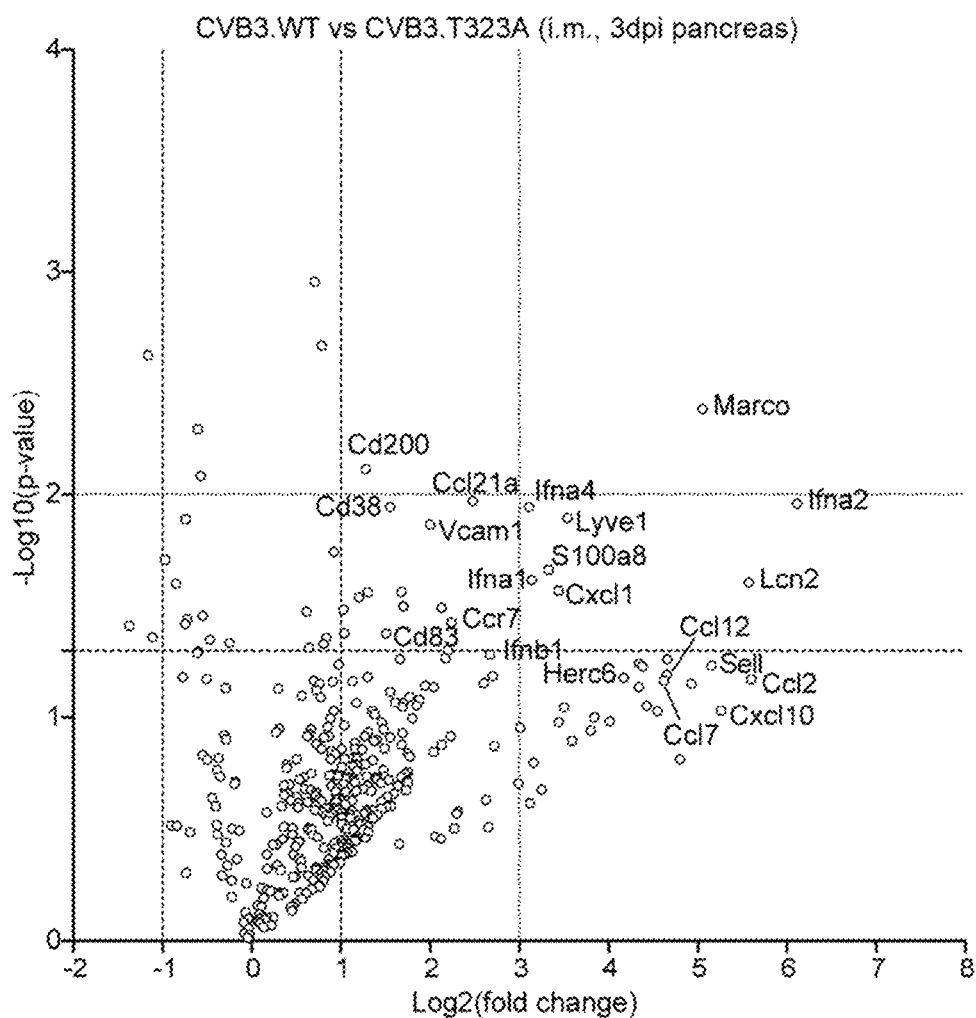
FIG. 14O shows a volcano plot of differentially expressed genes in pancreas (3 dpi) from CVB3-T323A infected mice versus CVB3-WT infected mice.

Next, the systemic immune responses were evaluated by quantifying cytokine and chemokine production in serum during early infection (2 and 3 days post-infection). A broad panel of proinflammatory cytokines and chemokines were more highly induced by CVB3-T323A as compared to CVB3-WT (FIGS. 14H-14N). Consistent with this, select chemokine mRNAs from pancreata were significantly elevated in CVB3-T323A infected mice, as were genes involved in apoptosis including CD3, Sell, and Lcn2 (FIG. 14O). These data were consistent with findings in CVB3-T323A infected mice that dramatically lost weight and had significant visceral fat necrosis.

Figure 7F:
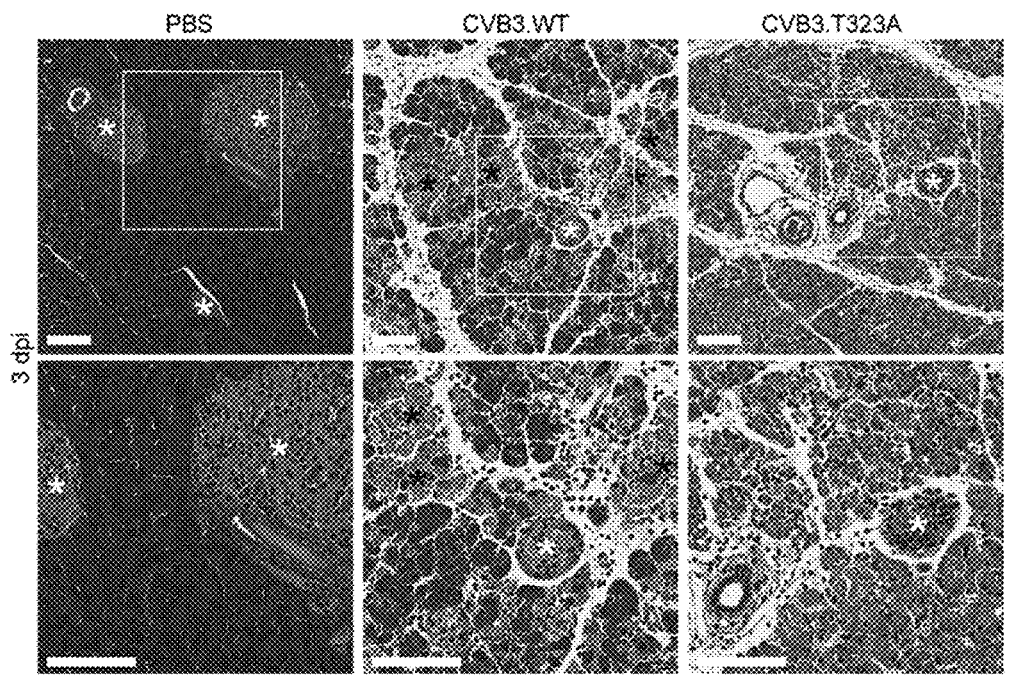
Figure 7G:
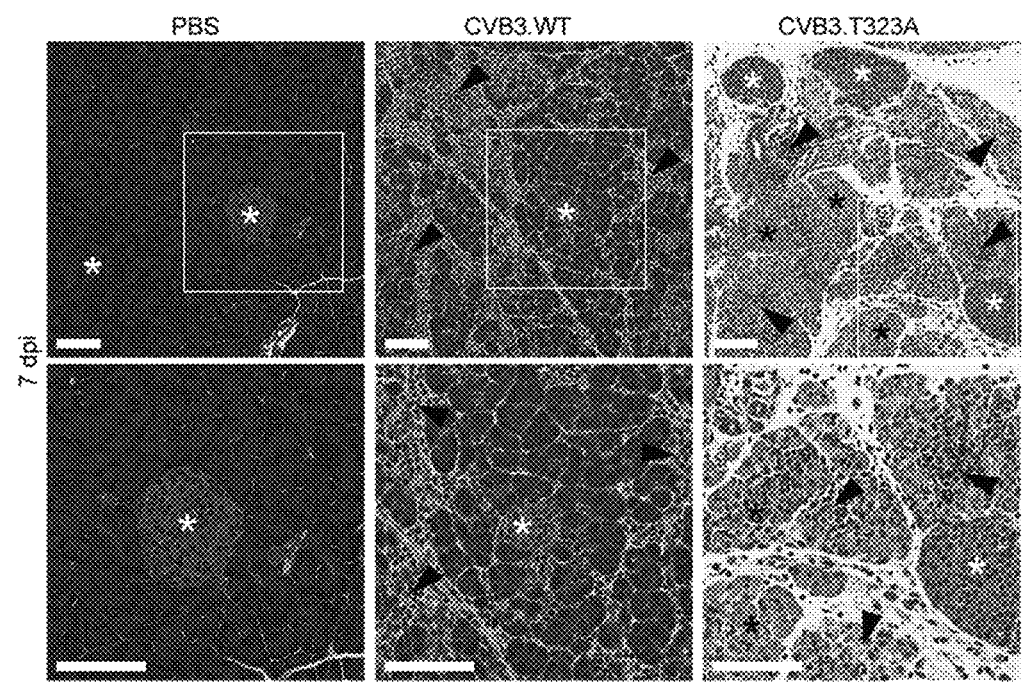
Figure 7H:
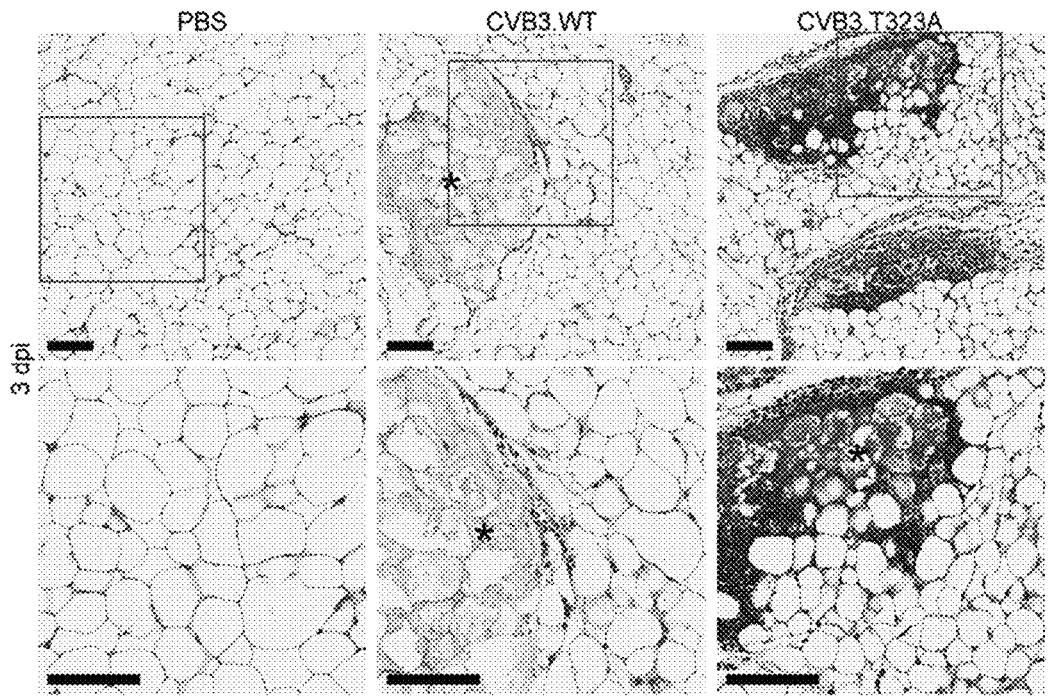
Figure 7I:
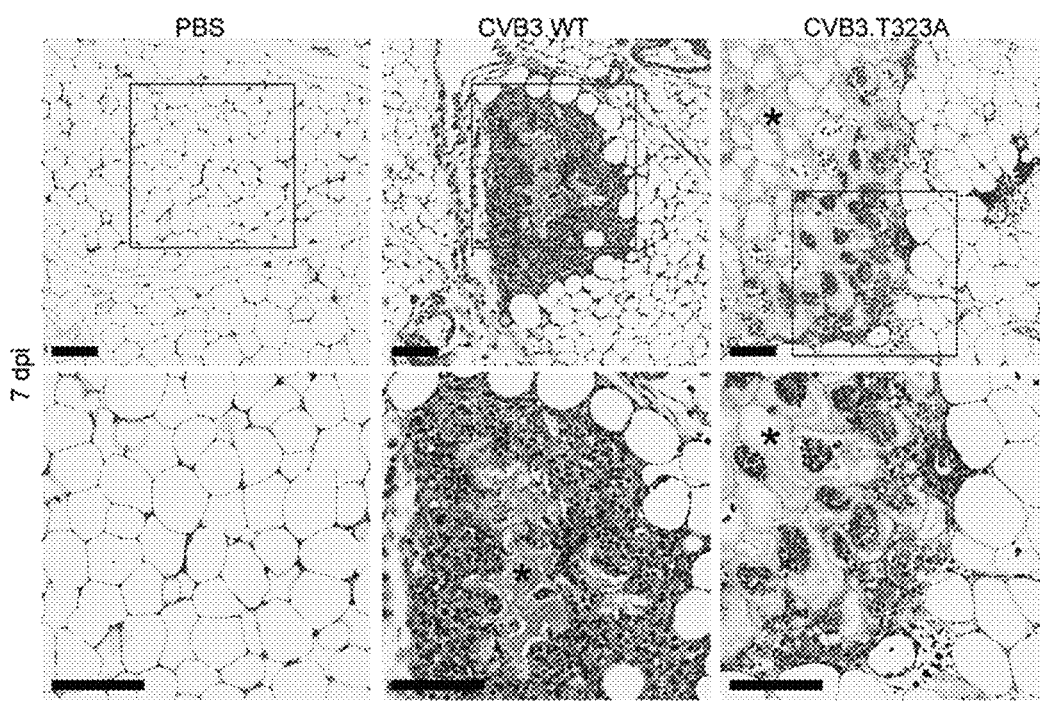
Figure 14P:
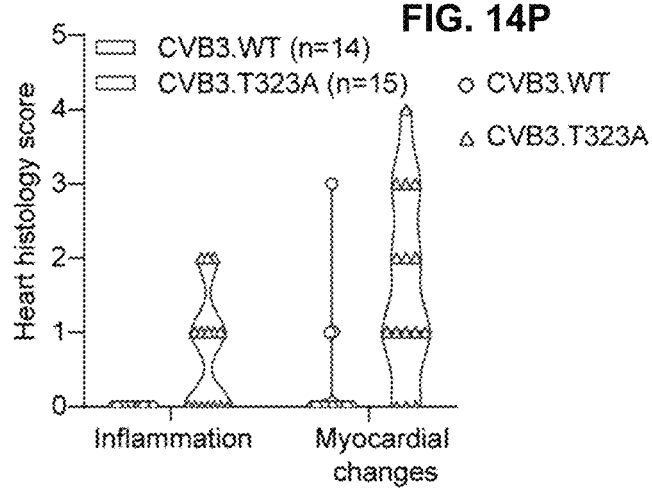
FIG. 14P shows histo-pathogenesis score of hearts (7 dpi) based on H&E sections. Scoring was based on severity of pathology using the following descriptors: Inflammation score: 0=Normal; 1=few inflammatory cells; 2=multifocal clusters with small numbers of cells; 3=Multifocal clusters with moderate numbers of cells; 4=Multifocal clusters with large numbers of cells. Myocardial Changes score: 0=Normal; 1=few foci of change (1-3); 2=Multiple foci with degeneration/necrosis/mineralization (<5%); 3=Multiple foci with degeneration/necrosis/mineralization (5-15%); 4=Multiple foci/coalescing area with degeneration/necrosis/mineralization (>15%).

Finally, histology was used to characterize the pathologic damage of multiple organs, including thigh muscle, heart, liver, spleen, pancreas, kidney, colon, ileum, and white and brown adipose tissue (3 and 7 days post-infection). Most organs (thigh muscle, liver, kidney, spleen, colon, ileum and brown adipose) were normal when comparing PBS treatment to viral infection at 3 or 7 days (data not shown). At 3 days post-infection, hearts were normal in PBS-injected and infected mice, but on day 7, a greater proportion of CVB3-T323A infected mice showed myocardial changes and inflammation in heart tissue (FIG. 14P). At 3 days post-infection, the pancreas of CVB3-T323A infected mice exhibited irreversible injury in most acinar cells and an influx of inflammatory cells between the pancreatic lobules (FIG. 7F). By contrast, the pancreas from mice infected with CVB3-WT had fewer injured acini. At 7 days post-infection, the pancreatic parenchyma showed significant inflammation, consisting of macrophages and lymphocytes, with marked acinar loss in CVB3-T323A infected pancreas (FIG. 7G). Notably, in all mice, CVB3 infection did not have apparent effects on the islets of Langerhans. Consistent with visible visceral fat necrosis (FIGS. 7C-7D), histopathologic analysis of white adipose tissue revealed that CVB3-T323A caused more severe damage than CVB-WT, with large regions of necrotic adipocytes surrounded by inflammatory cells (FIGS. 7H-7I). Thus, the marked lethality observed with CVB3-T323A was likely due primarily to a severe form of pancreatitis, consisting of high viral replication, exacerbated immunopathology, and irreversible pancreatic destruction.

SUMMARY AND CONCLUSIONS OF EXAMPLES 1-8

To control viral infection, vertebrates rely on both inducible interferon responses and less well-characterized cell-intrinsic responses composed of "at the ready" antiviral effector proteins. The data within Examples 1-8 showed that E3 ubiquitin ligase TRIM7 was a cell-intrinsic antiviral effector that restricted multiple human enteroviruses by targeting viral 2BC, a membrane remodeling protein, for ubiquitination and proteasome-dependent degradation. Selective pressure exerted by TRIM7 resulted in emergence of a TRIM7-resistant coxsackievirus with a single point mutation in the viral 2C ATPase/helicase. In cultured cells, the mutation helped the virus evade TRIM7 but impaired optimal viral replication, and this correlated with a hyper-active and structurally plastic 2C ATPase. Unexpectedly, the TRIM7-resistant virus had a replication advantage in mice and caused lethal pancreatitis. These findings in Examples 1-8 revealed unique mechanisms for targeting enterovirus replication and provided molecular insight into the benefits and trade-offs of viral evolution imposed by a host restriction factor.

Methods Used in Examples 1-8

The following provides descriptions of some exemplary methods and materials used in Examples 1-8 as disclosed herein:

Cell lines. 293T, HeLa, Huh7.5, C2C12, RD, and HepG2 cells were maintained in Dulbecco's Modified Eagle Medium (DMEM, Gibco) supplemented with 10% FBS (Gibco), 1% Penicillin-streptomycin (Gibco), and 1× non-essential amino acids (NEAA; Gibco). Vero-E6 cells were maintained Eagle's Minimum Essential Medium (MEM, Gibco) supplemented with 10% FBS, 1% Penicillin-streptomycin, and 1×NEAA. All these cells were cultured at 37° C. with 5% $CO_2$.

Virus. The following viruses were propagated as previously described: HCV-YPet, YFV-Venus, and VEEV-GFP (Schoggins et al., 2011), ONNV-GFP, CVB3-GFP, PV-GFP, and PIV3-GFP (Schoggins et al., 2014). ZIKV-GFP (Schwarz et al., 2016). Mengovirus, PV (Mahoney strain), and CVB3 (Nancy and H3 strain) were provided by J. Pfeiffer. EVD68 (US/MO14 strain) was provided by R. Orchard. Echovirus 11 (Gregory strain) and EV71 (1095 strain) were provided by C. Coyne. Ad5V-GFP was provided by R. Gerard. HeLa cells were used to propagate MenV, PV, and CVB3. EV71 and E11 viral stocks were prepared in Vero cells. EVD68 viral stocks were propagated in RD cells. The viral titers of MenV, PV, and CVB3 were quantified by plaque assay in HeLa cells. Virus yields of E11, EV71, and EVD68 were measured by TCI D50 assay in HeLa or RD cells. Non-human primate enterovirus Simian Agent-5 (SA5 picornavirus 17) was purchased from ATCC (Cat NO.: VR-952), amplified in Vero-E6 cells and titered by TCID50 assay. Echovirus 18 strain Jena/AN1367 (E18/T323) and Jena/AN1370 (E18/I323) were rescued in our lab from infectious DNA construct pT7-E18/AN1367 and pT7-E18/AN1370.

Mice. 2-day-old neonatal mice were bred in mouse facility. 5-week-old wild type C57Bl/6J mice were purchased from Jackson Laboratory. 6 to 7-week-old mice were used for virus infection.

Plasmid constructs. 118 RING type E3 ubiquitin ligase pENTR clones (Table 2) were obtained from N. Alto. These 118 E3 genes were subcloned into Lentivirus-based expression vector pTRIP.CMV.IVSb.ires.TagRFP-DEST (Schoggins et al., 2011) or pSCRPSY-DEST (Schoggins et al., 2012) using Gateway cloning.

To generate N-terminal HA-tagged gene expression constructs, the empty pTarget vector (Promega) was reengineered by inserting HA-tag coding sequence between BamHI and XhoI, and the new expression vector was named pTT-HA-C. All viral protein coding genes used in this study were subcloned into pTT-HA-C using XhoI and SacII. N-terminal StrepII-tagged wild type and mutated ubiquitin (K48 only and K48R) were custom-synthesized by Integrated DNA Technologies, Inc. and cloned into pRK5-HA-ubiquitin-WT plasmid (Addgene #17608) using SalI and NotI. For protein expression and purification, TRIM7 PRY/SPRY domain was cloned into pGEX4T-1 vector using EcoRI and XhoI. CVB3 N-terminal transmembrane region (1-115) deleted 2C (116-329) and its single mutation T323A and pocket-binding motif deletion were cloned into pHis-MBP-His vector using BamHI and NotI using Gibson Assembly. All constructs were verified by DNA sequencing.

Lentivirus production, transduction, and viral infection assays. Lentiviral production and transduction was performed as previous described (Schoggins et al., 2011). Briefly, $5 \times 10^5$ 293 T cells in 6-well plates or $1 \times 10^5$ cells in 24-well plates were co-transfected with plasmids expressing E3 (pTRIP-E3 or pSCRPSY-E3), HIV-1 gag-pol and VSV-G in a ratio of 1/0.8/0.2, respectively. For 6-well plate transfection, 6 μl X-tremeGENE HP (Roche) was combined with 2.0 μg total DNA in 100 μl Opti-MEM (Gibco). For 24-well plate transfection, 1.5 μl FuGENE (Roche) was combined with 0.5 μg total DNA in 25 μl Opti-MEM. Transfections were carried out for 6 h, followed by a medium change to DMEM containing 3% FBS. Supernatants were collected at 48 h and 72 h, pooled, cleared by centrifugation and stored at −80° C. For lentiviral transduction, HeLa or Huh7.5 cells were seeded in to 24-well plates at a density of $2 \times 10^4$ cells per well and transduced with lentivirus by spinoculation at 1000×g at 37° C. for 45 minutes (min) in medium containing 3% FBS, 20 mM HEPES, and 4 μg/mL polybrene.

For virus infection assay, then lentivirus transduced cells were split and reseeded in to 24-well plates 48 hours (h) post-transduction at a density of $4 \times 10^4$ cells per well. 16-24 h later, the cells were infected with the indicated reporter virus at low multiplicity of infection (MOI. 1 MOI=1 plaque formation unit per cell). The cells were harvested for FACS-based infectivity analysis. The harvest time for each virus was: CVB3-GFP, 8 h, ONNV-GFP, 24 h, VEEV-GFP, 24 h, PIV3-GFP 24 h, Adv5-GFP at 12 h, YFV-venus and ZIKV-GFP at 48 h.

Generation of CVB3 infectious clones and replicons. To generate a non-reporter wild type infectious clone of CVB3 [strain Woodruff, also known as H3 strain], the total RNA from wild type CVB3 infected cells was extracted. Subsequently, the cDNA was generated using SuperScript™ IV First-Strand Synthesis System (Invitrogen, Cat #18091050) to be template. Then, PCR was used to clone the full length CVB3 genome using Herculase II Fusion DNA Polymerase kit (Agilent Technologies, Inc., Cat #600675). It was then cloned into pCR-BluntII-TOPO vector (Invitrogen, Cat #K280002). This plasmid was named pCRII-T7-CVB3. The constructs were sequenced to verify the original sequence. The 2C mutated CVB3 used in these Examples was engineered by using overlap PCR to generate a fragment containing the mutation, then inserted into CVB3 infectious cDNA constructs using SpeI and PmlI.

For CVB3 replicon constructs, pCVB3-eGFP infectious clone (Feuer et al., 2002) was modified by inserting Rluc2A coding sequence using BstBI and NdeI restriction sites. The wild type CVB3 replicon was termed pCVB3-Rluc2A-RepWT. To make a replication-deficient replicon, the codons of the GDD polymerase active site "ggt gac gat" in viral 3D gene were replaced with "acg cgt", which encoded amino acids TR, and was recognized by restriction enzyme MluI. This plasmid was named pCVB3-RLuc2A-RepMut.

In vitro transcription of viral infectious RNA and replicon RNA. CVB3 viral RNA and replicon RNA were in vitro transcribed using T7 RiboMAX™ Express Large Scale RNA Production System (Promega, Cat #P1320). RNA was purified from the transcription reaction using RNeasy mini kit (Qiagen, Cat #74106) and quantified by Nanodrop.

Transfection of viral infectious RNA and replicon RNA. The TransIT®-mRNA Transfection Kit (Mirus Bio, Cat #MIR2250) was used for the transfection of infectious viral RNA and replicon RNA. To produce virus from in vitro transcribed RNA, HeLa cells were seeded in a 100 cm dish at a density of $4 \times 10^6$ cells the day before transfection. A total of 4 μg of viral RNA was transfected in each dish, and virus was harvested 36 to 48 hours post-transfection. For CVB3 replicon assays, cells were plated at a density of $5 \times 10^4$ cells per well in 24-well plates the day before transfection. 100 ng viral replicon RNA was transfected into the cells. The transfected cells were harvested at the indicated time points using Renilla lysis buffer. Renilla luciferase activity was quantified using the Renilla Luciferase Assay System (Promega, Cat #E2820) and LUMIstar OPTIMA Microplate Reader (BMG LABTECH).

CVB3 binding and entry assay. Confocal microscopy analysis of binding and entry: cells were seeded in Falcon 8-well culture slide (Cat #354118) at a density of $5 \times 10^3$ cells per well the day before infection. The cells were infected with CVB3 at 1,000 MOI and adsorbed to cells for 1.5 h at 4° C. with horizontal shaking. After adsorption, the cells were washed five times with cold FBS-free DMEM. For the binding assays, the cells were fixed using 4% PFA at the end of washing. For entry assays, the washed cells were incubated with pre-warmed medium containing 5% FBS at 37° C. for 30 min. The cells were then immediately chilled on ice and washed with cold DMEM three times, followed by three washes each of cold glycine buffer (pH 3.5) and cold DMEM. The cells were fixed with 4% PFA, PFA was removed, and the cells were washed with PBS three time at room temperature. Virus was visualized using anti-VP1 antibody staining according to the "Immunofluorescence assay and microscopy" procedure described below.

Plaque assay of binding and entry: cells were seeded in 24-well plates at a density of $1 \times 10^5$ cells per well the day before infection. The cells were infected with CVB3 at 100 MOI and adsorbed to cells for 1.5 h at 4° C. with horizontal shaking. The cells were processed as described in the preceding section. After the final wash, 200 μL FBS free DMEM was added into the wells, and the plates were placed in −80° C. for 1 h. After three freeze-thaw cycles, bound or internalized virus was quantified by plaque assay.

RNA extraction, reverse transcription PCR, and real-time PCR. Total RNA from tissue culture cells was extracted using RNeasy mini kit (Qiagen, Cat #74106) following the manufacturer's instructions. Total RNA from mouse tissue was extracted using TRIzol (Invitrogen). For RT-PCR assays, SuperScript IV First-strand synthesis system (Invitrogen, Cat #18091050) was used to generate the complementary DNA template.

For CVB3 strand-specific real-time RT-PCR, CVB3-5'UTR-forward primer (UTJS19202) was used to synthesize viral minus strand RNA, and CVB3-3'UTR-reverse primer (UTJS19203) was used to synthesize viral plus strand RNA. CVB3 genomic RNA copies were determined by quantitative RT-PCR using primer pairs targeting viral RNA encoding the 3C protein. Plasmid pTT-HA-3C was used as standard template. The real-time PCR was performed using Fast SYBR Green Master Mix (Applied Biosystem, Cat #4385612). All RT-qPCR reactions were performed using a 7500 FAST Real-time PCR machine (Applied Biosystems). Primer sequences are listed in Table S2.

Generation of TRIM7-resistant CVB3. CVB3 was serially passaged in HeLa-TRIM7 cells or control cells expressing Fluc. Briefly, the cells were infected with CVB3 at 10 MOI, and the supernatants were harvested 12 h post-infection. Then, 50% of the supernatant was used for the next round of infection. CPE was observed after the 4th passage. Plaque purification was used to isolate single clonal variants. The full-length viral genomes of TRIM7-resistant CVB3 or control passaged CVB3 were amplified by PCR and cloned into pCR-BluntII-TOPO vector. Plasmid were sequenced using fourteen primers spanning the CVB3 full-length genome (Table 3).

Immunofluorescence assay and confocal microscopy. For CVB3 infections, after fixation, the cells were permeabilized with 0.1% saponin in 1×PBS containing 3% BSA at 4° C. for 20 min and blocked in 1×PBS containing 3% BSA at RT for 1 h. Then the cells were incubated with VP1 primary antibody (EMD Millipore, Cat #MAB948, 1:1000) or anti-dsRNA antibody (J2, 1:1,000) in 1×PBS containing 1% BSA for 1 h at RT. Cells were washed five time with PBS, incubated with 1:5,000 Alexa Fluor-488 secondary antibodies (Invitrogen) in 1×PBS containing 1% BSA for 1 h at room temperature (23° C.±5° C.) in the dark, followed by five washes with PBS, and staining with ProLong™ Diamond Antifade Mountant with DAPI (Invitrogen, Cat #P36962).

For confocal immunofluorescence studies, the indicated antibodies and dyes were diluted as below: mouse anti-Flag (Sigma, M2, 1:1,000), rabbit anti-HA (Pierce, 1:1,000), goat-anti-mouse Alexa Fluor-488 (Invitrogen, 1:1,000), goat-anti-rabbit Alexa Fluor-488 (Invitrogen, 1:1,000), goat-anti-mouse Alexa Fluor-555 (Invitrogen, 1:1,000), goat-anti-rabbit Alexa Fluor-647 (Invitrogen, 1:1,000), Bodipy493/503 (ThermoFisher, Cat #3922, 15 μg/mL), ProLong™ Diamond Antifade Mountant with DAPI.

Protein lysate preparation and Western blot. Tissue culture cells were lysed in Nonidet P-40 (NP-40) buffer (50 mM Tris pH 7.4, 150 mM NaCl, 1% (v/v) NP-40, 1 mM EDTA, protease inhibitor cocktail) and incubated on ice for 30 min, followed by centrifugation at 13,000 rpm for 20 min at 4° C. For mouse tissue lysates, fresh tissues were collected in 2 ml round-bottom Eppendorf tubes containing NP40 lysis buffer and cut to small pieces using scissors. Then the tissues were homogenized with a Bullet Blender homogenizer (Next Advanced Inc., Averill Park, NY), and centrifuged at 13,000 rpm for 20 min at 4° C. Western blot analyses were performed as previously described (Mar et al., 2018).

The following antibodies were used for immunoblotting: mouse anti-Flag (Sigma, M2, 1:5,000), rabbit anti-Flag (Sigma, 1:5,000), mouse anti-HA (Pierce, 1:5,000), rabbit anti-HA (Pierce, 1:5,000), HRP-conjugated Actin (Sigma, Cat #A3854 1:10,000), mouse anti-GAPDH (Abclonal, Cat #AC002, 1:5,000), mouse anti-Strep (ThermoFisher, Cat #MA5-17283, 1:1,000), rabbit anti-TRIM7 (Sigma, Cat #HPA039213, 1:1,000), mouse anti-CVB3 VP1 (provided by C. Coyne, 1:1,000), rabbit anti-CVB3 3A and 2C were kindly provided by J. L. Whitton (3A, 1:5,000; 2C, 1:1,000) (Cornell et al., 2007).

Co-immunoprecipitation and StrepII-3×Flag tandem affinity purification. For Co-IP assays, plasmids expressing genes of interest were co-transfected into 293T cells in 6-well plate. The cells were harvested at 30 h post-transfection and lysed in 400 μL NP40 lysis buffer containing protease inhibitors. After incubation on ice for 30 min, lysates were cleared by centrifugation at 13,000 rpm for 20 min at 4° C. Subsequently, a proportion of the cell lysate was saved for analysis as input, and another proportion was subjected to precipitation with anti-HA magnetic beads (Pierce, Cat #88837) or Anti-Flag M2 affinity Gel (Sigma, Cat #A2220) overnight at 4° C. with rocking. The next day, the beads or gel were washed seven times with IP wash buffer (50 mM Tris pH 7.4, 500 mM NaCl, 0.1% (v/v) NP-40, 1 mM EDTA). Precipitated proteins were eluted from beads or gel by heating sample in SDS loading buffer at 75° C. for 15 min.

For cell-based ubiquitination assays, plasmids expressing HA-2BC, StrepII-Ubi, and TRIM7-3F were co-transfected into 293T cells in 6-well plates. Proteasome inhibitor MG132 (10 μM) was added into culture medium at 24 h post-transfection, and the cells were harvested at 30 h post-transfection. The cell lysates were subjected to precipitation with HA-Beads or Strep-beads overnight at 4° C. clod room. Precipitated proteins were eluted from beads or gel by heating samples in SDS loading buffer at 75° C. for 15 min.

To identify TRIM7-interacting proteins, StrepII-3×Flag tandem affinity purification was performed as described (Ma et al., 2017) with the following modifications. Briefly, HeLa-TRIM7 cells in two 150-cm dishes were infected with CVB3 at 25 MOI in the presence of MG132 for 6 h. Total cell lysate (1.5 mL) was separated into two equal volumes and subjected to first affinity with anti-Flag or anti-IgG beads overnight at 4° C. cold room with rolling. The next day, beads were washed seven times with IP wash buffer. The precipitated proteins were eluted using 3×Flag peptides (Sigma, Cat #F4799). The volume of eluted proteins was adjusted to 400 μL with IP wash buffer, then incubated with Strep-Tactin Beads (IBA, Cat #2-1206-002) for 4 h at 4° C. with rocking for a second affinity purification. After seven washes, the precipitated proteins were eluted with Strep-Tactin elution buffer (IBA, Cat #2-1000-025: 100 mM Tris-HCl pH 8.0, 150 mM NaCl, 1 mM EDTA, and 2.5 mM Desthiobiotin). To identify TRIM7 interacting proteins, the eluted proteins were separated on a gradient gel (BioRad, 4-20% precast polyacrylamide gel) at 120V for 5-10 min, until the protein ladder run ~1 cm into gel. Then the gel was stained with Coomassie blue for 1 h at RT. After destaining of the gel, the stained area was cut into slices and each slice was placed into an Eppendorf 1.5 mL tube, which had been previously rinsed with 50% acetone and millipure water. Proteins were identified by mass spectrometry by the UT Southwestern Proteomics Core.

Gene silencing use shRNA and siRNA. To knockdown endogenous TRIM7 expression in HepG2 cells, the cells were transduced with lentivirus-expressing short hairpin RNA (shRNA) that targets TRIM7 or control LacZ gene. To knockdown endogenous Trim7 expression in C2C12 cells, the cells were transfected with 50 nM siRNA that targets mouse Trim7 using lipofectamine RNAiMax transfection reagent (Invitrogen, Cat #13778030) following the manufacturer's instructions. Non-targeting siRNA was used as control. The custom-synthesized shRNA sequences were ordered from Sigma, then cloned into pLKO.1 vector. The custom-synthesized siRNA duplexes were ordered from Sigma. All synthesized sequences are listed in Table 3. Knockdown efficiency of endogenous TRIM7 expression was confirmed by Western blot using an antibody against TRIM7.

Recombinant protein expression and purification. For experiments to study interactions between TRIM7 and wild type or mutated 2C, GST-tagged TRIM7 PRY/SPRY domain, His-MBP-His-tagged 2C 116-329 region and its mutants with T323A or pocket-binding motif deletion were expressed on E. coli BL21 (DE3) cells. To express 2C proteins and a control protein His-MBP-His, the cells were grown at 37° C. and induced overnight at 18° C. with isopropyl-b-D-thiogalactopyranoside (IPTG, 0.1 or 0.3 mM). To express GST-TRIM7-PRY/SPRY, the cells were grown at 37° C. and induced overnight at 12° C. with 0.3 mM IPTG. Bacteria expressing 2C proteins were harvested by centrifugation and resuspended in lysis buffer containing 50 mM Tris-HCl (pH 7.5), 150 mM NaCl, 25 mM imidazole, 0.5 mM TCEP, and 1×EDTA-free protease inhibitor. The cells were disrupted using high pressure homogenization with Avestin Emulsiflex-05 machine. The lysates were cleared by centrifuging at 9,000×g for 30 min at 4° C. Lysates were then incubated with Ni-NTA agarose (Qiagen, Cat #30210) at 4° C. for 2 h with rocking. After multiple washes in wash buffer (50 mM Tris-HCl (pH7.5), 150 mM NaCl, 50 mM imidazole), proteins were eluted in buffer containing 50 mM Tris-HCl (pH7.5), 150 mM NaCl, and 500 mM imidazole. For GST-TRIM7PRY/SPRY purification, a similar strategy was employed, using Glutathione Sepharose 4B (GE, 17-0756-05) for pulldown and 10 mM reduced glutathione (Fisher Scientific, Cat #BP2521-100), 1 mM DTT for elution.

In vitro binding assay. 20 μg of purified protein His-MBP-His, His-MBP-His-2CΔN.WT, His-MBP-His-2CΔN.T323A, and His-MBP-His-2CΔN.ΔPBM were preincubated with Ni-NTA magnetic beads (NEB, Cat #514235) in binding buffer (50 mM Tris-HCl (pH 7.5), 150 mM NaCl, 25 mM imidazole, 0.5 mM TCEP) in a total volume of 500 μL for 1 h at room temperature. Beads were washed five times with wash buffer. Subsequently, 20 μg GST-TRIM7PRY/SPRY was resuspended in 500 μL binding buffer (50 mM Tris-HCl (pH7.5), 150 mM NaCl, 0.1 mM EDTA), and incubated with the pretreated Ni-NTA beads for 1 h at room temperature (RT). The bound proteins were eluted with 500 mM imidazole elution buffer. The eluted proteins were boiled in SDS loading buffer at 75° C. for 15 min, then separated using SDS-PAGE gel, followed by staining with Coomassie blue.

ATPase activity assay. The concentration of purified proteins was determined by the Pierce BCA protein assay kit (ThermoFisher Scientific, Cat #23227) according to the manufacturer's instructions. The 2C ATPase activity was performed using the QuantiChrom ATPase assay kit (BioAssay Systems, Cat #DATG-200) according to the manufacturer's protocol.

Isolation of endoplasmic reticulum and lipid droplets. For isolation of endoplasmic reticulum (ER) and lipid droplets (LDs) from CVB3 infected cells, HeLa-TRIM7CA-3F cells were mock-infected or infected with 10 MOI CVB3. Cells were harvested 6 h post-infection by trypsinization, and collected by centrifugation at 4° C., 1500×g, for 5 min. The cells were then washed twice with 10 volumes of ice chilled 1×PBS, followed by two washes with 10 volumes of cold hypotonic buffer (50 mm HEPES pH7.4, 2 mM MgCl2, 1 mM EDTA, 250 mM sucrose). Next, cell pellets were resuspended in 5 volume of hypotonic buffer and incubated on ice for 30 minutes. Cells were collected by centrifugation at 4° C., 1500×g for 5 min. Cells were then resuspended in hypotonic buffer containing protease inhibitors and homogenized by dounce homogenizer to achieve at least 90% disruption. Post-nuclear supernatants (PNS) were isolated by centrifugation at 4° C., 1500×g for 10 min. Subsequently, the post-mitochondria supernatants (PMS) were isolated by centrifugation at 4° C., 15,000×g for 15 min. The protein concentration of PMS isolated from infected and mock-infected cells were determined using BCA assay. Equal amounts of protein in PMS fractions were adjusted to 3 mL using hypotonic buffer containing protease inhibitors. 3 mL of isotonic buffer (50 mM HEPES pH 7.4, 100 mM KCl, 2 mM MgCl2) containing 60% sucrose was added, for a total of 6 mL of 30% sucrose solution. The 6 mL were overlaid in ultracentrifugation tubes with 2 mL of 18% sucrose in isotonic buffer, 2 mL of 10% sucrose in isotonic buffer and 2 mL of isotonic buffer. Samples were centrifuged at 35,000 rpm for 3 hours at 4° C. using SW40Ti rotor (Beckman Coulter). 0.6 ml fractions containing lipid droplets were collected from the top and transferred to 2 mL microcentrifuge tubes containing 1 mL of isotonic buffer. Fractions were centrifuged at 20,000×g for 30 minutes at 4° C. A gel loading tip was used to remove the underlying solution until the sample volume was minimized to 50 μL. Samples were mixed with 1 volume of 2×SDS loading buffer, boiled and analyzed by Western blot. For ER isolation, following LDs fractionation, the bottom pellets were resuspended in cold 1×PBS and collected by centrifugation at 4° C., 15,000×g for 10 min. Pellets were washed three times with cold PBS and dissolved in NP40 lysis buffer containing protease inhibitors. The protein concentration of ER fraction was determined by BCA assay and equal protein amount was used for Western blot analysis. Two independent isolation were performed for each experimental condition.

2C modeling and molecular simulation. A dimer model of CVB3 was constructed using the crystal structure of EV71 (pdb id: 5gq1) (Guan et al., 2017). Point mutations were performed on this EV71 structure to obtain the corresponding CVB3 WT and mutant dimer structures, by using COOT software (Emsley et al., 2010). The two Zn ions (one for each monomer) were included and the missing residues were inserted with their most probable rotomeric forms. Then, dodecahedron simulation boxes were generated for each system imposing periodic boundary conditions, with the inclusions of SPCE explicit waters and neutralizing ions. AMBER99sb-ildn force-field (Lindorff-Larsen et al., 2010) was used for all simulations. After an initial converged steepest descent energy minimization, 10 ns of NVT and 20 ns of NPT (first 10 with Berendsen (Eslami et al., 2010) and the last 10 with Parrinello-Rahman (Parrinello and Rahman, 1981) barostats) thermal equilibrations at T=300 K and P=1 atm were performed. We employed 2 fs time steps in production level trajectories where simulations were run under NPT ensemble with Parrinello-Rahman barostat. Long-range electrostatics were handled with Particle Mesh Ewald (PME) (Darden et al., 1993) summation. All simulations were performed by Gromacs package (Abraham et al., 2015) on UTSW's biohpc computing cluster.

500 ns production level MD trajectory were obtained for each mutant. Two post-simulation analyses were carried out. First, the (mass-weighted) covariance matrix was calculated and diagonalized to obtain eigenvalues and eigenvectors, by fitting each MD frame to the initially equilibrated crystal structure. Then, principal component analyses were done by projecting the overall MD trajectory along each of the first 3 largest eigenvectors. This procedure to extract important dynamical information is also commonly known as "essential dynamics" (Amadei et al., 1993; David and Jacobs, 2014). As a second analysis, radius of gyration of the ATP binding pocket was calculated, and associated probability distributions were obtained. Here, the ATP binding residues from crystallographic structures were used to define the binding pocket (Guan et al., 2017). Simulation convergences were assessed by calculating associated errors as the half of the difference between first and second halves of a given simulation.

Virus infection in mice. All mice were handled according to the Guide for the Care of Laboratory Animals of the National Institutes of Health. All mouse studies were performed in a manner designed to minimize pain, and any animals that exhibited severe disease were euthanized immediately. Female C57BL/6J mice were inoculated by i.m. route with $1 \times 10^6$ PFU or i.p. $1 \times 10^4$ PFU of CVB3-WT or CVB3-T323A per mouse. Mice were sacrificed at 2-day post-infection, and thigh muscle (i.m. only), heart, liver, and spleen were harvested. Viral titers in pancrease were determined 3 days post-infection via i.m. route. To determine viral titers, fresh tissues were weighed and homogenized with a Bullet Blender homogenizer (Next Advanced Inc., Averill Park, NY), followed by plaque assay to quantitate viral genomes as described above.

To assess the antiviral activity of TRIM7 in vivo using lipid nanoparticle-delivered mRNAs, synthetic RNAs were purchased from Trilink Biotechnologies. This included the manufacturer's "CleanCap Fluc mRNA" and a pseodouridylated, capped, and polyadenylated murine Trim7 RNA. mRNA delivery to the liver was achieved via Selective ORgan Targeting Lipid Nanoparticles (SORT LNPs) (Cheng et al., 2020). Liver SORT LNPs consisted of five lipids with fixed 5A2-SC8:DOPE:cholesterol:DMG-PEG2000: DODAP ratio of 15:15:30:3:15.8 (molar), wherein 5A2-SC8 was synthesized as reported previously (Zhou et al., 2016). Commercial lipids 1,2-dioleoyl-sn-glycero-3-phosphoethanolamine (DOPE), cholesterol, 1,2-dimyristoyl-rac-glycero-3-methoxypolyethylene glycol-2000 (DMG-PEG2000) and 1,2-dioleoyl-3-dimethylammonium-propane (DODAP) were purchased from Avanti Polar Lipids. To form LNPs-mRNA formulations, all required lipids were dissolved in ethanol and mRNA in 10 mM citrate buffer (pH 4.0), followed by rapidly mixing the above two solutions at a volume ratio of 1:3 (ethanol to buffer) to reach the final weight ratio of 40:1 (total lipids to mRNA). After standing at room temperature 15 min, LNPs-mRNA formulations were dialyzed against 1×PBS for 2 hours before intravenous injection into mice. Wild type female mice were administrated 10 μg mRNA per mouse via intravenous injection (i.v.) to tail vein (n=7 each group). At 6 hours post i.v. administration, mice were challenged i.p. with CVB3 at $10^4$ PFU per mouse. Livers were harvested at 2-day post infection. Virus loading in liver and spleen were determined by plaque assay. The expression and antiviral potential of mTrim7 from LNPs was independently confirmed in cell culture by delivering mRNA to HeLa cells, followed by Western blot and a CVB3-GFP inhibition assay, as described above.

For in vivo growth-competition assay, female C57BL/6J mice were co-infected by i.m. and i.p. route with an equal amount of CVB3-WT and CVB3-T323A, for a total of $10^6$ (i.m.) or $10^4$ (i.p.) PFU virus. The liver and spleen were harvested at 2-day post-infection. Viral RNA was isolated and reverse transcription was performed using oligo-dT to generate cDNA template. Primer pairs forward-UTJS19019 and reverse-UTJS20101 (Table 3) were used in a PCR reaction to amplify a 505 bp fragment that containing the T323A mutation site. Due to introduction of a BglI restriction site at the T323A mutation, BglI digestion was performed on the PCR products to distinguish the cDNA templates that came from CVB3-WT and CVB3-T323A. Only PCR products amplified from the CVB3-T323A, but not CVB3-WT could be cut, resulting in two fragments of 155 bp and 305 bp (Figure S7A). To quantify the proportion of CVB3-WT and CVB3-T323A, the intensity reduction of the 505 bp bands post BglI digestion was analyzed using ImageJ (FIG. 13D) (Schindelin et al., 2012). The intensity of individual 505 bp bands was measured, and the intensity scores were used to label peak images in Figure S7B. To quantify the proportion of CVB3-WT and CVB3-T323A, the intensity reduction of the 505 bp bands post BglI digestion was analyzed using ImageJ (FIGS. 13E-13F) (Schindelin et al., 2012). The intensity of individual 505 bp bands were measured, the intensity score inserted in peak images in FIGS. 13E-13F. To present the proportion of CVB3-WT and CVB3-T323A, the value of band intensity. The PCR products were also sequenced using sanger DNA sequencing to analyze the mixture of CVB3-WT and CVB3-T323A by analyzing the sequencing chromatogram (FIGS. 13I-13K).

Metabolic phenotyping and histology. Blood urea nitrogen (BUN), alanine transaminase (ALT), amylase (AMYL), and lipase (LIPA) were measured in fresh, unfrozen serum using VITROS MicroSlide Technology by the UTSW Mouse Metabolic Phenotyping Core. Muscle, heart, liver, pancreas, perigonadal white fat, and other mouse organs were fixed in 10% neutral buffer formalin, dehydrated, cleared, and infiltrated with paraffin. 5 μm paraffin sections were prepared from harvested organs and independently reviewed by a pair of blinded pathologists.

RNA expression profiling. Thigh muscle and liver were harvested at 2 dpi and pancreas was harvested at 3 dpi. The total tissue RNA was isolated using TRIzol (Invitrogen). The concentration and quality of RNA samples were determined using Bioanalyzer 2100 (Agilent). Gene expression profiling was performed with the nCounter PanCancer Immune Profiling Panel (NanoString, Cat #115000142, XT_PGX_MmV1_CancerImm_CSO) using the nCounter Analysis System (NanoString) per manufacturer's protocol. RNA quantification, processing, and gene expression profiling were performed by the UTSW Microarray and Immune Phenotyping Core Facility. Gene expression data for all tissues was analyzed with nSolver 4.0 using the Advanced Analysis plugin, version 2.0 (NanoString), per manufacturer's protocol. The background signal was calculated as the average of negative controls multiplied by 2 times the standard deviation of negative controls. The threshold background value was determined independently for each tissue by multiplying the maximum background signal by two. A frequency cutoff was applied with nSolver, such that genes with detection levels below a tissue-specific threshold background value in greater than 40% of samples (liver and muscle) or 70% of samples (pancreas) were automatically omitted from the data set prior to gene set and differential expression analysis. Clustering of differentially expressed genes was performed with Morpheus (Broad Institute).

Luminex assays. The profiling of mouse chemokines and inflammatory cytokines from serum samples were detected and quantified using Bio-Plex Mouse Chemokine Panel 31-Plex assay (Cat #12009159). The assay was carried out by the UTSW Microarray and Immune Phenotyping Core Facility according to the manufacturer's protocol. A single analysis was done for each mouse. In results presentation, a heat map was generated using the average of log 2-fold change in concentration of each infected group of mice compared to PBS treated mice. Violin plots present the concentration of the indicated cytokines or chemokines (picograms/milliliter).

Quantification and Statistical Analysis. All data were presented as means±SD and analyzed using GraphPad Prism software (version 8). Individual statistical tests are specified within the figure legends. For data with two groups, unpaired students' t-tests were used under the assumption of normality. Data with more than two groups were analyzed by analysis of variance (ANOVA) under assumption of normality. In general, at least three independent biological replicates (n) were carried out for each experiment. Data were reproduced in independent experiments as indicated in the legends.

TABLE 3

| Name (UTJS) | Sequence | Notes | SEQ ID NO: |
|---|---|---|---|
| UTJS18422 | GCAGGCTTGGAAGGAGTTCGAACCATGGGTCCTGCATTTGAATTTGC | CVB3C-F: | 7 |
| UTJS18423 | CCAAGCGCTCCCTCCTCCGGATCCTTGTTCATCATTGAAATAGTGC | CVB3C-R: | 8 |
| UTJS18474 | GAGttcgaa ccATGGCGGCTGTGGGACCGCGGACC | TRIM7-F(BsfBI) | 9 |
| UTJS18475 | GGAagatct AGGCCAGATTCGCAAGTAGGTG | TRIM7-R (BgIII) | 10 |
| UTJS18476 | GGAagatctCATCCCTTTTAAGACAAAGG | TRIM7dSPRY-R (BgIII) | 11 |
| UTJS18477 | GAGCTGCAGGGCGAGGCGACGGCCTCCATCGCCCTAGAGCTCTTTCGTGAGCCGGTG | TRIM7CA-F | 12 |
| UTJS18478 | CACCGGCTCACGAAAGAGCTCTAGGGCGATGGAGGCCGTCGCCTCGCCCTGCAGCTC | TRIM7CA-R | 13 |
| UTJS18479 | CGGactagt accATGGCGGCTGTGGGACCGCGG | TRIM7-RFP-F (SpeI) | 14 |
| UTJS18509 | GGAACTCAAGCACAGTGAAG | qCVB3-3C-F | 15 |
| UTJS18510 | AGCCTCTGATGTCTCTGAAC | qCVB3-3C-F | 16 |
| UTJS18511 | TACAGACATGGTGCGAAGAG | qCVB3-5'UTR-F | 17 |
| UTJS18512 | AACACGGACACCCAAAGTAG | qCVB3-5'UTR-F | 18 |
| UTJS18541 | CCGGCTGGAGGACTGTGAGGTGTTCCTCGAGGAACACCTCACAGTCCTCCAGTTTTT | shTRIM7-1F | 19 |
| UTJS18542 | AATTAAAAACTGGAGGACTGTGAGGTGTTCCTCGAGGAACACCTCACAGTCCTCCAG | shTRIM7-1R | 20 |
| UTJS18543 | CCGGCCATCTGCCTAGAGCTCTTTCCTCGAGGAAAGAGCTCTAGGCAGATGGTTTTT | shTRIM7-2F | 21 |
| UTJS18544 | AATTAAAAACCATCTGCCTAGAGCTCTTTCCTCGAGGAAAGAGCTCTAGGCAGATGG | shTRIM7-2R | 22 |
| UTJS18545 | CCGGCGCTAAATACTGGCAGGCGTTCTCGAGAACGCCTGCCAGTATTTAGCGTTTTT | shLacZ-F | 23 |
| UTJS18546 | AATTAAAAACGCTAAATACTGGCAGGCGTTCTCGAGAACGCCTGCCAGTATTTAGCG | shLacZ-R | 24 |
| UTJS19007 | GTGGCATGCCATCTGGATGTTCTGGCACAAGC | CVB3-3Dd-F(SphI) | 25 |
| UTJS19008 | GATCAATTCAGGATGATTGCTTATACGCGTGTGATTGCATCATACCCGTGGC | CVB3-dDD-OF(MIuI) | 26 |
| UTJS19009 | GCCACGGGTATGATGCAATCACACGCGTATAAGCAATCATCCTGAATTGATC | CVB3-dDD-OR(MIuI) | 27 |
| UTJS19010 | CCCCCTCGA GGTCGACGGTATCGATTT | CVB3-3Dd-R(XhoI) | 28 |
| UTJS19019 | tccCCGCGG CTACTGCACTTTTGCTTGCCTTAG | 3AB-R(SacII) | 29 |
| UTJS19020 | ccgCTCGAGGGTCCACCAGTATACAGAGAG | CVB3-3A-F(XhoI) | 30 |
| UTJS19021 | tccCCGCGG CTATTGAAAGCCTGCAAAGAGCTTG | CVB3-3A-R(SacII) | 31 |
| UTJS19022 | ccgCTCGA GGGTCCTGCATTTGAATTTGCTG | CVB3-3C-F(XhoI) | 32 |
| UTJS19023 | tccCCGCG GCTATTGTTCATCATTGAAATAGTG | CVB3-3C-R(SacII) | 33 |
| UTJS19024 | ccgCTCGA GGGAGAGATCGAGTTTATTGAGAG | CVB3-3D-F(XhoI) | 34 |
| UTJS19025 | tccCCGCGG CTAGAAAGAGTCCAACCACTTCCTAC | CVB3-3D-R(SacII) | 35 |

TABLE 3-continued

| Name (UTJS) | Sequence | Notes | SEQ ID NO: |
|---|---|---|---|
| UTJS19026 | ccg*CTCGAG* GGACAACAATCAGGGGCAGTATAC | CVB3-2A-F(XhoI) | 36 |
| UTJS19027 | tcc*CCGCGG* CTACTGTTCCATTGCATCATCTTCCAG | CVB3-2A-R(SacII) | 37 |
| UTJS19028 | ccg*CTCGAG* GGAGTGAAGGACTATGTGGAAC | CVB3-2B-F(XhoI) | 38 |
| UTJS19029 | tcc*CCGCGG* CTATTGGCGTTCAGCCATGGGTATTC | CVB3-2B-R(SacII) | 39 |
| UTJS19030 | ccg*CTCGAG* AACAACGGATGGCTAAAAAAGTTC | CVB3-2C-F(XhoI) | 40 |
| UTJS19031 | tcc*CCGCGG* CTACTGGAACAGTGCCTCAAGGGTAG | CVB3-2C-R(SacII) | 41 |
| UTJS19190 | TGGCCATCCGGTGTCTAATAGA | CVB3-Gseq-F1 | 42 |
| UTJS19191 | AGGACTGTTTGGGCAGAACATG | CVB3-Gseq-F2 | 43 |
| UTJS19192 | CGTCACGCCAGAGATGAGGATA | CVB3-Gseq-F3 | 44 |
| UTJS19193 | GCCCAAAGCTCCTGTTACATCA | CVB3-Gseq-F4 | 45 |
| UTJS19194 | TGTGTTTTGGACCGAGGGAAAC | CVB3-Gseq-F5 | 46 |
| UTJS19195 | AGGAGATACCAATCCCATGTGCT | CVB3-Gseq-F6 | 47 |
| UTJS19196 | CTGAGGTCAGGGAAAAACACGA | CVB3-Gseq-F7 | 48 |
| UTJS19197 | AACGCTCCAACTGTGTCAGACA | CVB3-Gseq-F8 | 49 |
| UTJS19198 | ACGTTTGTGTCAGTAGCTGGAA | CVB3-Gseq-F9 | 50 |
| UTJS19199 | TACAACTTCCCCACGAGAGCAG | CVB3-Gseq-F10 | 51 |
| UTJS19200 | TGTGAAAGACGAACTCAGATCTGC | CVB3-Gseq-F11 | 52 |
| UTJS19201 | TGCAACTCCCATCACCTGTACA | CVB3-Gseq-F12 | 53 |
| UTJS19202 | GTG***GCGGCCGC***TTAAAACAGCCTGTGGGTTG ATCCCACC | CVB3-5utr-F/NotI | 54 |
| UTJS19203 | GGT***ATCGAT***TTTTTTTTTTTTTTTCCGCACCG AATGCGGAGAATTTAC | CVB3-3utr-R/CIaI | 55 |
| UTJS19204 | GAACTGTATGTAATTACTCATCCGCTTCTCAA GGGAGAACACTC | CVB3.2C(K107R)-OR | 56 |
| UTJS19205 | GAGTGTTCTCCCTTGAGAAGCGGATGAGTAAT TACATACAGTTC | CVB3.2C(K107R)-OF | 57 |
| UTJS19303 | GAGttcgaaccATGGCGGCTGTGGGACCGCGGA CCGGCCCCGGAACCGGCGCCGAGGCTC | TRIM7-F(BstBI) | 58 |
| UTJS19331 | tCCCCGCGGCTACTGGAACAGTGCCTCAAGGG CAGC | CVB3-2Ct323a R(SacII) | 59 |
| UTJS19332 | ccgCTCGAGGGCGTATCTGATTACATTAAAG | EV71-2BC-F/xhoI | 60 |
| UTJS19333 | tCCCCGCGGCTATTGGAAAAGAGCTTCAATGGT G | EV71-2BC-R/sacII | 61 |
| UTJS19334 | *TGTTCCAGATTACGCTCTCGAG* GGCCTCACCAATTACATAGA | PV-2BC-F | 62 |
| UTJS19335 | *CGGCCGCAGTCGACGGTACCCC* CTATTGAAACAAAGCCTCCATAC | PV-2BC-R | 63 |
| UTJS19336 | CcgCTCGAGGGCATTACTGATTATATTCAAAAT C | EVD68-2BC-F/XhoI | 64 |
| UTJS19337 | tccCCGCGGCTACTGAAACAGAGCTTCCAGCTT ATC | EVD68-2BC-R/SacII | 65 |
| UTJS19338 | CCgCTCGAGGGGCCGAGCTTGGACTTCG | EV71-3C-F/xhoI | 66 |

TABLE 3-continued

| Name (UTJS) | Sequence | Notes | SEQ ID NO: |
|---|---|---|---|
| UTJS19339 | tCCCCGCGGCTATTGTTCACTGCAAAAGTATC | EV71-3C-R/sacII | 67 |
| UTJS19340 | ccgCTCGAGGGACCAGGGTTCGATTACG | PV-3C-F/xhoI | 68 |
| UTJS19341 | tCCCCGCGGCTAACTCTGAGTGAAGTATGATC | PV-3C-R/sacII | 69 |
| UTJS19342 | CcgCTCGAGGGACCAGGGTTCGATTTTGC | EVD68-3C-F/XhoI | 70 |
| UTJS19343 | tccCCGCGGCTAAAAAACTTGATGGAAAACAC | EVD68-3C-R/SacII | 71 |
| UTJS19361 | tccCCGCGGCTAAGCCCCGACACTGTGCCTGTGG | CVB3-2CdC7-R/SacII | 72 |
| UTJS19368 | cgcGTCGACGGCGTATCTGATTACATTAAAG | EV71-2BC-F/SaII | 73 |
| UTJS19369 | cgcGTCGACGGCCTCACCAATTACATAGA | PV-2BC-F/SaII | 74 |
| UTJS19370 | tccCCGCGGCTATTGAAACAAAGCCTCCATAC | PV-2BC-R/SacII | 75 |
| UTJS19375 | CATGGCGGTGGCTTAAGCAGAGAGTGTCCCAATATTACGGAATAC | 2BC.K86R-F | 76 |
| UTJS19376 | GTATTCCGTAATATTGGGACACTCTCTGCTTAAGCCACCGCCATG | 2BC.K86R-R | 77 |
| UTJS19377 | CTGAGATGACAAACGCCTGCAGGGGCATGGAATGGATAGCCAT | 2BC.K115R-F | 78 |
| UTJS19378 | ATGGCTATCCATTCCATGCCCCTGCAGGCGTTTGTCATCTCAG | 2BC.K115R-R | 79 |
| UTJS19379 | GTAATTACATACAGTTCAAGTCCAGATGCCGTATTGAGCCTGTATG | 2BC.K216R-F | 80 |
| UTJS19380 | CATACAGGCTCAATACGGCATCTGGACTTGAACTGTATGTAATTAC | 2BC.K216R-R | 81 |
| UTJS19381 | CATGGGAGTCCCGGTGCAGGTAGGTCAGTTGCAACAAATCTGATC | 2BC.K234R-F | 82 |
| UTJS19382 | GATCAGATTTGTTGCAACTGACCTACCTGCACCGGGACTCCCATG | 2BC.K234R-R | 83 |
| UTJS19383 | GTTGCCCAGTCAACTTTAAGAGATGTTGCCCGTTAGTCTGTGGAAAG | 2BC.K379R-F | 84 |
| UTJS19384 | CTTTCCACAGACTAACGGGCAACATCTCTTAAAGTTGACTGGGCAAC | 2BC.K379R-R | 85 |
| UTJS19395 | ccgCTCGAGCCTTTCACGTTTAAACCAAGAC | MenV-2B/F-XhoI | 86 |
| UTJS19396 | tccCCGCGGCTACTGCTGTTGGAAAAGTGAGATC | MenV-2B/R-SacII | 87 |
| UTJS19397 | ccgCTCGAGTCCCCCCTTAAACAGGTCAATG | MenV-2C/F-XhoI | 88 |
| UTJS19398 | tccCCGCGGCTATTGGGCCACAAGGGTCTGCAC | MenV-2C/R-SacII | 89 |
| UTJS19424 | AATCACTAGTGGGTCAAGACTCCATC | CVB3-2B/SpeI-F | 90 |
| UTJS19425 | CATCCACGTGTGTGTTAACATTCCCG | CVB3-3D/PmII-R | 91 |
| UTJS19426 | AGGCACAGTGTCGGGGCTGTCCTTGAGGCACTGTTCCAGGGTC | CVB3-2C/T323V-F | 92 |
| UTJS19427 | GACCCTGGAACAGTGCCTCAAGGACAGCCCCGACACTGTGCCT | CVB3-2C/T323V-F | 93 |
| UTJS20027 | GTACTTCCAATCCGGAGCGGCTGTGGGACCGCGGAC | MBP-hTRIM7-F | 94 |
| UTJS20028 | ggtggtgctcgagTGCGGCCGCTCAAGGCCAGATTCGCAAGTAGGTG | MBP-hTRIM7-R | 95 |

TABLE 3-continued

| Name (UTJS) | Sequence | Notes | SEQ ID NO: |
|---|---|---|---|
| UTJS20029 | GTACTTCCAATCCGGA TCCAAATGCCGTATTGAGCCTG | MBP-2CDN-F | 96 |
| UTJS20030 | ggtggtgctcgagTGCGGCCGCCTACTGGA ACAGTGCCTCAAG | MBP-2CDN_WT/T323A-R | 97 |
| UTJS20031 | ggtggtgctcgagTGCGGCCGCTCAAGCCC CGACACTGTGCCTGTG | MBP-2CDNDPBM-R | 98 |
| UTJS20091 | GTACTTCCAATCCGGA GACGAGGCGGTGCAGGAGGCC | MBP-hTRIM7CSP-F | 99 |
| UTJS20092 | GTACTTCCAATCCGGA CTCAGCAGCCAGATCCAGGAG | MBP-hTRIM7SP-F | 100 |
| UTJS20093 | CAACCACAGGCACAGTGTCGCGGCTACCCTT GAGGCACTGTTC | CVB3/G321A-F | 101 |
| UTJS20094 | GAACAGTGCCTCAAGGGTAGCCGCGACACTG TGCCTGTGGTTG | CVB3/G321A-R | 102 |
| UTJS20099 | CAACCACAGGCACAGTGTCGCGGCTGCCCTT GAGGCACTGTTC | CVB3/G321A_T323A-F | 103 |
| UTJS20100 | GAACAGTGCCTCAAGGGCAGCCGCGACACTG TGCCTGTGGTTG | CVB3/G321A_T323A-R | 104 |
| UTJS20168 | CAGGCACAGTGTCGGGGCTAGCCTTGAGGCA CTGTTCCAGG | CVB3-2C/T323S-F | 105 |
| UTJS20169 | CCTGGAACAGTGCCTCAAGGCTAGCCCCGAC ACTGTGCCTG | CVB3-2C/T323S-R | 106 |
| UTJS20170 | CAGGCACAGTGTCGGGGCTGGCCTTGAGGCA CTGTTCCAGG | CVB3-2C/T323G-F | 107 |
| UTJS20171 | CCTGGAACAGTGCCTCAAGGCCAGCCCCGAC ACTGTGCCTG | CVB3-2C/T323G-R | 108 |

REFERENCES CITED IN EXAMPLES 1-8

Abraham et al., *SoftwareX.* 2015; 1-2 (15): 19.
Amadei et al., *Proteins.* 1993; 17: 412-425.
Cheng et al., *Adv. Mater.* 2018; 30: e1805308.
Cheng et al., *Nat. Nanotechnol.* 2020; 15: 313-320.
Cornell et al., *J. Virol.* 2007; 81: 6785-6797.
Darden et al., *J. Chem. Phys.* 1993; 98: 10089-10092.
David & Jacobs, *Methods Mol. Biol.* 2014; 1084: 193-226.
Emsley et al., *Acta Crystallogr. D Biol. Crystallogr.* 2010; 66: 486-501.
Eslami et al., *J. Chem. Phys.* 2010; 133: 084105.
Feuer et al., *J. Virol.* 2002; 76: 4430-4440.
Guan et al., *Sci. Adv.* 2017; 3: e1602573.
Guan et al., *PLoS Pathog.* 2018; 14: e1007304.
Lindorff-Larsen et al., *Proteins.* 2010; 78: 1950-1958.
Ma et al., *J. Vis. Exp.* 2017; 119: 55236.
Mar et al., *Nat. Commun.* 2018; 9: 3603.
Nozawa et al., *Cell.* 2017; 169: 1214-1227.e18
Parrinello & Rahman, *J. Appl. Physiol.* 1981; 52: 7182.
Schindelin et al., *Nat. Methods.* 2012; 9: 676-682.
Schoggins et al., *Nature.* 2011; 472: 481-485.
Schoggins et al., *Proc. Natl. Acad. Sci. USA.* 2012; 109: 14610-14615.
Schoggins et al., *Nature.* 2014; 505: 691-695.
Schwarz et al., *MSphere.* 2016; 1: 1-12.
Zhou et al., *Proc. Natl. Acad. Sci. USA.* 2016; 113: 520-525.

What is claimed is:

1. A method of treating an enterovirus infection, comprising administering to a subject a composition comprising at least one mRNA encoding a tripartite motif containing 7 (TRIM7) protein and at least one lipid nanoparticle (LNP), wherein the subject has or is suspected of having an enterovirus infection.

2. The method of claim 1, wherein the composition is administered at an effective dose and an administration interval such that at least one symptom of the enterovirus infection is reduced in intensity, severity, frequency, onset, or any combination thereof.

3. The method of claim 2, wherein the at least one symptom of the enterovirus infection comprises fever, chills, sore throat, nasal congestion, cough, or any combination thereof.

4. The method of claim 2, wherein the effective dose comprises a dose ranging from about 0.01-5.0 mg/kg mRNA to body weight.

5. The method of claim 1, wherein the composition is administered intravenously.

6. The method of claim 1, wherein the administering of the composition results in a decreased viral titer in the subject compared to an untreated subject with identical enterovirus infection.

7. The method of claim 1, wherein the at least one mRNA encoding a TRIM7 protein comprises a polynucleotide sequence at least 80% identical to any one of SEQ ID NOs: 1-6.

8. The method of claim 1, wherein the at least one mRNA encoding a TRIM7 protein is codon optimized.

9. The method of claim 1, wherein the at least one LNP comprises an ionizable cationic lipid, an ionizable phospholipid, a cholesterol, a cholesterol derivative, or any combination thereof.

10. The method of claim 1, wherein the composition further comprises at least one pharmaceutically acceptable excipient.

* * * * *

SEQUENCE LISTING

```
<160> NUMBER OF SEQ ID NOS: 110

<210> SEQ ID NO 1
<211> LENGTH: 2864
<212> TYPE: DNA
<213> ORGANISM: Homo sapiens

<400> SEQUENCE: 1
agtgggccct cggcgcccag ctccgcgtcc tgtgaggtcc agtggccgcc caggcgcgac      60
cagatctggg tgcgcggaga gcgcgcatgg cggctgtggg accgcggacc ggccccggaa     120
```

```
ccggcgccga ggctctagcg ctggcggcag agctgcaggg cgaggcgacg tgctccatct      180
gcctagagct ctttcgtgag ccggtgtccg tcgagtgcgg ccacagcttc tgccgcgcct      240
gcatagggcg ctgctgggag cgcccgggcg cggggtctgt tggggccgcc accgcgcgc      300 ccccttccc actgccctgt ccgcagtgcc gcgagcccgc gcgcccagt cagctgcggc       360 ccaaccggca gctggcggca gtggccacgc tcctgcggcg cttcagcctg cccgcggctg      420
ccccgggaga gcacgggtct caggcggccg cggcccgggc agcggctgcc cgctgcgggc      480
agcatggcga acccttcaag ctctactgcc aggacgacgg acgcgccatc tgcgtggtgt      540
gcgaccgcgc ccgcgagcac cgcgagcacg ccgtgctgcc gctggacgag gcggtgcagg      600
aggccaagga gctcttggag tccaggctga gggtcttgaa gaaggaactg gaggactgtg      660
aggtgttccg gtccacggaa aagaaggaga gcaaggagct gctgaaacag atggcagcgg      720
agcaggagaa ggtgggggca gagttccagg cactgagggc tttcctggtg gagcaggagg      780
gtcggctgct aggccgcctg gaggaactgt cccgggaggt ggcacagaag cagaatgaga      840
acctggccca gctcggggtt gagatcaccc agctgtccaa gctcagcagc cagatccagg      900
agacagctca aaagcctgac cttgactttc tccaggaatt caaaagcacg ctgagcaggt      960
gtagcaatgt gcctggcccc aagccaacca cagtctcttc tgagatgaag aataaagtct     1020
ggaatgtttc tctcaagacc tttgtcttaa aagggatgct gaagaagttc aaagaggacc     1080
ttcggggaga gctggagaaa gaggagaaag tggagctcac cttggatccc gacacggcca     1140
acccgcgcct catcctctct ctggatctta agggcgtgcg cctcggcgag cgggcccagg     1200
acctgcccaa ccacccctgc cgcttcgaca ccaacacccg cgtcctggcg tcctgcggct     1260
tctcctcggg ccggcatcac tgggaggtgg aggtgggctc taaggacggc tgggcctttg     1320
gcgtggcccg cgagagcgtg cgccgaaagg gcctgacgcc cttcactccc gaggagggcg     1380
tctgggccct gcagctcaac ggcggccagt actgggccgt gaccagcccc gagcggtcgc     1440
ccctcagctg cggcacctg tcgcgcgtgc gggtggccct ggacctggag gtgggagccg      1500
tgtccttcta cgctgtggag gacatgcgcc acctctacac cttccgcgtc aacttccagg     1560
agcgcgtgtt cccgcttttc tctgtttgct ccacgggcac ctacttgcga atctggcctt     1620
gaggggcact gctggggagc tcctgtctct gggctgccgg tgggagggga tgtcgcctcc     1680
ccagagatgc ctggtccgtc ttgggtctgc cctccgtgct cctgacccct gctgcccaag     1740
agagcctgct acagacacaa ccccgaggca ggagagtgac tgtggccaac cgagcagggg     1800 aacagggggct ttggactcct gagggtgttc ccttcctgag gtcacatgtg gatttggcca    1860
gagccttcag gaggtggagg ccggtgaggt caggagccca gctctccagg gggcttctgc     1920
cctgactggg aagggtgcct ggctccctaa aacaatgtca aagccagtcc tgctgttctc     1980
tgttgccagg gggcaggtct gggcctgggc caaccacgtt tgttatcatg gctgctgcct     2040 tctgacagc tgccagctct gccttgagag gttgtgggac ctctggatcc agctgacctg      2100
acaggtcatc tactcaggga ggagcccgt gctcccagct cagaggacag tctgggccag      2160
aactggaagg agacatctgt cccgtctttg agtgacaagc ccgggacaac agccagtggg     2220
catcacggct ctccagcact ccttagccgg aggatacaga gtgatgggtg catcctgacc      2280
aatgcgacaa ccaacacgtg ctctcacaaa ccctgactc ccgcactttc cagtgccaaa      2340
gtacaaacgc tgcttggata aggagagcaa agcttctgga actttattta ctctttcttt     2400
ttaattttct tttaagagac tgggtcttgc tatgttgccc aggctggtct tgaactcctg     2460
gcctcaagtg atcctccagt ttccatctcc ctaagagctg ggattacagg tgtgagccgc     2520
```

```
tgtacccgaa cttttttgt ttttgcttct ggaactttga aacacaaaac acaagttggc      2580
acttacaatt ttaaagatgc agccagctct aaacaacaca cagagcacaa atatgctcct      2640
gacggactca ggaaaatgcc aacagcagag caccctggtg ccaaggcctt ctcagcccat      2700
gccctggagg gcattcccct ggccagcctc agcccttgt ctacttgttc tccagcttct       2760
gggtagctgg gcttctggaa gggtggcagt gggctactcc ctgctcagcg ctcccctggg      2820 aaggggtga ggagatgaaa atgaaactat gagctgtctt tgga                        2864

<210> SEQ ID NO 2
<211> LENGTH: 3009
<212> TYPE: DNA
<213> ORGANISM: Homo sapiens

<400> SEQUENCE: 2
ctgcagcctg cctggaagct gaaggaaagg tgggggcatt gtaggacacc ttgaacccag        60
gtctcccaac ttcacaggac tcccttcctc cgcccaggag ttttaaggaa gaggaacttc       120
ctggtgggac atattgagtg ccaaacgtgt gttcacataa aaaatcaaga gatcagggca       180
tgagtctgca tctgaaaact cgagtaaaaa atccggtgta tgctgttaat ggaaagaaca       240
gaatatgaca cttgcatgcc gcatattctc acttcgttcc ttgggggtgt gctgctacct       300
ctggtcactg gcatcggact tttcttcctt cttctacttt cctacatct cccaagtttt        360 gtattttgag catgtgttag cattataact gctaaacagg aaagatggcc tttaaaaga        420 aagtgaagtg taaagttttg agggtgatga aataaatgtg cttgaggaag aaaaagcaat       480
ctcagtttaa tcctatggtt gccccaggag gcactaattt atcccttctg cttttcaagt       540
gaggaagctg cagcttggcg tagttctggg ggagtatga agctgccttg gtttaggtga        600
tggagcacag gtccacagac atgtgtgggt gcatctgtgg caggggagaa aagagcatgt       660
gtccagacta cagcttgttc agagctggga cactgacaat agagcacgca ctgcgtgcgt       720
aggtgggtgt gtctccgatc ctccagcagt gacagggacg aagccttgcc ctgtgggatg       780
actcaggcca ctggccaaat gttatgtctc catgttcaag tccctctcca acttctcctc       840
ctgggacaga aacagatggc agcggagcag agaaggtgg gggcagagtt ccaggcactg        900
agggctttcc tggtggagca ggagggtcgg ctgctaggcc gcctggagga actgtcccgg       960
gaggtggcac agaagcagaa tgagaacctg gcccagctcg gggttgagat cacccagctg      1020
tccaagctca gcagccagat ccaggagaca gctcaaaagc ctgaccttga ctttctccag      1080
gaattcaaaa gcacgctgag caggtgtagc aatgtgcctg gccccaagcc aaccacagtc      1140
tcttctgaga tgaagaataa agtctggaat gtttctctca agacctttgt cttaaaaggg      1200
atgctgaaga agttcaaaga ggaccttcgg ggagagctgg agaaagagga gaaagtggag      1260
ctcaccttgg atcccgacac ggccaacccg cgcctcatcc tctctctgga tcttaagggc      1320
gtgcgcctcg gcgagcgggc ccaggacctg cccaaccacc cctgccgctt cgacaccaac      1380
acccgcgtcc tggcgtcctg cggcttctcc tcgggccggc atcactggga ggtggaggtg      1440
ggctctaagg acggctgggc ctttggcgtg gcccgcgaga gcgtgcgccg aaagggcctg      1500
acgcccttca ctcccgagga gggcgtctgg gccctgcagc tcaacggcgg ccagtactgg      1560
gccgtgacca gccccgagcg gtcgcccctc agctgcgggc acctgtcgcg cgtgcgggtg      1620
gccctggacc tggaggtggg agccgtgtcc ttctacgctg tggaggacat gcgccacctc      1680
tacaccttcc gcgtcaactt ccaggagcgc gtgttcccgc ttttctctgt ttgctccacg      1740
```

```
ggcacctact tgcgaatctg gccttgaggg gcactgctgg ggagctcctg tctctgggct    1800
gccggtggga ggggatgtcg cctccccaga gatgcctggt ccgtcttggg tctgccctcc    1860
gtgctcctga cccctgctgc caagagagc ctgctacaga cacaaccccg aggcaggaga     1920
gtgactgtgg ccaaccgagc aggggaacag gggctttgga ctcctgaggg tgttcccttc    1980
ctgaggtcac atgtggattt ggccagagcc ttcaggaggt ggaggccggt gaggtcagga    2040
gcccagctct ccagggggct ctgccctga ctgggaaggg tgcctggctc cctaaaacaa     2100
tgtcaaagcc agtcctgctg ttctctgttg ccaggggca ggtctgggcc tgggccaacc     2160
acgtttgtta tcatggctgc tgccttctgg acagctgcca gctctgcctt gagaggttgt    2220
gggacctctg gatccagctg acctgacagg tcatctactc agggaggagc cctgtgctcc    2280
cagctcagag gacagtctgg gccagaactg gaaggagaca tctgtcccgt ctttgagtga    2340
caagcccggg acaacagcca gtgggcatca cggctctcca gcactcctta gccggaggat    2400
acagagtgat gggtgcatcc tgaccaatgc gacaaccaac acgtgctctc acaaacccct    2460
gactcccgca ctttccagtg ccaaagtaca aacgctgctt ggataaggag agcaaagctt    2520
ctggaacttt atttactctt tctttttaat tttcttttaa gagactgggt cttgctatgt    2580
tgcccaggct ggtcttgaac tcctggcctc aagtgatcct ccagtttcca tctccctaag    2640
agctgggatt acaggtgtga ccgctgtac ccgaactttt tttgttttg cttctggaac      2700 tttgaaacac aaaacacaag ttggcactta caattttaaa gatgcagcca gctctaaaca    2760
acacacagag cacaaatatg ctcctgacgg actcaggaaa atgccaacag cagagcaccc    2820
tggtgccaag gccttctcag cccatgccct ggagggcatt cccctggcca gcctcagccc    2880
cttgtctact tgttctccag cttctgggta gctgggcttc tggaagggtg gcagtgggct    2940
actccctgct cagcgctccc ctgggaaggg ggtgaggaga tgaaaatgaa actatgagct    3000
gtctttgga                                                            3009

<210> SEQ ID NO 3
<211> LENGTH: 2852
<212> TYPE: DNA
<213> ORGANISM: Homo sapiens

<400> SEQUENCE: 3
tgcgcgacgt cccccacgga cttggcgatg ttcttcctgt ctgttcggag cctctagcct      60
ggtctgcgtc tccgcagctc tctgcccgcg ggaagtctcc ggcacagcca cgcagccgct     120
gcccccactc ttatctcttt ccccgaagcg ggctctgctc aaagtcccca cctcgtggaa     180
ctgagtgaga ggacctcgcc aagatgtcca gggagggggc tcccgggtta agccgcgcac     240
ctagagccgt ctgactgtgc caacgctgtc gattctgggg gccctttctt tgctattttc     300
tcgctgagcc tcagcgaggg tgtgtgcagg ggtgagggcg gggcggggag gctcgggcgg     360
cagtccccag tctctccttg ctggcccatc ctgctccaac tctcccagcc acggggcttc     420
ctggtggggg gcggagagt agaggagacg actaggggta gggctgccgg agcttgtgtt      480
tcagtctggc tggtccagca gatgcttttg gggaagcaag atcccgagac cttcagagtc     540
acctcgcagt gtaacctgta gcctgtagag atgacttcta cccggcctcc ccctcagagc     600
tcttggagtc caggctgagg gtcttgaaga aggaactgga ggactgtgag gtgttccggt     660
ccacggaaaa gaaggagagc aaggagctgc tgaaacagat ggcagcggag caggagaagg     720
tgggggcaga gttccaggca ctgagggctt tcctggtgga gcaggaggt cggctgctag      780 gccgcctgga ggaactgtcc cggaggtgg cacagaagca gaatgagaac ctggcccagc      840
```

```
tcggggttga gatcacccag ctgtccaagc tcagcagcca gatccaggag acagctcaaa      900
agcctgacct tgactttctc caggaattca aaagcacgct gagcaggtgt agcaatgtgc      960
ctggccccaa gccaaccaca gtctcttctg agatgaagaa taaagtctgg aatgtttctc     1020
tcaagacctt tgtcttaaaa gggatgctga agaagttcaa agaggacctt cggggagagc     1080
tggagaaaga ggagaaagtg gagctcacct tggatcccga cacggccaac ccgcgcctca     1140
tcctctctct ggatcttaag ggcgtgcgcc tcggcgagcg ggcccaggac ctgcccaacc     1200 accctgccg cttcgacacc aacacccgcg tcctggcgtc ctgcggcttc tcctcgggcc     1260
ggcatcactg ggaggtggag gtgggctcta aggacggctg ggcctttggc gtggcccgcg     1320
agagcgtgcg ccgaaagggc ctgacgccct cactcccga ggagggcgtc tgggccctgc     1380
agctcaacgg cggccagtac tgggccgtga ccagccccga gcggtcgccc tcagctgcg     1440 ggcacctgtc gcgcgtgcgg gtggccctgg acctggaggt gggagccgtg tccttctacg     1500
ctgtggagga catgcgccac ctctacacct tccgcgtcaa cttccaggag cgcgtgttcc     1560
cgcttttctc tgtttgctcc acgggcacct acttgcgaat ctggccttga ggggcactgc     1620
tggggagctc ctgtctctgg gctgccggtg ggaggggatg tcgcctcccc agagatgcct     1680
ggtccgtctt gggtctgccc tccgtgctcc tgacccctgc tgcccaagag agcctgctac     1740
agacacaacc ccgaggcagg agagtgactg tggccaaccg agcaggggaa caggggcttt     1800
ggactcctga gggtgttccc ttcctgaggt cacatgtgga tttggccaga gccttcagga     1860
ggtggaggcc ggtgaggtca ggagcccagc tctccagggg gcttctgccc tgactgggaa     1920
gggtgcctgg ctccctaaaa caatgtcaaa gccagtcctg ctgttctctg ttgccagggg     1980
gcaggtctgg gcctgggcca accacgtttg ttatcatggc tgctgccttc tggacagctg     2040
ccagctctgc cttgagaggt tgtgggacct ctggatccag ctgacctgac aggtcatcta     2100
ctcagggagg agccctgtgc tcccagctca gaggacagtc tgggccagaa ctggaaggag     2160
acatctgtcc cgtctttgag tgacaagccc gggacaacag ccagtgggca tcacggctct     2220
ccagcactcc ttagccggag gatacagagt gatgggtgca tcctgaccaa tgcgacaacc     2280
aacacgtgct ctcacaaacc cctgactccc gcactttcca gtgccaaagt acaaacgctg     2340
cttggataag gagagcaaag cttctggaac tttatttact cttctttttt aattttcttt     2400
taagagactg ggtcttgcta tgttcccag gctggtcttg aactcctggc tcaagtgat     2460 cctccagttt ccatctccct aagagctggg attacaggtg tgagccgctg tacccgaact     2520
ttttttgttt ttgcttctgg aactttgaaa cacaaaacac aagttggcac ttacaatttt     2580
aaagatgcag ccagctctaa acaacacaca gagcacaaat atgctcctga cggactcagg     2640
aaaatgccaa cagcagagca ccctggtgcc aaggccttct cagcccatgc cctggagggc     2700
attcccctgg ccagcctcag ccccttgtct acttgttctc cagcttctgg gtagctgggc     2760
ttctggaagg gtggcagtgg gctactccct gctcagcgct cccctgggaa gggggtgagg     2820
agatgaaaat gaaactatga gctgtctttg ga                                   2852

<210> SEQ ID NO 4
<211> LENGTH: 2643
<212> TYPE: DNA
<213> ORGANISM: Homo sapiens

<400> SEQUENCE: 4
tgcgcgacgt cccccacgga cttggcgatg ttcttcctgt ctgttcggag cctctagcct       60
```

| | | | | |
|---|---|---|---|---|
| ggtctgcgtc | tccgcagctc | tctgcccgcg | ggaagtctcc | ggcacagcca cgcagccgct | 120 |
| gcccccactc | ttatctcttt | ccccgaagcg | ggctctgctc | aaagtcccca cctcgtggaa | 180 |
| ctgagtgaga | ggacctcgcc | aagatgtcca | gggaggggc | tcccgggtta agccgcgcac | 240 |
| ctagagccgt | ctgactgtgc | caacgctgtc | gattctgggg | gcccttttctt tgctattttc | 300 |
| tcgctgagcc | tcagcgaggg | agctcttgga | gtccaggctg | agggtcttga agaaggaact | 360 |
| ggaggactgt | gaggtgttcc | ggtccacgga | aagaaggag | agcaaggagc tgctggtgag | 420 |
| ccaggcaccc | gcaggccccc | cgtgggacat | tacagaggcc | tgagaactca gcaccagggc | 480 |
| tcgaaacaga | tggcagcgga | gcaggagaag | gtggggggcag | agttccaggc actgagggct | 540 |
| ttcctggtgg | agcaggaggg | tcggctgcta | ggccgcctgg | aggaactgtc ccgggaggtg | 600 |
| gcacagaagc | agaatgagaa | cctgcccag | ctcggggttg | agatcaccca gctgtccaag | 660 |
| ctcagcagcc | agatccagga | gacagctcaa | aagcctgacc | ttgactttct ccaggaattc | 720 |
| aaaagcacgc | tgagcaggtg | tagcaatgtg | cctggcccca | agccaaccac agtctcttct | 780 |
| gagatgaaga | ataaagtctg | gaatgtttct | ctcaagacct | tgtcttaaa agggatgctg | 840 |
| aagaagttca | agaggacct | tcggggagag | ctggagaaag | aggagaaagt ggagctcacc | 900 |
| ttggatcccg | acacgccaa | cccgcgcctc | atcctctctc | tggatcttaa gggcgtgcgc | 960 |
| ctcggcgagc | gggcccagga | cctgcccaac | caccccctgcc | gcttcgacac caacacccgc | 1020 |
| gtcctggcgt | cctgcggctt | ctcctcgggc | cggcatcact | gggaggtgga ggtgggctct | 1080 |
| aaggacggct | gggcctttgg | cgtggcccgc | gagagcgtgc | gccgaaaggg cctgacgccc | 1140 |
| ttcactcccg | aggagggcgt | ctgggccctg | cagctcaacg | gcggcagta ctgggccgtg | 1200 |
| accagccccg | agcggtcgcc | cctcagctgc | gggcacctgt | cgcgcgtgcg ggtggccctg | 1260 |
| gacctggagg | tgggagccgt | gtccttctac | gctgtggagg | acatgcgcca cctctacacc | 1320 |
| ttccgcgtca | acttccagga | gcgcgtgttc | ccgcttttct | ctgtttgctc cacgggcacc | 1380 |
| tacttgcgaa | tctggccttg | aggggcactg | ctggggagct | cctgtctctg gctgccggt | 1440 |
| gggaggggat | gtcgcctccc | cagagatgcc | tggtccgtct | tgggtctgcc ctccgtgctc | 1500 |
| ctgacccctg | ctgcccaaga | gagcctgcta | cagacacaac | cccgaggcag agagtgact | 1560 |
| gtggccaacc | gagcagggga | acaggggctt | tggactcctg | agggtgttcc cttcctgagg | 1620 |
| tcacatgtgg | atttggccag | agccttcagg | aggtggaggc | cggtgaggtc aggagcccag | 1680 |
| ctctccaggg | ggcttctgcc | ctgactggga | agggtgcctg | gctccctaaa acaatgtcaa | 1740 |
| agccagtcct | gctgttctct | gttgccaggg | ggcaggtctg | ggcctgggcc aaccacgttt | 1800 |
| gttatcatgg | ctgctgcctt | ctggacagct | gccagctctg | ccttgagagg ttgtgggacc | 1860 |
| tctggatcca | gctgacctga | caggtcatct | actcagggag | gagccctgtg ctcccagctc | 1920 |
| agaggacagt | ctgggccaga | actggaagga | gacatctgtc | ccgtctttga gtgacaagcc | 1980 |
| cgggacaaca | gccagtgggc | atcacggctc | tccagcactc | cttagccgga ggatacagag | 2040 |
| tgatgggtgc | atcctgacca | atgcgacaac | caacacgtgc | tctcacaaac ccctgactcc | 2100 |
| cgcactttcc | agtgccaaag | tacaaacgct | gcttggataa | ggagagcaaa gcttctggaa | 2160 |
| ctttatttac | tctttctttt | taattttctt | ttaagagact | gggtcttgct atgttgccca | 2220 |
| ggctggtctt | gaactcctgg | cctcaagtga | tcctccagtt | tccatctccc taagagctgg | 2280 |
| gattacaggt | gtgagccgct | gtacccgaac | tttttttgtt | tttgcttctg gaactttgaa | 2340 |
| acacaaaaca | caagttggca | cttacaattt | taaagatgca | gccagctcta aacaacacac | 2400 |
| agagcacaaa | tatgctcctg | acggactcag | gaaaatgcca | acagcagagc accctggtgc | 2460 |

```
caaggccttc tcagcccatg ccctggaggg cattccctg gccagcctca gcccttgtc      2520 tacttgttct ccagcttctg ggtagctggg cttctggaag ggtggcagtg ggctactccc    2580
tgctcagcgc tccctggga aggggtgag gagatgaaaa tgaaactatg agctgtcttt      2640
gga                                                                  2643

<210> SEQ ID NO 5
<211> LENGTH: 2575
<212> TYPE: DNA
<213> ORGANISM: Homo sapiens

<400> SEQUENCE: 5
tgcgcgacgt cccccacgga cttggcgatg ttcttcctgt ctgttcggag cctctagcct      60
ggtctgcgtc tccgcagctc tctgcccgcg gaagtctcc ggcacagcca cgcagccgct      120
gcccccactc ttatctcttt ccccgaagcg ggctctgctc aaagtcccca cctcgtggaa     180
ctgagtgaga ggacctcgcc aagatgtcca gggaggggc tcccgggtta agccgcgcac      240
ctagagccgt ctgactgtgc aacgctgtc gattctgggg gccctttctt tgctatttc       300 tcgctgagcc tcagcgaggg agctcttgga gtccaggctg agggtcttga agaaggaact     360
ggaggactgt gaggtgttcc ggtccacgga aagaaggag agcaaggagc tgctgaaaca     420
gatggcagcg gagcaggaga aggtgggggc agagttccag gcactgaggg ctttcctggt    480
ggagcaggag ggtcggctgc taggccgcct ggaggaactg tcccgggagg tggcacagaa    540
gcagaatgag aacctggccc agctcggggt tgagatcacc cagctgtcca agctcagcag    600
ccagatccag gagacagctc aaaagcctga ccttgacttt ctccaggaat caaaagcac     660 gctgagcagg tgtagcaatg tgcctggccc caagccaacc acagtctctt ctgagatgaa    720
gaataaagtc tggaatgttt ctctcaagac ctttgtctta aaagggatgc tgaagaagtt    780
caaagaggac cttcggggag agctggaaa agaggagaaa gtggagctca ccttggatcc     840
cgacacggcc aacccgcgcc tcatcctctc tctggatctt aagggcgtgc gcctcggcga    900
gcgggcccag gacctgccca accacccctg ccgcttcgac accaacaccc gcgtcctggc    960
gtcctgcggc ttctcctcgg gccggcatca ctggaggtg gaggtgggct ctaaggacgg     1020
ctgggccttt ggcgtggccc gcgagagcgt gcgccgaaag ggcctgacgc ccttcactcc    1080
cgaggagggc gtctgggccc tgcagctcaa cggcggccag tactgggccg tgaccagccc    1140
cgagcggtcg cccctcagct gcgggcacct gtcgcgcgtg cgggtggccc tggacctgga    1200
ggtgggagcc gtgtccttct acgctgtgga ggacatgcgc cacctctaca ccttccgcgt    1260
caacttccag gagcgcgtgt tcccgctttt ctctgtttgc tccacgggca cctacttgcg    1320
aatctggcct tgagggcac tgctggggag ctcctgtctc tgggctgccg gtgggagggg    1380
atgtcgcctc cccagagatg cctggtccgt cttgggtctg ccctccgtgc tcctgaccc     1440 tgctgcccaa gagagcctgc tacagacaca ccccgaggc aggagagtga ctgtggccaa    1500
ccgagcaggg gaacaggggc tttggactcc tgagggtgtt cccttcctga ggtcacatgt    1560
ggatttggcc agagccttca ggaggtggag gccggtgagg tcaggagccc agctctccag   1620
ggggcttctg ccctgactgg gaaggtgcc tggctcccta aaacaatgtc aaagccagtc    1680
ctgctgttct ctgttgccag ggggcaggtc tgggcctggg ccaaccacgt tgttatcat    1740 ggctgctgcc ttctggacag ctgccagctc tgccttgaga ggttgtggga cctctggatc    1800
cagctgacct gacaggtcat ctactcaggg aggagccctg tgctcccagc tcagaggaca    1860
```

| | | |
|---|---|---|
| gtctgggcca gaactggaag gagacatctg tcccgtctttt gagtgacaag cccgggacaa | 1920 | |
| cagccagtgg gcatcacggc tctccagcac tccttagccg gaggatacag agtgatgggt | 1980 | |
| gcatcctgac caatgcgaca accaacacgt gctctcacaa acccctgact cccgcacttt | 2040 | |
| ccagtgccaa agtacaaacg ctgcttggat aaggagagca aagcttctgg aactttattt | 2100 | |
| actctttctt tttaattttc ttttaagaga ctgggtcttg ctatgttgcc caggctggtc | 2160 | |
| ttgaactcct ggcctcaagt gatcctccag tttccatctc cctaagagct gggattacag | 2220 | |
| gtgtgagccg ctgtacccga acttttttttg tttttgcttc tggaactttg aaacacaaaa | 2280 | |
| cacaagttgg cacttacaat tttaaagatg cagccagctc taaacaacac acagagcaca | 2340 | |
| aatatgctcc tgacggactc aggaaaatgc caacagcaga gcaccctggt gccaaggcct | 2400 | |
| tctcagccca tgccctggag ggcattcccc tggccagcct cagcccttg tctacttgtt | 2460 | |
| ctccagcttc tgggtagctg ggcttctgga agggtggcag tgggctactc cctgctcagc | 2520 | |
| gctcccctgg aagggggtg aggagatgaa aatgaaacta tgagctgtct ttgga | 2575 | |

<210> SEQ ID NO 6
<211> LENGTH: 1131
<212> TYPE: DNA
<213> ORGANISM: Homo sapiens

<400> SEQUENCE: 6

| | | |
|---|---|---|
| agtgggccct cggcgcccag ctccgcgtcc tgtgaggtcc agtggccgcc caggcgcgac | 60 | |
| cagatctggg tgcgcggaga gcgcgcatgg cggctgtggg accgcggacc ggccccggaa | 120 | |
| ccggcgccga ggctctagcg ctggcggcag agctgcaggg cgaggcgacg tgctccatct | 180 | |
| gcctagagct ctttcgtgag ccggtgtccg tcgagtgcgg ccacagcttc tgccgcgcct | 240 | |
| gcataggcg ctgctgggag cgccggggcg cggggtctgt tggggccgcc acccgcgcgc | 300 | |
| cccccttccc actgccctgt ccgcagtgcc gcgagcccgc gcgcccagt cagctgcggc | 360 | |
| ccaaccggca gctggcggca gtggccacgc tcctgcggcg cttcagcctg cccgcggctg | 420 | |
| ccccgggaga gcacgggtct caggcggccg cggcccgggc agcggctgcc cgctgcgggc | 480 | |
| agcatggcga acccttcaag ctctactgcc aggacgacgg acgcgccatc tgcgtggtgt | 540 | |
| gcgaccgcgc ccgcgagcac cgcgagcacg ccgtgctgcc gctggacgag gcggtgcagg | 600 | |
| aggccaagga gctcttggag tccaggctga gggtcttgaa gaaggaactg gaggactgtg | 660 | |
| aggtgttccg gtccacggaa aagaaggaga gcaaggagct gctggtgagc caggcacccg | 720 | |
| caggccccc gtgggacatt acagaggcct gagaactcag caccagggct cggtgtgtgt | 780 | |
| ggtgttggag tgtgtgctat ggaaccgcag aatcgatttc agaaagataa tagagtccat | 840 | |
| attatatagg gtgtccacat aattgttgta caaaccagag cttttttaaag tgaaaagcag | 900 | |
| tgctaaaata attattgcaa aacaactggc ttaaactgga gctgtcccag cgaatcagga | 960 | |
| cgctcagtca ctctgatatt acgtaacata ccagttaggg cctgcggaag catcttgtaa | 1020 | |
| tggaacacat tactatttct gcagagaaac atggatattc aataagtggg aatattaata | 1080 | |
| caataaagag cctcatggca tgttttgtca acaaaacagt agtgaaaaaa a | 1131 | |

<210> SEQ ID NO 7
<211> LENGTH: 47
<212> TYPE: DNA
<213> ORGANISM: Artificial Sequence
<220> FEATURE:
<223> OTHER INFORMATION: Synthetic Construct

<400> SEQUENCE: 7

```
gcaggcttgg aaggagttcg aaccatgggt cctgcatttg aatttgc                    47
```

<210> SEQ ID NO 8
<211> LENGTH: 46
<212> TYPE: DNA
<213> ORGANISM: Artificial Sequence
<220> FEATURE:
<223> OTHER INFORMATION: Synthetic Construct

<400> SEQUENCE: 8

```
ccaagcgctc cctcctccgg atccttgttc atcattgaaa tagtgc                     46
```

<210> SEQ ID NO 9
<211> LENGTH: 35
<212> TYPE: DNA
<213> ORGANISM: Artificial Sequence
<220> FEATURE:
<223> OTHER INFORMATION: Synthetic Construct

<400> SEQUENCE: 9

```
gagttcgaac catggcggct gtgggaccgc ggacc                                 35
```

<210> SEQ ID NO 10
<211> LENGTH: 31
<212> TYPE: DNA
<213> ORGANISM: Artificial Sequence
<220> FEATURE:
<223> OTHER INFORMATION: Synthetic Construct

<400> SEQUENCE: 10

```
ggaagatcta ggccagattc gcaagtaggt g                                     31
```

<210> SEQ ID NO 11
<211> LENGTH: 29
<212> TYPE: DNA
<213> ORGANISM: Artificial Sequence
<220> FEATURE:
<223> OTHER INFORMATION: Synthetic Construct

<400> SEQUENCE: 11

```
ggaagatctc atccctttta agacaaagg                                        29
```

<210> SEQ ID NO 12
<211> LENGTH: 57
<212> TYPE: DNA
<213> ORGANISM: Artificial Sequence
<220> FEATURE:
<223> OTHER INFORMATION: Synthetic Construct

<400> SEQUENCE: 12

```
gagctgcagg gcgaggcgac ggcctccatc gccctagagc tctttcgtga gccggtg         57
```

<210> SEQ ID NO 13
<211> LENGTH: 57
<212> TYPE: DNA
<213> ORGANISM: Artificial Sequence
<220> FEATURE:
<223> OTHER INFORMATION: Synthetic Construct

<400> SEQUENCE: 13

```
caccggctca cgaaagagct ctagggcgat ggaggccgtc gcctcgccct gcagctc         57
```

<210> SEQ ID NO 14
<211> LENGTH: 33
<212> TYPE: DNA

<213> ORGANISM: Artificial Sequence
<220> FEATURE:
<223> OTHER INFORMATION: Synthetic Construct

<400> SEQUENCE: 14
cggactagta ccatggcggc tgtgggaccg cgg                         33

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
ggaactcaag cacagtgaag                                        20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
agcctctgat gtctctgaac                                        20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
tacagacatg gtgcgaagag                                        20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
aacacggaca cccaaagtag                                        20

<210> SEQ ID NO 19
<211> LENGTH: 57
<212> TYPE: DNA
<213> ORGANISM: Artificial Sequence
<220> FEATURE:
<223> OTHER INFORMATION: Synthetic Construct

<400> SEQUENCE: 19
ccggctggag gactgtgagg tgttcctcga ggaacacctc acagtcctcc agttttt    57

<210> SEQ ID NO 20
<211> LENGTH: 57
<212> TYPE: DNA
<213> ORGANISM: Artificial Sequence
<220> FEATURE:
<223> OTHER INFORMATION: Synthetic Construct

<400> SEQUENCE: 20
aattaaaaac tggaggactg tgaggtgttc ctcgaggaac acctcacagt cctccag    57

<210> SEQ ID NO 21
<211> LENGTH: 57
<212> TYPE: DNA
<213> ORGANISM: Artificial Sequence
<220> FEATURE:
<223> OTHER INFORMATION: Synthetic Construct

<400> SEQUENCE: 21
ccggccatct gcctagagct ctttcctcga ggaaagagct ctaggcagat ggttttt       57

<210> SEQ ID NO 22
<211> LENGTH: 57
<212> TYPE: DNA
<213> ORGANISM: Artificial Sequence
<220> FEATURE:
<223> OTHER INFORMATION: Synthetic Construct

<400> SEQUENCE: 22
aattaaaaac catctgccta gagctctttc ctcgaggaaa gagctctagg cagatgg       57

<210> SEQ ID NO 23
<211> LENGTH: 57
<212> TYPE: DNA
<213> ORGANISM: Artificial Sequence
<220> FEATURE:
<223> OTHER INFORMATION: Synthetic Construct

<400> SEQUENCE: 23
ccggcgctaa atactggcag gcgttctcga gaacgcctgc cagtatttag cgttttt       57

<210> SEQ ID NO 24
<211> LENGTH: 57
<212> TYPE: DNA
<213> ORGANISM: Artificial Sequence
<220> FEATURE:
<223> OTHER INFORMATION: Synthetic Construct

<400> SEQUENCE: 24
aattaaaaac gctaaatact ggcaggcgtt ctcgagaacg cctgccagta tttagcg       57

<210> SEQ ID NO 25
<211> LENGTH: 32
<212> TYPE: DNA
<213> ORGANISM: Artificial Sequence
<220> FEATURE:
<223> OTHER INFORMATION: Synthetic Construct

<400> SEQUENCE: 25
gtggcatgcc atctggatgt tctggcacaa gc       32

<210> SEQ ID NO 26
<211> LENGTH: 52
<212> TYPE: DNA
<213> ORGANISM: Artificial Sequence
<220> FEATURE:
<223> OTHER INFORMATION: Synthetic Construct

<400> SEQUENCE: 26
gatcaattca ggatgattgc ttatacgcgt gtgattgcat catacccgtg gc       52

<210> SEQ ID NO 27
<211> LENGTH: 52
<212> TYPE: DNA
<213> ORGANISM: Artificial Sequence
<220> FEATURE:

<223> OTHER INFORMATION: Synthetic Construct

<400> SEQUENCE: 27
gccacgggta tgatgcaatc acacgcgtat aagcaatcat cctgaattga tc    52

<210> SEQ ID NO 28
<211> LENGTH: 27
<212> TYPE: DNA
<213> ORGANISM: Artificial Sequence
<220> FEATURE:
<223> OTHER INFORMATION: Synthetic Construct

<400> SEQUENCE: 28
ccccctcgag gtcgacggta tcgattt    27

<210> SEQ ID NO 29
<211> LENGTH: 33
<212> TYPE: DNA
<213> ORGANISM: Artificial Sequence
<220> FEATURE:
<223> OTHER INFORMATION: Synthetic Construct

<400> SEQUENCE: 29
tccccgcggc tactgcactt ttgcttgcct tag    33

<210> SEQ ID NO 30
<211> LENGTH: 30
<212> TYPE: DNA
<213> ORGANISM: Artificial Sequence
<220> FEATURE:
<223> OTHER INFORMATION: Synthetic Construct

<400> SEQUENCE: 30
ccgctcgagg gtccaccagt atacagagag    30

<210> SEQ ID NO 31
<211> LENGTH: 34
<212> TYPE: DNA
<213> ORGANISM: Artificial Sequence
<220> FEATURE:
<223> OTHER INFORMATION: Synthetic Construct

<400> SEQUENCE: 31
tccccgcggc tattgaaagc ctgcaaagag cttg    34

<210> SEQ ID NO 32
<211> LENGTH: 31
<212> TYPE: DNA
<213> ORGANISM: Artificial Sequence
<220> FEATURE:
<223> OTHER INFORMATION: Synthetic Construct

<400> SEQUENCE: 32
ccgctcgagg gtcctgcatt tgaatttgct g    31

<210> SEQ ID NO 33
<211> LENGTH: 33
<212> TYPE: DNA
<213> ORGANISM: Artificial Sequence
<220> FEATURE:
<223> OTHER INFORMATION: Synthetic Construct

<400> SEQUENCE: 33
tccccgcggc tattgttcat cattgaaata gtg    33

```
<210> SEQ ID NO 34
<211> LENGTH: 32
<212> TYPE: DNA
<213> ORGANISM: Artificial Sequence
<220> FEATURE:
<223> OTHER INFORMATION: Synthetic Construct

<400> SEQUENCE: 34
ccgctcgagg gagagatcga gtttattgag ag                              32

<210> SEQ ID NO 35
<211> LENGTH: 35
<212> TYPE: DNA
<213> ORGANISM: Artificial Sequence
<220> FEATURE:
<223> OTHER INFORMATION: Synthetic Construct

<400> SEQUENCE: 35
tccccgcggc tagaaagagt ccaaccactt cctac                           35

<210> SEQ ID NO 36
<211> LENGTH: 33
<212> TYPE: DNA
<213> ORGANISM: Artificial Sequence
<220> FEATURE:
<223> OTHER INFORMATION: Synthetic Construct

<400> SEQUENCE: 36
ccgctcgagg gacaacaatc aggggcagta tac                             33

<210> SEQ ID NO 37
<211> LENGTH: 36
<212> TYPE: DNA
<213> ORGANISM: Artificial Sequence
<220> FEATURE:
<223> OTHER INFORMATION: Synthetic Construct

<400> SEQUENCE: 37
tccccgcggc tactgttcca ttgcatcatc ttccag                          36

<210> SEQ ID NO 38
<211> LENGTH: 31
<212> TYPE: DNA
<213> ORGANISM: Artificial Sequence
<220> FEATURE:
<223> OTHER INFORMATION: Synthetic Construct

<400> SEQUENCE: 38
ccgctcgagg gagtgaagga ctatgtggaa c                               31

<210> SEQ ID NO 39
<211> LENGTH: 35
<212> TYPE: DNA
<213> ORGANISM: Artificial Sequence
<220> FEATURE:
<223> OTHER INFORMATION: Synthetic Construct

<400> SEQUENCE: 39
tccccgcggc tattggcgtt cagccatggg tattc                           35

<210> SEQ ID NO 40
<211> LENGTH: 33
<212> TYPE: DNA
<213> ORGANISM: Artificial Sequence
<220> FEATURE:
<223> OTHER INFORMATION: Synthetic Construct
```

```
<400> SEQUENCE: 40
ccgctcgaga acaacggatg gctaaaaaag ttc                          33

<210> SEQ ID NO 41
<211> LENGTH: 35
<212> TYPE: DNA
<213> ORGANISM: Artificial Sequence
<220> FEATURE:
<223> OTHER INFORMATION: Synthetic Construct

<400> SEQUENCE: 41
tccccgcggc tactggaaca gtgcctcaag ggtag                        35

<210> SEQ ID NO 42
<211> LENGTH: 22
<212> TYPE: DNA
<213> ORGANISM: Artificial Sequence
<220> FEATURE:
<223> OTHER INFORMATION: Synthetic Construct

<400> SEQUENCE: 42
tggccatccg gtgtctaata ga                                      22

<210> SEQ ID NO 43
<211> LENGTH: 22
<212> TYPE: DNA
<213> ORGANISM: Artificial Sequence
<220> FEATURE:
<223> OTHER INFORMATION: Synthetic Construct

<400> SEQUENCE: 43
aggactgttt gggcagaaca tg                                      22

<210> SEQ ID NO 44
<211> LENGTH: 22
<212> TYPE: DNA
<213> ORGANISM: Artificial Sequence
<220> FEATURE:
<223> OTHER INFORMATION: Synthetic Construct

<400> SEQUENCE: 44
cgtcacgcca gagatgagga ta                                      22

<210> SEQ ID NO 45
<211> LENGTH: 22
<212> TYPE: DNA
<213> ORGANISM: Artificial Sequence
<220> FEATURE:
<223> OTHER INFORMATION: Synthetic Construct

<400> SEQUENCE: 45
gcccaaagct cctgttacat ca                                      22

<210> SEQ ID NO 46
<211> LENGTH: 22
<212> TYPE: DNA
<213> ORGANISM: Artificial Sequence
<220> FEATURE:
<223> OTHER INFORMATION: Synthetic Construct

<400> SEQUENCE: 46
tgtgttttgg accgagggaa ac                                      22

<210> SEQ ID NO 47
<211> LENGTH: 23
```

```
<212> TYPE: DNA
<213> ORGANISM: Artificial Sequence
<220> FEATURE:
<223> OTHER INFORMATION: Synthetic Construct

<400> SEQUENCE: 47
aggagatacc aatcccatgt gct                                              23

<210> SEQ ID NO 48
<211> LENGTH: 22
<212> TYPE: DNA
<213> ORGANISM: Artificial Sequence
<220> FEATURE:
<223> OTHER INFORMATION: Synthetic Construct

<400> SEQUENCE: 48
ctgaggtcag ggaaaaacac ga                                               22

<210> SEQ ID NO 49
<211> LENGTH: 22
<212> TYPE: DNA
<213> ORGANISM: Artificial Sequence
<220> FEATURE:
<223> OTHER INFORMATION: Synthetic Construct

<400> SEQUENCE: 49
aacgctccaa ctgtgtcaga ca                                               22

<210> SEQ ID NO 50
<211> LENGTH: 22
<212> TYPE: DNA
<213> ORGANISM: Artificial Sequence
<220> FEATURE:
<223> OTHER INFORMATION: ACGTTTGTGTCAGTAGCTGGAA

<400> SEQUENCE: 50
acgtttgtgt cagtagctgg aa                                               22

<210> SEQ ID NO 51
<211> LENGTH: 22
<212> TYPE: DNA
<213> ORGANISM: Artificial Sequence
<220> FEATURE:
<223> OTHER INFORMATION: Synthetic Construct

<400> SEQUENCE: 51
tacaacttcc ccacgagagc ag                                               22

<210> SEQ ID NO 52
<211> LENGTH: 24
<212> TYPE: DNA
<213> ORGANISM: Artificial Sequence
<220> FEATURE:
<223> OTHER INFORMATION: Synthetic Construct

<400> SEQUENCE: 52
tgtgaaagac gaactcagat ctgc                                             24

<210> SEQ ID NO 53
<211> LENGTH: 22
<212> TYPE: DNA
<213> ORGANISM: Artificial Sequence
<220> FEATURE:
<223> OTHER INFORMATION: Synthetic Construct

<400> SEQUENCE: 53
```
tgcaactccc atcacctgta ca                                                    22

<210> SEQ ID NO 54
<211> LENGTH: 39
<212> TYPE: DNA
<213> ORGANISM: Artificial Sequence
<220> FEATURE:
<223> OTHER INFORMATION: Synthetic Construct

<400> SEQUENCE: 54
gtggcggccg cttaaaacag cctgtgggtt gatcccacc                                  39

<210> SEQ ID NO 55
<211> LENGTH: 49
<212> TYPE: DNA
<213> ORGANISM: Artificial Sequence
<220> FEATURE:
<223> OTHER INFORMATION: Synthetic Construct

<400> SEQUENCE: 55
ggtatcgatt tttttttttt tttttccgca ccgaatgcgg agaatttac                        49

<210> SEQ ID NO 56
<211> LENGTH: 44
<212> TYPE: DNA
<213> ORGANISM: Artificial Sequence
<220> FEATURE:
<223> OTHER INFORMATION: Synthetic Construct

<400> SEQUENCE: 56
gaactgtatg taattactca tccgcttctc aagggagaac actc                            44

<210> SEQ ID NO 57
<211> LENGTH: 44
<212> TYPE: DNA
<213> ORGANISM: Artificial Sequence
<220> FEATURE:
<223> OTHER INFORMATION: Synthetic Construct

<400> SEQUENCE: 57
gagtgttctc ccttgagaag cggatgagta attacataca gttc                            44

<210> SEQ ID NO 58
<211> LENGTH: 60
<212> TYPE: DNA
<213> ORGANISM: Artificial Sequence
<220> FEATURE:
<223> OTHER INFORMATION: Synthetic Construct

<400> SEQUENCE: 58
gagttcgaac catggcggct gtgggaccgc ggaccggccc cggaaccggc gccgaggctc            60

<210> SEQ ID NO 59
<211> LENGTH: 36
<212> TYPE: DNA
<213> ORGANISM: Artificial Sequence
<220> FEATURE:
<223> OTHER INFORMATION: Synthetic Construct

<400> SEQUENCE: 59
tccccgcggc tactggaaca gtgcctcaag ggcagc                                     36

<210> SEQ ID NO 60
<211> LENGTH: 31
<212> TYPE: DNA
<213> ORGANISM: Artificial Sequence

```
<220> FEATURE:
<223> OTHER INFORMATION: Synthetic Construct

<400> SEQUENCE: 60
ccgctcgagg gcgtatctga ttacattaaa g                                    31

<210> SEQ ID NO 61
<211> LENGTH: 34
<212> TYPE: DNA
<213> ORGANISM: Artificial Sequence
<220> FEATURE:
<223> OTHER INFORMATION: Synthetic Construct

<400> SEQUENCE: 61
tccccgcggc tattggaaaa gagcttcaat ggtg                                 34

<210> SEQ ID NO 62
<211> LENGTH: 42
<212> TYPE: DNA
<213> ORGANISM: Artificial Sequence
<220> FEATURE:
<223> OTHER INFORMATION: Synthetic Construct

<400> SEQUENCE: 62
tgttccagat tacgctctcg agggcctcac caattacata ga                        42

<210> SEQ ID NO 63
<211> LENGTH: 45
<212> TYPE: DNA
<213> ORGANISM: Artificial Sequence
<220> FEATURE:
<223> OTHER INFORMATION: Synthetic Construct

<400> SEQUENCE: 63
cggccgcagt cgacggtacc ccctattgaa acaaagcctc catac                     45

<210> SEQ ID NO 64
<211> LENGTH: 34
<212> TYPE: DNA
<213> ORGANISM: Artificial Sequence
<220> FEATURE:
<223> OTHER INFORMATION: Synthetic Construct

<400> SEQUENCE: 64
ccgctcgagg gcattactga ttatattcaa aatc                                 34

<210> SEQ ID NO 65
<211> LENGTH: 36
<212> TYPE: DNA
<213> ORGANISM: Artificial Sequence
<220> FEATURE:
<223> OTHER INFORMATION: Synthetic Construct

<400> SEQUENCE: 65
tccccgcggc tactgaaaca gagcttccag cttatc                               36

<210> SEQ ID NO 66
<211> LENGTH: 28
<212> TYPE: DNA
<213> ORGANISM: Artificial Sequence
<220> FEATURE:
<223> OTHER INFORMATION: Synthetic Construct

<400> SEQUENCE: 66
ccgctcgagg ggccgagctt ggacttcg                                        28
```

<210> SEQ ID NO 67
<211> LENGTH: 32
<212> TYPE: DNA
<213> ORGANISM: Artificial Sequence
<220> FEATURE:
<223> OTHER INFORMATION: Synthetic Construct

<400> SEQUENCE: 67
tccccgcggc tattgttcac tgcaaaagta tc                                   32

<210> SEQ ID NO 68
<211> LENGTH: 28
<212> TYPE: DNA
<213> ORGANISM: Artificial Sequence
<220> FEATURE:
<223> OTHER INFORMATION: Synthetic Construct

<400> SEQUENCE: 68
ccgctcgagg gaccagggtt cgattacg                                        28

<210> SEQ ID NO 69
<211> LENGTH: 32
<212> TYPE: DNA
<213> ORGANISM: Artificial Sequence
<220> FEATURE:
<223> OTHER INFORMATION: Synthetic Construct

<400> SEQUENCE: 69
tccccgcggc taactctgag tgaagtatga tc                                   32

<210> SEQ ID NO 70
<211> LENGTH: 29
<212> TYPE: DNA
<213> ORGANISM: Artificial Sequence
<220> FEATURE:
<223> OTHER INFORMATION: Synthetic Construct

<400> SEQUENCE: 70
ccgctcgagg gaccagggtt cgattttgc                                       29

<210> SEQ ID NO 71
<211> LENGTH: 32
<212> TYPE: DNA
<213> ORGANISM: Artificial Sequence
<220> FEATURE:
<223> OTHER INFORMATION: Synthetic Construct

<400> SEQUENCE: 71
tccccgcggc taaaaaactt gatggaaaac ac                                   32

<210> SEQ ID NO 72
<211> LENGTH: 34
<212> TYPE: DNA
<213> ORGANISM: Artificial Sequence
<220> FEATURE:
<223> OTHER INFORMATION: Synthetic Construct

<400> SEQUENCE: 72
tccccgcggc taagccccga cactgtgcct gtgg                                 34

<210> SEQ ID NO 73
<211> LENGTH: 31
<212> TYPE: DNA
<213> ORGANISM: Artificial Sequence
<220> FEATURE:
<223> OTHER INFORMATION: Synthetic Construct

```
<400> SEQUENCE: 73
cgcgtcgacg gcgtatctga ttacattaaa g                              31

<210> SEQ ID NO 74
<211> LENGTH: 29
<212> TYPE: DNA
<213> ORGANISM: Artificial Sequence
<220> FEATURE:
<223> OTHER INFORMATION: Synthetic Construct

<400> SEQUENCE: 74
cgcgtcgacg gcctcaccaa ttacataga                                 29

<210> SEQ ID NO 75
<211> LENGTH: 32
<212> TYPE: DNA
<213> ORGANISM: Artificial Sequence
<220> FEATURE:
<223> OTHER INFORMATION: Synthetic Construct

<400> SEQUENCE: 75
tccccgcggc tattgaaaca aagcctccat ac                             32

<210> SEQ ID NO 76
<211> LENGTH: 45
<212> TYPE: DNA
<213> ORGANISM: Artificial Sequence
<220> FEATURE:
<223> OTHER INFORMATION: Synthetic Construct

<400> SEQUENCE: 76
catggcggtg gcttaagcag agagtgtccc aatattacgg aatac               45

<210> SEQ ID NO 77
<211> LENGTH: 45
<212> TYPE: DNA
<213> ORGANISM: Artificial Sequence
<220> FEATURE:
<223> OTHER INFORMATION: Synthetic Construct

<400> SEQUENCE: 77
gtattccgta atattgggac actctctgct taagccaccg ccatg               45

<210> SEQ ID NO 78
<211> LENGTH: 43
<212> TYPE: DNA
<213> ORGANISM: Artificial Sequence
<220> FEATURE:
<223> OTHER INFORMATION: Synthetic Construct

<400> SEQUENCE: 78
ctgagatgac aaacgcctgc aggggcatgg aatggatagc cat                 43

<210> SEQ ID NO 79
<211> LENGTH: 43
<212> TYPE: DNA
<213> ORGANISM: Artificial Sequence
<220> FEATURE:
<223> OTHER INFORMATION: Synthetic Construct

<400> SEQUENCE: 79
atggctatcc attccatgcc cctgcaggcg tttgtcatct cag                 43

<210> SEQ ID NO 80
```

<211> LENGTH: 46
<212> TYPE: DNA
<213> ORGANISM: Artificial Sequence
<220> FEATURE:
<223> OTHER INFORMATION: Synthetic Construct

<400> SEQUENCE: 80
gtaattacat acagttcaag tccagatgcc gtattgagcc tgtatg    46

<210> SEQ ID NO 81
<211> LENGTH: 46
<212> TYPE: DNA
<213> ORGANISM: Artificial Sequence
<220> FEATURE:
<223> OTHER INFORMATION: Synthetic Construct

<400> SEQUENCE: 81
catacaggct caatacggca tctggacttg aactgtatgt aattac    46

<210> SEQ ID NO 82
<211> LENGTH: 45
<212> TYPE: DNA
<213> ORGANISM: Artificial Sequence
<220> FEATURE:
<223> OTHER INFORMATION: Synthetic Construct

<400> SEQUENCE: 82
catgggagtc ccggtgcagg taggtcagtt gcaacaaatc tgatc    45

<210> SEQ ID NO 83
<211> LENGTH: 45
<212> TYPE: DNA
<213> ORGANISM: Artificial Sequence
<220> FEATURE:
<223> OTHER INFORMATION: Synthetic Construct

<400> SEQUENCE: 83
gatcagattt gttgcaactg acctacctgc accgggactc ccatg    45

<210> SEQ ID NO 84
<211> LENGTH: 47
<212> TYPE: DNA
<213> ORGANISM: Artificial Sequence
<220> FEATURE:
<223> OTHER INFORMATION: Synthetic Construct

<400> SEQUENCE: 84
gttgcccagt caactttaag agatgttgcc cgttagtctg tggaaag    47

<210> SEQ ID NO 85
<211> LENGTH: 47
<212> TYPE: DNA
<213> ORGANISM: Artificial Sequence
<220> FEATURE:
<223> OTHER INFORMATION: Synthetic Construct

<400> SEQUENCE: 85
ctttccacag actaacgggc aacatctctt aaagttgact gggcaac    47

<210> SEQ ID NO 86
<211> LENGTH: 31
<212> TYPE: DNA
<213> ORGANISM: Artificial Sequence
<220> FEATURE:
<223> OTHER INFORMATION: Synthetic Construct

<400> SEQUENCE: 86

```
ccgctcgagc ctttcacgtt taaaccaaga c                               31
```

<210> SEQ ID NO 87
<211> LENGTH: 34
<212> TYPE: DNA
<213> ORGANISM: Artificial Sequence
<220> FEATURE:
<223> OTHER INFORMATION: Synthetic Construct

<400> SEQUENCE: 87

```
tccccgcggc tactgctgtt ggaaaagtga gatc                            34
```

<210> SEQ ID NO 88
<211> LENGTH: 31
<212> TYPE: DNA
<213> ORGANISM: Artificial Sequence
<220> FEATURE:
<223> OTHER INFORMATION: Synthetic Construct

<400> SEQUENCE: 88

```
ccgctcgagt cccccttaa acaggtcaat g                                31
```

<210> SEQ ID NO 89
<211> LENGTH: 33
<212> TYPE: DNA
<213> ORGANISM: Artificial Sequence
<220> FEATURE:
<223> OTHER INFORMATION: Synthetic Construct

<400> SEQUENCE: 89

```
tccccgcggc tattgggcca caagggtctg cac                             33
```

<210> SEQ ID NO 90
<211> LENGTH: 26
<212> TYPE: DNA
<213> ORGANISM: Artificial Sequence
<220> FEATURE:
<223> OTHER INFORMATION: Synthetic Construct

<400> SEQUENCE: 90

```
aatcactagt gggtcaagac tccatc                                     26
```

<210> SEQ ID NO 91
<211> LENGTH: 26
<212> TYPE: DNA
<213> ORGANISM: Artificial Sequence
<220> FEATURE:
<223> OTHER INFORMATION: Synthetic Construct

<400> SEQUENCE: 91

```
catccacgtg tgtgttaaca ttcccg                                     26
```

<210> SEQ ID NO 92
<211> LENGTH: 43
<212> TYPE: DNA
<213> ORGANISM: Artificial Sequence
<220> FEATURE:
<223> OTHER INFORMATION: Synthetic Construct

<400> SEQUENCE: 92

```
aggcacagtg tcggggctgt ccttgaggca ctgttccagg gtc                  43
```

<210> SEQ ID NO 93
<211> LENGTH: 43
<212> TYPE: DNA

<213> ORGANISM: Artificial Sequence
<220> FEATURE:
<223> OTHER INFORMATION: Synthetic Construct

<400> SEQUENCE: 93
gaccctggaa cagtgcctca aggacagccc cgacactgtg cct         43

<210> SEQ ID NO 94
<211> LENGTH: 36
<212> TYPE: DNA
<213> ORGANISM: Artificial Sequence
<220> FEATURE:
<223> OTHER INFORMATION: Synthetic Construct

<400> SEQUENCE: 94
gtacttccaa tccggagcgg ctgtgggacc gcggac         36

<210> SEQ ID NO 95
<211> LENGTH: 47
<212> TYPE: DNA
<213> ORGANISM: Artificial Sequence
<220> FEATURE:
<223> OTHER INFORMATION: Synthetic Construct

<400> SEQUENCE: 95
ggtggtgctc gagtgcggcc gctcaaggcc agattcgcaa gtaggtg         47

<210> SEQ ID NO 96
<211> LENGTH: 38
<212> TYPE: DNA
<213> ORGANISM: Artificial Sequence
<220> FEATURE:
<223> OTHER INFORMATION: Synthetic Construct

<400> SEQUENCE: 96
gtacttccaa tccggatcca aatgccgtat tgagcctg         38

<210> SEQ ID NO 97
<211> LENGTH: 43
<212> TYPE: DNA
<213> ORGANISM: Artificial Sequence
<220> FEATURE:
<223> OTHER INFORMATION: Synthetic Construct

<400> SEQUENCE: 97
ggtggtgctc gagtgcggcc gcctactgga acagtgcctc aag         43

<210> SEQ ID NO 98
<211> LENGTH: 46
<212> TYPE: DNA
<213> ORGANISM: Artificial Sequence
<220> FEATURE:
<223> OTHER INFORMATION: Synthetic Construct

<400> SEQUENCE: 98
ggtggtgctc gagtgcggcc gctcaagccc cgacactgtg cctgtg         46

<210> SEQ ID NO 99
<211> LENGTH: 37
<212> TYPE: DNA
<213> ORGANISM: Artificial Sequence
<220> FEATURE:
<223> OTHER INFORMATION: Synthetic Construct

<400> SEQUENCE: 99
gtacttccaa tccggagacg aggcggtgca ggaggcc         37

<210> SEQ ID NO 100
<211> LENGTH: 37
<212> TYPE: DNA
<213> ORGANISM: Artificial Sequence
<220> FEATURE:
<223> OTHER INFORMATION: Synthetic Construct

<400> SEQUENCE: 100
gtacttccaa tccggactca gcagccagat ccaggag                                37

<210> SEQ ID NO 101
<211> LENGTH: 43
<212> TYPE: DNA
<213> ORGANISM: Artificial Sequence
<220> FEATURE:
<223> OTHER INFORMATION: Synthetic Construct

<400> SEQUENCE: 101
caaccacagg cacagtgtcg cggctaccct tgaggcactg ttc                         43

<210> SEQ ID NO 102
<211> LENGTH: 43
<212> TYPE: DNA
<213> ORGANISM: Artificial Sequence
<220> FEATURE:
<223> OTHER INFORMATION: Synthetic Construct

<400> SEQUENCE: 102
gaacagtgcc tcaagggtag ccgcgacact gtgcctgtgg ttg                         43

<210> SEQ ID NO 103
<211> LENGTH: 43
<212> TYPE: DNA
<213> ORGANISM: Artificial Sequence
<220> FEATURE:
<223> OTHER INFORMATION: Synthetic Construct

<400> SEQUENCE: 103
caaccacagg cacagtgtcg cggctgccct tgaggcactg ttc                         43

<210> SEQ ID NO 104
<211> LENGTH: 43
<212> TYPE: DNA
<213> ORGANISM: Artificial Sequence
<220> FEATURE:
<223> OTHER INFORMATION: Synthetic Construct

<400> SEQUENCE: 104
gaacagtgcc tcaagggcag ccgcgacact gtgcctgtgg ttg                         43

<210> SEQ ID NO 105
<211> LENGTH: 41
<212> TYPE: DNA
<213> ORGANISM: Artificial Sequence
<220> FEATURE:
<223> OTHER INFORMATION: Synthetic Construct

<400> SEQUENCE: 105
caggcacagt gtcggggcta gccttgaggc actgttccag g                           41

<210> SEQ ID NO 106
<211> LENGTH: 41
<212> TYPE: DNA
<213> ORGANISM: Artificial Sequence
<220> FEATURE:

```
<223> OTHER INFORMATION: Synthetic Construct

<400> SEQUENCE: 106
cctggaacag tgcctcaagg ctagccccga cactgtgcct g                              41

<210> SEQ ID NO 107
<211> LENGTH: 41
<212> TYPE: DNA
<213> ORGANISM: Artificial Sequence
<220> FEATURE:
<223> OTHER INFORMATION: Synthetic Construct

<400> SEQUENCE: 107
caggcacagt gtcggggctg gccttgaggc actgttccag g                              41

<210> SEQ ID NO 108
<211> LENGTH: 41
<212> TYPE: DNA
<213> ORGANISM: Artificial Sequence
<220> FEATURE:
<223> OTHER INFORMATION: Synthetic Construct

<400> SEQUENCE: 108
cctggaacag tgcctcaagg ccagccccga cactgtgcct g                              41

<210> SEQ ID NO 109
<211> LENGTH: 11
<212> TYPE: DNA
<213> ORGANISM: Artificial Sequence
<220> FEATURE:
<223> OTHER INFORMATION: synthetic construct

<400> SEQUENCE: 109
gcccttgagg c                                                               11

<210> SEQ ID NO 110
<211> LENGTH: 11
<212> TYPE: DNA
<213> ORGANISM: Artificial Sequence
<220> FEATURE:
<223> OTHER INFORMATION: Synthetic construct

<400> SEQUENCE: 110
acccttgagg c                                                               11
```